US008445000B2

(12) United States Patent
Sellman et al.

(10) Patent No.: US 8,445,000 B2
(45) Date of Patent: May 21, 2013

(54) IMMUNOGENIC COMPOSITIONS OF STAPHYLOCOCCUS EPIDERMIDIS POLYPEPTIDE ANTIGENS

(75) Inventors: Bret Richard Sellman, Warwick, NY (US); Steven Morris Baker, Highland Mills, NY (US)

(73) Assignee: Wyeth LLC, Madison, NJ (US)

( * ) Notice: Subject to any disclaimer, the term of this patent is extended or adjusted under 35 U.S.C. 154(b) by 294 days.

(21) Appl. No.: 11/665,940

(22) PCT Filed: Oct. 19, 2005

(86) PCT No.: PCT/US2005/037746
§ 371 (c)(1),
(2), (4) Date: Apr. 20, 2007

(87) PCT Pub. No.: WO2007/001423
PCT Pub. Date: Jan. 4, 2007

(65) Prior Publication Data
US 2007/0292450 A1    Dec. 20, 2007

Related U.S. Application Data

(60) Provisional application No. 60/620,788, filed on Oct. 21, 2004.

(51) Int. Cl.
*A61K 39/085* (2006.01)
*A61K 39/02* (2006.01)
*A61K 39/00* (2006.01)
*A61K 51/00* (2006.01)
*A61M 36/14* (2006.01)
*C07K 14/00* (2006.01)
*C07K 17/00* (2006.01)

(52) U.S. Cl.
USPC ............. 424/243.1; 424/234.1; 424/190.1; 424/1.11; 424/198.1; 530/350; 435/69.1; 435/69.7; 536/23.1; 536/23.7

(58) Field of Classification Search
None
See application file for complete search history.

(56) References Cited

U.S. PATENT DOCUMENTS

| | | | |
|---|---|---|---|
| 5,700,928 A | 12/1997 | Hodgson et al. | |
| 5,801,234 A | 9/1998 | Hodgson et al. | |
| 6,380,370 B1 * | 4/2002 | Doucette-Stamm et al. | 536/23.1 |
| 6,703,492 B1 | 3/2004 | Kimmerly | |
| 6,995,008 B1 | 2/2006 | Liu et al. | |
| 7,060,458 B1 * | 6/2006 | Doucette-Stamm et al. | 435/69.1 |
| 2004/0147734 A1 | 7/2004 | Doucette-Stamm et al. | |
| 2006/0018881 A1 | 1/2006 | Liu et al. | |

FOREIGN PATENT DOCUMENTS

| | | |
|---|---|---|
| WO | 93/09811 | 5/1993 |
| WO | 93/19373 | 9/1993 |
| WO | 94/16737 | 8/1994 |
| WO | WO 96/09321 * | 3/1996 |
| WO | 00/12689 | 3/2000 |
| WO | 01/34809 A2 | 5/2001 |
| WO | 01/98499 A1 | 12/2001 |
| WO | WO 02/059148 | 8/2002 |
| WO | WO 03/011899 | 2/2003 |
| WO | 2004/043405 A2 | 5/2004 |
| WO | 2004/087746 A2 | 10/2004 |
| WO | 2006/032472 A2 | 3/2006 |

OTHER PUBLICATIONS

Rupp et al. The Journal of Infectious Diseases 2001;183:1038-42.*
Rupp et al. The Journal of Infectious Disease 2001; 183:1038-42.*
Josefsson et al, The Journal of Infectious Diseases 2001; 184:1572-80.*
Houghten et al. (New Approaches to Immunization, Vaccines 86, Cold Spring Harbor Laboratory, p. 21-25, 1986).*
Colman et al. (Research in Immunology 145: 33-36, 1994, p. 33 col. 2, p. 35 col. 1).*
(Greenspan et al, Nature Biotechnology 17:936-937, 1999).*
Harlow et al , Antibodies a Laboratory Manual, Cold Spring Harbor Laboratory Press Inc., 1988). pp. 23-25, 27-33 and 72-74.*
Sellman, B.R.; et al.—Infection and Immunity 73(10):6591-6600—Oct. 2005.
Bowden MG, et al.; The Journal of Biological Chemistry 277(45)43017-43023 (2002).
Cockayne A, et al.; Infection and Immunity 66(8):3767-3774 (1998).
Davis SL, et al.; The Journal of Biological Chemistry 276(30)27799-27805 (2001).
Diekema, DJ, et al.; International Journal of Antimicrobial Agents 20:412-418 (2002).
Edmond MB, et al.; Clinical Infectious Diseases 29:239-244 (1999).
Grifantini R, et al.; Nature Biotechnology 20:914-921 (2002).
Haas G, et al.; Proteomics 2:313-324 (2002).
Heilmann C, et al.; Molecular Microbiology 24(5):1013-1024 (1997).
Hussain M, et al.; Infection and Immunity 65(2):519-524 (1997).
Josefsson E, et al.; The Journal of Infectious Diseases 184:1572-1580 (2001).
McKenney D, et al.; Infection and Immunity 66(10):4711-4720 (1998).
McKenney D, et al.; Science 284 1523-1527 1999.
Nilsson M, et al.; Infection and Immunity 66(6):2666-2673 (1998).
Rupp ME, et al.; The Journal of Infectious Diseases 183:1038-1042 (2001).
Shepard BD and Gilmore MS; Infection and Immunity 70(8):4344-4352 (2002).
Swialto E, et al.; Infection and Immunity 71(12):7149-7153 (2003).
Veenstra GJC, et al.; Journal of Bacteriology 178(2):537-541 (1996).
Von Eiff C, et al.; Eur J Clin Microbiol Infect Dis 18:843-846 (1999).
Von Eiff C, et al.; The Lancet Infectious Diseases 2:677-685 (2002).

(Continued)

*Primary Examiner* — Larry Helms
*Assistant Examiner* — Oluwatosin Ogunbiyi
(74) *Attorney, Agent, or Firm* — Victoria S. Molenda

(57) ABSTRACT

The present invention relates to immunogenic compositions, comprising polypeptides isolated from *Staphylococcus epidermidis*. The invention also relates to polynucleotides encoding *Staphylococcus epidermidis* polypeptides and their use in immunogenic compostions. In addition, the invention relates to methods of inducing an immune response in mammals against *Staphylococcus epidermidis* and *Staphylococcus aureus* using immunogenic compostions of the *Staphylococcus epidermidis* polypeptides and polynucleotides. The invention also relates to methods for detecting *Staphylococcus epidermidis* in a biological sample.

21 Claims, 4 Drawing Sheets

OTHER PUBLICATIONS

Vuong C, et al.; The Journal of Infectious Diseases 188:706-718 (2003).
Vytvytska O, et al.; Proteomics 2:580-590 (2002).
Wang X, et al.; J. of Bacteriology 186(9):2724-2734 (2004).
Williams RJ, et al.; Infection and Immunity 70(12):6805-6810 (2002).
Wiltshire MD and Foster SJ; Infection and Immunity 69(8)5198-5202 (2001).
Otto, M., et al., "ABC Transporters of *Staphylococci*", Res. Microbiol., 152:351-356 (2001).
Chen, et al., "Rapid screening of highly efficient vaccine candidates by immunoproteomics," Proteomics 4:3203-3213 (2004).

* cited by examiner

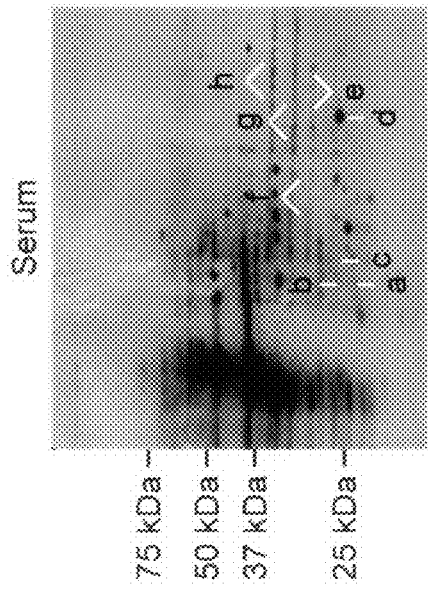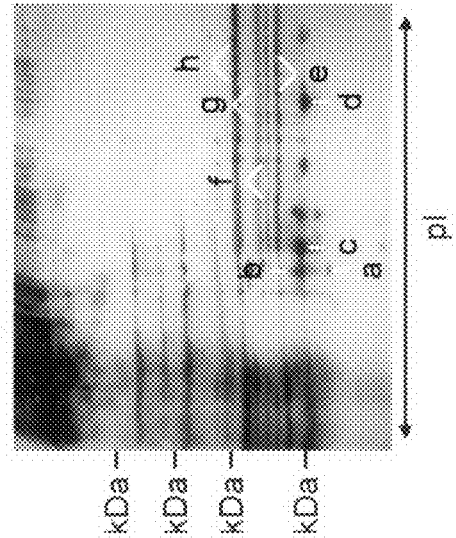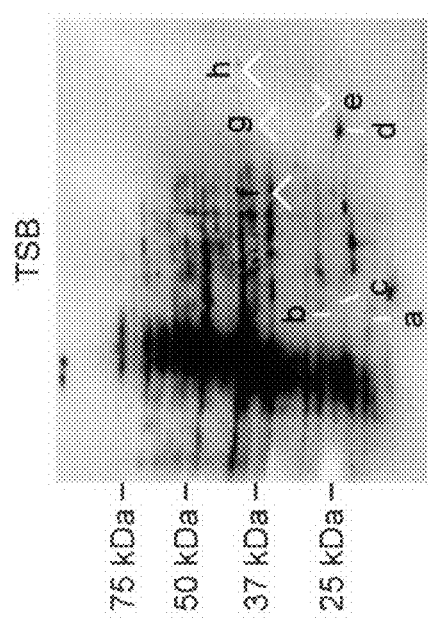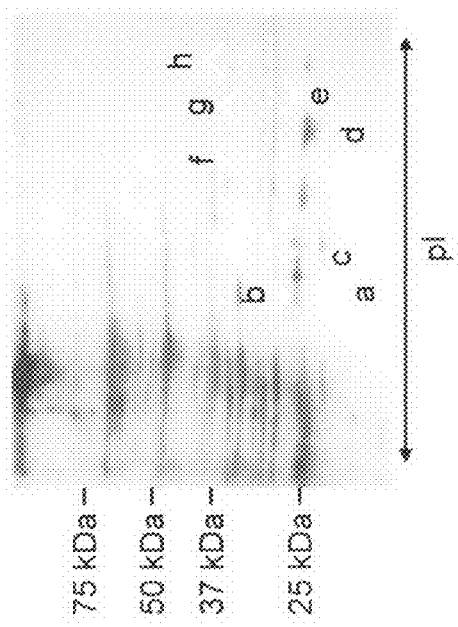

IMMUNOGENIC COMPOSITIONS OF *STAPHYLOCOCCUS EPIDERMIDIS* POLYPEPTIDE ANTIGENS

This application is a National Stage application filed under 35 U.S.C. §371 from PCT International Application No. PCT/US05/037746, filed on Oct. 19, 2005, which claims the benefit under 35 U.S.C. §119 (e) of U.S. Provisional Application No. 60/620,788, filed on Oct. 21, 2004, the entire disclosures of which are hereby incorporated by reference in their entirety.

FIELD OF THE INVENTION

The present invention relates to immunogenic compositions, comprising polypeptides isolated from *Staphylococcus epidermidis*. The invention also relates to polynucleotides encoding *Staphylococcus epidermidis* polypeptides and their use in immunogenic compositions. In addition, the invention relates to methods of inducing an immune response in mammals against *Staphylococcus epidermidis* and *Staphylococcus aureus* using immunogenic compositions of the *Staphylococcus epidermidis* polypeptides and polynucleotides. The invention also relates to methods for detecting *Staphylococcus epidermidis* in a biological sample.

BACKGROUND OF THE INVENTION

*Staphylococcus epidermidis* is a major component of the normal human microbial flora on the skin and mucous membranes and was once considered only a contaminant when cultured from an infected patient. See Heilmann, C. and G. Peters, Biology and pathogenicity of Staphylococcus epidermidis, in Gram-positive pathogens, V. A. Fischetti, Editor. 2000, American Society for Microbiology: Washington, D.C. p. 442-449; von Eiff, C., et al., Lancet Infect Dis, 2(11): p. 677-85 (2002). It is now widely accepted to be an opportunistic pathogen of great importance and a leading cause of nosocomial bloodstream infections. See Am J Infect Control, 27: p. 520-32 (1999); Diekema, D. J., et al., Int J Antimicrob Agents, 20(6): p. 412-8 (2002); Edmond, M. B., et al., Clin Infect Dis, 29(2): p. 239-44 (1999). These infections are primarily associated with the presence of an indwelling foreign polymer body such as a venous catheter, prosthetic joint or prosthetic heart valve. See Heilmann, C. and G. Peters, Biology and pathogenicity of Staphylococcus epidermidis, in Gram-positive pathogens, V. A. Fischetti, Editor. 2000, American Society for Microbiology: Washington, D.C. p. 442-449; von Eiff, C., et al., Lancet Infect Dis, 2(11): p. 677-85 (2002). Infection is thought to result from introduction of *Staphylcoccus epidermidis* from the patient's skin upon insertion of the prosthetic device. Colonization and subsequent biofilm formation can lead to bacteremia with the potential for hematogenous spread to other sites in the body. These infections are often difficult to treat, arising from the reduced killing of bacteria within a biofilm by antibiotics and also an increase in antibiotic resistance among clinical isolates. See Diekema, D. J., et al., Int J Antimicrob Agents, 20(6): p. 412-8 (2002); Edmond, M. B., et al., Clin Infect Dis, 29(2): p. 239-44 (1999); Lewis, K., Antimicrob Agents Chemother, 45(4): p. 999-1007 (2001); Raad, I. et al., Clin Infect Dis, 26(5): p.1182-7 (1998). *Staphylococcus epidermidis* with reduced susceptibility to vancomycin have been reported. See Sanyal, D. and D. Greenwood, J Med Microbiol, 39(3): p. 204-10(1993); Sanyal, D., et al., Lancet, 337 (8732): p. 54(1991). Difficulty treating these infections necessitates the use of immunization as a means to prevent infection.

Biofilm formation is a major virulence determinant for *Staphylcoccus epidermidis* infections. Consequently, research on *Staphylcoccus epidermidis* surface proteins has focused on those proteins involved in biofilm formation. These proteins have been subdivided into groups based on their involvement in the two major steps of biofilm formation: 1) primary attachment, *staphylococca*; surface protein-1 (SSP-1), autolysin (AtlE), Fbe (SdrG) and GehD and 2) bacterial cell accumulation, Bap homologous protein (Bhp), accumulation associated protein (AAP) and autolysin (AtlE). See von Eiff, C., et a., Lancet Infect Dis, 2002. 2(11): p. 677-85; Vuong, C., et al., J Infect Dis, 188(5): p. 706-18 (2003); Veenstra, G. J., et al., J Bacteriol., 178(2): p. 537-41 (1996); Rupp, M. E., et al., J Infect Dis, 183(7): p. 1038-42 (2001); Hussain, M., et al., Infect Immun, 65(2): p. 519-24 (1997); Nilsson, M., et al., Infect Immun, 66(6): p. 2666-73 (1998); Davis, S. L., et al., J Biol Chem, 276(30): p. 27799-805 (2001); and Bowden, M. G., et al., J Biol Chem, 277(45): p. 43017-43023 (2002). Comparatively less effort has been exerted towards the identification of surface proteins expressed upon exposure to the environmental cues within the host or those involved in host-parasite interactions.

*Staphylococcus epidermidis* must undergo a transition from commensal to pathogen and adapt to its microenvironment within the host. For a commensal to transition to a pathogen it must gain access to host tissue, sense changes in its environment, alter gene expression so that it is able to evade host defenses, attach and adhere to host factors, grow and divide in the presence of different nutrients and host defenses. Proteins on the bacterial surface make initial contact with the new environment within the host. The many functions of these proteins include sensing the environment, scavenging and transporting nutrients, defending against the host immune system and binding host proteins. Surface exposed proteins can also serve as points of contact or recognition by the host immune system and can be targets for a humoral immune response against the bacterium. Josefsson, E., et al., J Infect Dis, 184(12): p. 1572-80 (2001); Swiatlo, E., et al., Infect Immun, 71(12): p. 7149-53 (2003); Grifantini, R., et al., Nat Biotechnol, 20(9): p. 914-21 (2002). Thus, there is an immediate need for identifying promising candidates among *Staphylococcus epidermidis* proteins for use in immunogenic compositions that induce immune responses to disease causing serotypes of *Staphylococcus epidermidis*.

SUMMARY OF THE INVENTION

The present invention provides an immunogenic composition comprising a polypeptide having an amino acid sequence chosen from one or more of SEQ ID NO: 1 through SEQ ID NO: 32, a biological equivalent thereof, or a fragment thereof. In a particular embodiment, the polypeptide is immunoreactive with antibodies in the serum of rabbits infected with *Staphylococcus epidermidis*. In another embodiment, the polypeptide binds to one or more rabbit serum proteins.

In certain embodiments, the immunogenic composition further comprises a pharmaceutically acceptable carrier. In other embodiments, the immunogenic compositions of the invention also comprise one or more adjuvants. In still another embodiment, the immunogenic composition further comprises a *Staphylococcus epidermidis* polysaccharide antigen. In still another embodiment, the immunogenic composition further comprises a *Staphylococcus aureus* polysaccharide or polypeptide antigen.

The present invention provides immunogenic compositions, comprising a polypeptide isolated from *Staphylococcus epidermidis*.

The present invention provides an immunogenic composition comprising a *Staphylococcus epidermidis* polypeptide wherein the polypeptide further comprises heterologous amino acids. In a particular embodiment, the polypeptide is a fusion polypeptide. In another embodiment, the polypeptide is a recombinant polypeptide. In still another embodiment, the invention provides an immunogenic composition comprising a *Staphylococcus epidermidis* polypeptide wherein the polypeptide comprises a neutralizing epitope of *Staphylococcus epidermidis*. In a certain embodiment, the polypeptide is a lipoprotein.

The present invention further provides immunogenic compositions, comprising a *Staphylococcus epidermidis* polypeptide, wherein the polypeptide is encoded by a polynucleotide comprising a nucleotide sequence having at least about 95% identity to a nucleotide sequence chosen from one of SEQ ID NO: 33 through SEQ ID NO: 64 or a degenerate variant thereof, or a fragment thereof. In a particular embodiment, the *Staphylococcus epidermidis* polynucleotide sequence is selected from the group consisting of SEQ ID NO: 40, SEQ ID NO: 42, SEQ ID NO: 43, SEQ ID NO: 44, SEQ ID NO: 46, SEQ ID NO: 50, SEQ ID NO: 51, SEQ ID NO: 52, SEQ ID NO: 55, SEQ ID NO: 58, SEQ ID NO: 59, and SEQ ID NO: 62, or a degenerate variant thereof, or a fragment thereof.

The present invention provides an immunogenic composition, wherein the polynucleotide is derived from *Staphylococcus epidermidis*. In a particular embodiment, the polynucleotide further comprises heterologous nucleotides. In another embodiment, the polynucleotide is in an expression vector. In still another embodiment, the expression vector is plasmid DNA. In a certain embodiment, the polynucleotide is a recombinant polynucleotide. In another embodiment, the polynucleotide is operatively linked to one or more gene expression regulatory elements. In still another embodiment, the polynucleotide directs the expression of a neutralizing epitope of *Staphylococcus epidermidis*.

The invention also provides an immunogenic composition comprising a *Staphylococcus epidermidis* polypeptide encoded by a polynucleotide, wherein the immunogenic composition further comprises a transfection facilitating agent. In a particular embodiment, said transfection facilitating agent is bupivicaine.

The present invention also provides a method of inducing an immune response against *Staphylococcus epidermidis* comprising administering to a mammal an immunogenic amount of a composition comprising: a polypeptide having an amino acid sequence chosen from one or more of SEQ ID NO: 1 through SEQ ID NO: 32 or a biological equivalent thereof, or a fragment thereof, and a pharmaceutically acceptable carrier.

In addition, the present invention provides a method of inducing an immune response against *Staphylococcus epidermidis* comprising administering to a mammal an immunogenic amount of a composition comprising: a polynucleotide having a nucleotide sequence chosen from one or more of SEQ ID NO: 33 through SEQ ID NO: 64, a degenerate variant thereof, or a fragment thereof and a pharmaceutically acceptable carrier.

In one embodiment, the invention provides an immunogenic composition comprising a polynucleotide having a nucleotide sequence chosen from one of SEQ ID NO: 33 through SEQ ID NO: 64, a degenerate variant thereof, or a fragment thereof and is comprised in an expression vector. In another embodiment, the polynucleotide is derived from *Staphylococcus epidermidis*. In still another embodiment the polynucleotide comprises heterologous nucleotides.

In a certain embodiment, the invention provides a method for the detection and/or identification of *Staphylococcus epidermidis* in a biological sample comprising: (a) contacting the sample with an oligonucleotide probe of a polynucleotide comprising the nucleotide sequence chosen from one of SEQ ID NO:33 through SEQ ID NO: 64, or a degenerate variant thereof, or a fragment thereof, under conditions permitting hybridization; and (b) detecting the presence of hybridization complexes in the sample, wherein hybridization complexes indicate the presence of *Staphylococcus epidermidis* in the sample.

In other embodiments, the invention provides a method for the detection and/or identification of antibodies to *Staphylococcus epidermidis* in a biological sample comprising: (a) contacting the sample with a polypeptide comprising an amino acid sequence chosen from one of SEQ ID NO: 1 through SEQ ID NO: 32 or a biological equivalent thereof, or a fragment thereof, under conditions permitting immune complex formation; and detecting the presence of immune complexes in the sample, wherein immune complexes indicate the presence of *Streptococcus pneumoniae* in the sample.

In a particular embodiment, the immunogenic composition comprises a *Staphylococcus epidermidis* polypeptide sequence selected from the group consisting of SEQ ID NO: 8, SEQ ID NO: 10, SEQ ID NO: 11, SEQ ID NO: 12, SEQ ID NO: 14, SEQ ID NO: 18, SEQ ID NO: 19, SEQ ID NO: 20, SEQ ID NO: 23, SEQ ID NO: 26, SEQ ID NO: 27, SEQ ID NO: 30, a biological equivalent thereof, or a fragment thereof. In another embodiment, the immunogenic composition comprises a *Staphylococcus epidermidis* polynucleotide sequence selected from the group consisting of SEQ ID NO: 40, SEQ ID NO: 42, SEQ ID NO: 43, SEQ ID NO: 44, SEQ ID NO: 46, SEQ ID NO: 50, SEQ ID NO: 51, SEQ ID NO: 52, SEQ ID NO: 55, SEQ ID NO: 58, SEQ ID NO: 59, SEQ ID NO: 62, or a degenerate variant thereof, or a fragment thereof.

In yet another embodiment, the invention provides a method of inducing an immune response against *Staphylococcus aureus* comprising administering to a mammal an immunogenic amount of a composition comprising: a *Staphylococcus epidermidis* polypeptide sequence selected from the group consisting of SEQ ID NO: 8, SEQ ID NO: 10, SEQ ID NO: 11, SEQ ID NO: 12, SEQ ID NO: 14, SEQ ID NO: 18, SEQ ID NO: 19, SEQ ID NO: 20, SEQ ID NO: 23, SEQ ID NO: 26, SEQ ID NO: 27, SEQ ID NO: 30, a biological equivalent thereof, or a fragment thereof.

In a particular embodiment, the invention provides a method of inducing an immune response against *Staphylococcus aureus* comprising administering to a mammal an immunogenic amount of a composition comprising: a *Staphylococcus epidermidis* polynucleotide sequence selected from the group consisting of SEQ ID NO: 40, SEQ ID NO: 42, SEQ ID NO: 43, SEQ ID NO: 44, SEQ ID NO: 46, SEQ ID NO: 50, SEQ ID NO: 51, SEQ ID NO: 52, SEQ ID NO: 55, SEQ ID NO: 58, SEQ ID NO: 59, SEQ ID NO: 62, or a degenerate variant thereof, or a fragment thereof.

BRIEF DESCRIPTION OF THE DRAWINGS

FIG. 1 depicts protein expression profiles of cell wall fractions from *S. epidermidis* 0-47 grown in TSB (1A and 1C) or 70% rabbit serum (1B and 1D), which were compared by 2D gel electrophoresis. Proteins were separated on pH 4-7 IPG strips in the first dimension followed by SDS-PAGE in the second dimension, transferred to nitrocellulose and detected by fluorescent stain (1A and 1C). Immunoreactive proteins were visualized with immune sera (1B and 1D) from rabbits infected with *S. epidermidis* 0-47. Molecular weight markers are labeled to the left.

DETAILED DESCRIPTION OF THE INVENTION

Figure 2A:
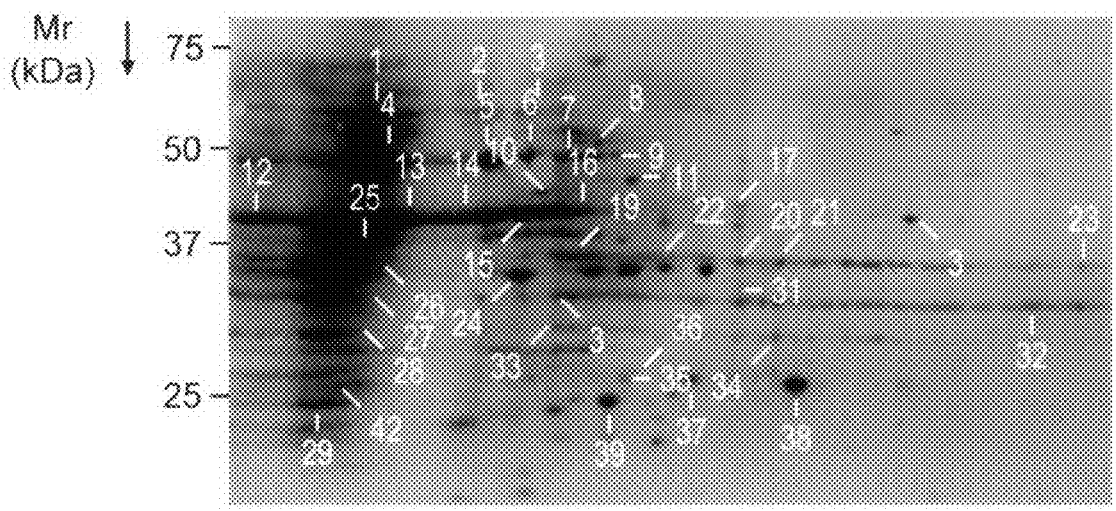
FIG. 2 depicts fluorescent stained blot (2A) and immunoblot (2B) of a cell surface fraction from *S. epidermidis* 0-47 grown in 70% rabbit serum separated on pH 4-7 IPG strips in the first dimension and SDS-PAGE in the second dimension. The proteins in the spots were identified by mass spec analysis.

Upon exposure to the bloodstream of the host, invading bacteria encounter environmental cues specific to the new environment. These cues are detected by the bacteria and signal adaptive changes in protein expression that may be detectable in cell wall purified proteins. Often, proteins and carbohydrates at the bacterial cell wall are candidates for inclusion in immunogenic compositions for treating or preventing bacterial infections. Whether an upregulated protein interacts with the host or plays a role in nutrient acquisition, it is important to the bacteria and therefore plays a role in survival of the bacteria and pathogenesis. Growth of bacteria in body fluids (ie. serum, peritoneal dialysate fluid, and urine) has been used as a model system to mimic some of the signals bacteria encounter within the host. See Wiltshire, M. D. and S. J. Foster, Infect Immun, 69(8): p. 5198-202 (2001); Shepard, B. D. and M. S. Gilmore, Infect Immun, 70(8): p. 4344-52 (2002); Smith, D. G., et al., Infect Immun, 59(2): p. 617-24 (1991); McDermid, K. P., et al., Infect Immun, 61(5): p.1743-9 (1993). One or more of these culture conditions was found to alter gene expression in *Enterococcus faecalis, S. aureus* and *Staphylcoccus epidermidis* and those proteins identified as being increased in expression in the altered culture conditions were found to belong to different classes of proteins having a variety of functions. See Wiltshire, M. D. and S. J. Foster, Infect Immun, 69(8): p. 5198-202 (2001); Shepard, B. D. and M.S. Gilmore, Infect Immun, 70(8): p. 4344-52 (2002).

The most common predisposing factor for a *Staphylcoccus epidermidis* infection is the implantation of a prosthetic device. An implanted prosthetic device becomes coated with plasma and matrix proteins including fibrinogen, vitronectin, von Willebrand factor and fibronectin. See von Eiff, C., et al., Eur J Clin Microbiol Infect Dis, 18(12): p. 843-6 (1999). These proteins often act as ligands for *Staphylococcal epidermidis* surface proteins, thus allowing the bacteria to bind and colonize the prosthetic device. *Staphylcoccus epidermidis* is known to express proteins that bind to fibrinogen, vitronectin and fibronectin. See Nilsson, M., et al., A fibrinogen-binding protein of *Staphylococcus epidermidis*. Infect Immun, 66(6), p. 2666-73 (1998); Davis, S. L., et al., J Biol Chem, 276(30), p. 27799-805 (2001); Williams, R. J., et al., Infect Immun, 70(12), p. 6805-10 (2002); Heilmann, C., et al., Mol Microbiol, 24(5), p. 1013-24 (1997). It is reasonable to expect that *Staphylcoccus epidermidis* will bind additional serum proteins in making the transition from commensal to pathogen.

The invention described hereinafter addresses the need for *Staphylococcus epidermidis* immunogenic compositions that effectively prevent or treat most or all of the disease caused by serotypes of *Staphylococcus epidermidis*. The invention further addresses the need for methods of diagnosing *Staphylococcus epidermidis* infection. The present invention has identified *Staphylococcus epidermidis* open reading frames, hereinafter ORFs, which encode antigenic polypeptides. More particularly, the *Staphylococcus epidermidis* ORFs encode polypeptides that serve as potential antigenic polypeptides in immunogenic compositions. In certain embodiments, the invention comprises *Staphylococcus epidermidis* polynucleotide ORFs encoding surface localized, exposed, secreted or membrane associated polypeptide antigens.

In other embodiments, the invention comprises vectors comprising ORF sequences and host cells or animals transformed, transfected or infected with these vectors. The invention also comprises transcriptional gene products of *Staphylococcus epidermidis* ORFs, such as, for example, mRNA, antisense RNA, antisense oligonucleotides and ribozyme molecules, which can be used to inhibit or control growth of the microorganism. The invention relates also to methods of detecting these nucleic acids or polypeptides and kits for diagnosing *Staphylococcus epidermidis* infection. The invention also relates to immunogenic compositions for the prevention and/or treatment of bacterial infection, in particular infection caused by or exacerbated by *Staphylococcus epidermidis*. In particular embodiments, the immunogenic compositions are used for the treatment or prevention of systemic diseases, which are induced or exacerbated by *Staphylococcus epidermidis*. In other embodiments, the immunogenic compositions are used for the treatment or prevention of non-systemic diseases, which are induced or exacerbated by *Staphylococcus epidermidis*.

A. *Staphylococcus epidermidis* ORF Polynucleotides and Polypeptides

Isolated and purified *Staphylococcus epidermidis* ORF polynucleotides are identified which are used in the production of *Staphylococcus epidermidis* polypeptides for inclusion in immunogenic compositions. More specifically, in certain embodiments, the ORFs encode *Staphylococcus epidermidis* surface localized, exposed, membrane associated or secreted polypeptides, particularly antigenic polypeptides. Thus, in one aspect, the present invention identifies isolated and purified polynucleotides (ORFs) that encode *Staphylococcus epidermidis* surface localized, exposed, membrane associated or secreted polypeptides for inclusion in immunogenic compositions. In particular embodiments, a polynucleotide of the present invention is a DNA molecule, wherein the DNA may be genomic DNA, chromosomal DNA, plasmid DNA or cDNA. In another embodiment, a polynucleotide is a recombinant polynucleotide, which encodes a *Staphylococcus epidermidis* polypeptide comprising an amino acid sequence that has at least 95% identity to an amino acid sequence of one of SEQ ID NO: 1 through SEQ ID NO: 32 or a fragment thereof. In another embodiment, an isolated and purified ORF polynucleotide comprises a nucleotide sequence that has at least 95% identity to one of the ORF nucleotide sequences of SEQ ID NO: 33 through SEQ ID NO: 64, a degenerate variant thereof, or a complement thereof. In one embodiment, an ORF polynucleotide of one of SEQ ID NO: 33 through SEQ ID NO: 64 is comprised in a plasmid vector and expressed in a prokaryotic host cell.

As used hereinafter, the term "polynucleotide" means a sequence of nucleotides connected by phosphodiester linkages. Polynucleotides are presented hereinafter in the direction from the 5' to the 3' direction. A polynucleotide of the present invention can comprise from about 10 to about several hundred thousand base pairs. In one embodiment, a polynucleotide comprises from about 10 to about 3,000 base pairs. Example lengths of particular polynucleotide are set forth hereinafter.

A polynucleotide as described herein can be a deoxyribonucleic acid (DNA) molecule, a ribonucleic acid (RNA) molecule, or analogs of the DNA or RNA generated using nucleotide analogs. The nucleic acid molecule can be single-stranded or double-stranded, but preferably is double-stranded DNA. Where a polynucleotide is a DNA molecule, that molecule can be a gene, a cDNA molecule or a genomic DNA molecule. Nucleotide bases are indicated hereinafter by a single letter code: adenine (A), guanine (G), thymine (T), cytosine (C), inosine (I) and uracil (U).

"Isolated" means altered "by the hand of man" from the natural state. If a composition or substance occurs in nature, in order for it to be considered "Isolated" it must have been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed hereinafter.

As used herein, an "isolated" polynucleotide is free of sequences which naturally flank the nucleic acid (i.e., sequences located at the 5' and 3' ends of the nucleic acid) in the genomic DNA of the organism from which the nucleic acid is derived. For example, in various embodiments, the isolated *Staphylococcus epidermidis* nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. However, the *Staphylococcus epidermidis* nucleic acid molecule can be fused to other protein encoding or regulatory sequences and still be considered isolated.

ORF polynucleotides and thus the polypeptides described herein may be obtained using standard cloning and screening techniques from a cDNA library derived from mRNA. Polynucleotides of the invention can also be obtained from natural sources such as genomic DNA libraries (e.g., a *Staphylococcus epidermidis* library) or can be synthesized using well known and commercially available techniques.

Also encompassed herein are nucleic acid molecules that differ from the nucleotide sequences shown in SEQ ID NO:33 through SEQ ID NO:64 (and fragments thereof) due to degeneracy of the genetic code and thus encode the same *Staphylococcus epidermidis* polypeptide as that encoded by the nucleotide sequence shown in SEQ ID NO:33 through SEQ ID NO:64.

Orthologues and allelic variants of the *Staphylococcus epidermidis* polynucleotides can readily be identified using methods well known in the art. Allelic variants and orthologues of the polynucleotides will comprise a nucleotide sequence that is typically at least about 70-75%, more typically at least about 80-85%, and most typically at least about 90-95% or more homologous to the nucleotide sequence shown in SEQ ID NO:33 through SEQ ID NO:64, or a fragment of these nucleotide sequences. Such nucleic acid molecules can readily be identified as being able to hybridize under stringent conditions, to the nucleotide sequence shown in SEQ ID NO:33 through SEQ ID NO:64, or a fragment of these nucleotide sequences.

Moreover, the polynucleotides can comprise only a fragment of the coding region of a *Staphylococcus epidermidis* polynucleotide or gene, such as a fragment of one of SEQ ID NO:33 through SEQ ID NO:64. In certain embodiments, such fragments encode immunogenic fragments.

When these *Staphylococcus epidermidis* ORF polynucleotides of the invention are used for the recombinant production of *Staphylococcus epidermidis* polypeptides for inclusion in immunogenic compositions, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be linked to the coding sequence (see Gentz et al., *Proc. Natl. Acad. Sci. USA*, 86:821-824, 1989, incorporated by reference hereinafter in its entirety). Thus, contemplated herein is the preparation of polynucleotides encoding fusion polypeptides permitting His-tag purification of expression products. The polynucleotide may also contain non-coding 5' and 3' sequences, such as transcribed, non-translated sequences, splicing and polyadenylation signals.

Thus, a polynucleotide encoding a polypeptide for inclusion in immunogenic compositions of the present invention, including homologs and orthologs from species other than *Staphylococcus epidermidis*, such as *Staphylococcus aureus* may be obtained by a process which comprises the steps of screening an appropriate library under stringent hybridization conditions with a labeled probe having the sequence of one of SEQ ID NO:33 through SEQ ID NO:64, a fragment thereof; and isolating full-length cDNA and genomic clones containing the polynucleotide sequence. Such hybridization techniques are well known to the skilled artisan. The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low "processivity" (a measure of the ability of the enzyme to remain attached to the template during the polymerization reaction), failing to complete a DNA copy of the mRNA template during first strand cDNA synthesis.

Thus, in certain embodiments, the polynucleotide sequence information provided herein allows for the preparation of relatively short DNA (or RNA) oligonucleotide sequences having the ability to specifically hybridize to gene sequences of the selected polynucleotides disclosed hereinafter. The term "oligonucleotide" as used hereinafter is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. Thus, in particular embodiments, nucleic acid probes of an appropriate length are prepared based on a consideration of a selected nucleotide sequence, e.g., a sequence such as that shown in SEQ ID NO:33 through SEQ ID NO:64. The ability of such nucleic acid probes to specifically hybridize to a polynucleotide encoding a *Staphylococcus epidermidis* polypeptide lends them particular utility in a variety of embodiments. Most importantly, the probes can be used in a variety of assays for detecting the presence of complementary sequences in a given sample.

In certain embodiments, it is advantageous to use oligonucleotide primers. These primers may be generated in any manner, including chemical synthesis, DNA replication, reverse transcription, or a combination thereof. The sequence of such primers is designed using a polynucleotide described herein for use in detecting, amplifying or mutating a defined segment of an ORF polynucleotide that encodes a *Staphylococcus epidermidis* polypeptide from prokaryotic cells using polymerase chain reaction (PCR) technology.

In certain embodiments, it is advantageous to employ a polynucleotide described herein in combination with an appropriate label for detecting hybrid formation. A wide variety of appropriate labels are known in the art, including radioactive, enzymatic or other ligands, such as avidin/biotin, which are capable of giving a detectable signal.

Polynucleotides which are identical or sufficiently identical to a nucleotide sequence contained in one of SEQ ID NO:33 through SEQ ID NO:64, or a fragment thereof, may be used as hybridization probes for cDNA and genomnic DNA or as primers for a nucleic acid amplification (PCR) reaction, to isolate full-length cDNAs and genomic clones encoding polypeptides described herein and to isolate cDNA and genomic clones of other genes (including genes encoding homologs and orthologs from species other than *Staphylococcus epidermidis*) that have a high sequence similarity to the polynucleotide sequences set forth in of SEQ ID NO:33 through SEQ ID NO:64, or a fragment thereof. Typically these nucleotide sequences are from at least about 70% identical to at least about 95% identical to that of the reference polynucleotide sequence. The probes or primers will generally comprise at least 15 nucleotides, preferably, at least 30 nucleotides and may have at least 50 nucleotides. Particularly preferred probes will have between 30 and 50 nucleotides.

There are several methods available and well known to those skilled in the art to obtain full-length cDNAs, or extend short cDNAs, for example those based on the method of Rapid Amplification of cDNA ends (RACE). See Frohman et al., *Proc. Natl. Acad. Sci. USA* 85, 8998-9002, 1988. Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an "adaptor" sequence ligated onto each end. Nucleic acid amplification (PCR) is then carried out to amplify the "missing" 5' end of the cDNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

To provide certain of the advantages in accordance with the present invention, a preferred nucleic acid sequence employed for hybridization studies or assays includes probe molecules that are complementary to at least a 10 to about 70 nucleotides long stretch of a polynucleotide that encodes a *Staphylococcus epidermidis* polypeptide, such as that shown in one of SEQ ID NO:33 through SEQ ID NO:64. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 40 nucleotides, 55 to 70 nucleotides, or even longer where desired. Such fragments can be readily prepared by, for example, directly synthesizing the fragment by chemical means, by application of nucleic acid reproduction technology, such as the PCR technology of (U.S. Pat. No. 4,683,202, incorporated hereinafter by reference) or by excising selected DNA fragments from recombinant plasmids containing appropriate inserts and suitable restriction enzyme sites.

In another embodiment, it is contemplated that an isolated and purified polynucleotide comprises a nucleotide sequence that is identical or complementary to a segment of at least 10 contiguous bases of one of SEQ ID NO:33 through SEQ ID NO:64, wherein the polynucleotide hybridizes to a polynucleotide that encodes a *Staphylococcus epidermidis* polypeptide. Preferably, the isolated and purified polynucleotide comprises a base sequence that is identical or complementary to a segment of at least 25 to about 70 contiguous bases of one of SEQ ID NO:33 through SEQ ID NO:64. For example, the polynucleotide can comprise a segment of bases identical or complementary to 40 or 55 contiguous bases of the disclosed nucleotide sequences.

Accordingly, a polynucleotide probe molecule can be used for its ability to selectively form duplex molecules with complementary stretches of the gene. Depending on the application envisioned, one will desire to employ varying conditions of hybridization to achieve varying degree of selectivity of the probe toward the target sequence (see Table 1 below). For applications requiring a high degree of selectivity, one will typically desire to employ relatively stringent conditions to form the hybrids. For some applications, for example, where one desires to prepare mutants employing a mutant primer strand hybridized to an underlying template or where one seeks to isolate a *Staphylococcus epidermidis* homologous polypeptide coding sequence from other cells, functional equivalents, or the like, less stringent hybridization conditions are typically needed to allow formation of the heteroduplex (see Table 1). Cross-hybridizing species can thereby be readily identified as positively hybridizing signals with respect to control hybridizations. Thus, hybridization conditions are readily manipulated, and thus will generally be a method of choice depending on the desired results.

For some applications, for example, where one desires to prepare mutants employing a mutant primer strand hybridized to an underlying template or where one seeks to isolate a homologous polypeptide coding sequence from other cells, functional equivalents, or the like, less stringent hybridization conditions are typically needed to allow formation of the heteroduplex. Cross-hybridizing species are thereby readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions are readily manipulated, and thus will generally be a method of choice depending on the desired results.

Also described herein are polynucleotides capable of hybridizing under reduced stringency conditions, more preferably stringent conditions, and most preferably highly stringent conditions, to polynucleotides described hereinafter. Examples of stringency conditions are shown in Table 1 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 1

Stringency Conditions

| Stringency Condition | Polynucleotide Hybrid | Hybrid Length (bp)[I] | Hybridization Temperature and Buffer[H] | Wash Temperature and Buffer[H] |
|---|---|---|---|---|
| A | DNA:DNA | >50 | 65° C.; 1xSSC -or- 42° C.; 1xSSC, 50% formamide | 65° C.; 0.3xSSC |
| B | DNA:DNA | <50 | $T_B$; 1xSSC | $T_B$; 1xSSC |
| C | DNA:RNA | >50 | 67° C.; 1xSSC -or- 45° C.; 1xSSC, 50% formamide | 67° C.; 0.3xSSC |
| D | DNA:RNA | <50 | $T_D$; 1xSSC | $T_D$; 1xSSC |
| E | RNA:RNA | >50 | 70° C.; 1xSSC -or- 50° C.; 1xSSC, 50% formamide | 70° C.; 0.3xSSC |
| F | RNA:RNA | <50 | $T_F$; 1xSSC | $T_F$; 1xSSC |
| G | DNA:DNA | >50 | 65° C.; 4xSSC -or- 42° C.; 4xSSC, 50% formamide | 65° C.; 1xSSC |
| H | DNA:DNA | <50 | $T_H$; 4xSSC | $T_H$; 4xSSC |
| I | DNA:RNA | >50 | 67° C.; 4xSSC -or- 45° C.; 4xSSC, 50% formamide | 67° C.; 1xSSC |
| J | DNA:RNA | <50 | $T_J$; 4xSSC | $T_J$; 4xSSC |
| K | RNA:RNA | >50 | 70° C.; 4xSSC -or- 50° C.; 4xSSC, 50% formamide | 67° C.; 1xSSC |
| L | RNA:RNA | <50 | $T_L$; 2xSSC | $T_L$; 2xSSC |
| M | DNA:DNA | >50 | 50° C.; 4xSSC -or- 40° C.; 6xSSC, 50% formamide | 50° C.; 2xSSC |
| N | DNA:DNA | <50 | $T_N$; 6xSSC | $T_N$; 6xSSC |
| O | DNA:RNA | >50 | 55° C.; 4xSSC -or- 42° C.; 6xSSC, 50% formamide | 55° C.; 2xSSC |
| P | DNA:RNA | <50 | $T_P$; 6xSSC | $T_P$; 6xSSC |
| Q | RNA:RNA | >50 | 60° C.; 4xSSC -or- 45° C.; 6xSSC, 50% formamide | 60° C.; 2xSSC |
| R | RNA:RNA | <50 | $T_R$; 4xSSC | $T_R$; 4xSSC |

(bp)[I]: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
Buffer[H]: SSPE (1xSSPE is 0.15M NaCl, 10 mM NaH$_2$PO$_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
$T_B$ through $T_R$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6(log$_{10}$[Na$^+$]) + 0.41(% G + C) − (600/N), where N is the number of bases in the hybrid, and [Na$^+$] is the concentration of sodium ions in the hybridization buffer ([Na$^+$] for 1xSSC = 0.165 M).

Additional examples of stringency conditions for polynucleotide hybridization are provided in Sambrook et al., 1989, Molecular Cloning: A Laboratory Manual, Cold Spring Harbor Laboratory Press, Cold Spring Harbor, N.Y., chapters 9 and 11, and Ausubel et al., 1995, Current Protocols in Molecular Biology, eds., John Wiley & Sons, Inc., sections 2.10 and 6.3-6.4, incorporated hereinafter by reference.

B. *Staphylococcus epidermidis* Polypeptides

In particular embodiments, the present invention provides isolated and purified *Staphylococcus epidermidis* polypeptides for use in immunogenic compositions. Preferably, a *Staphylococcus epidermidis* polypeptide used in an immunogenic composition of the invention is a recombinant polypeptide. In certain embodiments, a *Staphylococcus epidermidis* polypeptide comprises the amino acid sequence that has at least 95% identity to the amino acid sequence of one of SEQ ID NO: 1 through SEQ ID NO: 32, a biological equivalent thereof, or a fragment thereof.

A *Staphylococcus epidermidis* polypeptide used in an immunogenic composition of the present invention encompasses a polypeptide that comprises: 1) the amino acid sequence shown in one of SEQ ID NO: 1 through SEQ ID NO: 32; 2) functional and non-functional naturally occurring variants or biological equivalents of *Staphylococcus epidermidis* polypeptides of SEQ ID NO: 1 through SEQ ID NO: 32; 3) recombinantly produced variants or biological equivalents of *Staphylococcus epidermidis* polypeptides of SEQ ID NO: 1 through SEQ ID NO: 32; and 4) polypeptides isolated from organisms other than *Staphylococcus epidermidis* (orthologues of *Staphylococcus epidermidis* polypeptides).

A biological equivalent or variant of such a *Staphylococcus epidermidis* polypeptide encompasses 1) a polypeptide isolated from *Staphylococcus epidermidis*; and 2) a polypeptide that contains substantially homology to a *Staphylococcus epidermidis* polypeptide.

Biological equivalents or variants of *Staphylococcus epidermidis* include both functional and non-functional *Staphylococcus epidermidis* polypeptides. Functional biological equivalents or variants are naturally occurring amino acid sequence variants of a *Staphylococcus epidermidis* polypeptide that maintains the ability to elicit an immunological or antigenic response in a subject. Functional variants will typically contain only conservative substitutions of one or more amino acids of one of SEQ ID NO: 1 through SEQ ID NO: 32, or substitution, deletion or insertion of non-critical residues in non-critical regions of the polypeptide (e.g., not in regions containing antigenic determinants or protective epitopes).

The present invention further provides non-*Staphylococcus epidermidis* orthologues of *Staphylococcus epidermidis* polypeptides. Orthologues of *Staphylococcus epidermidis* polypeptides are polypeptides that are isolated from non-*Staphylococcus epidermidis* organisms and possess antigenic capabilities of the *Staphylococcus epidermidis* polypeptide. Orthologues of a *Staphylococcus epidermidis* polypeptide can readily be identified as comprising an amino acid sequence that is substantially homologous to one of SEQ ID NO: 1 through SEQ ID NO: 32.

Modifications and changes can be made in the structure of a polypeptide of the present invention and still obtain a molecule having *Staphylococcus epidermidis* antigenicity. For example, certain amino acids can be substituted for other amino acids in a sequence without appreciable loss of antigenicity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte and Doolittle, J Mol Biol, 157: p. 105-132, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within +/−2 is preferred, those that are within +/−1 are particularly preferred, and those within +/−0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated hereinafter by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 2, below). The present invention thus contemplates immunogenic compositions comprising functional or biological equivalents of a *Staphylococcus epidermidis* polypeptide as set forth above.

TABLE 2

Amino Acid Substitutions

| Original Residue | Exemplary Residue Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the encoding DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a phage vector which can exist in both a single stranded and double stranded form. Typically, site-directed mutagenesis in accordance herewith is performed by first obtaining a single-stranded vector which includes within its sequence a DNA sequence which encodes all or a portion of the *Staphylococcus epidermidis* polypeptide sequence selected. An oligonucleotide primer bearing the desired mutated sequence is prepared (e.g., synthetically). This primer is then annealed to the singled-stranded vector, and extended by the use of enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as *E. coli* cells and clones are selected which include recombinant vectors bearing the mutation. Commercially available kits come with all the reagents necessary, except the oligonucleotide primers.

A *Staphylococcus epidermidis* polypeptide or polypeptide antigen used in an immunogenic composition of the present invention is understood to be any *Staphylococcus epidermidis* polypeptide comprising substantial sequence similarity, structural similarity and/or functional similarity to a *Staphylococcus epidermidis* polypeptide comprising the amino acid sequence of one of SEQ ID NO: 1 through SEQ ID NO: 32. In addition, such a *Staphylococcus epidermidis* polypeptide or polypeptide antigen is not limited to a particular source. Thus, the invention provides for the general detection and isolation of the polypeptides from a variety of sources.

It is contemplated in the present invention, that a *Staphylococcus epidermidis* polypeptide may advantageously be cleaved into fragments for use in further structural or functional analysis, or in the generation of reagents such as *Staphylococcus epidermidis*-related polypeptides and *Staphylococcus epidermidis*-specific antibodies. This can be accomplished by treating purified or unpurified *Staphylococcus epidermidis* polypeptides with a peptidase such as endoproteinase glu-C (Boehringer, Indianapolis, Ind.). Treatment with CNBr is another method by which peptide fragments may be produced from natural *Staphylococcus epidermidis* polypeptides. Recombinant techniques also can be used to produce specific fragments of a *Staphylococcus epidermidis* polypeptide.

Fragments of the *Staphylococcus epidermidis* polypeptides are also included in the immunogenic compositions of the invention. A fragment is a polypeptide having an amino acid sequence that is entirely the same as part, but not all, of the amino acid sequence. The fragment can comprise, for example, at least 7 or more (e.g., 8, 10, 12, 14, 16, 18, 20, or more) contiguous amino acids of an amino acid sequence of one of SEQ ID NO: 1 through SEQ ID NO: 32. Fragments may be "freestanding" or comprised within a larger polypeptide of which they form a part or region, most preferably as a single, continuous region. In one embodiment, the fragments include at least one epitope of the mature polypeptide sequence.

"Fusion protein" refers to a protein or polypeptide encoded by two, often unrelated, fused genes or fragments thereof. For example, fusion proteins or polypeptides comprising various portions of constant region of immunoglobulin molecules together with another human protein or part thereof have been described. In many cases, employing an immunoglobulin Fc region as a part of a fusion protein or polypeptide is advantageous for use in therapy and diagnosis resulting in, for example, improved pharmacokinetic properties (see e.g., International Application EP-A 0232 2621). On the other hand, for some uses it is desirable to be able to delete the Fc part after the fusion protein or polypeptide has been expressed, detected and purified.

It is contemplated that *Staphylococcus epidermidis* polypeptides may be isolated from *Staphylococcus epidermidis* or prepared recombinantly as described herein.

C. *Staphylococcus epidermidis* Polynucleotide and Polypeptide Variants

"Variant" as the term is used hereinafter, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Methods to determine identity and similarity are codified in publicly available computer programs. Computer program methods to determine identity and similarity between two sequences include, but are not limited to, the GCG program package (Devereux et al., *Nucleic Acids Research* 12(1):387, 1984), BLASTP, BLASTN, TBLASTN and FASTA (Altschul et al., *J. Molec. Biol.* 215:403-410,1990). The BLASTX program is publicly available from NCBI and other sources (BLAST Manual, Altschul, S., et al., NCBI NLM NIH Bethesda, Md. 20894; Altschul et al., *J. Molec. Biol.* 215:403-410, 1990.). The well known Smith-Waterman algorithm may also be used to determine identity.

By way of example, a polynucleotide sequence described herein may be identical to the reference sequence of one of SEQ ID NO: 33 through SEQ ID NO: 64, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in one of SEQ ID NO: 33 through SEQ ID NO: 64 by the numerical percent of the respective percent identity (divided by 100) and subtracting that product from said total number of nucleotides in one of SEQ ID NO: 33 through SEQ ID NO: 64.

For example, an isolated *Staphylococcus epidermidis* polynucleotide comprising a polynucleotide sequence that has at least 70% identity to the nucleic acid sequence of one of SEQ ID NO: 33 through SEQ ID NO: 64; a degenerate variant thereof or a fragment thereof, wherein the polynucleotide sequence may include up to $n_n$ nucleic acid alterations over the entire polynucleotide region of the nucleic acid sequence of one of SEQ ID NO: 33 through SEQ ID NO: 64, wherein $n_n$ is the maximum number of alterations and is calculated by the formula:

$$n_n \leq x_n - (x_n \cdot y),$$

in which $x_n$ is the total number of nucleic acids of one of SEQ ID NO: 33 through SEQ ID NO: 64 and y has a value of 0.70, wherein any non-integer product of $x_n$ and y is rounded down to the nearest integer prior to subtracting such product from $x_n$. Of course, y may also have a value of 0.80 for 80%, 0.85 for 85%, 0.90 for 90% 0.95 for 95%, etc. Alterations of a polynucleotide sequence encoding one of the polypeptides of SEQ ID NO: 1 through SEQ ID NO: 32 may create nonsense, missense or frameshift mutations in this coding sequence and thereby alter the polypeptide encoded by the polynucleotide following such alterations.

Similarly, a polypeptide sequence described herein may be identical to the reference sequence of SEQ ID NO: 1 through SEQ ID NO: 32, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in one of SEQ ID NO: 1 through SEQ ID NO: 32 by the numerical percent of the respective percent identity (divided by 100) and then subtracting that product from said total number of amino acids in one of SEQ ID NO: 1 through SEQ ID NO: 32, or:

$$n_a \leq x_a - (x_a \cdot y),$$

wherein $n_a$ is the number of amino acid alterations, $x_a$ is the total number of amino acids in one of SEQ ID NO: 1 through SEQ ID NO: 32, and y is, for instance 0.70 for 70%, 0.80 for 80%, 0.85 for 85% etc., and wherein any non-integer product of $x_a$ and y is rounded down to the nearest integer prior to subtracting it from $x_a$.

D. Vectors, Host Cells And Recombinant *Staphylococcus epidermidis* Polypeptides In one embodiment, the present invention provides expression vectors comprising ORF polynucleotides that encode *Staphylococcus epidermidis* polypeptides for use in immunogenic compositions. The *Staphylococcus epidermidis* expression vectors comprise ORF polynucleotides that encode Staphylococcus epidermidis polypeptides comprising the amino acid residue sequence of one of SEQ ID NO: 1 through SEQ ID NO: 32. Alternatively, the expression vectors comprise a polynucleotide comprising the nucleotide base sequence of one of SEQ ID NO: 33 through SEQ ID NO: 64. In other embodiments, the expression vectors of the invention comprise a polynucleotide operatively linked to an enhancer-promoter. In still other embodiments, the expression vectors comprise a polynucleotide operatively linked to a prokaryotic promoter. Alternatively, the expression vectors comprise a polynucleotide operatively linked to an enhancer-promoter that is a eukaryotic promoter. The expression vectors further comprise a polyadenylation signal that is positioned 3' of the carboxy-terminal amino acid and within a transcriptional unit of the encoded polypeptide.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith and Johnson, Gene 67:31-40,1988), pMAL (New England Biolabs, Beverly; Mass.) and pRIT5 (Pharmacia, Piscataway, N.J.) which fuse glutathione S-transferase (GST), maltose E binding protein, or protein A, respectively, to the target recombinant protein.

In one embodiment, the coding sequence of the *Staphylococcus epidermidis* polynucleotide is cloned into a pGEX expression vector to create a vector encoding a fusion protein comprising, from the N-terminus to the C-terminus, GST-thrombin cleavage site-*Staphylococcus epidermidis* polypeptide. The fusion protein can be purified by affinity chromatography using glutathione-agarose resin. Recombinant *Staphylococcus epidermidis* polypeptide unfused to GST can be recovered by cleavage of the fusion protein with thrombin.

Examples of suitable inducible non-fusion *E. coli* expression vectors include pTrc (Amann et al., Gene 69:301-315, 1988), pET lid (Studier et al. "Gene Expression Technology" Methods in Enzymology 185, 60-89,1990), pBAD and pCRT7. Target gene expression from the pTrc vector relies on host RNA polymerase transcription from a hybrid trp-lac fusion promoter. Target gene expression from the pET lid vector relies on transcription from a T7 gn1 0-lac fusion promoter mediated by a coexpressed viral RNA polymerase J7 gn1. This viral polymerase is supplied by host strains BL21 (DE3) or HMS I 74(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein. Another strategy is to alter the nucleic acid sequence of the nucleic acid to be inserted into an expression vector so that the individual codons for each amino acid are those preferentially utilized in *E. coli*. Such alteration of nucleic acid sequences of the invention can be carried out by standard DNA mutagenesis or synthesis techniques.

In another embodiment, the *Staphylococcus epidermidis* polynucleotide expression vector is a yeast expression vector. Examples of vectors for expression in yeast *S. cerevisiae* include pYepSec I (Baldari, et al., Embo J, 6: p. 229-234, 1987), pMFa (Kurjan and Herskowitz, Cell, p. 933-943, 1982), pJRY88 (Schultz et al., Gene, 54: p. 113-123,1987), and pYES2 (Invitrogen Corporation, San Diego, Calif.).

Alternatively, a *Staphylococcus epidermidis* polynucleotide can be expressed in insect cells using, for example, baculovirus expression vectors. Baculovirus vectors available for expression of proteins in cultured insect cells (e.g., Sf 9 cells) include the pAc series (Smith et al., Mol Cell Biol, 3: p. 2156-2165,1983) and the pVL series (Lucklow and Summers, Virology, 170: p. 31-39, 1989).

In yet another embodiment, a nucleic acid of the invention is expressed in mammalian cells using a mammalian expression vector. Examples of mammalian expression vectors include pCDM8 (Seed, Nature, 329: p. 840, 1987) and pMT2PC (Kaufman et al., EMBO J, 6: p. 187-195,1987). When used in mammalian cells, the expression vector's control functions are often provided by viral regulatory elements.

As used hereinafter, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used hereinafter, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used hereinafter, the phrase "enhancer-promoter" means a composite unit that contains both enhancer and promoter elements. An enhancer-promoter is operatively linked to a coding sequence that encodes at least one gene product. As used hereinafter, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct described herein can be any enhancer-promoter that drives expression in a cell to be transfected. By employing an enhancer-promoter with well-known properties, the level and pattern of gene product expression can be optimized.

For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., "Molecular Cloning: A Laboratory Manual" 2nd, ed, Cold Spring Harbor Laboratory, Cold Spring Harbor Laboratory Press, Cold Spring Harbor, N.Y., 1989, incorporated hereinafter by reference.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., Genes Dev, 1: p. 268-277,1987), lymphoid-specific promoters (Calame and Eaton, Adv Immunol, 43: p. 235-275, 1988), in particular, promoters of T cell receptors (Winoto and Baltimore, EMBO J, 8: p. 729-733,1989) and immunoglobulins (Banerji et al., Cell, 33: p. 729-740,1983), (Queen and Baltimore, Cell, 33: p. 741-748,1983), neuron-specific promoters (e.g., the neurofilament promoter; Byrne and Ruddle, PNAS, 86: p. 5473-5477, 1989), pancreas-specific promoters (Edlund et al., Science, 230: p. 912-916, 1985), and mammary gland-specific promoters (e.g., milk whey promoter; U.S. Pat. No. 4,873,316 and International Application EP 264,166). Developmentally-regulated promoters are also encompassed, for example the murine hox promoters (Kessel and Gruss, Science, 249: p. 374-379, 1990) and the α-fetoprotein promoter (Campes and Tilghman, Genes Dev, 3: p. 537-546,1989).

Also provided herein is a recombinant expression vector comprising a DNA molecule encoding a *Staphylococcus epidermidis* polypeptide cloned into the expression vector in an antisense orientation. That is, the DNA molecule is operatively linked to a regulatory sequence in a manner which allows for expression (by transcription of the DNA molecule) of an RNA molecule which is antisense to *Staphylococcus epidermidis* mRNA. Regulatory sequences operatively linked to a nucleic acid cloned in the antisense orientation can be chosen which direct the continuous expression of the antisense RNA molecule in a variety of cell types. For instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

The recombinant expression vectors described herein may be inserted into any suitable host cell. The terms "host cell" and "recombinant host cell" are used interchangeably hereinafter. It is understood that such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used hereinafter. A host cell can be any prokaryotic or eukaryotic cell. For example, a *Staphylococcus epidermidis* polypeptide can be expressed in bacterial cells such as *E. coli*, insect cells (such as Sf9, Sf21), yeast or mammalian cells (such as Chinese hamster ovary cells (CHO), VERO, chick embryo fibroblasts, BHK cells or COS cells). Other suitable host cells are known to those skilled in the art.

Vector DNA is introduced into prokaryotic or eukaryotic cells via conventional transformation, infection or transfection techniques. As used hereinafter, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, ultrasound or electroporation. Suitable methods for transforming or transfecting host cells can be found in Sambrook, et al. ("Molecular Cloning: A Laboratory Manual" 2nd, ed, Cold Spring Harbor Laboratory, Cold Spring Harbor Laboratory Press, Cold Spring Harbor, N.Y., 1989), and other laboratory manuals.

A host cell described herein, such as a prokaryotic or eukaryotic host cell in culture, is used to produce (i.e., express) a *Staphylococcus epidermidis* polypeptide. Accordingly, also described herein are methods for producing a Staphylococcus epidermidis polypeptide using such host cells. In one embodiment, the method comprises culturing the host cell (into which a recombinant expression vector encoding a Staphylococcus epidermidis polypeptide has been introduced) in a suitable medium until the Staphylococcus epidermidis polypeptide is produced. In another embodiment, the method further comprises isolating the Staphylococcus epidermidis polypeptide from the medium or the host cell.

A coding sequence of an expression vector is operatively linked to a transcription termination region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to hereinafter as transcription-termination regions. Those regions are required for efficient polyadenylation of transcribed messenger RNA (mRNA). Transcription-termination regions are well known in the art. Examples of such transcription-termination regions are the polyadenylation signal of SV40 and the protamine gene.

An expression vector comprises a polynucleotide that encodes a Staphylococcus epidermidis polypeptide. Such a polypeptide is meant to include a sequence of nucleotide bases encoding a Staphylococcus epidermidis polypeptide sufficient in length to distinguish the segment from a polynucleotide segment encoding a non-Staphylococcus epidermidis polypeptide. Such a polypeptide can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed hereinafter using a mutagenic procedure such as site-directed mutagenesis.

In certain embodiments, the expression vectors described herein comprise polynucleotides that encode polypeptides comprising the amino acid residue sequence of one of SEQ ID NO: 1 through SEQ ID NO: 32. An expression vector can include a Staphylococcus epidermidis polypeptide coding region itself of any of the Staphylococcus epidermidis polypeptides noted above or it can contain coding regions bearing selected alterations or modifications in the basic coding region of such a Staphylococcus epidermidis polypeptide. Alternatively, such vectors or fragments can encode larger polypeptides or polypeptides which nevertheless include the basic coding region. In any event, it should be appreciated that due to codon redundancy as well as biological functional equivalence, this aspect is not limited to the particular DNA molecules corresponding to the polypeptide sequences noted above.

Exemplary vectors include the mammalian expression vectors of the pCMV family including pCMV6b and pCMV6c (Chiron Corp., Emeryville Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing Staphylococcus epidermidis polypeptides by virtue of DNA incorporated into such expression vectors can be detected.

A DNA molecule can be incorporated into a vector by a number of techniques that are well known in the art. For instance, the vector pUC18 has been demonstrated to be of particular value in cloning and expression of genes. Likewise, the related vectors M13mp18 and M13mp19 can be used in certain embodiments of the invention, in particular, in performing dideoxy sequencing.

An expression vector described herein is useful both as a means for preparing quantities of the Staphylococcus epidermidis polypeptide-encoding DNA itself, and as a means for preparing the encoded polypeptide and peptides. It is contemplated that where Staphylococcus epidermidis polypeptides are made by recombinant means, one can employ either prokaryotic or eukaryotic expression vectors as shuttle systems.

In another aspect, the recombinant host cells are prokaryotic host cells. Preferably, the recombinant host cells of the invention are bacterial cells of the DH5 α strain of Escherichia coli. In general, prokaryotes are preferred for the initial cloning of DNA sequences and constructing the vectors useful in the invention. For example, E. coli K12 strains can be particularly useful. Other microbial strains that can be used include E. coli B, and E. coli$_X$1976 (ATCC No. 31537). These examples are, of course, intended to be illustrative rather than limiting.

The aforementioned strains, as well as E. coli W3110 (ATCC No. 273325), E. coli BL21 (DE3), E. coli Top10, bacilli such as Bacillus subtilis, or other enterobacteriaceae such as Salmonella typhimurium (or other attenuated Salmonella strains as described in U.S. Pat. No. 4,837,151) or Serratia marcesans, and various Pseudomonas species can be used.

In general, plasmid vectors containing replicon and control sequences, which are derived from species compatible with the host cell are used in connection with these hosts. The vector ordinarily carries a replication site, as well as marking sequences which are capable of providing phenotypic selection in transformed cells. For example, E. coli can be transformed using pBR322, a plasmid derived from an E. coli species (Bolivar, et al. 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang, et al. 1978; Itakura., et al. 1977, Goeddel, et al. 1979; Goeddel, et al. 1980) and a tryptophan (TRP) promoter system (EP 0036776; Siebwenlist et al. 1980). While these are the most commonly used, other microbial promoters have been discovered and utilized, and details concerning their nucleotide sequences have been published, enabling a skilled worker to introduce functional promoters into plasmid vectors (Siebwenlist, et al. 1980).

In addition to prokaryotes, eukaryotic microbes such as yeast can also be used. Saccharomyces cerevisiae or common baker's yeast is the most commonly used among eukaryotic microorganisms, although a number of other strains are commonly available. For expression in Saccharomyces, the plasmid YRp7, for example, is commonly used (Stinchcomb, et al. 1979; Kingsman, et al. 1979; Tschemper, et al. 1980). This plasmid already contains the trpI gene which provides a selection marker for a mutant strain of yeast lacking the ability to grow in tryptophan, for example ATCC No. 44076 or PEP4-1 (Jones, 1977). The presence of the trpI lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman., et al.

1980) or other glycolytic enzymes (Hess, et al. 1968; Holland, et al. 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any-plasmid vector containing a yeast-compatible promoter, origin or replication and termination sequences are suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are AtT-20, VERO, HeLa, NSO, PER C6, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

Where expression of recombinant *Staphylococcus epidermidis* polypeptides is desired and a eukaryotic host is contemplated, it is most desirable to employ a vector such as a plasmid that incorporates a eukaryotic origin of replication. Additionally, for the purposes of expression in eukaryotic systems, one desires to position the *Staphylococcus epidermidis* encoding sequence adjacent to and under the control of an effective eukaryotic promoter such as promoters used in combination with Chinese hamster ovary cells. To bring a coding sequence under control of a promoter, whether it is eukaryotic or prokaryotic, the 5' end of the translation initiation region of the proper translational reading frame of the polypeptide must be positioned between about 1 and about 50 nucleotides 3' of or downstream with respect to the promoter chosen. Furthermore, where eukaryotic expression is anticipated, one would typically desire to incorporate into the transcriptional unit a polynucleotide which encodes the *Staphylococcus epidermidis* polypeptide.

Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (see e.g., Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet, et al. 1992).

A transfected cell can be prokaryotic or eukaryotic. Preferably, the host cells of the invention are prokaryotic host cells. Where it is of interest to produce a *Staphylococcus epidermidis* polypeptide, cultured prokaryotic host cells are of particular interest.

Also contemplated herein is a process or method of preparing *Staphylococcus epidermidis* polypeptides comprising transforming, transfecting or infecting cells with a polynucleotide that encodes a *Staphylococcus epidermidis* polypeptide to produce transformed host cells; and maintaining the transformed host cells under biological conditions sufficient for expression of the polypeptide. In a particular embodiment, the transformed host cells are prokaryotic cells. Alternatively, the host cells are eukaryotic cells. More particularly, the prokaryotic cells are bacterial cells of the DH5-α strain of *Escherichia coli*. Alternatively, the polynucleotide transfected into the transformed cells comprise the nucleic acid sequence of one of SEQ ID NO: 33 through SEQ ID NO: 64. Additionally, transfection is accomplished using an expression vector disclosed above. A host cell used in the process is capable of expressing a functional, recombinant *Staphylococcus epidermidis* polypeptide.

Following transfection, the cell is maintained under culture conditions for a period of time sufficient for expression of a *Staphylococcus epidermidis* polypeptide. Culture conditions are well known in the art and include ionic composition and concentration, temperature, pH and the like. Typically, transfected cells are maintained under culture conditions in a culture medium. Suitable media for various cell types are well known in the art. In certain embodiments, culture temperature is from about 20° C. to about 50° C., more preferably from about 30° C. to about 40° C. and, even more preferably about 37° C.

The pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of a *Staphylococcus epidermidis* polypeptide. A suitable time depends inter alia upon the cell type used and is readily determinable by a skilled artisan. Typically, maintenance time is from about 2 to about 14 days.

Recombinant *Staphylococcus epidermidis* polypeptide is recovered or collected either from the transfected cells or the medium in which those cells are cultured. Recovery comprises isolating and purifying the *Staphylococcus epidermidis* polypeptide. Isolation and purification techniques for polypeptides are well known in the art and include such procedures as precipitation, filtration, chromatography, electrophoresis and the like.

E. Immunogenic Compositions

The present invention provides immunogenic compositions comprising one or more *Staphylococcus epidermidis* polypeptides selected as described in the Examples below, and physiologically acceptable carriers. In certain embodiments, the immunogenic compositions comprise one or more *Staphylococcus epidermidis* polypeptides comprising the amino acid residue sequence of one or more of SEQ ID NO: 1 through SEQ ID NO: 32. In other embodiments, the immunogenic compositions of the invention comprise polynucleotides that encode *Staphylococcus epidermidis* polypeptides, and physiologically acceptable carriers. For example, the immunogenic compositions of the present invention comprise *Staphylococcus epidermidis* polypeptides comprising the amino acid sequence of one or more of SEQ ID NO: 1 through SEQ ID NO: 32. Alternatively, the immunogenic compositions comprise polynucleotides comprising the nucleotide sequence of one or more of SEQ ID NO: 33 through SEQ ID NO: 64.

Various tests are used to assess the in vitro immunogenicity of the polypeptides of the invention. For example, an in vitro opsonic assay is conducted by incubating together a mixture of *Staphylococcus epidermidis* cells, heat inactivated human serum containing specific antibodies to the polypeptide in question, and an exogenous complement source. Opsonophagocytosis proceeds during incubation of freshly isolated human polymorphonuclear cells (PMN's) and the antibody/complement/*Staphylococcus* cell mixture. Bacterial cells that are coated with antibody and complement are killed upon opsonophagocytosis. Colony forming units (cfu) of surviving bacteria that escape from opsonophagocytosis are determined by plating the assay mixture. Titers are reported as the reciprocal of the highest dilution that gives ≧50% bacterial killing, as determined by comparison to assay controls. Specimens that demonstrate less than 50% killing at the lowest serum dilution tested (1:8), are reported as having an OPA titer of 4. The highest dilution tested is 1:2560. Samples with ≧50% killing at the highest dilution are repeated, beginning with a higher initial dilution. The method described above is a modification of Gray's method (Gray, Conjugate Vaccines Supplement, p. 694-697,1990).

A test serum control, which contains test serum plus bacterial cells and heat inactivated complement, is included for each individual serum. This control is used to assess whether the presence of antibiotics or other serum components are capable of killing the bacterial strain directly (i.e. in the absence of complement or PMN's). A human serum with known opsonic titer is used as a positive human serum control. The opsonic antibody titer for each unknown serum is calculated as the reciprocal of the initial dilution of serum giving 50% cfu reduction compared to the control without serum.

A whole cell ELISA assay is also used to assess in vitro immunogenicity and surface exposure of the polypeptide antigen, wherein the bacterial strain of interest (*Staphylococcus epidermidis*) is coated onto a plate, such as a 96 well plate, and test sera from an immunized animal is reacted with the bacterial cells. If any antibody, specific for the test polypeptide antigen, is reactive with a surface exposed epitope of the polypeptide antigen, it can be detected by standard methods known to one skilled in the art.

Any polypeptide demonstrating the desired in vitro activity is then tested in an in vivo animal challenge model. In certain embodiments, immunogenic compositions are used in the immunization of an animal (e.g., a mouse) by methods and routes of immunization known to those of skill in the art (e.g., intranasal, parenteral, oral, rectal, vaginal, transdermal, intraperitoneal, intravenous, subcutaneous, etc.). Following immunization of the animal with a particular *Staphylococcus epidermidis* immunogenic composition, the animal is challenged with *Staphylococcus epidermidis* and assayed for resistance to *Staphylococcus epidermidis* infection.

The *Staphylococcus epidermidis* polynucleotides and polypeptides are incorporated into immunogenic compositions suitable for administration to a subject, e.g., a human. Such compositions typically comprise the nucleic acid molecule or protein, together with a pharmaceutically acceptable carrier. As used hereinafter the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

An immunogenic composition of the invention is formulated to be compatible with its intended route of administration. Examples of routes of administration include parenteral (e.g., intravenous, intradermal, subcutaneous, intraperitoneal), transmucosal (e.g., oral, rectal, intranasal, vaginal, respiratory) and transdermal (topical). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and the like. In many cases, isotonic agents are included, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a *Staphylococcus epidermidis* polypeptide or anti-*Staphylococcus epidermidis* antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated hereinafter by reference.

It is especially advantageous to formulate oral or parenteral compositions in dosage unit form for ease of administration and uniformity of dosage. Dosage unit form as used hereinafter refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Combination immunogenic compositions are provided by including two or more of the polypeptides of the invention, as well as by combining one or more of the polypeptides of the invention with one or more known non-*Staphylococcus epidermidis* polypeptides such as *Staphylococcus aureus* polypeptides.

The following twelve *Staphylococcus epidermidis* polypeptide sequences SEQ ID NO: 8, SEQ ID NO: 10, SEQ ID NO: 11, SEQ ID NO: 12, SEQ ID NO: 14, SEQ ID NO: 18, SEQ ID NO: 19, SEQ ID NO: 20, SEQ ID NO: 23, SEQ ID NO: 26, SEQ ID NO: 27, and SEQ ID NO: 30 have polypeptide sequences with at least 90% identity to the homologs from *Staphylococcus aureus*. Therefore, these twelve polypeptides may also be used in immunogenic compositions against *Staphylococcus aureus*. In addition, the following twelve *Staphylococcus epidermidis* polynucleotide sequences encoding the the polypeptides with at least 90% identity to the *Staphylococcus aureus* homologs may also be used in immunogenic compositions: SEQ ID NO: 40, SEQ ID NO: 42, SEQ ID NO: 43, SEQ ID NO: 44, SEQ ID NO: 46, SEQ ID NO: 50, SEQ ID NO: 51, SEQ ID NO: 52, SEQ ID NO: 55, SEQ ID NO: 58, SEQ ID NO: 59, and SEQ ID NO: 62, or a degenerate variant thereof, or a fragment thereof.

In other embodiments, combination immunogenic compositions are provided by combining one or more of the polypeptides of the invention with one or more known *S. epidermidis* polysaccharides or polysaccharide-protein conjugates. See, for example, the *Staphylococcus epidermidis* and *Staphylococcus aureus* capsular polysaccharide adhesin, PNSG, poly-N-succinyl beta-1-6 N-acetyl glucosamine (also known as PIA, PS/A, PNAG). See Mckenney, D., et al., *Infect. Immun.* 66:4711 (1998) and Mckenney, D., et al., *Science* 284:1523 (1998), the disclosures of which are hereby incorporated by reference in their entirety.

In other embodiments, combination immunogenic compositions are provided by combining one or more polypeptides of the invention with one or more known *S. aureus* polysaccharides or *S. aureus* polysaccharide-protein conjugates. For example, of the 12 known capsular serotypes of *S. aureus*, serotype 5 (CP5) and serotype 8 (CP8) account for approximately 85-90% of all clinical isolates []. Most methicillin-resistant *S. aureus* isolates express CP5 ]. Antibodies to CP5 and CP8 induce type-specific opsonophagocytic killing by human polymorphonuclear neutrophils in vitro and confer protection in animals [Karakawa, W. W., Sutton, A., et al., *Infect Immun* 56(5):1090-1095 (1988); Fattom, A. I., Sarwar, J., et al., *Infection & Immunity* 64(5):1659-1665 (1996)]. Several laboratories have synthesized immunogenic conjugates consisting of CP5 and CP8 covalently linked to protein. These conjugates are highly immunogenic in mice and humans and induce antibodies that opsonize microencapsulated *S. aureus* for phagocytosis [Fattom, A., Schneerson, R, et al., *Infect Immun* 61(3):1023-1032 (1993); Gilbert, F. B., Poutrel, B., et al., *Vaccine* 12(4):369-374 (1994); Reynaud-Rondier, L., Voiland, A., et al., FEMS Microbiol Immunol 3(4):193-199 (1991)]. Monovalent immunogenic compositions containing CP5 conjugated to *Pseudomonas aeruginosa* recombinant exotoxin A are immunogenic and well tolerated in healthy adults and in patients with end-stage renal disease [Welch, P. G., Fattom, A., Moore, J. Jr., et al., *J. Am. Soc. Nephrol.* 7:247-253 [Abstract] (1996)]. In a double-blind trial involving patients with end-stage renal disease who were receiving hemodialysis, a bivalent conjugate vaccine composed of CP5 and CP8 covalently bound to *Pseudomonas aeruginosa* recombinant exotoxin A conferred partial immunity against *S. aureus* bacteremia for approximately 40 weeks, after which protection decreased as antibody levels decreased [Shinefield, H., Black, S., et al., *N Engl J Med* 346(7):491-496 (2002)]. The outcome of this trial indicates a need for an improved immunogenic composition that could contribute to broader and more complete protection.

As described above, in certain embodiments, combination immunogenic compositions are provided by combining one or more polypeptides of the invention with one or more known *S. aureus* polysaccharide-protein conjugates. The "protein component" of the carbohydrate-protein conjugates is known as a carrier protein. The term "carrier proteins", as a group are preferably proteins that are non-toxic and non-reactogenic and obtainable in sufficient amount and purity. Carrier proteins should be amenable to standard conjugation procedures. In a particular embodiment of the present invention, $CRM_{197}$ is used as the carrier protein. $CRM_{197}$, (Wyeth, Sanford, N.C.) is a non-toxic variant (i.e., toxoid) of diphtheria toxin isolated from cultures of *Corynebacterium diphtheria* strain C7 (β197) grown in casamino acids and yeast extract-based medium. $CRM_{197}$ is purified through ultra-filtration, ammonium sulfate precipitation, and ion-exchange chromatography. Other diphtheria toxoids are also suitable for use as carrier proteins. The immunogenic composition may further comprise an adjuvant, such as an aluminum-based adjuvant, such as aluminum phosphate, aluminum sulfate and aluminum hydroxide.

Other suitable carrier proteins include inactivated bacterial toxins such as tetanus toxoid, pertussis toxoid, cholera toxoid (e.g., as described in International Patent Application WO2004/083251 [38]), *E. coli* LT, *E. coli* ST, and exotoxin A from *Pseudomonas aeruginosa*. Bacterial outer membrane proteins such as outer membrane complex c (OMPC), porins, transferrin binding proteins, pneumolysin, pneumococcal surface protein A (PspA), pneumococcal adhesin protein (PsaA), or *Haemophilus influenzae* protein D, can also be used. Other proteins, such as ovalbumin, keyhole limpet hemocyanin (KLH), bovine serum albumin (BSA) or purified protein derivative of tuberculin (PPD) can also be used as carrier proteins.

Immunogenic compositions comprising polynucleotides are delivered to the recipient by a variety of vectors and expression systems. Such systems include, among others, chromosomal, episomal and virus-derived systems, e.g., vectors derived from bacterial plasmids, attenuated bacteria such as *Salmonella* (U.S. Pat. No. 4,837,151), from bacteriophage, from transposons, from yeast episomes, from insertion elements, from yeast chromosomal elements, from viruses such as vaccinia and other poxviruses, adenovirus, baculoviruses, papova viruses, such as SV40, fowl pox viruses, pseudorabies viruses and retroviruses, alphaviruses such as Venezuelan equine encephalitis virus (U.S. Pat. No. 5,643,576), sindbis virus and semiliki forest virus, nonsegmented negative-stranded RNA viruses such as vesicular stomatitis virus (U.S. Pat. No. 6,168,943), and vectors derived from combinations thereof, such as those derived from plasmid and bacteriophage genetic elements, such as cosmids and phagemids. The expression systems should include control regions that regulate as well as engender expression, such as promoters and other regulatory elements (such as a polyadenylation signal). Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., "Molecular Cloning: A Laboratory Manual" 2nd, ed, Cold Spring Harbor Laboratory, Cold Spring Harbor Laboratory Press, Cold Spring Harbor, N.Y., 1989.

A pharmaceutically acceptable vehicle is understood to designate a compound or a combination of compounds entering into a pharmaceutical or immunogenic composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen.

As defined hereinafter, an "adjuvant" is a substance that serves to enhance the immunogenicity of an "antigen" or the immunogenic compositions comprising one or more polypeptide antigens having an amino acid sequence chosen from one of SEQ ID NO: 1 through SEQ ID NO: 32. Thus, adjuvants are often given to boost or modulate the immune response and are well known to the skilled artisan. Examples of adjuvants contemplated in the present invention include, but are not limited to, aluminum salts (alum) such as aluminum phosphate and aluminum hydroxide, *Mycobacterium tuberculosis*, bacterial lipopolysaccharides, aminoalkyl glucosamine phosphate compounds (AGP), or derivatives or analogs thereof, which are available from Corixa (Hamilton, Mont.), and which are described in U.S. Pat. No. 6,113,918; one such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyoxytetradecanoylamino]-b-D-glucopyranoside, which is also known as 529 (formerly known as RC529), which is formulated as an aqueous form or as a stable emulsion, MPL™ (3-O-deacylated monophosphoryl lipid A) (Corixa) described in U.S. Pat. No. 4,912,094, synthetic polynucleotides such as oligonucleotides containing a CpG motif (U.S. Pat. No. 6,207,646), polypeptides, saponins such as Quil A or STIMULON™ QS-21 (Antigenics, Framingham, Mass.), described in U.S. Pat. No. 5,057,540, a pertussis toxin (PT), or an *E. coli* heat-labile toxin (LT), particularly LT-K63, LT-R72, CT-Si09, PT-K9/G129; see, e.g., International Patent Publication Nos. WO 93/13302 and WO 92/19265, cholera toxin (either in a wild-type or mutant form, e.g., wherein the glutamic acid at amino acid position 29 is replaced by another amino acid, preferably a histidine, in accordance with published International Patent Application number WO 00/18434). Similar cholera toxin mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other cholera toxin mutants are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36).

Various cytokines and lymphokines are suitable for use as adjuvants. One such adjuvant is granulocyte-macrophage colony stimulating factor (GM-CSF), which has a nucleotide sequence as described in U.S. Pat. No. 5,078,996. A plasmid containing GM-CSF cDNA has been transformed into *E. coli* and has been deposited with the American Type Culture Collection (ATCC), 1081 University Boulevard, Manassas, Va. 20110-2209, under Accession Number 39900. The cytokine Interleukin-12 (IL-12) is another adjuvant which is described in U.S. Pat. No. 5,723,127. Other cytokines or lymphokines have been shown to have immune modulating activity, including, but not limited to, the interleukins 1-alpha, 1-beta, 2, 4, 5,6, 7, 8, 10, 13, 14, 15, 16, 17 and 18, the interferons-alpha, beta and gamma, granulocyte colony stimulating factor, and the tumor necrosis factors alpha and beta, and are suitable for use as adjuvants.

A composition of the present invention is typically administered parenterally in unit dosage formulations containing standard, well-known nontoxic physiologically acceptable carriers, adjuvants, and vehicles as desired.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, when administering viral vectors, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art (see, e.g. Gabizon et al., 1990; Ferruti et al., 1986; and Ranade, 1989).

The immunogenic compositions of this invention also comprise a polynucleotide sequence of this invention operatively associated with a regulatory sequence that controls gene expression. The polynucleotide sequence of interest is engineered into an expression vector, such as a plasmid, under the control of regulatory elements which will promote expression of the DNA, that is, promoter and/or enhancer elements. In a preferred embodiment, the human cytomegalovirus immediate-early promoter/enhancer is used (U.S. Pat. No. 5,168,062). The promoter may be cell-specific and permit substantial transcription of the polynucleotide only in predetermined cells.

The polynucleotides of the invention are introduced directly into the host either as "naked" DNA (U.S. Pat. No. 5,580,859) or formulated in compositions with facilitating agents, such as bupivicaine and other local anesthetics (U.S. Pat. No. 5,593,972) and cationic polyamines (U.S. Pat. No. 6,127,170), which are hereby incorporated by reference in their entirety.

In this polynucleotide immunization procedure, the polypeptides of the invention are expressed on a transient basis in vivo; no genetic material is inserted or integrated into the chromosomes of the host. This procedure is to be distinguished from gene therapy, where the goal is to insert or integrate the genetic material of interest into the chromosome. An assay is used to confirm that the polynucleotides administered by immunization do not give rise to a transformed phenotype in the host (U.S. Pat. No. 6,168,918).

H. Uses and Methods of the Invention

The *Staphylococcus epidermidis* polynucleotides, polypeptides and polypeptide homologues described herein are used in methods of immunization. The isolated polynucleotides are used to express *Staphylococcus epidermidis* polypeptides (e.g., via a recombinant expression vector in a host cell or in polynucleotide immunization applications).

As described in detail in the Examples herein, *Staphylococcus epidermidis* was grown in the presence of serum to stimulate the expression of proteins and carbohydrates at the bacterial cell wall that may be significant to systemic bacterial infection. As a result, thirty two polypeptides and the corresponding polynucleotides were identified as expressed by *Staphylococcus epidermidis* when grown in 70% serum. In addition, twenty-four of these proteins were found to be reactive with immune sera from rabbits infected with *Staphylococcus epidermidis*.

The genes corresponding to the proteins expressed when *Staphylococcus epidermidis* was grown in serum were cloned and used to express the proteins recombinantly. The recombinant proteins were used to immunize mice and twenty five of twenty six proteins induced antibodies that reacted with whole cell lysates of *Staphylococcus epidermidis*. In addition, eighteen of these sera also reacted with whole cell lysates of *Staphylococcus aureus*. Finally, when immunized mice were challenged with *Staphylococcus epidermidis* it was found that eleven of the proteins had induced antibodies that reduced the amount of detectable bacteria found in the spleen after challenge.

The invention further provides immunogenic compositions comprising one or more polypeptides just described, which have an amino acid sequence chosen from one SEQ ID NO: 1 through SEQ ID NO: 32, a biological equivalent thereof or a fragment thereof. The immunogenic composition may further comprise a pharmaceutically acceptable carrier. In certain embodiments, the immunogenic composition will comprise one or more adjuvants.

In another embodiment, the invention provides immunogenic compositions comprising a polynucleotide having a nucleotide sequence chosen from one of SEQ ID NO: 33 through SEQ ID NO: 64, wherein the polynucleotide is comprised in a recombinant expression vector. Preferably the vector is plasmid DNA. The polynucleotide may further comprise heterologous nucleotides, e.g., the polynucleotide is operatively linked to one or more gene expression regulatory elements, and further comprise one or more adjuvants. In a preferred embodiment, the immunogenic polynucleotide composition directs the expression of one or more neutralizing epitopes of *Staphylococcus epidermidis*.

Provided also are methods for immunizing a host against *Staphylococcus epidermidis* infection. In a preferred embodiment, the host is human. Thus, a host or subject is administered an immunizing amount of an immunogenic composition comprising a polypeptide having an amino acid sequence chosen from one of SEQ ID NO: 1 through SEQ ID NO: 32, a biological equivalent thereof or a fragment thereof and a pharmaceutically acceptable carrier. An immunizing amount of an immunogenic composition is determined by performing a dose response study in which subjects are immunized with gradually increasing amounts of the immunogenic composition and the immune response analyzed to determine the optimal dosage. Starting points for the study are inferred from immunization data in animal models. The dosage amount can vary depending upon specific conditions of the individual. The amount is determined in routine trials by means known to those skilled in the art.

An immunologically effective amount of the immunogenic composition in an appropriate number of doses is administered to the subject to elicit an immune response. Immunologically effective amount, as used herein, means the administration of that amount to a mammalian host (preferably human), either in a single dose or as part of a series of doses, sufficient to at least cause the immune system of the individual treated to generate a response that reduces the clinical impact of the bacterial infection. Ideally, the treated individual will not exhibit the more serious clinical manifestations of the *Staphloccocal epidermidis* or *Staphlocccal aureus* infection. The dosage amount can vary depending upon specific conditions of the individual, such as age and weight. This amount can be determined in routine trials by means known to those skilled in the art.

All patents and publications cited herein are hereby incorporated by reference.

EXAMPLES

The following examples were carried out using standard techniques, which are well known and routine to those of skill in the art, except where otherwise described in detail. All chemicals were obtained from Sigma (Sigma Chemical Co., St. Louis, Mo.) unless stated otherwise. The following examples are presented for illustrative purpose, and should not be construed in any way limiting the scope of this invention.

Example 1

Bacterial Growth in 70% Serum

The following examples were performed using the clinical isolate *Staphylcoccus epidermidis* 0-47. The unannotated genomic sequence was available for this isolate from Incyte Corporation of Palo Alto, Calif. See Heilmann, C., et al., Infect Immun, 64(1): p. 277-82 (1996). To stimulate the expression of proteins, which may be clinically relevant to pathogenicity, cultures of bacteria were grown overnight in either 100% tryptic soy broth (TSB) or 70:30 rabbit serum:TSB with shaking (200 rpm) at 37° C. The rabbit serum was obtained from Life Technologies, Rockville, Md. Bacteria were diluted from an overnight culture to an $OD_{600}$~0.1 and grown for 4 h until mid log phase. At mid log phase, the cells were harvested by centrifugation and further processed as described in the following examples.

Example 2

Preparation Of Cell Wall Fractions For 2-D Gel Electrophoresis

The cell walls of *Staphylcoccus epidermidis* 0-47 grown as described in Example 1 were isolated and then prepared for two-dimensional gel electrophoresis. Bacterial pellets were resuspended to an $OD_{600}$~20 and washed twice with rocking for 15 minutes at 4° C. using Tris buffered saline (TBS, 20 mM Tris, pH 8.0, 150 mM NaCl). Serum proteins bound to the surface of the bacteria were removed by washing for 15 minutes at 4° C. with 20 mM Tris, pH 8.0 containing 1M NaCl. Bacteria grown in TSB were treated in the same manner as the bacteria grown in serum. The bacteria were again pelleted by centrifugation. To create protoplasts, the bacteria were then resuspended to $OD_{600}$~40 in TBS containing 30% sucrose, 100 µg/ml lysostaphin, 10 µg/ml DNase, 1 µg/ml Pefablock (Boehringer Mannheim, Indianapolis, Ind.), 10 µg/ml lysozyme and 100 units/ml mutanolysin and incubated at 37° C. for 1 hour. The resulting protoplasts were pelleted by centrifugation at 5000 rpm for 10 minutes and the supernatant containing the cell wall material was decanted. The decanted supernatants containing the cell wall fractions were supplemented with Complete Mini protease inhibitor tablets (Roche Diagnostics, Indianapolis, Ind.) and dialyzed overnight against water at 4° C. using a 10,000 kD MWCO dialysis membrane (Pierce Biotechnology, Inc., Rockford, Ill.). After dialysis, the cell wall fractions were frozen at −20° C.

Following isolation, the cell wall fraction samples were prepared for 2-D gel electrophoresis as follows: the frozen cell wall extracts were thawed and precipitated with 70% acetone on ice for 4 hours. The protein precipitate was pelleted, dried in a SpeedVac (Thermo Savant, Holbrook, N.Y.) and solubilized with ReadyPrep (BioRad) SEQUENTIAL EXTRACTION REAGENT 3, which contains 5 M urea, 2 M thiourea, 2% (w/v) CHAPS, 2% (w/v) SB 3-10, 40 mM Tris and 0.2% Bio-Lyte 3/10.

The prepared cell wall fraction samples were loaded onto 11 cm immobilized pH gradient (IPG) strips, pH 4-7 (Bio-Rad) by allowing each sample to re-hydrate a gel strip during an overnight incubation at room temperature. The sample size was 250 µg in a total volume of 200 µl. During the overnight incubation, the strips were covered with mineral oil (BioRad) to prevent evaporation. Following completion of rehydration of the strips, excess mineral oil was removed onto blotting paper that was saturated with water and the hydrated strips were then loaded into a pHaser Iso-electric focusing (IEF) apparatus (Genomic Solutions Inc., Ann Arbor, Mich.). The strips were prefocused with a current limit of 50 mA/strip with the voltage gradually increasing from 250 V to 5,000 V. Voltage was then held constant at 5,000 V for a total 50 kVh (~16h). Second dimension SDS-PAGE was carried out using 12.5% Criterion precast gels (BioRad). For mass spectrometric analysis, gels were stained with Sypro Ruby protein gel stain (BioRad) according to the manufacturer's instructions.

Two-dimensional (2D) gel profiles of cell wall associated proteins from Staphylococcus epidermidis grown in TSB or 70% rabbit serum were compared. See FIG. 1. Growth in 70% rabbit serum resulted in a change in the protein expression profile of cell wall associated proteins from Staphylcoccus epidermidis that was easily detectable in fluorescent stained transfers of 2D gels (FIGS. 1A and 1B).

Eight proteins were detected by fluorescent stain to be differentially regulated between Staphylcoccus epidermidis grown in TSB or in the presence of rabbit serum. See Table 3 and FIG. 1. Most notable was an increase in the fluorescent staining of three protein streaks between 25 kDa and 37 kDa in the cells grown in 70% serum (FIG. 1B, spots e, g and h).

TABLE 3

List of Spots Identified[a]

| [b]Spot # | Protein SEQ ID NO: | [c]Method of detection |
|---|---|---|
| 1, 2 | 12 | I, S |
| 3 | 12 | I, S |
| 3 | 19 | I, S |
| 4[c] | 11 | I, S |
| 4 | 18 | I, S |
| 5-7, 9 | 11 | I, S |
| 8 | 21 | I |
| 10[c] | 11 | I, S |
| 10 | 18 | I, S |
| 10 | 28 | I, S |
| 11 | 3 | I, S |
| 12 | 10 | I, S |
| 13 | 10 | I, S |
| 13 | 26 | I, S |
| 14 | [d]NGID | I, S |
| 15-16 | 10 | I, S |
| 17 | 25 | I |
| 18 | 4 | I |
| 19 | 17 | I, S |
| 19 | 23 | I, S |
| 20-23, 25 | 17 | I, S |
| 24 | 30 | I, S |
| 26 | 30 | I, S |
| 26 | 8 | I, S |
| 26 | 7 | I, S |
| 27, 30-32 | 2 | I, S |
| 28, 33 | 22 | I, S |
| 29 | 5 | I, S |
| 34 | 13 | I, S |
| 35 | NGID | I |
| 36 | NGID | I |
| 37 | NGID | I, S |
| 38 | 29 | I, S |
| 38 | 3 | I, S |
| 39 | 32 | I, S |
| 40 | 14 | S |
| 40 | 20 | S |
| 40 | 27 | S |
| 41 | 14 | S |
| 42 | 6 | I |
| 43 | 32 | S |
| 43 | 16 | S |
| 43 | 24 | S |
| 44 | 15 | S |

[a]List of spots detected on 2D blots by reactivity with immune sera or binding to serum components.
[b]Some spots contained more that one protein.
[c]Method by which the spot was detected following transfer to nitrocellulose, reactive immune sera from infected rabbits, I, or binding serum components, S.
[d]NGID = no gene in database Example 3

Binding of Immune Serum and Biotinylated Serum Proteins to Cell Wall Proteins

After completion of the first and second dimensions of electrophoresis, the protein content of the gels was transferred onto nitrocellulose for binding assays. Specifically, the protein content of the gels was electro-blotted to nitrocellulose membranes (BioRad) using a semi-dry blotting apparatus (Owl Separations Systems, Portsmouth, N.H.) at 12V for 1 hour. The protein containing nitrocellulose membranes (blots) were then stained with Sypro Ruby protein blot stain (BioRad) following the manufacturer's instructions and visualized in a FluorS Imager (BioRad). Each blot was incubated in blocking buffer (PBS with 0.05% Tween 20 and 5% dry milk) for 10 minutes at room temperature then incubated overnight with either a 1:2000 dilution of immune sera (Western blot) or 40 µg/ml biotinylated serum proteins (see below). Following overnight incubation, blots were washed 3× with wash buffer (PBS with 0.5% Tween 20) and incubated with either goat anti-rabbit IgG alkaline phosphatase conjugate (Biosource International, Camarillo, Calif.) or streptavidin alkaline phosphatase conjugate (Biosource) for 2 hours at room temperature in blocking buffer. Blots were again washed three times with wash buffer and visualized with BCIP/NBT membrane phosphatase substrate system (KPL, Inc., Gaithersburg, Md.). Pictures were taken in the FluorS. All analysis of 2D gels was performed using Melanie 3.0 software.

Protein concentration was assayed using the BioRad protein assay kit (BioRad).

Changes in the protein expression profile of cell wall associated proteins was more pronounced by considering the Western blots of the nitrocellulose membranes containing the proteins transferred from the 2D gels. In the Western blots, the nitrocellulose membranes were incubated with pooled immune sera from rabbits repeatedly infected with Staphylcoccus epidermidis 0-47. See FIGS. 1C and 1D. These upregulated proteins are also strongly immunoreactive, suggesting they were expressed during infection of the rabbits. Five other immunoreactive streaks or spots from the serum-grown cells were expressed at either lower or undetectable levels in TSB grown cells. See FIG. 1, spots a, b, c, d and f.

Example 4

Analysis of Serum Proteins that Interact With Staphylcoccus epidermidis Cell Wall Associated Proteins Elution of Serum Proteins from Staphylococcus epidermidis Staphylcoccus epidermidis 0-47 was grown in 70% rabbit serum at 37° C. to $OD_{600}$~0.8 and the cells were pelleted. The cells were resuspended at $OD_{600}$~20 and washed three times with TBS while rocking at 4° C. The bound serum proteins were eluted sequentially with 20 mM Tris, pH 8.0 containing either 0.5 M NaCl, 1.0 M NaCl or 4.0 M urea for 1 hour with rocking at 4° C. The bacteria were then removed by centrifugation and the supernatant collected. The supernatants contained the serum proteins eluted from the surface of the bacteria. Proteins eluted under the different conditions were analyzed by SDS-PAGE using 4-20% gradient Tris-glycine gels (Cambrex Biosciences Rockland, Inc., Rockland, Me.)
Biotinylation of Serum Proteins The eluted serum proteins were dialyzed overnight against PBS at 4° C. IgG's were depleted by overnight incubation with protein G sepharose (Amersham-Pharmacia, Piscataway, N.J.) at 4° C. Assuming an average protein mass of 50 kDa in the eluted fraction, the proteins were labeled with a 15-molar excess of EZ-Link® NHS-biotin (Pierce Biotechnology) for 1.5 hour at 4° C. The reaction was quenched with excess glycine and dialyzed (10,0000 MWCO, Pierce) overnight against PBS.

Identification Of Serum Proteins Bound To The Surface Of *Staphylcoccus epidermidis*

Figure 3:
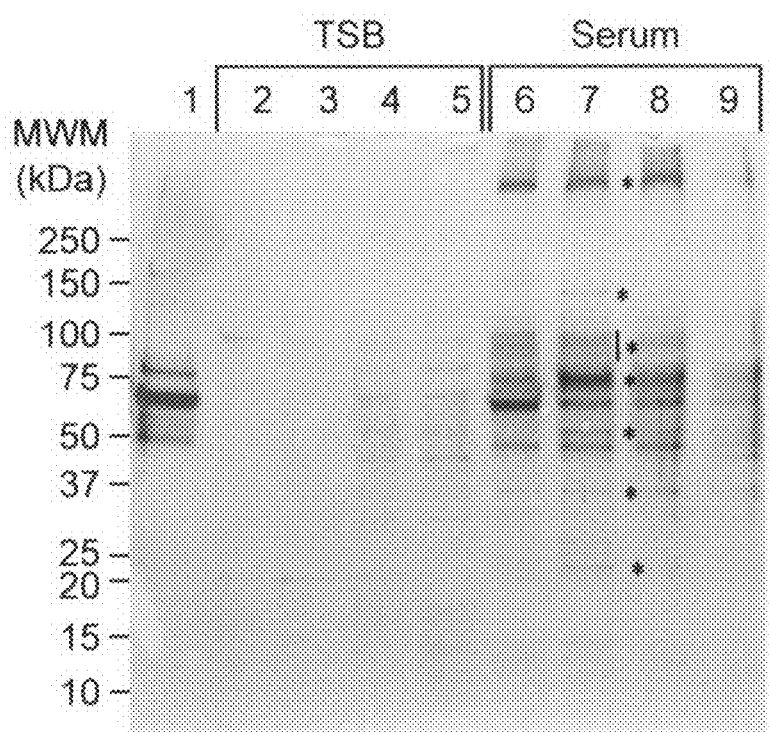
FIG. 3 depicts proteins, which were eluted from the surface of *S. epidermidis* 0-47 grown in TSB or 70% rabbit serum with increasing concentrations of NaCl or 4.0M urea. Asteriks indicate enriched proteins eluted from the surface of S. Epi grown in the presence of serum. Bacteria were washed 3× with TBS then sequentially with 0.5 M and 1.0 M NaCl and 4.0 M urea. Protein concentrations were determined for each of the samples and 0.75 µg was run on a 4-20% gradient gel. No protein was detected by protein assay in the samples eluted from the surface of TSB-grown bacteria (lanes 2-5), so 25 µl was loaded onto the gel. Lane 1, rabbit serum; Lanes 2 and 6—0.15M NaCl eluate; Lanes 3 and 7—0.5M NaCl, Lanes 4 and 8—1.0 M NaCl; Lane 5 and 9—4.0 M urea.

Serum proteins eluted from the bacteria under these conditions were compared by SDS-PAGE to normal rabbit serum and to the bacterial proteins eluted from the surface of *Staphylcoccus epidermidis* grown in TSB. See FIG. 3. Buffers containing 0.5 NaCl, 1 M NaCl and 4 M urea each eluted bound serum proteins from the bacterial cells. These eluted serum proteins represent a pool of proteins eluted from the bacterial surface that is enriched for serum proteins. Some bacterial proteins are likely present in this pool, however no bacterial proteins detectable by protein assay were eluted from bacteria grown in TSB. Although some faint protein bands were detected by silver stain to be eluted from TSB grown bacteria, they did not correspond to the more intensely stained proteins eluted from the surface of the bacteria grown in serum. Elution with 1 M NaCl was the least denaturing condition that eluted the most proteins and was used to elute proteins for the following examples.

Figure 2B:
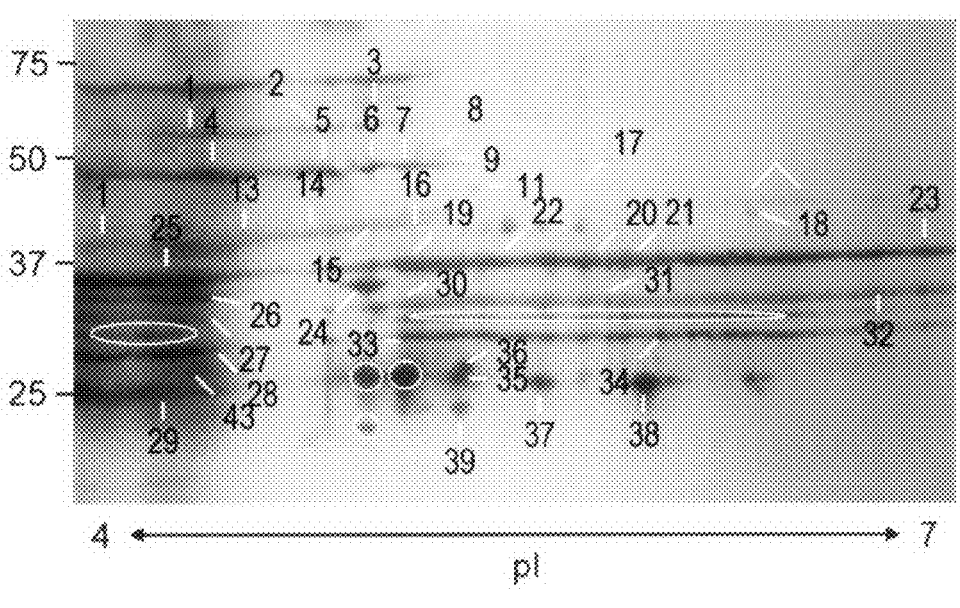
Figure 4A:
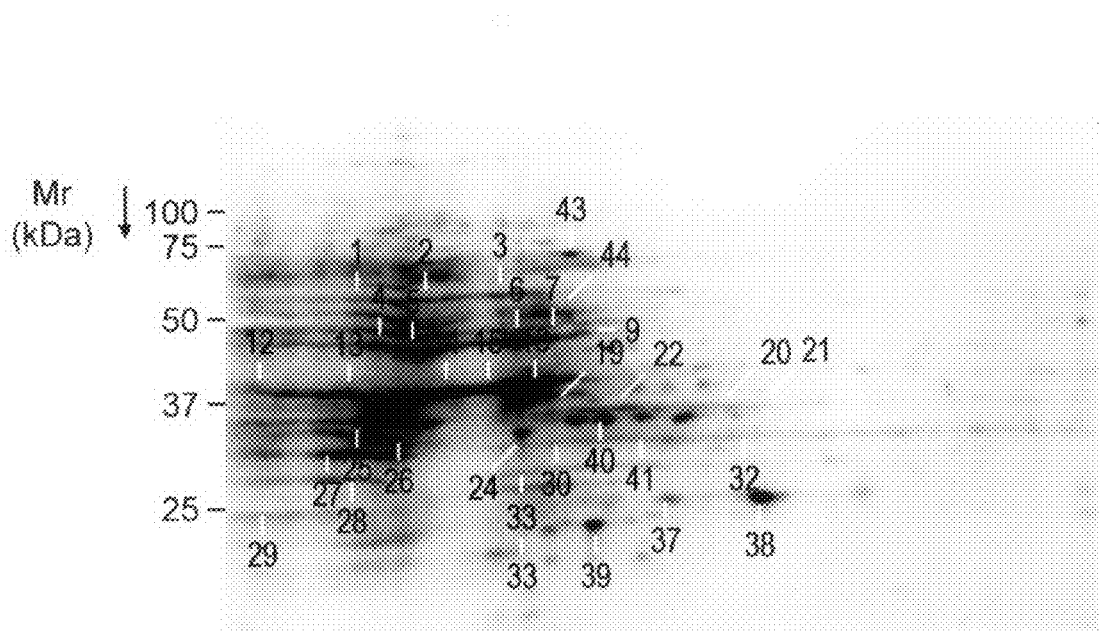
FIG. 4 depicts a 2D transfer of cell surface proteins from *S. epidermidis*, which was fluorescently stained for protein (4A) and probed with biotinylated serum proteins (4B) eluted from *S. epidermidis* grown in 70% rabbit serum. The spots were visualized with a streptavidin-alkaline phosphatase conjugate. The proteins in the spots were identified by mass spectroscopy.
Figure 4B:
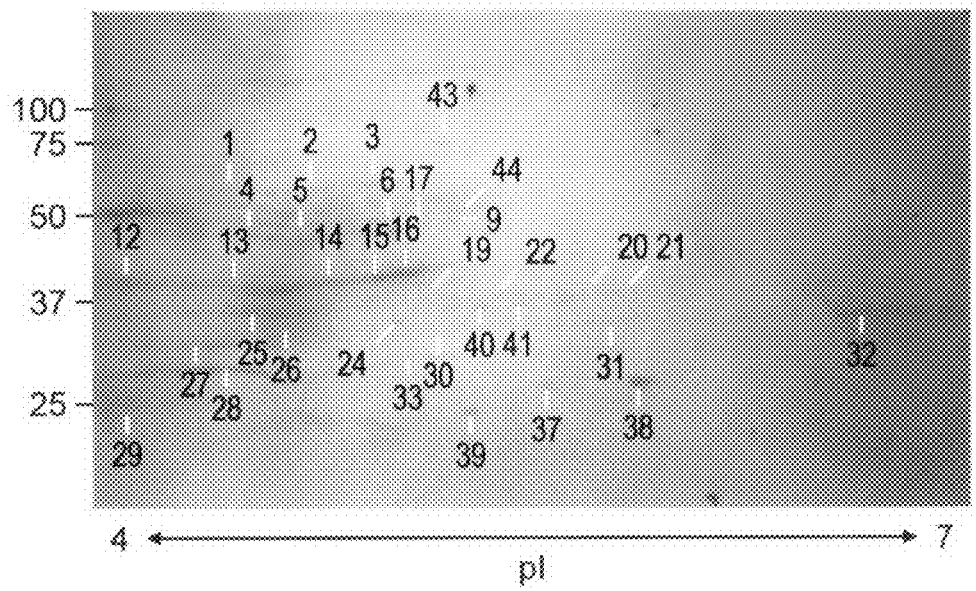

In order to identify cell wall associated proteins involved in binding serum components, biotin labeled serum proteins were used to probe 2D transfers by incubating a solution of the labeled proteins with the nitrocellulose bound cell wall proteins transferred from a 2D gel. To isolate serum proteins that bind to *Staphylcoccus epidermidis*, bacteria grown in 70% rabbit serum were washed with 1 M NaCl. The eluted serum proteins were collected and dialyzed into PBS. Next, the naturally occurring immune IgG that may be present in the eluted serum proteins was depleted by incubation with protein G sepharose. Removal of IgG reduces the likelihood of identifying a protein that is reactive with host antibodies. The eluted serum proteins were then biotin labeled as described above and used to probe a 2D blot of *Staphylcoccus epidermidis* cell surface proteins. See FIGS. 4A and 4B. Thirty-four spots and regions were visualized by this method and are likely involved in the interaction of *Staphylcoccus epidermidis* with host serum proteins. Of the 34 spots consistently found to interact with serum components all but 4 were found to react with the immune sera from infected rabbits. See FIG. 2 and Table 3.

*Staphylcoccus epidermidis* grown in serum had serum proteins bound to bacterial surface proteins that were eluted with 0.5 M and 1 M NaCl. Under the same conditions few staphylococcal proteins were eluted from bacteria grown in TSB however it is possible that a staphylococcal protein expressed only in the serum is eluted by the high salt treatment.

Example 5

Mass Spectroscopy Identification of Serum Upregulated Proteins

Bacteria grown in 70% serum were used in subsequent proteomic experiments and analyses, working under the assumption that the changes detected during growth in serum may more accurately reflect alterations in gene expression made by the bacteria in response to environmental cues seen within a host. In the following mass spectroscopy studies, proteins isolated from spots on 2D gel electrophoresis separations were first subjected to time-of-flight mass spectroscopy. If a positive, unambiguous identification was obtained then no further mass spectrometric analysis was performed. See Table 4. In the cases where some ambiguity remained after time-of-flight mass spectroscopy, such as when multiple proteins resolved to the same spot on the 2D gel, then electrospray mass spectroscopy was performed to resolve the ambiguity. See Table 4.

TABLE 4

Proteins Identified by Mass Spectroscopy

| Orf | Protein SEQ ID NO: | DNA SEQ ID NO: | 2-D Gel Spot Number |
|-----|---|---|---|
| 121 | 1 | 33 | 38 |
| 305 | 2 | 34 | 27, 30-32 |
| 321 | 3 | 35 | 11 |
| 373 | 4 | 36 | 18 |
| 554 | 5 | 37 | 29 |
| 639 | 6 | 38 | 42 |
| 608 | 7 | 39 | 26, |
| 702 | 8 | 40 | 26 |
| 793 | 9 | 41 | 39 |
| 847 | 10 | 42 | 12, 13, 15, 16 |
| 854 | 11 | 43 | 4, 5-7, 9, 10 |
| 1015 | 12 | 44 | 1, 2, 3 |
| 1069 | 13 | 45 | 34 |
| 1238 | 14 | 46 | 40, 41 |
| 1382 | 15 | 47 | 44 |
| 1405 | 16 | 48 | 43 |
| 1450 | 17 | 49 | 19, 20-23, 25 |
| 1522 | 18 | 50 | 4, 10 |
| 1545 | 19 | 51 | 3 |
| 1653 | 20 | 52 | 40, |
| 1690 | 21 | 53 | 8 |
| 1703 | 22 | 54 | 28, 33 |
| 2006 | 23 | 55 | 19 |
| 2180 | 24 | 56 | 43 |
| 2214 | 25 | 57 | 17 |
| 2482 | 26 | 58 | 13 |
| 2580 | 27 | 59 | 40 |
| 2649 | 28 | 60 | 10 |
| 2653 | 29 | 61 | 38 |
| 2736 | 30 | 62 | 24, 26 |
| 2907 | 31 | 63 |  |
| 2975 | 32 | 64 | 39, 43 |

Sample Preparation

Prior to performing mass spectrometry, the target protein spots were subjected to in-gel tryptic digestion. Protein spots were removed from the gel and cut into ~1 mm pieces. The gel pieces were washed three times with 0.2 ml of 50% (v/v) acetonitrile (Burdick & Jackson, Muskegon, Mich.) in 10 mM ammonium bicarbonate (J. T. Baker, Phillipsburg, N.J.) for 15 minutes with occasional vortexing. The gel pieces were dehydrated with acetonitrile for 5 minutes, lyophilized, and stored frozen at −20° C. Proteins in the gel were then digested with 50 µl of 12 ng/ml sequencing grade modified trypsin (Promega Corporation, Madison, Wis.) overnight at 37° C. The trypsin solution was then removed and the gel again dehydrated in 50 µl acetonitrile. The peptide-containing acetonitrile was then removed and the gel pieces washed in 50 µl 5% formic acid (Riedel-de Haën, Seelze, Germany) for 15 minutes at room temperature in a bath sonicator (Branson Cleaning Equipment Co., Shelton, Conn.). The peptide-containing supernatant was removed and combined with the initial acetonitrile wash. The gel was again washed in acetonitrile and the supernatant combined with two previous extraction steps and dried in a SpeedVac (Thermo Savant) to ~10 µl, then diluted to 100 µl with 0.1% (v/v) aqueous formic acid. The sample was then loaded onto a Zip-Tip$_{C18}$ P10 column (Waters Corporation, Milford, Mass.) and eluted in 50 µl of 50% acetonitrile/0.1% formic acid. Samples were transferred to a 96×2 well Teflon coated stainless steel plate (PerSeptive Biosystems, Framingham, Mass.) for mass fingerprinting analysis on the MALDI-ToF instrument (PerSeptive Biosystems) glass nanospray tips (New Objective Inc., Woburn, Mass.) to be sprayed in the orifice of the ion trap mass spectrometer.

Peptide Mass Fingerprinting Using ToF Mass Spectrometry

Each sample was applied to the Teflon coated stainless steel 96×2 well plate with the α-cyano-4-hydroxycinnamic acid thin-layer application. The samples were allowed to dry at room temperature. Mass spectral data were acquired on a Voyager DE-STR MALDI-ToF mass spectrometer (PerSeptive Biosystems) equipped with delayed extraction technology, and a reflector. The mass spectrometer was equipped with a nitrogen laser at 337 nm and a laser rate of 3 Hz. Accelerating voltage was set at 20 kV, mode of operation (reflector), extraction mode (delayed), polarity (positive), grid voltage (65%), mirror voltage ratio (1.12), extraction delay time (200 nsec), mass range (800-3500 Da), and laser shots per spectrum (200).

Static Nanospray Ion Trap-Mass Spectrometry

Mass spectral data were acquired on a ThermoFinnigan LCQ DECA quadrupole ion trap mass spectrometer (ThermoFinnigan, San Jose, Calif.) equipped with a nano-electrospray interface. The nano-electrospray interface consisted of a silica spray needle, ~27 mm length by 120/69 µm OD/ID, 2 µm orifice diameter (New Objective Inc.). The glass tip was mounted in a x,y,z axis holder (ThermoFinnigan) held on a base positioned at the front of the mass spectrometer detector. Electrical current was applied to the standard coating of the glass tip to supply an electrical connection for the electrospray interface through a metal connection on the static nanospray probe (ThermoFinnigan). The nanospray delivered a flow of 20-80 nl/min.

Two to five microliters of the tryptic digest was analyzed using a nanospray glass tip spraying directly into the orifice of the mass spectrometer. Peptide analyses were conducted on the LCQ-DECA ion trap mass spectrometer (Thermofinnigan) operating at a variable spray voltage of ~1 kV, and using a heated capillary temperature of 200° C. Data sets were acquired in automated MS/MS mode using the data acquisition software provided with the instrument. The acquisition method included 1 MS scan (400-1800 m/z) followed by MS/MS scans of the top three most abundant ions in the MS scan. The dynamic exclusion function was employed to increase the number of peptide ions that were analyzed (settings: 3 amu=exclusion width, 0.5 minutes=exclusion duration). The current experiment was analyzed in groups of samples and in a manual fashion.

Automated analysis of mass fingerprinting data was performed using MSFIT (Protein Prospector) and MASCOT (Matrix Science) software database search engines using Incyte's PathoSeq(c) *Staphylcoccus epidermidis* 0-47 database. The resultant spectra were processed with baseline correction, noise removal, and peak de-isotoping before utilizing the search engines. The database search parameters were set at the following levels: MW (1000-150 kDa), pI (3-10), Digest (trypsin), max. number of missed cleavages (2), missed cleavages pfactor (0.4), static modification (cysteine modified by acrylamide), N terminus (hydrogen), C terminus (free acid), variable mods (oxidation of methionine, N-terminus acetylation, phosphorylation of serine, threonine, and tyrosine), Mass (monoisotopic), min. number of peptides required to match (4) with a mass tolerance of 300 ppm, and the application of iterative calibration (Intelcast) with a mass tolerance of 15 ppm. Protein identifications were determined by MOWSE score and a 95% confidence score by MS-FIT and MASCOT respectively.

Automated analysis of MS/MS data was performed using SEQUEST incorporated into the Finnigan Bioworks data analysis package (ThermoFinnigan). See Eng, J. K., et al., J Amer Soc Mass Spec, 5(11): p. 976-89 (1994). The following variable modifications were allowed in the software: cysteine acrylamide modification and oxidation of methionine. The search parameters were set at the following designations: mass range (400-3500 Da), lower intensity MS signal (1e$^{+5}$), peptide tolerance (2.0 Da), min. number of fragment ions (15), min. number of scans in a group (1), and maximum number of missed cleavages (2). All protein identifications were manually verified for accuracy.

Identification Of Proteins By Mass Spectrometry

Spots consistently detected on both fluorescent and immunostained transfers from *Staphylcoccus epidermidis* grown in 70% serum, were located and labeled for identification by mass spectrometry. See FIGS. 2A and 2B. A total of 40 immunoreactive spots were cut and subjected to mass spectrometric analysis for identification. See Table 4. The complete protein sequences are shown in the sequence listing (SEQ ID NOS:1-32). The protein-containing gel spots were cut out of a gel and identified by mass fingerprint analysis using MALDI-TOF followed by searching Incyte's PathSeq (c) *Staphylcoccus epidermidis* 0-47 database for the corresponding coding region. See Table 4. Spots with multiple protein hits or questionable signal were further analyzed using static nanospray. A total of 32 proteins was identified, with some spots containing more than one protein. See Tables 3 and 4. Twenty-four of the proteins identified were immunoreactive, 26 bound to serum components and 20 of the proteins were both immunoreactive and serum binding. This large overlap was expected, as most proteins on the surface of *Staphylcoccus epidermidis* involved in binding to serum factors would likely elicit an immune response.

Six proteins were consistently present in immunostained blots, but no corresponding spots were visibly present on the fluorescent stained transfers. See FIG. 2B, white circles and arrow. Although these proteins are likely expressed during an infection and elicit an immune response they are not expressed at levels that allow for their detection by fluorescent protein staining under the conditions used in these experiments.

Example 6

Prediction of Protein Function

The predicted function of the proteins was determined by comparison with complete genome homologs from ATCC12228. See Zhang, Y. Q., et a., Mol Microbiol, 49(6), p.

1577-93 (2003). The predicted functions shown in Table 5, are attributed to the respective ORFs by prior publications involving the specific protein or by homology to previously characterized proteins occurring in other organisms.

TABLE 5

Predicted Functions of S. epidermidis proteins

| Spot # | [a]Predicted function | Protein SEQ ID NO: | [b]Method of detection |
|---|---|---|---|
| 1, 2 | dihydrolipoamide dehydrogenase | 12 | I, S |
| 3 | " | 12 | I, S |
|  | glutamate-1-semialdehyde 2,1-aminomutase | 19 | I, S |
| 4 | enolase | 11 | I, S |
|  | elongation factor TU (EF-TU) | 18 | I, S |
| 5-7, 9 | enolase | 11 | I, S |
| 8 | phosphogluconate dehydrogenase | 21 | I |
| 10 | enolase | 11 | I, S |
|  | elongation factor TU (EF-TU) | 18 | I, S |
|  | Na+/H+ antiporter | 28 | I, S |
| 11 | alanine dehydrogenase | 3 | I, S |
| 12 | glyceraldehyde-3-phosphate dehydro (GAPDH) | 10 | I, S |
| 13 | " |  | I, S |
|  | elongation factor (EF-TS) | 26 | I, S |
| 14 | no match |  | I, S |
| 15-16 | glyceraldehyde-3-phosphate dehydro (GAPDH) | 10 | I, S |
| 17 | acetyl-CoA C-acetyltransferase | 25 | I |
| 18 | cystathionine gamma-synthase | 4 | I |
| 19 | ferrichrome binding lipoprotein | 17 | I, S |
|  | oligopeptide permease | 23 | I, S |
| 20-23, 25 | ferrichrome binding lipoprotein | 17 | I, S |
| 24 | fructose-bisphosphate aldolase | 30 | I, S |
| 26 | " |  | I, S |
|  | hypothetical protein | 8 | I, S |
|  | hypothetical protein | 7 | I, S |
| 27, 30-32 | lipoprotein (SitC) | 2 | I, S |
| 28, 33 | amino acid-binding lipoprotein | 22 | I, S |
| 29 | putative hexulose-6-phosphate synthase | 5 | I, S |
| 34 | lipoate ligase | 13 | I, S |
| 35 | no match |  | I |
| 36 | no match |  | I |
| 37 | no match |  | I, S |
| 38 | immunodominant antigen A | 29 | I, S |
|  | Putative protein | 1 | I, S |
| 39 | extracellular matrix binding protein (Embp) | 32 | I, S |
| 40 | cysteine synthase | 14 | S |
|  | fructose-bisphosphate aldolase homologue | 20 | S |
|  | thioredoxine reductase | 27 | S |
| 41 | cysteine synthase | 14 | S |
| 42 | putative transaldolase | 6 | I |
| 43 | extracellular matrix binding protein (Embp) | 32 | S |
|  | transketolase | 16 | S |
|  | hypothetical protein | 24 | S |
| 44 | glutamyl-tRNAGln amidotransferase subunit | 15 | S |

[a]The predicted function of the proteins was determined by comparison with complete genome homologs from ATCC12228.
[b]Method by which the spot was detected following transfer to nitrocellulose, reactive immune sera from infected rabbits, I, or binding serum components, S.

As discussed above, the expression profile of cell wall associated proteins from Staphylococcus epidermidis 0-47 grown in 70% rabbit serum was analyzed by 2D gel electrophoresis. The overall expression profile in serum was determined to be significantly different from that occurring following growth in TSB. Numerous proteins that were upregulated during growth in serum were identified by mass spectroscopy and their functions predicted by sequence comparison. See Table 5. Three proteins predicted to be involved in nutrient acquisition, 305,1450, and 1703 were all significantly increased. See Tables 4 and 5. All three proteins form streaks across the gel. See FIG. 4. Without being bound by theory, this may be the consequence of multiple charge isomers or related to their predicted lipoprotein composition. Additionally, all three proteins are highly reactive with immune sera from rabbits infected with Staphylcoccus epidermidis 0-47 suggesting that these proteins are also expressed in the host during an infection. See FIG. 2 and Table 5. In total, 24 of these proteins were identified as reactive with immune sera from infected rabbits. Not only are these proteins expressed during growth in serum, but they also elicited an immune response in an infected animal. See Example 8. Taken together, these data suggest that these antigens are all expressed during an infection. Expression of the transcripts from these ORFs within the bloodstream of an infected mouse was confirmed by RT-PCR for all of the identified proteins (data not shown).

Example 7

Cloning And Expression Of Recombinant Proteins

Genes were cloned using primers designed based on the proteins identified by mass spectrometry of the expressed proteins and the *Staphylcoccus epidermidis* 0-47 database. Individual genes were amplified by polymerase chain reaction (PCR) using Pfu Turbo DNA polymerase (Stratagene, La Jolla, Calif.) and adenine overhangs were added with Taq DNA polymerase (Roche Diagnostics). The reaction products were cloned into pCRT7/NT-TOPO or pBAD/TO-POThio (Invitrogen, Carlsbad, Calif.) following the manufacturer's instructions and transformed into *E. coli* Top10 (Invitrogen). Positive clones were detected by colony PCR using ReddyMix PCR mastermix (ABgene, Rochester, N.Y.) and sequenced to ensure that no spurious mutations had arisen. Plasmids from pCRT7 clones were purified and transformed into *E. coli* BL21 (DE3) (Invitrogen) for expression using the T7 polymerase. Proteins were expressed by growth of the positive clones in HySoy broth (1% HySoy, Quest Intl, Stockbridge, Ga.), 0.5% yeast extract, 100 mM NaCl, 50 mM $Na_2HPO_4$-$7H_2O$, 40 mM $NaH_2PO_4$—$H_2O$) supplemented with 100 µg/ml ampicillin at 37° C. with shaking (200 rpm) until $OD_{600}$~1.0. Protein expression was induced with either 1 mM IPTG (pCRT7) or 0.2% arabinose (pBAD) and the cultures were grown an additional 3 hours. The cells were then harvested by centrifugation and expression was assessed by SDS-PAGE of whole cell lysates.

Purification Of Recombinant Proteins

Cell pellets were resuspended in 100 ml TBS (20 mM Tris, pH 8.0, 150 mM NaCl) and lysed by one passage through a French pressure cell (SLM-Aminco, Rochester, N.Y.). Samples were then separated into a soluble fraction or insoluble pellet by centrifugation at 10,000×g for 10 minutes. The location of recombinant protein was assessed by SDS-PAGE. If a recombinant protein was in the soluble fraction, then the protein was loaded onto iminodiacetic acid agarose resin charged with $Ni^{2+}$. See Table 6. Next, the column was washed with 30 mM imidazole in TBS. Bound proteins were eluted with 300 mM imidazole in TBS. If an additional purification step was required, the proteins were dialyzed into 20 mM Tris, pH 8.0, containing 50 mM NaCl, 1 mM EDTA and loaded onto a column packed with POROS-Q resin (Applied Biosystems, Foster City, Calif.). Bound proteins were eluted with a 50 mM to 500 mM NaCl gradient in 20 mM Tris, pH 8.0, 1 mM EDTA. Fractions containing the protein of interest were determined by SDS-PAGE and frozen at −20° C.

If a recombinant protein was found in the insoluble fraction, then the insoluble fraction was treated with 100 ml 1% Triton X-100 in TBS for 4 hours at 4° C. See Table 6. The insoluble proteins were pelleted by centrifugation and the supernatant discarded. The insoluble pellet was then extracted with 100 ml of 8 M urea in TBS for at least 8 hours at room temperature. Insoluble debris was pelleted and the protein was purified as above except all buffers contained 2M urea. Following purification Triton X-100 was added to a final concentration of 0.1%. The proteins were then dialyzed into TBS containing 0.1% Triton and stored at −20° C.

All liquid chromatography was performed using an AKTA explorer (Amersham-Pharmacia Biotech, Piscataway, N.J.). All SDS-PAGE was performed using 4-20% gradient Tris-glycine gels (Cambrex).

TABLE 6

Recombinant Protein Solubility

| Protein | | Location of Recombinant Protein | |
|---|---|---|---|
| Orf | SEQ ID NO: | Soluble Fraction | Insoluble Fraction |
| 121 | 1 | | X |
| 305 | 2 | X | |
| 321 | 3 | | X |
| 373 | 4 | | X |
| 554 | 5 | X | |
| 639 | 6 | X | |
| 608 | 7 | | X |
| 702 | 8 | | X |
| 793 | 9 | | X |
| 847 | 10 | X | |
| 854 | 11 | | X |
| 1015 | 12 | | X |
| 1069 | 13 | | X |
| 1238 | 14 | | X |
| 1382 | 15 | | X |
| 1405 | 16 | | X |
| 1450 | 17 | X | |
| 1522 | 18 | | X |
| 1545 | 19 | | X |
| 1653 | 20 | | X |
| 1690 | 21 | X | |
| 1703 | 22 | X | |
| 2006 | 23 | NT | |
| 2180 | 24 | | X |
| 2214 | 25 | | X |
| 2482 | 26 | X | |
| 2580 | 27 | X | |
| 2649 | 28 | | X |
| 2653 | 29 | X | |
| 2736 | 30 | | X |
| 2907 | 31 | NT | |
| 2975 | 32 | NT | |

X indicates the protein was found in that fraction.
NT indicates not tested.

Example 8

Immunogenic Compositions Using Recombinant *Staphylcoccus epidermidis* Proteins

Four week-old female Balb/C mice (Charles River Laboratories, Wilmington, Mass.) were immunized at 0, 3 and 6 weeks with 10 µg recombinant protein formulated with 20 µg STIMULON™ QS-21 by subcutaneous injection. The mice were bled on week 0 prior to the first immunization and on week 8. Two days following the final bleed, the mice were challenged by intraperitoneal injection of $5 \times 10^8$ cfu *Staphylococcus epidermidis* 0-47 grown overnight on Columbia salt agar (1× Columbia agar, 0.1% glucose, 1% yeast extract, 0.5% NaCl). Twenty-four hours following challenge, the mice were sacrificed and the bacteria were enumerated in the spleen and blood.

Active Immunization of Mice With Recombinant Proteins

Twenty-seven orfs encoding either serum-binding or immunoreactive proteins were cloned from *Staphylococcus epidermidis* 0-47 and the recombinant proteins were expressed in *E. coli* with a hexahistidine tag (The His-tag was used as a matter of convenience; an immunogenic composition of this invention would contain proteins expressed without a His-tag). See Table 7. These proteins were purified using a $Ni^{2+}$ chelate column followed by ion exchange chromatography. The three remaining cloned orfs (2006, 2975 and 2907) were cloned but not expressed at levels sufficient for purification. Balb/C mice were immunized at 0, 3 and 6 weeks with individual recombinant proteins. The animals were bled at 0 and 8 weeks and challenged (i.p.) on week 8 with *Staphylococcus epidermidis* 0-47. Twenty-four hours following challenge, the animals were euthanized and the number of bacteria present in the blood and spleen enumerated. This initial screen of immunogenic composition candidates was performed on groups of 5 animals to enable for the screening of numerous proteins. The resulting data are not statistically significant but they did provide valuable information as to the immunogenic composition potential of a large number of candidates. Eight of twenty-seven recombinant proteins reduced the number of bacteria recovered from the spleen and/or blood by one log or more. See Table 7 (NT=not tested).

TABLE 7

Reductions in Bacterial Counts Following Immunization

| Protein | | Log CFU Reduction | |
|---|---|---|---|
| Orf | SEQ ID NO: | Spleen | Blood |
| 121 | 1 | NT | NT |
| 305 | 2 | 0.8 | 1 |
| 321 | 3 | 0 | 1 |
| 373 | 4 | 0 | 0 |
| 554 | 5 | 0.5 | 0 |
| 639 | 6 | 0 | 0 |
| 608 | 7 | 0.5 | 0 |
| 702 | 8 | 0 | 0 |
| 793 | 9 | NT | NT |
| 847 | 10 | 0 | 0 |
| 854 | 11 | 1.5 | 0.7 |
| 1015 | 12 | 0 | 0 |
| 1069 | 13 | 1.1 | 0 |
| 1238 | 14 | 1 | 0.8 |
| 1382 | 15 | 0 | 0 |
| 1405 | 16 | 0 | 0 |
| 1450 | 17 | 0 | 0 |
| 1522 | 18 | 0 | 0 |
| 1545 | 19 | 0 | 0 |
| 1653 | 20 | 1 | 0 |
| 1690 | 21 | 0 | 0 |
| 1703 | 22 | 2 | 0 |
| 2006 | 23 | NT | NT |
| 2180 | 24 | 0 | 0 |
| 2214 | 25 | 1.2 | 0.9 |
| 2482 | 26 | 0 | 0 |
| 2580 | 27 | 0 | 0 |
| 2649 | 28 | 0.9 | 0 |
| 2653 | 29 | 0 | 0 |
| 2736 | 30 | 0 | 0 |
| 2907 | 31 | NT | NT |
| 2975 | 32 | NT | NT |

NT indicates not tested.

The sera obtained from the immunized mice were evaluated for antibody reactivity to the bacterial proteins. See Table 8. Twenty-three of twenty-four immune sera tested reacted with the native proteins, as determined by western blots of whole cell lysates of *Staphylococcus epidermidis* grown to mid-log phase in rabbit serum. See Table 8 (NT=not tested).

TABLE 8

Antibody Reactivity to *Staphylococcal* Protein

| Protein | | Antibody Reactivity to *Staphylococcal* Protein | |
|---|---|---|---|
| Orf | SEQ ID NO: | *S. epidermidis* | *S. aureus* |
| 121 | 1 | NT | NT |
| 305 | 2 | + | + |
| 321 | 3 | + | − |
| 373 | 4 | + | NT |
| 554 | 5 | − | NT |
| 639 | 6 | + | − |
| 608 | 7 | + | + |
| 702 | 8 | + | + |
| 793 | 9 | + | + |
| 847 | 10 | + | + |
| 854 | 11 | + | |
| 1015 | 12 | + | + |
| 1069 | 13 | + | + |
| 1238 | 14 | + | NT |
| 1382 | 15 | + | + |
| 1405 | 16 | + | + |
| 1450 | 17 | + | + |
| 1522 | 18 | + | + |
| 1545 | 19 | + | + |
| 1653 | 20 | + | NT |
| 1690 | 21 | + | + |
| 1703 | 22 | + | + |
| 2006 | 23 | NT | NT |
| 2180 | 24 | NT | NT |
| 2214 | 25 | + | + |
| 2482 | 26 | + | + |
| 2580 | 27 | + | NT |
| 2649 | 28 | + | + |
| 2653 | 29 | − | NT |
| 2736 | 30 | + | + |
| 2907 | 31 | NT | NT |
| 2975 | 32 | NT | NT |

NT indicates not tested.

As shown in Table 8, many of the animals immunized with *Staphylcoccus epidermidis* antigens also developed antibody responses to *Staphylcoccus aureus*. Therefore, immunogenic compositions against *Staphylcoccus epidermidis* antigens could be effective in the treatment or prevention of *Staphylcoccus aureus* as well as *Staphylcoccus epidermidis*. See Table 8.

A subset of the recombinant proteins used in immunogenic compositions above were used to immunize larger groups of mice. Groups of 10 female (4 week-old) Balb/C mice were immunized by subcutaneous injection with saline or 10 μg of antigen with 20 μg STIMULON™ QS-21 as adjuvant. Two weeks following the last immunization, the mice ere challenged with ~5×10$^8$ cfu *S. epidermidis* 0-47 by intraperitoneal injection. Twenty-four hours after challenge, bacteria were enumerated in the blood and spleen. See Table 9. Reduction in log CFU was determined as compared to a control of STIMULON™ QS-21 in saline. Data were analyzed by student's-T test with resulting p-values of *0.05 or **0.01.

TABLE 9

Proteins Used in Immunogenic Compositions

| | LOG CFU REDUCTION | |
|---|---|---|
| Orf | Spleen | Blood |
| 305 | 0.5 | |
| 321 | 0.7 | 1.2* |
| 554 | — | |
| 608 | 0.3 | |
| 793 | 0.7 | |
| 854 | 0.9 | |
| 1069 | 1.6** | |
| 1238 | 1.2* | 1.2* |

TABLE 9-continued

Proteins Used in Immunogenic Compositions

| Orf | LOG CFU REDUCTION | |
|---|---|---|
| | Spleen | Blood |
| 1653 | 0.4 | |
| 1703 | 0.8 | |
| 2214 | 1.4* | |
| 2649 | 1.2* | |

*p-value <0.05
**p-value <0.01

The *Staphylcoccus epidermidis* proteins shown in Table 9 showed the greatest effectiveness when used in immunogenic compositions that reduced the severity of a bacterial infection following a subsequent challenge.

Example 9

Protection from *Staphylcoccus aureus* Challenge Following Immunization With *Staphylcoccus epidermidis* Proteins As suggested by the antibody binding data in Example 8, (Table 8), immunogenic compositions against *Staphylcoccus epidermidis* antigens could be effective in the treatment or prevention of *Staphylcoccus aureus*. Therefore, a challenge was performed using *Staphylcoccus aureus* following immunization with immunogenic compositions of *Staphylcoccus epidermidis* antigens.

Four week-old female CD-1 mice (Charles River Laboratories, Wilmington, Mass.) were immunized at 0, 3 and 6 weeks with 10 μg recombinant protein in 20 μg STIMU-LON™ QS-21 by subcutaneous injection. The mice were bled on week 0 prior to the first immunization and on week 8. Two days following the final bleed the mice were challenged by intraperitoneal injection of $3 \times 10^8$ cfu *S. aureus* Reynolds grown overnight on Columbia salt agar (1× Columbia agar, 0.1% glucose, 1% yeast extract, 0.5% NaCl). Twenty-four hours following challenge, the mice were sacrificed and the bacteria were enumerated in the kidney.

TABLE 10

Challenge with *Staphylococcus. aureus*

| ORF | Protein SEQ ID NO: | Predicted Function | CFU reduction |
|---|---|---|---|
| 2653 | 29 | immunodominant Ag A | 0.9 log |
| 321 | 3 | alanine dehydrogenase | 0.7 log |
| 1015 | 12 | dihydrolipoamide dehydrogenase | none |
| 608 | 7 | unknown | 0.6 log |
| 1069 | 13 | lipoate ligase | 1.7 log |
| 639 | 6 | hypothetical | none |

As shown in Table 10, certain *Staphylcoccus epidermidis* antigens were effective in inducing antibodies that recognized and bound to *Staphylcoccus aureus*. In addition, the induced antibodies had the beneficial effect of reducing the level of bacteria enumerated after a *Staphylcoccus aureus* challenge.

The percent identity of the amino acid sequence of the *Staphylcoccus epidermidis* polypeptide antigens of SEQ ID NOS:1 through SEQ ID NO:32 was compared to the amino acid sequence of their homologs from *Staphylcoccus aureus*. The results are shown in Table 11.

TABLE 11

Identity between *Staphylococcus epidermidis* and *Staphylococcus aureus*

| Orf | Polypeptide SEQ ID NO: | [a]% Identity with Homolog in *S. aureus* |
|---|---|---|
| 121 | 1 | 33% |
| 305 | 2 | 76% |
| 321 | 3 | 85% |
| 373 | 4 | 81% |
| 554 | 5 | 87% |
| 639 | 6 | 62% |
| 608 | 7 | 89% |
| 702 | 8 | 97% |
| 793 | 9 | 23% |
| 847 | 10 | 95% |
| 854 | 11 | 94% |
| 1015 | 12 | 96% |
| 1069 | 13 | 82% |
| 1238 | 14 | 94% |
| 1382 | 15 | 93% |
| 1405 | 16 | 82% |
| 1450 | 17 | 71% |
| 1522 | 18 | 96% |
| 1545 | 19 | 91% |
| 1653 | 20 | 95% |
| 1690 | 21 | 89% |
| 1703 | 22 | 82% |
| 2006 | 23 | 90% |
| 2180 | 24 | 87% |
| 2214 | 25 | 73% |
| 2482 | 26 | 91% |
| 2580 | 27 | 91% |
| 2649 | 28 | 78% |
| 2653 | 29 | 62% |
| 2736 | 30 | 92% |
| 2907 | 31 | |
| 2975 | 32 | 32% |

[a]Homology was determined between polypeptide sequences

What is claimed is:

1. An immunogenic composition comprising one or more isolated polypeptides consisting of the amino acid sequence selected from the group consisting of SEQ ID NO: 2, SEQ ID NO: 13, and SEQ ID NO: 17, wherein the at least one of the one or more isolated polypeptides is a lipoprotein, and at least one of the one or more isolated polypeptides is derived from *Staphylococcus epidermidis*.

2. The immunogenic composition of claim 1, wherein the one or more isolated polypeptides are immunoreactive with antibodies in the serum of rabbits infected with *Staphylococcus epidermidis*.

3. The immunogenic composition of claim 2, wherein the one or more isolated polypeptides bind to one or more rabbit serum proteins.

4. The immunogenic composition according to claim 1, further comprising a pharmaceutically acceptable carrier.

5. The immunogenic composition according to claim 4, further comprising one or more adjuvants.

6. An immunogenic composition comprising one or more isolated polypeptides consisting of an heterologous amino acid sequence and an amino acid sequence selected from the group consisting of SEQ ID NO: 2, SEQ ID NO: 13, and SEQ ID NO: 17.

7. The immunogenic composition according to claim 6, wherein the at least one of the one or more isolated polypeptides is a fusion polypeptide.

8. The immunogenic composition according to claim 7, wherein the at least one of the one or more isolated polypeptides is a recombinant polypeptide.

9. The immunogenic composition according to claim 1, said composition further comprising a *Staphylococcus epidermidis* polysaccharide antigen.

10. The immunogenic composition according to claim 1, said composition further comprising a *Staphylococcus aureus* polysaccharide or polypeptide antigen.

11. An immunogenic composition comprising one or more isolated polypeptides consisting of the amino acid sequence selected from the group consisting of SEQ ID NO: 2, SEQ ID NO: 13, SEQ ID NO: 17 and SEQ ID NO: 22 and further comprising an isolated Staphylococcus epidermidis polypeptide consisting of SEQ ID NO: 14.

12. A method of inducing an immune response against *Staphylococcus epidermidis* comprising administering to a mammal an immunogenic amount of an immunogenic composition according to claim 1.

13. The method of claim 12, wherein the immunogenic composition further comprises an adjuvant.

14. The method of claim 12, wherein at least one of the one or more isolated polypeptides is a recombinant polypeptide.

15. The immunogenic composition according to claim 1, wherein one of the one or more isolated polypeptides consists of the amino acid sequence of SEQ ID NO: 2.

16. The immunogenic composition according to claim 1, wherein one of the one or more isolated polypeptides consists of the amino acid sequence of SEQ ID NO: 13.

17. The immunogenic composition according to claim 1, wherein one of the one or more isolated polypeptides consists of the amino acid sequence of SEQ ID NO: 17.

18. An immunogenic composition comprising one or more isolated polypeptides consisting of the amino acid sequence selected from the group consisting of SEQ ID NO: 2, SEQ ID NO: 13, and SEQ ID NO: 17 and further comprising an isolated *Staphylococcus epidermidis* polypeptide consisting of SEQ ID NO: 22.

19. A method of inducing an immune response against Staphylococcus epidermidis comprising administering to a mammal an immunogenic amount of an immunogenic composition according to claim 6.

20. The method of claim 19, wherein at least one of the one or more isolated polypeptides is a fusion polypeptide.

21. The method of claim 19, wherein the immunogenic composition further comprises an adjuvant.

* * * * *

SEQUENCE LISTING

<160> NUMBER OF SEQ ID NOS: 64

<210> SEQ ID NO 1
<211> LENGTH: 338
<212> TYPE: PRT
<213> ORGANISM: Staphylococcus epidermidis

<400> SEQUENCE: 1

| | | | | | | | | | | | | | | |
|---|---|---|---|---|---|---|---|---|---|---|---|---|---|---|
| Leu | Arg | Lys | Asp | Val | Ile | Glu | Val | Val | Asn | Lys | Val | Glu | Asp | Tyr | Tyr |
| 1 | | | | 5 | | | | | 10 | | | | | 15 | |
| Phe | Lys | Ser | Tyr | Pro | Ile | Gln | Tyr | Asn | Pro | Ile | Ile | Glu | Tyr | Phe | Asn |
| | | | 20 | | | | | 25 | | | | | 30 | | |
| Gln | Ile | Lys | Asn | Lys | Val | Ile | Val | Ser | Leu | Lys | Ile | Tyr | Lys | Val | |
| | | | 35 | | | | 40 | | | | | 45 | | | |
| Tyr | Lys | Lys | Ile | Val | Glu | Asn | Ile | His | Asp | Thr | Glu | Ser | Gln | Trp | Ile |
| | 50 | | | | | 55 | | | | | 60 | | | | |
| Tyr | Ser | Pro | Glu | His | Ala | Leu | His | Pro | Ile | Glu | Phe | Ile | Glu | Ser | Phe |
| 65 | | | | | 70 | | | | | 75 | | | | | 80 |
| Cys | Lys | His | Ile | Lys | Gly | Lys | Tyr | Ala | Gly | Thr | Pro | Ile | Glu | Leu | Glu |
| | | | | 85 | | | | | 90 | | | | | 95 | |
| Leu | Trp | Gln | Lys | Ala | Gly | Ile | Ala | Thr | Ile | Phe | Gly | Phe | Ile | Asn | Lys |
| | | | 100 | | | | | 105 | | | | | 110 | | |
| Lys | Thr | Lys | Glu | Arg | Lys | Tyr | Gln | Glu | Ile | Phe | Trp | Val | Val | Ala | Arg |
| | | | 115 | | | | | 120 | | | | | 125 | | |
| Lys | Asn | Gly | Lys | Ser | Thr | Ile | Ser | Ser | Gly | Ile | Ala | Leu | Tyr | Leu | Leu |
| | 130 | | | | | 135 | | | | | 140 | | | | |
| Gly | Ala | Asp | Gly | Glu | Gly | Gly | Pro | Glu | Val | Tyr | Thr | Val | Ala | Thr | Lys |
| 145 | | | | | 150 | | | | | 155 | | | | | 160 |
| Lys | Asp | Gln | Ala | Lys | Ile | Val | Trp | Asn | Asp | Ala | Lys | Lys | Met | Val | Asn |
| | | | | 165 | | | | | 170 | | | | | 175 | |
| Lys | Ser | Pro | Leu | Leu | Lys | Leu | Asp | Phe | Val | Thr | Lys | Val | Ala | Glu | Ile |
| | | | 180 | | | | | 185 | | | | | 190 | | |
| Leu | Thr | Pro | Phe | Asn | Asp | Gly | Gln | Leu | Ile | Pro | Leu | Gly | Arg | Asp | Ser |
| | | | 195 | | | | | 200 | | | | | 205 | | |
| Asp | Thr | Thr | Asp | Gly | Leu | Asn | Val | His | Gly | Ala | Ile | Met | Asp | Glu | Val |
| | 210 | | | | | 215 | | | | | 220 | | | | |
| His | Ala | Trp | Lys | Thr | Met | Gln | Met | Tyr | Asp | Val | Val | Phe | Asp | Gly | Ile |
| 225 | | | | | 230 | | | | | 235 | | | | | 240 |
| Ser | Ala | Arg | Asp | Asn | Pro | Leu | Ile | Leu | Ala | Ile | Thr | Thr | Ala | Gly | Thr |
| | | | | 245 | | | | | 250 | | | | | 255 | |
| Ile | Arg | Asn | Ser | Val | Tyr | Asp | Ile | Lys | Tyr | Glu | Glu | Ser | Glu | Asn | Ile |
| | | | 260 | | | | | 265 | | | | | 270 | | |
| Ile | Asn | Gly | Leu | Trp | Glu | Asp | Glu | Gly | Tyr | Lys | Asn | Glu | Arg | Phe | Leu |
| | | | 275 | | | | | 280 | | | | | 285 | | |
| Pro | Leu | Ile | Tyr | Glu | Leu | Asp | Ser | Arg | Glu | Glu | Trp | Ile | Asp | Glu | Ser |
| | 290 | | | | | 295 | | | | | 300 | | | | |
| Cys | Trp | Leu | Lys | Ala | Asn | Pro | Gly | Leu | Gly | Ser | Ile | Lys | Lys | Ile | Asp |
| 305 | | | | | 310 | | | | | 315 | | | | | 320 |
| Ala | Ile | Lys | Thr | Lys | Val | Asn | Arg | Ala | Lys | Lys | Asn | Ala | Leu | Phe | Arg |
| | | | | 325 | | | | | 330 | | | | | 335 | |
| Ala | Thr | | | | | | | | | | | | | | |

<210> SEQ ID NO 2
<211> LENGTH: 309
<212> TYPE: PRT
<213> ORGANISM: Staphylococcus epidermidis

<400> SEQUENCE: 2

| | | | | | | | | | | | | | | |
|---|---|---|---|---|---|---|---|---|---|---|---|---|---|---|---|
| Val | Lys | Lys | Ile | Leu | Ala | Leu | Ala | Ile | Ala | Phe | Leu | Ile | Ile | Leu | Ala |
| 1 | | | | 5 | | | | | 10 | | | | | 15 | |
| Ala | Cys | Gly | Asn | His | Ser | Asn | His | Glu | His | His | Ser | His | Glu | Gly | Lys |
| | | | 20 | | | | | 25 | | | | | 30 | | |

```
Leu Lys Val Val Thr Thr Asn Ser Ile Leu Tyr Asp Met Val Lys Arg
        35                  40                  45

Val Gly Gly Asn Lys Val Asp Val His Ser Ile Val Pro Val Gly Gln
50                  55                  60

Asp Pro His Glu Tyr Glu Val Lys Pro Lys Asp Ile Lys Ala Leu Thr
65                  70                  75                  80

Asp Ala Asp Val Val Phe Tyr Asn Gly Leu Asn Leu Glu Thr Gly Asn
                85                  90                  95

Gly Trp Phe Glu Lys Ala Leu Asp Gln Ala Gly Lys Ser Thr Lys Asp
            100                 105                 110

Lys Asn Val Ile Ala Ala Ser Asn Val Lys Pro Ile Tyr Leu Asn
        115                 120                 125

Gly Glu Glu Gly Asn Lys Asn Lys Gln Asp Pro His Ala Trp Leu Ser
    130                 135                 140

Leu Glu Asn Gly Ile Lys Tyr Val Lys Thr Ile Gln Lys Ser Leu Glu
145                 150                 155                 160

His His Asp Lys Lys Asp Lys Ser Thr Tyr Glu Lys Gln Gly Asn Ala
                165                 170                 175

Tyr Ile Ser Lys Leu Glu Glu Leu Asn Lys Asp Ser Lys Asn Lys Phe
            180                 185                 190

Asp Asp Ile Pro Lys Asn Gln Arg Ala Met Met Thr Ser Glu Gly Ala
        195                 200                 205

Phe Lys Tyr Phe Ala Gln Gln Phe Asp Val Lys Pro Gly Tyr Ile Trp
    210                 215                 220

Glu Ile Asn Thr Glu Lys Gln Gly Thr Pro Gly Gln Met Lys Gln Ala
225                 230                 235                 240

Ile Lys Phe Val Lys Asp Asn His Leu Lys His Leu Leu Val Glu Thr
                245                 250                 255

Ser Val Asp Lys Lys Ala Met Gln Ser Leu Ser Glu Glu Thr Lys Lys
            260                 265                 270

Asp Ile Tyr Gly Glu Val Phe Thr Asp Ser Ile Gly Lys Ala Gly Thr
        275                 280                 285

Lys Gly Asp Ser Tyr Tyr Lys Met Met Lys Ser Asn Ile Asp Thr Ile
    290                 295                 300

His Gly Ser Met Lys
305

<210> SEQ ID NO 3
<211> LENGTH: 376
<212> TYPE: PRT
<213> ORGANISM: Staphylococcus epidermidis

<400> SEQUENCE: 3

Leu Glu Val Asp Asn Met Lys Ile Gly Ile Pro Lys Glu Ile Lys Asn
1               5                   10                  15

Asn Glu Asn Arg Val Gly Leu Ser Pro Ser Gly Val His Ala Leu Val
            20                  25                  30

Asp Gln Gly His Glu Val Leu Val Glu Thr Asn Ala Gly Leu Gly Ser
        35                  40                  45

Tyr Phe Glu Asp Gly Asp Tyr Gln Glu Ala Gly Ala Lys Ile Val Asp
    50                  55                  60

Glu Gln Ser Lys Ala Trp Asp Val Asp Met Val Ile Lys Val Lys Glu
65                  70                  75                  80

Pro Leu Glu Ser Glu Tyr Lys Phe Phe Lys Glu Glu Leu Ile Leu Phe
                85                  90                  95
```

```
Thr Tyr Leu His Leu Ala Asn Glu Gln Lys Leu Thr Gln Ala Leu Val
            100                 105                 110

Asp Asn Lys Val Ile Ser Ile Ala Tyr Glu Thr Val Gln Leu Pro Asp
        115                 120                 125

Gly Ser Leu Pro Leu Leu Thr Pro Met Ser Glu Val Ala Gly Arg Met
130                 135                 140

Ser Thr Gln Val Gly Ala Glu Phe Leu Gln Arg Phe Asn Gly Gly Met
145                 150                 155                 160

Gly Ile Leu Leu Gly Gly Ile Pro Gly Val Pro Lys Gly Lys Val Thr
                165                 170                 175

Ile Ile Gly Gly Gly Gln Ala Gly Thr Asn Ala Ala Lys Ile Ala Leu
            180                 185                 190

Gly Leu Gly Ala Glu Val Thr Ile Leu Asp Val Asn Pro Lys Arg Leu
        195                 200                 205

Glu Glu Leu Glu Asp Leu Phe Asp Gly Arg Val Arg Thr Ile Met Ser
    210                 215                 220

Asn Pro Leu Asn Ile Glu Met Tyr Val Lys Glu Ser Asp Leu Val Ile
225                 230                 235                 240

Gly Ala Val Leu Ile Pro Gly Ala Lys Ala Pro Asn Leu Val Thr Glu
                245                 250                 255

Asp Met Ile Lys Glu Met Lys Asp Gly Ser Val Ile Val Asp Ile Ala
            260                 265                 270

Ile Asp Gln Gly Gly Ile Phe Glu Thr Thr Asp Lys Ile Thr Thr His
        275                 280                 285

Asp Asn Pro Thr Tyr Thr Lys His Gly Val Val His Tyr Ala Val Ala
    290                 295                 300

Asn Met Pro Gly Ala Val Pro Arg Thr Ser Thr Ile Gly Leu Asn Asn
305                 310                 315                 320

Ala Thr Leu Pro Tyr Ala Gln Leu Leu Ala Asn Lys Gly Tyr Arg Glu
                325                 330                 335

Ala Phe Lys Val Asn His Pro Leu Ser Leu Gly Leu Asn Thr Phe Asn
            340                 345                 350

Gly His Val Thr Asn Lys Asn Val Ala Asp Thr Phe Asn Phe Glu Tyr
        355                 360                 365

Thr Ser Ile Glu Asp Ala Leu Lys
    370                 375

<210> SEQ ID NO 4
<211> LENGTH: 400
<212> TYPE: PRT
<213> ORGANISM: Staphylococcus epidermidis

<400> SEQUENCE: 4

Met Glu Ala Ile Asp Thr Cys Pro Asn Lys Tyr Ser Thr Ile Arg Arg
1               5                   10                  15

Val Leu Ile Met Asn Lys Lys Thr Gln Met Ile His Gly Gly His Thr
            20                  25                  30

Thr Asp Asn Tyr Thr Gly Ala Val Thr Thr Pro Ile Tyr Gln Thr Ser
        35                  40                  45

Thr Tyr Leu Gln Asp Asp Ile Gly Asp Leu Arg Gln Gly Tyr Glu Tyr
    50                  55                  60

Ser Arg Thr Ala Asn Pro Thr Arg Ala Ser Leu Glu Ser Val Ile Ala
65                  70                  75                  80

Asn Leu Glu His Gly Lys His Gly Phe Ala Phe Gly Ser Gly Met Ala
                85                  90                  95
```

```
Ala Ile Ser Ala Val Ile Met Leu Leu Asp Lys Gly Asp His Leu Val
            100                 105                 110

Leu Asn Ser Asp Val Tyr Gly Gly Thr Tyr Arg Ala Leu Thr Lys Val
            115                 120                 125

Phe Thr Arg Phe Gly Ile Asp Val Asp Phe Val Asp Thr Thr Lys Ile
            130                 135                 140

Glu Asn Ile Glu Gln Tyr Ile Lys Pro Glu Thr Lys Met Leu Tyr Val
145                 150                 155                 160

Glu Thr Pro Ser Asn Pro Leu Leu Arg Val Thr Asp Ile Lys Ala Ser
                165                 170                 175

Ala Lys Ile Ala Lys Lys Tyr Asp Leu Ile Ser Val Val Asp Asn Thr
            180                 185                 190

Phe Met Thr Pro Tyr Tyr Gln Asn Pro Leu Asp Phe Gly Ile Asp Ile
            195                 200                 205

Val Leu His Ser Ala Thr Lys Tyr Ile Gly Gly His Ser Asp Val Val
            210                 215                 220

Ala Gly Leu Val Ala Thr Ala Asp Asp Leu Ala Glu Arg Leu Gly
225                 230                 235                 240

Phe Ile Ser Asn Ser Thr Gly Gly Val Leu Gly Pro Gln Asp Ser Tyr
            245                 250                 255

Leu Leu Ile Arg Gly Ile Lys Thr Leu Gly Leu Arg Met Glu Gln Ile
            260                 265                 270

Asn Arg Asn Val Glu Gly Ile Val Gln Met Leu Gln Lys His Pro Lys
            275                 280                 285

Val Gln Gln Val Phe His Pro Ser Ile Lys Glu His Met Asn Tyr Thr
            290                 295                 300

Ile His Gln Asn Gln Ala Thr Gly His Thr Gly Val Val Ser Phe Glu
305                 310                 315                 320

Val Lys Asp Thr Glu Ala Ala Lys Gln Val Ile His Ala Thr Asn Tyr
            325                 330                 335

Phe Thr Leu Ala Glu Ser Leu Gly Ala Val Glu Ser Leu Ile Ser Val
            340                 345                 350

Pro Ala Leu Met Thr His Ala Ser Ile Pro Ser Asp Val Arg Ala Lys
            355                 360                 365

Glu Gly Ile Thr Asp Gly Leu Ile Arg Leu Ser Ile Gly Ile Glu Asp
            370                 375                 380

Thr Glu Asp Leu Val Asn Asp Leu Glu Gln Ala Leu Asn Thr Leu Arg
385                 390                 395                 400

<210> SEQ ID NO 5
<211> LENGTH: 210
<212> TYPE: PRT
<213> ORGANISM: Staphylococcus epidermidis

<400> SEQUENCE: 5

Leu Glu Leu Gln Leu Ala Ile Asp Leu Leu Asn Lys Glu Glu Ala Ala
1               5                   10                  15

Lys Leu Ala Gln Lys Val Glu Glu Tyr Val Asp Ile Val Glu Ile Gly
            20                  25                  30

Thr Pro Ile Val Ile Asn Glu Gly Leu Pro Ala Val Gln His Leu Asn
            35                  40                  45

Glu Asn Ile Asn Asn Ala Lys Val Leu Ala Asp Leu Lys Ile Met Asp
            50                  55                  60

Ala Ala Asp Tyr Glu Val Ser Gln Ala Val Lys Tyr Gly Ala Asp Ile
65                  70                  75                  80
```

```
Val Thr Ile Leu Gly Val Ala Glu Asp Ala Ser Ile Lys Ala Ala Val
                85                  90                  95

Glu Glu Ala His Lys His Gly Lys Ala Leu Leu Val Asp Met Ile Ala
            100                 105                 110

Val Gln Asn Leu Glu Gln Arg Ala Lys Glu Leu Asp Glu Met Gly Ala
        115                 120                 125

Asp Tyr Ile Ala Val His Thr Gly Tyr Asp Leu Gln Ala Glu Gly Lys
    130                 135                 140

Ser Pro Leu Asp Ser Leu Arg Thr Val Lys Ser Val Ile Lys Asn Ser
145                 150                 155                 160

Lys Val Ala Val Ala Gly Gly Ile Lys Pro Asp Thr Ile Lys Asp Ile
                165                 170                 175

Val Ala Glu Asp Pro Asp Leu Val Ile Val Gly Gly Ile Ala Asn
            180                 185                 190

Ala Asp Asp Pro Val Glu Ala Ala Lys Gln Cys Arg Ala Ala Ile Glu
                195                 200                 205

Gly Lys
    210

<210> SEQ ID NO 6
<211> LENGTH: 237
<212> TYPE: PRT
<213> ORGANISM: Staphylococcus epidermidis

<400> SEQUENCE: 6

Met Thr Lys Leu Asn Val Lys Val Phe Ala Asp Gly Ala Asp Ile Glu
1               5                   10                  15

Glu Met Lys Ser Ala Tyr Lys Asn Gln Leu Val Asp Gly Phe Thr Thr
            20                  25                  30

Asn Pro Ser Leu Met Ala Lys Ala Gly Val Thr Asp Tyr Lys Ala Phe
        35                  40                  45

Ala Glu Glu Val Val Ser Glu Ile Pro Asp Ala Ser Ile Ser Phe Glu
    50                  55                  60

Val Phe Ala Asp Asp Leu Pro Thr Met Glu Lys Glu Ala Glu Ile Leu
65                  70                  75                  80

Lys Gln Tyr Gly Asp Asn Val Phe Val Lys Ile Pro Ile Val Thr Thr
                85                  90                  95

Thr Gly Glu Ser Thr Leu Pro Leu Ile Lys Arg Leu Ser Ser Lys Gln
            100                 105                 110

Val Arg Leu Asn Val Thr Ala Val Tyr Thr Ile Glu Gln Val Lys Ala
        115                 120                 125

Ile Thr Asp Ala Val Thr Glu Gly Val Pro Thr Tyr Val Ser Val Phe
    130                 135                 140

Ala Gly Arg Ile Ala Asp Thr Gly Val Asp Pro Leu Pro Leu Met Lys
145                 150                 155                 160

Glu Ser Val Lys Val Thr His Ser Lys Glu Gly Val Gln Leu Leu Trp
                165                 170                 175

Ala Ser Cys Arg Glu Val Tyr Asn Val Ile Gln Ala Asp Glu Ile Gly
            180                 185                 190

Ala Asp Ile Ile Thr Cys Pro Ala Asp Val Val Lys Lys Val Asn Asn
        195                 200                 205

Asn Leu Gly Arg Asp Ile Gly Glu Leu Ser Val Asp Thr Val Lys Gly
    210                 215                 220

Phe Ala Lys Asp Ile Gln Ser Ser Gly Leu Ser Ile Leu
225                 230                 235
```

<210> SEQ ID NO 7
<211> LENGTH: 264
<212> TYPE: PRT
<213> ORGANISM: Staphylococcus epidermidis

<400> SEQUENCE: 7

Val Asn Ile Leu Lys Ile Gln Ile Leu Gln Phe Asn Val Glu Arg Gly
1               5                   10                  15

Asn Val Asp Lys Asn Met Gln Asn Ile Lys Thr Lys Phe Asn Gln Tyr
            20                  25                  30

Leu Asp Lys Asp Thr Ser Val Val Leu Pro Glu Met Trp Asn Asn
        35                  40                  45

Gly Tyr Ala Leu Glu Glu Leu Gln Lys Ala Asp Lys Asn Leu Lys
    50                  55                  60

Asp Ser Ser Leu Phe Ile Lys Asp Leu Ala His Thr Phe Asn Val Asp
65                  70                  75                  80

Ile Ile Ala Gly Ser Val Ser Asn Ile Arg Glu Asn His Ile Tyr Asn
                85                  90                  95

Thr Ala Phe Ala Ile Asn Lys Asn Lys Glu Leu Ile Asn Glu Tyr Asp
            100                 105                 110

Lys Val His Leu Val Pro Met Leu Arg Glu Pro Asp Phe Leu Cys Gly
        115                 120                 125

Gly Asn Val Val Pro Glu Pro Phe Tyr Leu Ser Asp Gln Thr Leu Val
    130                 135                 140

Thr Gln Ile Ile Cys Tyr Asp Leu Arg Phe Pro Glu Ile Leu Arg Tyr
145                 150                 155                 160

Pro Ala Arg Lys Gly Ala Lys Ile Ala Phe Tyr Val Ala Gln Trp Pro
                165                 170                 175

Ser Ser Arg Leu Asp His Trp Leu Ser Leu Leu Lys Ala Arg Ala Ile
            180                 185                 190

Glu Asn Asp Ile Phe Ile Val Ala Cys Asn Ser Cys Gly Asp Asp Gly
        195                 200                 205

His Thr Asn Tyr Ala Gly Asn Ser Ile Val Ile Asn Pro Asn Gly Glu
    210                 215                 220

Ile Leu Gly His Leu Asp Asp Lys Glu Gly Val Leu Thr Thr His Ile
225                 230                 235                 240

Asp Val Asp Leu Val Asp Gln Gln Arg Glu Tyr Ile Pro Val Phe Arg
                245                 250                 255

Asn Leu Lys Pro His Leu Tyr Lys
            260

<210> SEQ ID NO 8
<211> LENGTH: 295
<212> TYPE: PRT
<213> ORGANISM: Staphylococcus epidermidis

<400> SEQUENCE: 8

Met Ser Lys Ile Val Gly Ser Asp Arg Val Lys Arg Gly Met Ala Glu
1               5                   10                  15

Met Gln Lys Gly Gly Val Ile Met Asp Val Val Asn Ala Glu Gln Ala
            20                  25                  30

Lys Ile Ala Glu Glu Ala Gly Ala Val Ala Val Met Ala Leu Glu Arg
        35                  40                  45

Val Pro Ser Asp Ile Arg Ala Ala Gly Gly Val Ala Arg Met Ala Asn
    50                  55                  60

```
Pro Lys Ile Val Glu Glu Val Met Asn Ala Val Ser Ile Pro Val Met
 65                  70                  75                  80

Ala Lys Ala Arg Ile Gly His Ile Thr Glu Ala Arg Val Leu Glu Ser
                 85                  90                  95

Met Gly Val Asp Tyr Ile Asp Glu Ser Glu Val Leu Thr Pro Ala Asp
            100                 105                 110

Glu Glu Tyr His Leu Arg Lys Asp Gln Phe Thr Val Pro Phe Val Cys
        115                 120                 125

Gly Cys Arg Asn Leu Gly Glu Ala Ala Arg Arg Ile Gly Glu Gly Ala
    130                 135                 140

Ala Met Leu Arg Thr Lys Gly Pro Gly Thr Gly Asn Ile Val Glu
145                 150                 155                 160

Ala Val Arg His Met Arg Arg Val Asn Ser Glu Val Ser Arg Leu Thr
                165                 170                 175

Val Met Asn Asp Asp Glu Ile Met Thr Phe Ala Lys Asp Leu Gly Ala
            180                 185                 190

Pro Tyr Glu Val Leu Lys Gln Ile Lys Asp Asn Gly Arg Leu Pro Val
        195                 200                 205

Val Asn Phe Ala Ala Gly Val Ala Thr Pro Gln Asp Ala Ala Leu
210                 215                 220

Met Met Glu Leu Gly Ala Asp Gly Val Phe Val Gly Ser Gly Ile Phe
225                 230                 235                 240

Lys Ser Glu Asp Pro Glu Lys Phe Ala Lys Ala Ile Val Gln Ala Thr
                245                 250                 255

Thr His Tyr Gln Asp Tyr Glu Leu Ile Gly Lys Leu Ala Ser Glu Leu
            260                 265                 270

Gly Thr Ala Met Lys Gly Leu Asp Ile Asn Gln Ile Ser Leu Glu Glu
        275                 280                 285

Arg Met Gln Glu Arg Gly Trp
    290                 295

<210> SEQ ID NO 9
<211> LENGTH: 581
<212> TYPE: PRT
<213> ORGANISM: Staphylococcus epidermidis

<400> SEQUENCE: 9

Met Glu Asp Ala Val Val Glu Met Asp Ala Val Lys Tyr Leu Asn Lys
  1               5                  10                  15

Leu Asn Leu Asp Asn Ile Glu Leu Thr Lys Tyr Leu Phe Phe Thr Gly
             20                  25                  30

Lys Gly Gly Val Gly Lys Thr Thr Ile Ser Ser Phe Ile Ala Leu Asn
         35                  40                  45

Leu Ala Glu Asn Gly Lys Lys Val Ala Leu Val Ser Thr Asp Pro Ala
     50                  55                  60

Ser Asn Leu Gln Asp Val Phe Gln Met Glu Leu Ser Asn Lys Leu Thr
 65                  70                  75                  80

Lys Tyr Gln Pro Ile Pro Asn Leu Ser Ile Ala Asn Phe Asp Pro Ile
                 85                  90                  95

Val Ala Ala Asp Asp Tyr Lys Ala Gln Ser Ile Glu Pro Tyr Glu Gly
            100                 105                 110

Ile Leu Pro Glu Asp Val Leu Ser Glu Met Lys Glu Gln Leu Ser Gly
        115                 120                 125

Ser Cys Thr Val Glu Val Ala Phe Asn Glu Phe Thr Asn Phe Leu
    130                 135                 140
```

-continued

```
Ser Asp Lys Thr Leu Glu Gln Glu Phe Asp Phe Ile Ile Phe Asp Thr
145                 150                 155                 160

Ala Pro Thr Gly His Thr Leu Arg Met Leu Glu Leu Pro Ser Ala Trp
                165                 170                 175

Thr Asp Tyr Leu Asn Thr Thr Ser Asn Asp Ala Ser Cys Leu Gly Gln
            180                 185                 190

Leu Ser Gly Leu Asn Glu Asn Arg Val Lys Tyr Asn Ser Ala Leu Glu
        195                 200                 205

Lys Leu Arg Asn Gln Asp Asp Thr Thr Met Met Leu Val Ala Arg Pro
210                 215                 220

Thr His Ser Ser Ile Tyr Glu Ile Gln Arg Ala Gln Gln Glu Leu Gln
225                 230                 235                 240

Gln Leu Ser Ile Ser Lys Phe Lys Val Ile Ile Asn Asn Tyr Ile Glu
                245                 250                 255

Glu Ser His Gly Leu Ile Ser Ser Gln Met Lys Ser Glu Gln Asp Lys
            260                 265                 270

Asn Ile Asn His Phe Thr Glu Trp Leu Asn Asn His Ala Tyr Tyr
        275                 280                 285

Val Pro Tyr Lys Asn Gln Lys Glu Gly Ile Glu Ser Leu Thr Asn
290                 295                 300

Leu Leu Asn Asp Asp Asn Leu Ile Glu Asn Asp Phe Ile Val Glu
305                 310                 315                 320

Asp His Pro Gln Phe Asn Lys Leu Ile Asp Glu Ile Glu Asn Ser Lys
                325                 330                 335

Val Gln Tyr Leu Phe Thr Met Gly Lys Gly Val Gly Lys Thr Thr
            340                 345                 350

Val Ala Thr Gln Leu Ala Thr Thr Leu Ser Asn Lys Gly Tyr Arg Val
        355                 360                 365

Leu Leu Ala Thr Thr Asp Pro Thr Lys Glu Ile Asn Val Glu Thr Thr
370                 375                 380

Ser Asn Leu Asn Thr Ala Tyr Ile Asp Glu Glu Gln Ala Leu Glu Lys
385                 390                 395                 400

Tyr Lys Lys Glu Val Leu Ala Thr Val Asn Asp Asp Thr Pro Gln Asp
                405                 410                 415

Asp Ile Asp Tyr Ile Met Glu Asp Leu Lys Ser Pro Cys Thr Glu Glu
            420                 425                 430

Ile Ala Phe Phe Lys Ala Phe Ser Asp Ile Met Glu Asn Gln Asp Asp
        435                 440                 445

Met Asp Tyr Val Ile Val Asp Thr Ala Pro Thr Gly His Thr Leu Leu
450                 455                 460

Leu Leu Asp Ser Ser Glu Asn His His Arg Glu Leu Lys Lys Lys Ser
465                 470                 475                 480

Thr Gln Thr Thr Ser Asn Val Glu Thr Leu Leu Pro Lys Ile Gln Asn
                485                 490                 495

Lys Asn Leu Thr Gln Met Ile Ile Val Thr Leu Ala Glu Lys Thr Pro
            500                 505                 510

Tyr Leu Glu Ser Lys Arg Leu Val Glu Asp Leu Asn Arg Ala Asn Ile
        515                 520                 525

Gly His Asn Trp Trp Val Val Asn Gln Ser Leu Val Thr Leu Asn Gln
530                 535                 540

Arg Asp Asp Leu Phe Ser Asn Lys Lys Glu Asp Glu Ser Phe Trp Ile
545                 550                 555                 560

Asn Lys Ile Lys Asn Glu Ser Leu Asp Asn Tyr Phe Val Ile Pro Tyr
                565                 570                 575
```

```
Arg Val Leu Glu Tyr
            580

<210> SEQ ID NO 10
<211> LENGTH: 336
<212> TYPE: PRT
<213> ORGANISM: Staphylococcus epidermidis

<400> SEQUENCE: 10

Met Ala Ile Lys Val Ala Ile Asn Gly Phe Gly Arg Ile Gly Arg Leu
1               5                   10                  15

Ala Phe Arg Arg Ile Gln Asp Val Glu Gly Leu Glu Val Val Ala Val
            20                  25                  30

Asn Asp Leu Thr Asp Asp Met Leu Ala His Leu Leu Lys Tyr Asp
        35                  40                  45

Thr Met Gln Gly Arg Phe Thr Gly Glu Val Glu Val Ile Glu Gly Gly
    50                  55                  60

Phe Arg Val Asn Gly Lys Glu Ile Lys Ser Phe Asp Glu Pro Asp Ala
65                  70                  75                  80

Gly Lys Leu Pro Trp Gly Asp Leu Asp Ile Asp Val Val Leu Glu Cys
                85                  90                  95

Thr Gly Phe Tyr Thr Asp Lys Glu Lys Ala Gln Ala His Ile Asp Ala
            100                 105                 110

Gly Ala Lys Lys Val Leu Ile Ser Ala Pro Ala Lys Gly Asp Val Lys
        115                 120                 125

Thr Ile Val Phe Asn Thr Asn His Asp Thr Leu Asp Gly Ser Glu Thr
    130                 135                 140

Val Val Ser Gly Ala Ser Cys Thr Thr Asn Ser Leu Ala Pro Val Ala
145                 150                 155                 160

Lys Val Leu Ser Asp Glu Phe Gly Leu Val Glu Gly Phe Met Thr Thr
                165                 170                 175

Ile His Ala Tyr Thr Gly Asp Gln Asn Thr Gln Asp Ala Pro His Arg
            180                 185                 190

Lys Gly Asp Lys Arg Arg Ala Arg Ala Ala Glu Asn Ile Ile Pro
        195                 200                 205

Asn Ser Thr Gly Ala Ala Lys Ala Ile Gly Lys Val Ile Pro Glu Ile
210                 215                 220

Asp Gly Lys Leu Asp Gly Gly Ala Gln Arg Val Pro Val Ala Thr Gly
225                 230                 235                 240

Ser Leu Thr Glu Leu Thr Val Val Leu Asp Lys Gln Asp Val Thr Val
                245                 250                 255

Asp Gln Val Asn Ser Ala Met Lys Gln Ala Ser Asp Glu Ser Phe Gly
            260                 265                 270

Tyr Thr Glu Asp Glu Ile Val Ser Ser Asp Ile Val Gly Met Thr Tyr
        275                 280                 285

Gly Ser Leu Phe Asp Ala Thr Gln Thr Arg Val Met Thr Val Gly Asp
    290                 295                 300

Arg Gln Leu Val Lys Val Ala Trp Tyr Asp Asn Glu Met Ser Tyr
305                 310                 315                 320

Thr Ala Gln Leu Val Arg Thr Leu Ala His Leu Ala Glu Leu Ser Lys
                325                 330                 335

<210> SEQ ID NO 11
<211> LENGTH: 434
<212> TYPE: PRT
<213> ORGANISM: Staphylococcus epidermidis
```

```
<400> SEQUENCE: 11

Met Pro Ile Ile Thr Asp Val Tyr Ala Arg Glu Val Leu Asp Ser Arg
1               5                   10                  15

Gly Asn Pro Thr Val Glu Val Glu Val Leu Thr Glu Ser Gly Ala Phe
            20                  25                  30

Gly Arg Ala Leu Val Pro Ser Gly Ala Ser Thr Gly Glu His Glu Ala
        35                  40                  45

Val Glu Leu Arg Asp Gly Asp Lys Ser Arg Tyr Leu Gly Lys Gly Val
    50                  55                  60

Thr Lys Ala Val Glu Asn Val Asn Glu Met Ile Ala Pro Glu Ile Val
65                  70                  75                  80

Glu Gly Glu Phe Ser Val Leu Asp Gln Val Ser Ile Asp Lys Met Met
                85                  90                  95

Ile Gln Leu Asp Gly Thr His Asn Lys Gly Lys Leu Gly Ala Asn Ala
            100                 105                 110

Ile Leu Gly Val Ser Ile Ala Val Ala Arg Ala Ala Ala Asp Leu Leu
        115                 120                 125

Gly Gln Pro Leu Tyr Lys Tyr Leu Gly Gly Phe Asn Gly Lys Gln Leu
    130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Glu Ser
                165                 170                 175

Phe Lys Glu Ser Leu Arg Trp Gly Ala Glu Ile Phe His Asn Leu Lys
            180                 185                 190

Ser Ile Leu Ser Glu Arg Gly Leu Glu Thr Ala Val Gly Asp Glu Gly
        195                 200                 205

Gly Phe Ala Pro Arg Phe Glu Gly Thr Glu Asp Ala Val Glu Thr Ile
    210                 215                 220

Ile Lys Ala Ile Glu Lys Ala Gly Tyr Lys Pro Gly Glu Asp Val Phe
225                 230                 235                 240

Leu Gly Phe Asp Cys Ala Ser Ser Glu Phe Tyr Glu Asn Gly Val Tyr
                245                 250                 255

Asp Tyr Thr Lys Phe Glu Gly Glu His Gly Ala Lys Arg Ser Ala Ala
            260                 265                 270

Glu Gln Val Asp Tyr Leu Glu Glu Leu Ile Gly Lys Tyr Pro Ile Ile
        275                 280                 285

Thr Ile Glu Asp Gly Met Asp Glu Asn Asp Trp Glu Gly Trp Lys Gln
    290                 295                 300

Leu Thr Asp Arg Ile Gly Asp Lys Val Gln Leu Val Gly Asp Asp Leu
305                 310                 315                 320

Phe Val Thr Asn Thr Glu Ile Leu Ser Lys Gly Ile Glu Gln Gly Ile
                325                 330                 335

Gly Asn Ser Ile Leu Ile Lys Val Asn Gln Ile Gly Thr Leu Thr Glu
            340                 345                 350

Thr Phe Asp Ala Ile Glu Met Ala Gln Lys Ala Gly Tyr Thr Ala Val
        355                 360                 365

Val Ser His Arg Ser Gly Glu Thr Glu Asp Thr Thr Ile Ala Asp Ile
    370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
                405                 410                 415
```

```
Leu Tyr Glu Thr Ala Lys Phe Glu Gly Ile Lys Ser Phe Tyr Asn Leu
            420                 425                 430

Asp Lys

<210> SEQ ID NO 12
<211> LENGTH: 468
<212> TYPE: PRT
<213> ORGANISM: Staphylococcus epidermidis

<400> SEQUENCE: 12

Met Val Val Gly Asp Phe Pro Ile Glu Thr Asp Thr Ile Val Ile Gly
1               5                  10                  15

Ala Gly Pro Gly Gly Tyr Val Ala Ala Ile Arg Ala Ala Gln Leu Gly
            20                  25                  30

Gln Lys Val Thr Ile Val Glu Lys Gly Asn Leu Gly Gly Val Cys Leu
        35                  40                  45

Asn Val Gly Cys Ile Pro Ser Lys Ala Leu Leu His Ala Ser His Arg
    50                  55                  60

Phe Val Glu Ala Gln Asn Ser Glu Asn Leu Gly Val Ile Ala Glu Ser
65                  70                  75                  80

Val Ser Leu Asn Tyr Gln Lys Val Gln Glu Phe Lys Thr Ser Val Val
                85                  90                  95

Asn Lys Leu Thr Gly Gly Val Glu Gly Leu Leu Lys Gly Asn Lys Val
            100                 105                 110

Glu Ile Val Arg Gly Glu Ala Tyr Phe Val Asp Asn Asn Ser Leu Arg
        115                 120                 125

Val Met Asp Glu Lys Ser Ala Gln Thr Tyr Asn Phe Lys His Ala Ile
    130                 135                 140

Ile Ala Thr Gly Ser Arg Pro Ile Glu Ile Pro Asn Phe Glu Phe Gly
145                 150                 155                 160

Lys Arg Val Ile Asp Ser Thr Gly Ala Leu Asn Leu Gln Glu Val Pro
                165                 170                 175

Asn Lys Leu Val Val Val Gly Gly Gly Tyr Ile Gly Ser Glu Leu Gly
            180                 185                 190

Thr Ala Phe Ala Asn Phe Gly Ser Glu Val Thr Ile Leu Glu Gly Ala
        195                 200                 205

Lys Asp Ile Leu Gly Gly Phe Glu Lys Gln Met Thr Gln Pro Val Lys
    210                 215                 220

Lys Gly Met Lys Glu Lys Gly Ile Glu Ile Val Thr Glu Ala Met Ala
225                 230                 235                 240

Lys Ser Ala Glu Glu Thr Glu Asn Gly Val Lys Val Thr Tyr Glu Ala
                245                 250                 255

Lys Gly Glu Glu Gln Thr Ile Glu Ala Asp Tyr Val Leu Val Thr Val
            260                 265                 270

Gly Arg Arg Pro Asn Thr Asp Glu Leu Gly Leu Glu Glu Leu Gly Leu
        275                 280                 285

Lys Phe Ala Asp Arg Gly Leu Leu Glu Val Asp Lys Gln Ser Arg Thr
    290                 295                 300

Ser Ile Glu Asn Ile Phe Ala Ile Gly Asp Ile Val Pro Gly Leu Pro
305                 310                 315                 320

Leu Ala His Lys Ala Ser Tyr Glu Gly Lys Val Ala Ala Glu Ala Ile
                325                 330                 335

Asp Gly Gln Ala Ala Glu Val Asp Tyr Ile Gly Met Pro Ala Val Cys
        340                 345                 350
```

```
Phe Thr Glu Pro Glu Leu Ala Gln Val Gly Tyr Thr Glu Ala Gln Ala
            355                 360                 365

Lys Glu Glu Gly Leu Ser Ile Lys Ala Ser Lys Phe Pro Tyr Ala Ala
    370                 375                 380

Asn Gly Arg Ala Leu Ser Leu Asp Asp Thr Asn Gly Phe Val Lys Leu
385                 390                 395                 400

Ile Thr Leu Lys Glu Asp Asp Thr Leu Ile Gly Ala Gln Val Val Gly
                405                 410                 415

Thr Gly Ala Ser Asp Ile Ile Ser Glu Leu Gly Leu Ala Ile Glu Ser
                420                 425                 430

Gly Met Asn Ala Glu Asp Ile Ala Leu Thr Val His Ala His Pro Thr
        435                 440                 445

Leu Gly Glu Met Thr Met Glu Ala Ala Glu Lys Ala Ile Gly Tyr Pro
    450                 455                 460

Ile His Thr Met
465

<210> SEQ ID NO 13
<211> LENGTH: 279
<212> TYPE: PRT
<213> ORGANISM: Staphylococcus epidermidis

<400> SEQUENCE: 13

Met Asp Leu Ala Thr Lys Tyr Phe Asn Gln Ile Asn Trp Arg Tyr Val
1               5                   10                  15

Asp His Ser Ser Gly Leu Glu Pro Met Gln Ser Phe Ala Phe Asp Asp
            20                  25                  30

Thr Phe Ser Glu Ser Val Gly Lys Asp Leu Ser Cys Asn Val Val Arg
        35                  40                  45

Thr Trp Ile His Gln His Thr Val Ile Leu Gly Ile His Asp Ser Arg
    50                  55                  60

Leu Pro Phe Leu Ser Asp Gly Ile Arg Phe Leu Thr Asp Glu Gln Gly
65                  70                  75                  80

Tyr Asn Ala Ile Val Arg Asn Ser Gly Gly Leu Gly Val Val Leu Asp
                85                  90                  95

Gln Gly Ile Leu Asn Ile Ser Leu Ile Phe Lys Gly Gln Thr Glu Thr
            100                 105                 110

Thr Ile Asp Glu Ala Phe Thr Val Met Tyr Leu Leu Ile Asn Lys Met
        115                 120                 125

Phe Glu Asp Glu Asp Val Ser Ile Asp Thr Lys Glu Ile Glu Gln Ser
    130                 135                 140

Tyr Cys Pro Gly Lys Phe Asp Leu Ser Ile Asn Asp Lys Lys Phe Ala
145                 150                 155                 160

Gly Ile Ser Gln Arg Arg Val Arg Gly Ile Ala Val Gln Ile Tyr
                165                 170                 175

Leu Cys Ile Glu Gly Ser Gly Ser Glu Arg Ala Leu Met Met Gln Gln
            180                 185                 190

Phe Tyr Gln Arg Ala Leu Lys Gly Glu Thr Thr Lys Phe His Tyr Pro
        195                 200                 205

Asp Ile Asp Pro Ser Cys Met Ala Ser Leu Glu Thr Leu Leu Asn Arg
    210                 215                 220

Glu Ile Lys Val Gln Asp Val Met Phe Leu Leu Tyr Ala Leu Lys
225                 230                 235                 240

Asp Leu Gly Ala Asn Leu Asn Met Asp Pro Ile Thr Glu Asp Glu Trp
                245                 250                 255
```

```
Thr Arg Tyr Glu Gly Tyr Tyr Asp Lys Met Leu Glu Arg Asn Ala Lys
            260                 265                 270

Met Asn Glu Lys Leu Asp Phe
        275

<210> SEQ ID NO 14
<211> LENGTH: 310
<212> TYPE: PRT
<213> ORGANISM: Staphylococcus epidermidis

<400> SEQUENCE: 14

Met Ala Gln Lys Pro Val Asp Tyr Val Thr Gln Ile Ile Gly Asn Thr
1               5                   10                  15

Pro Val Val Lys Leu Arg Asn Val Val Asp Asp Ala Ala Asp Ile
            20                  25                  30

Tyr Val Lys Leu Glu Tyr Gln Asn Pro Gly Gly Ser Val Lys Asp Arg
            35                  40                  45

Ile Ala Leu Ala Met Ile Glu Lys Ala Glu Arg Glu Gly Lys Ile Lys
        50                  55                  60

Pro Gly Asp Thr Ile Val Glu Pro Thr Ser Gly Asn Thr Gly Ile Gly
65                  70                  75                  80

Leu Ala Phe Val Cys Ala Ala Lys Gly Tyr Lys Ala Val Phe Thr Met
                85                  90                  95

Pro Glu Thr Met Ser Gln Glu Arg Arg Asn Leu Leu Lys Ala Tyr Gly
            100                 105                 110

Ala Glu Leu Val Leu Thr Pro Gly Ser Glu Ala Met Lys Gly Ala Ile
            115                 120                 125

Lys Lys Ala Lys Glu Leu Lys Glu Glu His Gly Tyr Phe Glu Pro Gln
        130                 135                 140

Gln Phe Glu Asn Pro Ala Asn Pro Glu Ile His Glu Leu Thr Thr Gly
145                 150                 155                 160

Pro Glu Leu Val Glu Gln Phe Glu Gly Arg Gln Ile Asp Ala Phe Leu
                165                 170                 175

Ala Gly Val Gly Thr Gly Gly Thr Leu Ser Gly Val Gly Lys Val Leu
            180                 185                 190

Lys Lys Glu Tyr Pro Asn Val Glu Ile Val Ala Ile Glu Pro Glu Ala
        195                 200                 205

Ser Pro Val Leu Ser Gly Gly Glu Pro Gly Pro His Lys Leu Gln Gly
    210                 215                 220

Leu Gly Ala Gly Phe Val Pro Asp Thr Leu Asn Thr Glu Val Tyr Asp
225                 230                 235                 240

Ser Ile Ile Lys Val Gly Asn Asp Thr Ala Met Asp Met Ala Arg Arg
                245                 250                 255

Val Ala Arg Glu Glu Gly Ile Leu Ala Gly Ile Ser Ser Gly Ala Ala
            260                 265                 270

Ile Tyr Ala Ala Ile Gln Lys Ala Lys Glu Leu Gly Lys Gly Lys Thr
        275                 280                 285

Val Val Thr Val Leu Pro Ser Asn Gly Glu Arg Tyr Leu Ser Thr Pro
    290                 295                 300

Leu Tyr Ser Phe Asp Asn
305                 310

<210> SEQ ID NO 15
<211> LENGTH: 475
<212> TYPE: PRT
<213> ORGANISM: Staphylococcus epidermidis
```

<400> SEQUENCE: 15

```
Met His Phe Glu Thr Val Ile Gly Leu Glu Val His Val Glu Leu Lys
1               5                   10                  15

Thr Asp Ser Lys Met Phe Ser Pro Pro Ala His Phe Gly Ala Glu
            20                  25                  30

Pro Asn Ser Asn Thr Asn Val Ile Asp Leu Ala Tyr Pro Gly Val Leu
        35                  40                  45

Pro Val Val Asn Arg Arg Ala Val Asp Trp Ala Met Arg Ala Ser Met
50                  55                  60

Ala Leu Asn Met Asp Ile Ala Thr Asn Ser Lys Phe Asp Arg Lys Asn
65                  70                  75                  80

Tyr Phe Tyr Pro Asp Asn Pro Lys Ala Tyr Gln Ile Ser Gln Phe Asp
                85                  90                  95

Gln Pro Ile Gly Glu Asn Gly Tyr Ile Asp Ile Glu Val Asp Gly Glu
            100                 105                 110

Thr Lys Arg Ile Gly Ile Thr Arg Leu His Met Glu Glu Asp Ala Gly
        115                 120                 125

Lys Ser Thr His Lys Asp Gly Tyr Ser Leu Val Asp Leu Asn Arg Gln
130                 135                 140

Gly Thr Pro Leu Ile Glu Ile Val Ser Glu Pro Asp Ile Arg Ser Pro
145                 150                 155                 160

Lys Glu Ala Tyr Ala Tyr Leu Glu Lys Leu Arg Ser Ile Ile Gln Tyr
                165                 170                 175

Thr Gly Val Ser Asp Cys Lys Met Glu Glu Gly Ser Leu Arg Cys Asp
            180                 185                 190

Ala Asn Ile Ser Leu Arg Pro Tyr Gly Gln Lys Glu Phe Gly Thr Lys
        195                 200                 205

Thr Glu Leu Lys Asn Leu Asn Ser Phe Asn Tyr Val Lys Lys Gly Leu
210                 215                 220

Glu Tyr Glu Glu Lys Arg Gln Glu Glu Leu Leu Asn Gly Gly Glu
225                 230                 235                 240

Ile Gly Gln Glu Thr Arg Arg Phe Asp Glu Ser Thr Gly Lys Thr Ile
                245                 250                 255

Leu Met Arg Val Lys Glu Gly Ser Asp Asp Tyr Arg Tyr Phe Pro Glu
            260                 265                 270

Pro Asp Ile Val Pro Leu Tyr Val Asp Glu Asp Trp Lys Ala Arg Val
        275                 280                 285

Arg Glu Thr Ile Pro Glu Leu Pro Asp Glu Arg Lys Ala Lys Tyr Val
290                 295                 300

Asn Asp Leu Gly Leu Pro Glu Tyr Asp Ala His Val Leu Thr Leu Thr
305                 310                 315                 320

Lys Glu Met Ser Asp Phe Phe Glu Gly Ala Ile Asp His Gly Ala Asp
                325                 330                 335

Val Lys Leu Thr Ser Asn Trp Leu Met Gly Gly Val Asn Glu Tyr Leu
            340                 345                 350

Asn Lys Asn Gln Val Glu Leu Lys Asp Thr Gln Leu Thr Pro Glu Asn
        355                 360                 365

Leu Ala Gly Met Ile Lys Leu Ile Glu Asp Gly Thr Met Ser Ser Lys
370                 375                 380

Ile Ala Lys Lys Val Phe Pro Glu Leu Ala Glu Asn Gly Gly Asp Ala
385                 390                 395                 400

Lys Gln Ile Met Glu Asp Lys Gly Leu Val Gln Ile Ser Asp Glu Ala
                405                 410                 415
```

```
Thr Leu Leu Lys Phe Val Thr Asp Ala Leu Asp Asn Asn Pro Gln Ser
            420                 425                 430
Ile Glu Asp Tyr Lys Asn Gly Lys Gly Lys Ala Met Gly Phe Leu Val
            435                 440                 445
Gly Gln Ile Met Lys Ala Ser Lys Gly Gln Ala Asn Pro Gln Lys Val
            450                 455                 460
Asn Ser Leu Leu Lys Gln Glu Leu Asp Asn Arg
465                 470                 475

<210> SEQ ID NO 16
<211> LENGTH: 364
<212> TYPE: PRT
<213> ORGANISM: Staphylococcus epidermidis

<400> SEQUENCE: 16

Met Leu Lys Arg Ala Asn Glu Asn Glu Glu Ala Trp Asn Asn Met Leu
1               5                   10                  15
Lys Asn Tyr Ser Glu Ala Tyr Pro Glu Leu Ala Glu Glu Phe Lys Leu
            20                  25                  30
Ala Met Ser Gly Lys Leu Pro Asn Asn Tyr Ala Asp Ala Leu Pro Glu
            35                  40                  45
Tyr Asp Leu Asn His Ser Gly Ala Ser Arg Ala Asp Ser Gly Glu Ile
        50                  55                  60
Ile Gln Lys Leu Ser Glu Phe Val Pro Ser Phe Gly Gly Ser Ala
65                  70                  75                  80
Asp Leu Ala Gly Ser Asn Lys Ser Asn Val Lys Glu Ala Lys Asp Tyr
                85                  90                  95
Asn Lys Asp Thr Pro Glu Gly Lys Asn Val Trp Phe Gly Val Arg Glu
            100                 105                 110
Phe Ala Met Gly Ala Ala Ile Asn Gly Met Ala Ala His Gly Gly Leu
            115                 120                 125
His Pro Tyr Ala Ala Thr Phe Phe Val Phe Ser Asp Tyr Leu Lys Pro
        130                 135                 140
Ala Leu Arg Leu Ser Ser Ile Met Gly Leu Asn Ser Thr Phe Ile Phe
145                 150                 155                 160
Thr His Asp Ser Ile Ala Val Gly Glu Asp Gly Pro Thr His Glu Pro
                165                 170                 175
Ile Glu Gln Leu Ala Gly Leu Arg Ala Ile Pro Asn Met Asn Val Ile
            180                 185                 190
Arg Pro Ala Asp Gly Asn Glu Thr Arg Val Ala Trp Glu Val Ala Leu
            195                 200                 205
Glu Ser Glu Gln Thr Pro Thr Ser Leu Val Leu Thr Arg Gln Asn Leu
        210                 215                 220
Pro Thr Leu Asp Val Asp Lys Gln Thr Val Glu Asn Gly Val Arg Lys
225                 230                 235                 240
Gly Ala Tyr Ile Val Phe Glu Thr Glu Gln Leu Glu Tyr Leu Leu
                245                 250                 255
Leu Ala Ser Gly Ser Glu Val Asn Leu Ala Val Glu Ala Ala Lys Glu
            260                 265                 270
Leu Glu Gln Gln Gly Lys Gly Val Arg Val Ile Ser Met Pro Asn Trp
            275                 280                 285
Tyr Ala Phe Glu Gln Gln Ser Ser Tyr Lys Glu Ser Ile Leu Pro
        290                 295                 300
Ser Asp Val Thr Lys Arg Ile Ala Ile Glu Met Ala Ser Pro Leu Gly
305                 310                 315                 320
```

Trp His Lys Tyr Val Gly Ile Glu Gly Lys Val Ile Gly Ile Asn Ser
                325                 330                 335

Phe Gly Ala Ser Ala Pro Gly Asp Leu Val Val Glu Lys Tyr Gly Phe
            340                 345                 350

Thr Lys Glu Asn Ile Leu Lys Gln Val Arg Ser Leu
            355                 360

<210> SEQ ID NO 17
<211> LENGTH: 334
<212> TYPE: PRT
<213> ORGANISM: Staphylococcus epidermidis

<400> SEQUENCE: 17

Val Glu Ser Val Arg Gly Leu Lys Ile Leu Ser Val Ile Gly Leu Leu
1               5                   10                  15

Phe Val Leu Ile Ala Thr Ala Ala Cys Gly Asn Asn Ser Ser Ser Asn
            20                  25                  30

Ser Ser Lys Glu Ser Ser Lys Asp Gly Val Glu Ile Lys His Glu Glu
        35                  40                  45

Gly Thr Thr Lys Val Pro Lys His Pro Lys Arg Val Val Leu Glu
    50                  55                  60

Tyr Ser Phe Val Asp Ala Leu Val Ala Leu Asp Val Lys Pro Val Gly
65                  70                  75                  80

Ile Ala Asp Asp Asn Lys Lys Asn Arg Ile Ile Lys Pro Leu Arg Asp
                85                  90                  95

Lys Ile Gly Lys Tyr Thr Ser Val Gly Thr Arg Lys Pro Pro Asn Leu
            100                 105                 110

Glu Glu Ile Ser Lys Leu Lys Pro Asp Leu Ile Ile Ala Asp Asn Asn
        115                 120                 125

Arg His Lys Gly Ile Tyr Lys Asp Leu Asn Lys Ile Ala Pro Thr Ile
    130                 135                 140

Glu Leu Lys Ser Phe Asp Gly Asp Tyr Asn Glu Asn Ile Asp Ala Phe
145                 150                 155                 160

Lys Thr Ile Ser Lys Ala Leu Gly Lys Glu Glu Glu Gly Lys Lys Arg
                165                 170                 175

Leu Glu Glu His Asp Lys Lys Ile Glu Glu Tyr Lys Lys Glu Ile Thr
            180                 185                 190

Met Asp Lys Asn Gln Lys Val Leu Pro Ala Val Ala Ala Lys Ser Gly
        195                 200                 205

Leu Leu Ala His Pro Ser Asn Ser Tyr Val Gly Gln Phe Leu Ser Gln
    210                 215                 220

Leu Gly Phe Lys Glu Ala Leu Ser Asp Asp Val Thr Lys Gly Leu Ser
225                 230                 235                 240

Lys Tyr Leu Lys Gly Pro Tyr Leu Gln Met Asn Thr Glu Thr Leu Ser
                245                 250                 255

Gln Val Asn Pro Glu Arg Met Phe Ile Met Thr Asn Lys Ala Ser Ser
            260                 265                 270

Asn Glu Pro Ser Leu Lys Glu Leu Glu Lys Asp Pro Val Trp Lys Lys
        275                 280                 285

Leu Asn Ala Val Lys Asn Gln Arg Val Asp Ile Leu Asp Arg Asp Leu
    290                 295                 300

Trp Ala Arg Ser Arg Gly Leu Ile Ser Ser Glu Glu Met Ala Lys Glu
305                 310                 315                 320

Leu Val Glu Leu Ser Lys Thr Asp Ser Lys Lys Asp Asn Lys
                325                 330

<210> SEQ ID NO 18
<211> LENGTH: 411
<212> TYPE: PRT
<213> ORGANISM: Staphylococcus epidermidis

<400> SEQUENCE: 18

Met Arg Asp Lys Phe Glu Ile Thr Phe Ile Lys Asn Arg Arg Asp Leu
1               5                   10                  15

Ile Met Ala Lys Glu Lys Phe Asp Arg Ser Lys Glu His Ala Asn Ile
            20                  25                  30

Gly Thr Ile Gly His Val Asp His Gly Lys Thr Thr Leu Thr Ala Ala
        35                  40                  45

Ile Ala Thr Val Leu Ala Lys Asn Gly Asp Thr Val Ala Gln Ser Tyr
    50                  55                  60

Asp Met Ile Asp Asn Ala Pro Glu Glu Lys Glu Arg Gly Ile Thr Ile
65                  70                  75                  80

Asn Thr Ala His Ile Glu Tyr Gln Thr Asp Lys Arg His Tyr Ala His
                85                  90                  95

Val Asp Cys Pro Gly His Ala Asp Tyr Val Lys Asn Met Ile Thr Gly
            100                 105                 110

Ala Ala Gln Met Asp Gly Gly Ile Leu Val Val Ser Ala Ala Asp Gly
        115                 120                 125

Pro Met Pro Gln Thr Arg Glu His Ile Leu Leu Ser Arg Asn Val Gly
    130                 135                 140

Val Pro Ala Leu Val Val Phe Leu Asn Lys Val Asp Met Val Asp Asp
145                 150                 155                 160

Glu Glu Leu Leu Glu Leu Val Glu Met Glu Val Arg Asp Leu Leu Ser
                165                 170                 175

Glu Tyr Asp Phe Pro Gly Asp Asp Val Pro Val Ile Ala Gly Ser Ala
            180                 185                 190

Leu Lys Ala Leu Glu Gly Asp Ala Glu Tyr Gln Lys Ile Leu Asp
        195                 200                 205

Leu Met Gln Ala Val Asp Asp Tyr Ile Pro Thr Pro Glu Arg Asp Ser
    210                 215                 220

Asp Lys Pro Phe Met Met Pro Val Glu Asp Val Phe Ser Ile Thr Gly
225                 230                 235                 240

Arg Gly Thr Val Ala Thr Gly Arg Val Glu Arg Gly Gln Ile Lys Val
                245                 250                 255

Gly Glu Glu Val Glu Ile Ile Gly Met His Glu Thr Ser Lys Thr Thr
            260                 265                 270

Val Thr Gly Val Glu Met Phe Arg Lys Leu Leu Asp Tyr Ala Glu Ala
        275                 280                 285

Gly Asp Asn Ile Gly Ala Leu Leu Arg Gly Val Ala Arg Glu Asp Val
    290                 295                 300

Gln Arg Gly Gln Val Leu Ala Ala Pro Gly Ser Ile Thr Pro His Thr
305                 310                 315                 320

Lys Phe Lys Ala Glu Val Tyr Val Leu Ser Lys Asp Glu Gly Gly Arg
                325                 330                 335

His Thr Pro Phe Phe Thr Asn Tyr Arg Pro Gln Phe Tyr Phe Arg Thr
            340                 345                 350

Thr Asp Val Thr Gly Val Val Asn Leu Pro Glu Gly Thr Glu Met Val
        355                 360                 365

Met Pro Gly Asp Asn Val Glu Met Thr Val Glu Leu Ile Ala Pro Ile
    370                 375                 380

Ala Ile Glu Asp Gly Thr Arg Phe Ser Ile Arg Glu Gly Gly Arg Thr
385                 390                 395                 400

Val Gly Ser Gly Val Thr Glu Ile Phe Glu
                405                 410

<210> SEQ ID NO 19
<211> LENGTH: 428
<212> TYPE: PRT
<213> ORGANISM: Staphylococcus epidermidis

<400> SEQUENCE: 19

Met Met Ser Phe Glu Lys Ser Ile Lys Ala Met Glu Gln Ala Glu Lys
1               5                   10                  15

Leu Met Pro Gly Gly Val Asn Ser Pro Val Arg Ala Phe Lys Ser Val
                20                  25                  30

Asp Thr Pro Ala Ile Phe Met Asp His Gly Glu Gly Ser Lys Ile Tyr
            35                  40                  45

Asp Ile Asp Gly Asn Glu Tyr Ile Asp Tyr Val Leu Ser Trp Gly Pro
50                  55                  60

Leu Ile Leu Gly His Lys Asn Gln Gln Val Ile Ser Lys Leu His Glu
65                  70                  75                  80

Ala Val Asp Lys Gly Thr Ser Phe Gly Ala Ser Thr Leu Gln Glu Asn
                85                  90                  95

Lys Leu Ala Glu Leu Val Ile Asp Arg Val Pro Ser Ile Glu Lys Val
            100                 105                 110

Arg Met Val Ser Ser Gly Thr Glu Ala Thr Leu Asp Thr Leu Arg Leu
        115                 120                 125

Ala Arg Gly Tyr Thr Gly Arg Asn Lys Ile Ile Lys Phe Glu Gly Cys
130                 135                 140

Tyr His Gly His Ser Asp Ser Leu Leu Ile Lys Ala Gly Ser Gly Val
145                 150                 155                 160

Ala Thr Leu Gly Leu Pro Asp Ser Pro Gly Val Pro Glu Gly Ile Ala
                165                 170                 175

Lys Asn Thr Ile Thr Val Pro Tyr Asn Asp Leu Asp Ser Leu Lys Leu
            180                 185                 190

Ala Phe Glu Lys Tyr Gly Asp Asp Ile Ala Gly Val Ile Val Glu Pro
        195                 200                 205

Val Ala Gly Asn Met Gly Val Val Pro Pro Val Asn Gly Phe Leu Gln
210                 215                 220

Gly Leu Arg Asp Ile Thr Asn Glu Tyr Gly Ala Leu Leu Ile Phe Asp
225                 230                 235                 240

Glu Val Met Thr Gly Phe Arg Val Gly Tyr Asn Cys Ala Gln Gly Tyr
                245                 250                 255

Phe Gly Val Thr Pro Asp Leu Thr Cys Leu Gly Lys Val Ile Gly Gly
            260                 265                 270

Gly Leu Pro Val Gly Ala Phe Gly Gly Lys Lys Glu Ile Met Asp Tyr
        275                 280                 285

Ile Ala Pro Val Gly Thr Ile Tyr Gln Ala Gly Thr Leu Ser Gly Asn
290                 295                 300

Pro Leu Ala Met Thr Ser Gly Tyr Glu Thr Leu Ser Gln Leu Thr Pro
305                 310                 315                 320

Glu Ser Tyr Glu Tyr Phe Asn Ser Leu Gly Asp Ile Leu Glu Lys Gly
                325                 330                 335

Leu Lys Glu Val Phe Ala Lys Tyr Asn Val Pro Ile Thr Val Asn Arg
            340                 345                 350

```
Ala Gly Ser Met Ile Gly Tyr Phe Leu Asn Glu Gly Pro Val Thr Asn
        355                 360                 365

Phe Glu Glu Ala Asn Lys Ser Asp Leu Lys Leu Phe Ser Asn Met Tyr
370                 375                 380

Arg Glu Met Ala Lys Glu Gly Val Tyr Ile Pro Pro Ser Gln Phe Glu
385                 390                 395                 400

Gly Thr Phe Leu Ser Thr Ala His Thr Lys Asp Asp Ile Glu Lys Thr
                405                 410                 415

Ile Gln Ala Phe Asp Asn Ala Leu Ser Arg Ile Val
            420                 425

<210> SEQ ID NO 20
<211> LENGTH: 286
<212> TYPE: PRT
<213> ORGANISM: Staphylococcus epidermidis

<400> SEQUENCE: 20

Met Pro Leu Val Ser Met Lys Glu Met Leu Ile Asp Ala Lys Glu Asn
1               5                   10                  15

Gly Tyr Ala Val Gly Gln Tyr Asn Leu Asn Asn Leu Glu Phe Thr Gln
            20                  25                  30

Ala Ile Leu Glu Ala Ser Gln Glu Glu Asn Ala Pro Val Ile Leu Gly
        35                  40                  45

Val Ser Glu Gly Ala Ala Arg Tyr Met Ser Gly Phe Tyr Thr Val Val
50                  55                  60

Lys Met Val Glu Gly Leu Met His Asp Leu Asn Ile Thr Ile Pro Val
65                  70                  75                  80

Ala Ile His Leu Asp His Gly Ser Ser Phe Glu Lys Cys Lys Glu Ala
                85                  90                  95

Ile Asp Ala Gly Phe Thr Ser Val Met Ile Asp Ala Ser His Ser Pro
            100                 105                 110

Phe Glu Glu Asn Val Glu Ile Thr Ser Lys Val Val Glu Tyr Ala His
        115                 120                 125

Asp Arg Gly Val Ser Val Glu Ala Glu Leu Gly Thr Val Gly Gly Gln
130                 135                 140

Glu Asp Asp Val Val Ala Asp Gly Val Ile Tyr Ala Asp Pro Lys Glu
145                 150                 155                 160

Cys Gln Glu Leu Val Glu Lys Thr Gly Ile Asp Thr Leu Ala Pro Ala
                165                 170                 175

Leu Gly Ser Val His Gly Pro Tyr Lys Gly Glu Pro Lys Leu Gly Phe
            180                 185                 190

Lys Glu Met Glu Glu Ile Gly Ala Ser Thr Gly Leu Pro Leu Val Leu
        195                 200                 205

His Gly Gly Thr Gly Ile Pro Thr Lys Asp Ile Gln Lys Ala Ile Pro
210                 215                 220

Tyr Gly Thr Ala Lys Ile Asn Val Asn Thr Glu Asn Gln Ile Ala Ser
225                 230                 235                 240

Ala Lys Ala Val Arg Glu Val Leu Asn Asn Asp Lys Asp Val Tyr Asp
                245                 250                 255

Pro Arg Lys Tyr Leu Gly Pro Ala Arg Glu Ala Ile Lys Glu Thr Val
            260                 265                 270

Lys Gly Lys Ile Arg Glu Phe Gly Thr Ser Asn Arg Ala Lys
        275                 280                 285

<210> SEQ ID NO 21
<211> LENGTH: 468
```

<212> TYPE: PRT
<213> ORGANISM: Staphylococcus epidermidis

<400> SEQUENCE: 21

Met Thr Gln Gln Ile Gly Val Val Gly Leu Ala Val Met Gly Lys Asn
1               5                   10                  15

Leu Ala Trp Asn Ile Glu Ser Arg Gly Tyr Ser Val Ser Val Tyr Asn
            20                  25                  30

Arg Ser Arg Gln Lys Thr Asp Glu Met Val Lys Glu Ser Pro Gly Arg
        35                  40                  45

Glu Ile Tyr Pro Thr Tyr Ser Leu Glu Glu Phe Val Glu Ser Leu Glu
    50                  55                  60

Lys Pro Arg Lys Ile Leu Leu Met Val Lys Ala Gly Pro Ala Thr Asp
65                  70                  75                  80

Ala Thr Ile Asp Gly Leu Leu Pro Leu Leu Asp Asp Asp Ile Leu
            85                  90                  95

Ile Asp Gly Gly Asn Thr Asn Tyr Gln Asp Thr Ile Arg Arg Asn Lys
            100                 105                 110

Ala Leu Ala Glu Ser Ser Ile Asn Phe Ile Gly Met Gly Val Ser Gly
        115                 120                 125

Gly Glu Ile Gly Ala Leu Thr Gly Pro Ser Leu Met Pro Gly Gly Gln
    130                 135                 140

Lys Asp Ala Tyr Asn Lys Val Ser Asp Ile Leu Asp Ala Ile Ala Ala
145                 150                 155                 160

Lys Ala Gln Asp Gly Ala Ser Cys Val Thr Tyr Ile Gly Pro Asn Gly
            165                 170                 175

Ala Gly His Tyr Val Lys Met Val His Asn Gly Ile Glu Tyr Ala Asp
        180                 185                 190

Met Gln Leu Ile Ala Glu Ser Tyr Ala Met Met Lys Asp Leu Leu Gly
    195                 200                 205

Met Ser His Lys Glu Ile Ser Gln Thr Phe Lys Glu Trp Asn Ala Gly
    210                 215                 220

Glu Leu Glu Ser Tyr Leu Ile Glu Ile Thr Gly Asp Ile Phe Asn Lys
225                 230                 235                 240

Leu Asp Asp Asp Asn Glu Ala Leu Val Glu Lys Ile Leu Asp Thr Ala
            245                 250                 255

Gly Gln Lys Gly Thr Gly Lys Trp Thr Ser Ile Asn Ala Leu Glu Leu
        260                 265                 270

Gly Val Pro Leu Thr Ile Ile Thr Glu Ser Val Phe Ala Arg Phe Ile
    275                 280                 285

Ser Ser Ile Lys Glu Glu Arg Val Thr Ala Ser Lys Ser Leu Lys Gly
    290                 295                 300

Pro Lys Ala His Phe Glu Gly Asp Lys Lys Thr Phe Leu Glu Lys Ile
305                 310                 315                 320

Arg Lys Ala Leu Tyr Met Ser Lys Ile Cys Ser Tyr Ala Gln Gly Phe
            325                 330                 335

Ala Gln Met Arg Lys Ala Ser Glu Asp Asn Glu Trp Asn Leu Lys Leu
        340                 345                 350

Gly Glu Leu Ala Met Ile Trp Arg Glu Gly Cys Ile Ile Arg Ala Gln
    355                 360                 365

Phe Leu Gln Lys Ile Lys Asp Ala Tyr Asp Asn Glu Asn Leu Gln
    370                 375                 380

Asn Leu Leu Leu Asp Pro Tyr Phe Lys Asn Ile Val Met Glu Tyr Gln
385                 390                 395                 400

```
Asp Ala Leu Arg Glu Val Val Ala Thr Ser Val Tyr Asn Gly Val Pro
            405                 410                 415

Thr Pro Gly Phe Ser Ala Ser Ile Asn Tyr Tyr Asp Ser Tyr Arg Ser
            420                 425                 430

Glu Asp Leu Pro Ala Asn Leu Ile Gln Ala Gln Arg Asp Tyr Phe Gly
            435                 440                 445

Ala His Thr Tyr Glu Arg Lys Asp Arg Glu Gly Ile Phe His Thr Gln
            450                 455                 460

Trp Val Glu Glu
465

<210> SEQ ID NO 22
<211> LENGTH: 262
<212> TYPE: PRT
<213> ORGANISM: Staphylococcus epidermidis

<400> SEQUENCE: 22

Met Lys Arg Leu Leu Cys Ile Val Ala Leu Val Phe Val Leu Ala
1               5                   10                  15

Ala Cys Gly Asn Asn Ser Ser Asn Asn Lys Asp Asn Gln Ser Ser Ser
            20                  25                  30

Lys Asp Lys Asp Thr Leu Arg Val Gly Thr Glu Gly Thr Tyr Ala Pro
        35                  40                  45

Phe Thr Tyr His Asn Lys Lys Asp Gln Leu Thr Gly Tyr Asp Ile Asp
    50                  55                  60

Val Ile Lys Ala Val Ala Lys Glu Glu Asn Leu Lys Leu Lys Phe Asn
65                  70                  75                  80

Glu Thr Ser Trp Asp Ser Met Phe Ala Gly Leu Asp Ala Gly Arg Phe
                85                  90                  95

Asp Val Ile Ala Asn Gln Val Gly Val Asn Lys Asp Arg Glu Lys Lys
            100                 105                 110

Tyr Lys Phe Ser Glu Pro Tyr Thr Tyr Ser Ser Ala Val Leu Val Val
        115                 120                 125

Arg Glu Asn Glu Lys Asp Ile Thr Ser Phe Asn Asp Val Lys Gly Lys
130                 135                 140

Lys Leu Ala Gln Thr Phe Thr Ser Asn Tyr Gly Gln Leu Ala Lys Asp
145                 150                 155                 160

Lys Gly Ala Asp Ile Thr Lys Val Asp Gly Phe Asn Gln Ser Met Asp
                165                 170                 175

Leu Leu Leu Ser Lys Arg Val Asp Gly Thr Phe Asn Asp Ser Leu Ser
            180                 185                 190

Tyr Leu Asp Tyr Arg Lys Gln Lys Pro Asn Ala Lys Ile Lys Ala Ile
        195                 200                 205

Lys Gly His Ala Glu Gln Asn Lys Ser Ala Phe Ala Phe Ser Lys Lys
    210                 215                 220

Val Asp Glu Lys Thr Ile Glu Lys Phe Asn Lys Gly Leu Glu Lys Ile
225                 230                 235                 240

Arg Asp Asn Gly Glu Leu Ala Lys Ile Gly Lys Lys Trp Phe Gly Gln
                245                 250                 255

Asp Val Ser Lys Pro Glu
            260

<210> SEQ ID NO 23
<211> LENGTH: 310
<212> TYPE: PRT
<213> ORGANISM: Staphylococcus epidermidis
```

<400> SEQUENCE: 23

Val Tyr Met Thr Lys Tyr Val Leu Lys Arg Leu Cys Tyr Met Phe Val
1               5                   10                  15

Ser Leu Phe Ile Val Ile Thr Ile Thr Phe Phe Leu Met Lys Leu Met
            20                  25                  30

Pro Gly Ser Pro Phe Asn Asp Thr Lys Leu Asn Ala Gln Gln Lys Glu
        35                  40                  45

Ile Leu Asn Glu Lys Tyr Gly Leu Asn Asp Pro Val Ala Leu Gln Tyr
50                  55                  60

Val Asn Tyr Leu Lys Asn Val Val Thr Gly Asp Phe Gly Asn Ser Phe
65                  70                  75                  80

Gln Tyr His Asn Met Pro Val Trp Asp Leu Val Lys Pro Arg Leu Ile
            85                  90                  95

Pro Ser Met Glu Met Gly Ile Thr Ala Met Val Ile Gly Val Val Leu
            100                 105                 110

Gly Leu Val Leu Gly Val Ala Ala Ala Thr Lys Gln Asn Thr Trp Val
            115                 120                 125

Asp Tyr Thr Thr Thr Ile Ile Ser Val Ile Ala Val Ser Val Pro Ser
130                 135                 140

Phe Val Leu Ala Val Leu Leu Gln Tyr Val Phe Ala Val Lys Leu Glu
145                 150                 155                 160

Trp Phe Pro Val Ala Gly Trp Glu Gly Phe Ser Thr Ala Ile Leu Pro
                165                 170                 175

Ser Leu Ala Leu Ser Ala Thr Val Leu Ala Thr Val Ala Arg Tyr Ile
            180                 185                 190

Arg Ala Glu Met Ile Glu Val Leu Ser Ser Asp Tyr Ile Leu Leu Ala
            195                 200                 205

Arg Ala Lys Gly Asn Ser Thr Leu Lys Val Leu Phe Gly His Ala Leu
210                 215                 220

Arg Asn Ala Leu Ile Pro Ile Ile Thr Ile Ile Val Pro Met Leu Ala
225                 230                 235                 240

Gly Ile Leu Thr Gly Thr Leu Thr Ile Glu Asn Ile Phe Gly Val Pro
            245                 250                 255

Gly Leu Gly Asp Gln Phe Val Arg Ser Ile Thr Thr Asn Asp Phe Ser
            260                 265                 270

Val Ile Met Ala Thr Thr Ile Leu Phe Ser Thr Leu Phe Ile Val Ser
            275                 280                 285

Ile Phe Ile Val Asp Ile Leu Tyr Gly Val Ile Asp Pro Arg Ile Arg
            290                 295                 300

Val Gln Gly Gly Lys Lys
305                 310

<210> SEQ ID NO 24
<211> LENGTH: 514
<212> TYPE: PRT
<213> ORGANISM: Staphylococcus epidermidis

<400> SEQUENCE: 24

Val Asn Glu Glu Gln Arg Lys Ala Gly Thr Ile Asn Ile Leu Ala Glu
1               5                   10                  15

Arg Asp Arg Lys Ala Glu Lys Asp Tyr Ser Lys Tyr Phe Glu Gln Val
            20                  25                  30

Tyr Gln Pro Pro Ser Leu Lys Glu Ala Lys Lys Arg Gly Lys Gln Glu
        35                  40                  45

Val Gln Tyr Asn Arg Asp Phe His Ile Asp Glu Lys Tyr Lys Gly Met

-continued

```
            50                  55                  60
Gly Lys Gly Arg Thr Phe Leu Ile Lys Thr Tyr Gly Cys Gln Met Asn
 65                  70                  75                  80

Ala His Asp Thr Glu Val Met Ala Gly Ile Leu Asn Ala Leu Gly Tyr
                     85                  90                  95

Ser Ala Thr Ser Asp Ile Asn Glu Ala Asp Val Ile Leu Ile Asn Thr
                    100                 105                 110

Cys Ala Ile Arg Glu Asn Ala Glu Asn Lys Val Phe Ser Glu Ile Gly
                115                 120                 125

Asn Leu Lys His Leu Lys Lys Glu Arg Pro Asp Cys Leu Ile Gly Val
130                 135                 140

Cys Gly Cys Met Ser Gln Glu Glu Ser Val Val Asn Lys Ile Leu Lys
145                 150                 155                 160

Ser Tyr Gln Asn Val Asp Met Val Phe Gly Thr His Asn Ile His His
                165                 170                 175

Leu Pro Glu Ile Leu Glu Glu Ala Tyr Leu Ser Lys Ala Met Val Val
                180                 185                 190

Glu Val Trp Ser Lys Glu Gly Asp Ile Ile Glu Asn Leu Pro Lys Val
                195                 200                 205

Arg Asp Gly His Ile Lys Ala Trp Val Asn Ile Met Tyr Gly Cys Asp
210                 215                 220

Lys Phe Cys Thr Tyr Cys Ile Val Pro Phe Thr Arg Gly Lys Glu Arg
225                 230                 235                 240

Ser Arg Arg Pro Glu Asp Ile Ile Asp Glu Val Arg Glu Leu Ala Arg
                245                 250                 255

Glu Gly Tyr Gln Glu Ile Thr Leu Leu Gly Gln Asn Val Asn Ser Tyr
                260                 265                 270

Gly Lys Asp Ile Glu Gly Leu Asp Tyr Glu Leu Gly Asp Leu Leu Glu
                275                 280                 285

Asp Ile Ser Lys Ile Asp Ile Pro Arg Val Arg Phe Thr Thr Ser His
290                 295                 300

Pro Trp Asp Phe Thr Asp Arg Met Ile Glu Val Ile Ala Lys Gly Gly
305                 310                 315                 320

Asn Ile Val Pro His Ile His Leu Pro Val Gln Ser Gly Asn Asn Gln
                325                 330                 335

Val Leu Lys Ile Met Gly Arg Lys Tyr Thr Arg Glu Ser Tyr Leu Asp
                340                 345                 350

Leu Val Ser Arg Ile Lys Glu Ala Ile Pro Asn Val Ala Leu Thr Thr
                355                 360                 365

Asp Ile Ile Val Gly Tyr Pro Asn Glu Thr Val Glu Gln Phe Glu Glu
                370                 375                 380

Thr Leu Ser Leu Tyr Asp Asp Val Gln Phe Glu His Ala Tyr Thr Tyr
385                 390                 395                 400

Leu Tyr Ser Gln Arg Asp Gly Thr Pro Ala Ala Lys Met Lys Asp Asn
                405                 410                 415

Val Pro Leu Glu Val Lys Lys Gly Arg Leu Gln Arg Leu Asn Lys Lys
                420                 425                 430

Val Gly Ile Tyr Ser Gln Gln Ala Met Ser Gln Tyr Glu Gly Lys Ile
                435                 440                 445

Val Thr Val Leu Cys Glu Gly Ser Ser Lys Lys Asp Glu Asn Val Leu
                450                 455                 460

Ala Gly Tyr Thr Asp Lys Asn Lys Leu Val Asn Phe Lys Gly Pro Arg
465                 470                 475                 480
```

```
Glu Ser Ile Gly Lys Leu Val Asp Val Lys Ile Asp Glu Ala Lys Gln
                485                 490                 495

Tyr Ser Leu Asn Gly Thr Phe Ile Gln Glu His Gln Arg Ser Met Val
                500                 505                 510

Thr Gln

<210> SEQ ID NO 25
<211> LENGTH: 394
<212> TYPE: PRT
<213> ORGANISM: Staphylococcus epidermidis

<400> SEQUENCE: 25

Met Ser Arg Ile Val Leu Ala Glu Ala Tyr Arg Thr Pro Ile Gly Val
1                5                  10                  15

Phe Gly Gly Val Phe Lys Asp Ile Pro Ala Tyr Glu Leu Gly Ala Thr
                20                  25                  30

Val Ile Arg Gln Ile Leu Glu His Ser Gln Ile Asp Pro Asn Glu Ile
            35                  40                  45

Asn Glu Val Ile Leu Gly Asn Val Leu Gln Ala Gly Gln Gly Gln Asn
    50                  55                  60

Pro Ala Arg Ile Ala Ala Ile His Gly Gly Val Pro Glu Ala Val Pro
65                  70                  75                  80

Ser Phe Thr Val Asn Lys Val Cys Gly Ser Gly Leu Lys Ala Ile Gln
                85                  90                  95

Leu Ala Tyr Gln Ser Ile Val Ala Gly Asp Asn Glu Ile Val Ile Ala
                100                 105                 110

Gly Gly Met Glu Ser Met Ser Gln Ser Pro Met Leu Leu Lys Asn Ser
            115                 120                 125

Arg Phe Gly Phe Lys Met Gly Asn Gln Thr Leu Glu Asp Ser Met Ile
    130                 135                 140

Ala Asp Gly Leu Thr Asp Lys Phe Asn Asp Tyr His Met Gly Ile Thr
145                 150                 155                 160

Ala Glu Asn Leu Val Glu Gln Tyr Gln Ile Ser Arg Lys Glu Gln Asp
                165                 170                 175

Gln Phe Ala Phe Asp Ser Gln Lys Ala Ser Arg Ala Gln Gln Ala
                180                 185                 190

Gly Val Phe Asp Ala Glu Ile Val Pro Val Glu Val Pro Gln Arg Lys
            195                 200                 205

Gly Asp Pro Leu Ile Ile Ser Gln Asp Glu Gly Ile Arg Pro Gln Thr
    210                 215                 220

Thr Ile Asp Lys Leu Ala Gln Leu Arg Pro Ala Phe Lys Lys Asp Gly
225                 230                 235                 240

Ser Val Thr Ala Gly Asn Ala Ser Gly Ile Asn Asp Gly Ala Ala Ala
                245                 250                 255

Met Leu Val Met Thr Glu Asp Lys Ala Lys Ala Leu Gly Leu Gln Pro
                260                 265                 270

Ile Ala Val Leu Asp Ser Phe Gly Ala Ser Gly Val Ala Pro Ser Ile
            275                 280                 285

Met Gly Ile Gly Pro Val Glu Ala Ile His Lys Ala Leu Lys Arg Ser
    290                 295                 300

Asn Lys Val Ile Asn Asp Val Asp Ile Phe Glu Leu Asn Glu Ala Phe
305                 310                 315                 320

Ala Ala Gln Ser Ile Ala Val Asn Arg Glu Leu Gln Leu Pro Gln Asp
                325                 330                 335

Lys Val Asn Val Asn Gly Gly Ala Ile Ala Leu Gly His Pro Ile Gly
```

```
                         340                 345                 350
Ala Ser Gly Ala Arg Thr Leu Val Ser Leu Leu His Gln Leu Ser Asp
                355                 360                 365

Ala Lys Pro Thr Gly Val Ala Ser Leu Cys Ile Gly Gly Gly Gln Gly
            370                 375                 380

Ile Ala Thr Val Val Ser Lys Tyr Glu Val
385                 390

<210> SEQ ID NO 26
<211> LENGTH: 292
<212> TYPE: PRT
<213> ORGANISM: Staphylococcus epidermidis

<400> SEQUENCE: 26

Met Ala Ile Ser Ala Lys Leu Val Lys Glu Leu Arg Glu Lys Thr Gly
1               5                   10                  15

Ala Gly Met Met Asp Cys Lys Lys Ala Leu Thr Glu Thr Asp Gly Asp
                20                  25                  30

Ile Asp Lys Ala Ile Asp Tyr Leu Arg Glu Lys Gly Ile Ala Lys Ala
            35                  40                  45

Ala Lys Lys Ala Asp Arg Ile Ala Ala Glu Gly Leu Val His Val Glu
        50                  55                  60

Val Lys Asp Asn Glu Ala Ala Ile Val Glu Ile Asn Ser Glu Thr Asp
65                  70                  75                  80

Phe Val Ala Arg Asn Glu Gly Phe Gln Glu Leu Val Lys Glu Ile Ala
                85                  90                  95

Asn His Ile Leu Asp Ser Lys Val Glu Thr Val Asp Ala Leu Met Glu
            100                 105                 110

Ser Lys Leu Ser Ser Gly Lys Thr Val Asp Glu Arg Met Lys Glu Ala
        115                 120                 125

Ile Ser Thr Ile Gly Glu Lys Leu Ser Ile Arg Arg Phe Ser Ile Arg
130                 135                 140

Thr Lys Thr Asp Asn Asp Ala Phe Gly Ala Tyr Leu His Met Gly Gly
145                 150                 155                 160

Arg Ile Gly Val Leu Thr Val Val Glu Gly Thr Thr Asp Glu Glu Ala
                165                 170                 175

Ala Lys Asp Val Ala Met His Ile Ala Ala Ile Asn Pro Lys Tyr Val
            180                 185                 190

Ser Ser Glu Gln Val Ser Glu Glu Ile Asn His Glu Arg Glu Val
        195                 200                 205

Leu Lys Gln Gln Ala Leu Asn Glu Gly Lys Pro Glu Lys Ile Val Glu
210                 215                 220

Lys Met Val Glu Gly Arg Leu Arg Lys Tyr Leu Gln Glu Ile Cys Ala
225                 230                 235                 240

Val Asp Gln Asn Phe Val Lys Asn Pro Asp Glu Thr Val Glu Ala Phe
                245                 250                 255

Leu Lys Ala Lys Gly Gly Lys Leu Thr Asp Phe Val Arg Tyr Glu Val
            260                 265                 270

Gly Glu Gly Met Glu Lys Arg Glu Asn Phe Ala Glu Glu Val Lys
        275                 280                 285

Gly Gln Met Lys
    290

<210> SEQ ID NO 27
<211> LENGTH: 310
<212> TYPE: PRT
```

<213> ORGANISM: Staphylococcus epidermidis

<400> SEQUENCE: 27

| | | | | | | | | | | | | | | |
|---|---|---|---|---|---|---|---|---|---|---|---|---|---|---|
| Met<br>1 | Thr | Glu | Val | Asp<br>5 | Phe | Asp | Val | Ala | Ile<br>10 | Ile | Gly | Ala | Gly | Pro<br>15 | Ala |
| Gly | Met | Thr | Ala<br>20 | Ala | Val | Tyr | Ala | Ser<br>25 | Arg | Ala | Asn | Leu | Lys<br>30 | Thr | Val |
| Met | Ile | Glu<br>35 | Arg | Gly | Met | Pro | Gly<br>40 | Gly | Gln | Met | Ala | Asn<br>45 | Thr | Glu | Glu |
| Val | Glu<br>50 | Asn | Phe | Pro | Gly | Phe<br>55 | Glu | Met | Ile | Thr | Gly<br>60 | Pro | Asp | Leu | Ser |
| Thr<br>65 | Lys | Met | Phe | Glu | His<br>70 | Ala | Lys | Lys | Phe | Gly<br>75 | Ala | Glu | Tyr | Gln | Tyr<br>80 |
| Gly | Asp | Ile | Lys | Ser<br>85 | Val | Glu | Asp | Lys | Gly<br>90 | Asp | Tyr | Lys | Val | Ile<br>95 | Asn |
| Leu | Gly | Asn | Lys<br>100 | Glu | Ile | Thr | Ala | His<br>105 | Ala | Val | Ile | Ile | Ser<br>110 | Thr | Gly |
| Ala | Glu | Tyr<br>115 | Lys | Lys | Ile | Gly | Val<br>120 | Pro | Gly | Glu | Gln | Glu<br>125 | Leu | Gly | Gly |
| Arg | Gly<br>130 | Val | Ser | Tyr | Cys | Ala<br>135 | Val | Cys | Asp | Gly | Ala<br>140 | Phe | Phe | Lys | Asn |
| Lys<br>145 | Arg | Leu | Phe | Val | Ile<br>150 | Gly | Gly | Gly | Asp | Ser<br>155 | Ala | Val | Glu | Glu | Gly<br>160 |
| Thr | Phe | Leu | Thr | Lys<br>165 | Phe | Ala | Asp | Lys | Val<br>170 | Thr | Ile | Val | His | Arg<br>175 | Arg |
| Asp | Glu | Leu | Arg<br>180 | Ala | Gln | Asn | Ile | Leu<br>185 | Gln | Glu | Arg | Ala | Phe<br>190 | Lys | Asn |
| Asp | Lys | Val<br>195 | Asp | Phe | Ile | Trp | Ser<br>200 | His | Thr | Leu | Lys | Thr<br>205 | Ile | Asn | Glu |
| Lys | Asp<br>210 | Gly | Lys | Val | Gly | Ser<br>215 | Val | Thr | Leu | Glu | Ser<br>220 | Thr | Lys | Asp | Gly |
| Ala<br>225 | Glu | Gln | Thr | Tyr | Asp<br>230 | Ala | Asp | Gly | Val | Phe<br>235 | Ile | Tyr | Ile | Gly | Met<br>240 |
| Lys | Pro | Leu | Thr | Ala<br>245 | Pro | Phe | Lys | Asn | Leu<br>250 | Gly | Ile | Thr | Asn | Asp<br>255 | Ala |
| Gly | Tyr | Ile | Val<br>260 | Thr | Gln | Asp | Met | Ser<br>265 | Thr | Lys | Val | Arg<br>270 | Gly | Ile |
| Phe | Ala | Ala<br>275 | Gly | Asp | Val | Arg | Asp<br>280 | Lys | Gly | Leu | Arg | Gln<br>285 | Ile | Val | Thr |
| Ala | Thr<br>290 | Gly | Asp | Gly | Ser | Ile<br>295 | Ala | Ala | Gln | Ser | Ala<br>300 | Ala | Asp | Tyr | Ile |
| Thr<br>305 | Glu | Leu | Lys | Asp | Asn<br>310 | | | | | | | | | | |

<210> SEQ ID NO 28
<211> LENGTH: 465
<212> TYPE: PRT
<213> ORGANISM: Staphylococcus epidermidis

<400> SEQUENCE: 28

| | | | | | | | | | | | | | | | |
|---|---|---|---|---|---|---|---|---|---|---|---|---|---|---|---|
| Met<br>1 | Thr | Gln | Lys | Tyr<br>5 | Arg | Tyr | Pro | Thr | Phe<br>10 | Leu | Glu | Ser | Ile | Ser<br>15 | Thr |
| Ile | Leu | Val | Met<br>20 | Val | Val | Val | Val<br>25 | Ile | Gly | Phe | Val | Phe<br>30 | Phe | Asn |
| Val | Pro | Ile | Gln<br>35 | Ile | Leu | Leu | Leu<br>40 | Ile | Ser | Ser | Ala | Tyr<br>45 | Ala | Ala | Leu |

Ile Ala His Arg Val Gly Leu Lys Trp Lys Asp Leu Glu Glu Gly Ile
    50                  55                  60

Thr His Arg Leu Ser Thr Ala Met Pro Ala Ile Phe Ile Ile Leu Ala
65                  70                  75                  80

Val Gly Ile Ile Val Gly Ser Trp Met Tyr Ser Gly Thr Val Pro Ala
                85                  90                  95

Leu Ile Tyr Tyr Gly Leu Lys Phe Leu Asn Pro Ser Tyr Leu Leu Val
                100                 105                 110

Ser Ala Phe Ile Ile Ser Ala Met Thr Ser Ile Ala Thr Gly Thr Ala
                115                 120                 125

Trp Gly Ser Ala Ser Thr Ala Gly Ile Ala Leu Ile Ser Ile Ala Asn
    130                 135                 140

Gln Leu Gly Val Pro Ala Gly Met Ala Ala Gly Ala Ile Ile Ala Gly
145                 150                 155                 160

Ala Val Phe Gly Asp Lys Met Ser Pro Leu Ser Asp Thr Thr Asn Leu
                165                 170                 175

Ala Ala Leu Val Thr Lys Val Asn Ile Phe Ala His Ile Lys Ser Met
                180                 185                 190

Met Trp Thr Thr Ile Pro Ala Ser Ile Ile Gly Leu Ala Ile Trp Phe
    195                 200                 205

Ile Val Gly Leu Gln Tyr Lys Gly Asp Ala Asn Thr Gln Gln Ile Gln
    210                 215                 220

Asn Leu Leu Lys Glu Leu Thr Thr Ile Tyr Asn Leu Asn Phe Trp Val
225                 230                 235                 240

Trp Ile Pro Leu Ile Ile Ile Val Leu Cys Leu Ile Phe Arg Ile Ser
                245                 250                 255

Thr Val Pro Ser Met Leu Ile Ser Ile Ser Ala Leu Val Ile Gly
                260                 265                 270

Thr Phe Asp His Gln Phe Asn Met Lys Asp Gly Phe Lys Ala Ser Phe
    275                 280                 285

Asp Gly Phe Asn His Thr Met Leu His Gln Ser His Ile Ser Asp Asn
    290                 295                 300

Ala Lys Thr Leu Ile Glu Gln Gly Gly Met Met Ser Met Thr Gln Ile
305                 310                 315                 320

Ile Val Thr Ile Phe Cys Gly Tyr Ala Phe Ala Gly Ile Val Glu Lys
                325                 330                 335

Ala Gly Cys Leu Asp Val Ile Leu Glu Thr Ile Ala Lys Gly Val Lys
                340                 345                 350

Ser Val Gly Thr Leu Ile Leu Ile Thr Val Val Cys Ser Ile Met Leu
    355                 360                 365

Val Phe Ala Ala Gly Val Ala Ser Ile Val Ile Met Val Gly Val
    370                 375                 380

Leu Met Lys Asp Met Phe Glu Lys Met Asn Val Ser Lys Ser Val Leu
385                 390                 395                 400

Ser Arg Thr Leu Glu Asp Ser Ser Thr Met Val Leu Pro Leu Ile Pro
                405                 410                 415

Trp Gly Thr Ser Gly Ile Tyr Tyr Ala His Gln Leu Asn Val Ser Val
                420                 425                 430

Asp Gln Phe Phe Ile Trp Ala Ile Pro Cys Tyr Leu Cys Ala Phe Ile
                435                 440                 445

Ala Ile Ile Tyr Gly Phe Thr Gly Ile Gly Ile Lys Lys Ile Ser Arg
    450                 455                 460

Lys

<210> SEQ ID NO 29
<211> LENGTH: 235
<212> TYPE: PRT
<213> ORGANISM: Staphylococcus epidermidis

<400> SEQUENCE: 29

```
Met Lys Lys Thr Val Ile Ala Ser Thr Leu Ala Val Ser Leu Gly Ile
1               5                   10                  15

Ala Gly Tyr Gly Leu Ser Gly His Glu Ala His Ala Ser Glu Thr Thr
            20                  25                  30

Asn Val Asp Lys Ala His Leu Val Asp Leu Ala Gln His Asn Pro Glu
        35                  40                  45

Glu Leu Asn Ala Lys Pro Val Gln Ala Gly Ala Tyr Asp Ile His Phe
    50                  55                  60

Val Asp Asn Gly Tyr Gln Tyr Asn Phe Thr Ser Asn Gly Ser Glu Trp
65                  70                  75                  80

Ser Trp Ser Tyr Ala Val Ala Gly Ser Asp Ala Asp Tyr Thr Glu Ser
                85                  90                  95

Ser Ser Asn Gln Glu Val Ser Ala Asn Thr Gln Ser Ser Asn Thr Asn
            100                 105                 110

Val Gln Ala Val Ser Ala Pro Thr Ser Ser Glu Ser Arg Ser Tyr Ser
        115                 120                 125

Thr Ser Thr Thr Ser Tyr Ser Ala Pro Ser His Asn Tyr Ser Ser His
    130                 135                 140

Ser Ser Ser Val Arg Leu Ser Asn Gly Asn Thr Ala Gly Ser Val Gly
145                 150                 155                 160

Ser Tyr Ala Ala Ala Gln Met Ala Ala Arg Thr Gly Val Ser Ala Ser
                165                 170                 175

Thr Trp Glu His Ile Ile Ala Arg Glu Ser Asn Gly Gln Leu His Ala
            180                 185                 190

Arg Asn Ala Ser Gly Ala Ala Gly Leu Phe Gln Thr Met Pro Gly Trp
        195                 200                 205

Gly Ser Thr Gly Ser Val Asn Asp Gln Ile Asn Ala Ala Tyr Lys Ala
    210                 215                 220

Tyr Lys Ala Gln Gly Leu Ser Ala Trp Gly Met
225                 230                 235
```

<210> SEQ ID NO 30
<211> LENGTH: 296
<212> TYPE: PRT
<213> ORGANISM: Staphylococcus epidermidis

<400> SEQUENCE: 30

```
Met Asn Lys Glu Gln Leu Glu Lys Met Thr His Gly Lys Gly Phe Ile
1               5                   10                  15

Ala Ala Leu Asp Gln Ser Gly Gly Ser Thr Pro Lys Ala Leu Lys Glu
            20                  25                  30

Tyr Gly Val Asn Glu Asp Gln Tyr Ser Asn Glu Asp Glu Met Phe Gln
        35                  40                  45

Leu Val His Asp Met Arg Thr Arg Val Val Thr Ser Pro Ser Phe Ser
    50                  55                  60

Pro Asp Lys Ile Leu Gly Ala Ile Leu Phe Glu Gln Thr Met Asp Arg
65                  70                  75                  80

Glu Val Glu Gly Lys Tyr Thr Gly Asp Tyr Leu Ala Asp Lys Gly Val
                85                  90                  95
```

```
Val Pro Phe Leu Lys Val Asp Lys Gly Leu Ala Glu Glu Lys Asn Gly
                100                 105                 110

Val Gln Leu Met Lys Pro Ile Asp Asp Leu Asp Glu Thr Leu Asp Arg
            115                 120                 125

Ala Asn Glu Arg His Ile Phe Gly Thr Lys Met Arg Ser Asn Ile Leu
        130                 135                 140

Glu Leu Asn Glu Gln Gly Ile Lys Asp Val Val Glu Gln Gln Phe Glu
145                 150                 155                 160

Phe Ala Lys Lys Ile Ile Ala Lys Gly Leu Val Pro Ile Ile Glu Pro
                165                 170                 175

Glu Val Asn Ile Asn Ala Lys Asp Lys Ser Glu Ile Glu Lys Val Leu
            180                 185                 190

Lys Ala Glu Ile Lys Lys Gly Leu Asp Ser Leu Asn Asp Asp Gln Leu
        195                 200                 205

Val Met Leu Lys Leu Thr Ile Pro Thr Glu Ala Asn Leu Tyr Lys Asp
210                 215                 220

Leu Ala Asp His Pro Asn Val Val Arg Val Val Leu Ser Gly Gly
225                 230                 235                 240

Tyr Ser Arg Asp Glu Ala Asn Lys Leu Leu Lys Asp Asn Asp Glu Leu
                245                 250                 255

Ile Ala Ser Phe Ser Arg Ala Leu Ala Ser Asp Leu Arg Ala Ser Gln
            260                 265                 270

Ser Gln Glu Glu Phe Asp Lys Ala Leu Gly Asp Ala Val Asp Ser Ile
        275                 280                 285

Tyr Asp Ala Ser Val Asn Lys Asn
        290                 295

<210> SEQ ID NO 31
<211> LENGTH: 263
<212> TYPE: PRT
<213> ORGANISM: Staphylococcus epidermidis

<400> SEQUENCE: 31

Leu Lys Glu Arg Phe Ile Lys Lys Thr His Tyr Leu Asp Tyr Gln Phe
1               5                   10                  15

Asp Glu Pro Thr Asp Ile Lys Leu Gly Phe Thr Thr Arg Glu Asn Gly
            20                  25                  30

Leu Ser Pro Tyr Pro Asn His Ser Phe Asn Met Ala Arg Tyr Ile Ser
        35                  40                  45

Asp Ser Ala His His Ile Thr His His Gln Asp Ile Leu Ala Asn Leu
    50                  55                  60

Ile Gly Tyr Pro Arg Asp Glu Trp Val Phe Pro Ile Gln Thr His Asp
65                  70                  75                  80

Ser Arg Ile Val Glu Val Thr Ser Glu His Lys Gly Thr Asn Ile Asp
                85                  90                  95

Glu Leu Thr Asp Asp Leu His Gly Ile Asp Gly Met Tyr Thr Phe Asp
            100                 105                 110

Ser His Ile Leu Leu Thr Met Cys Tyr Ala Asp Cys Val Pro Val Tyr
        115                 120                 125

Phe Tyr Ser Glu Pro His Gly Tyr Ile Gly Leu Ala His Ala Gly Trp
    130                 135                 140

Arg Gly Thr Tyr Gly Gln Ile Val Lys Asp Met Leu Lys Lys Val Asp
145                 150                 155                 160

Phe Asp Tyr Glu Asp Leu Lys Ile Val Ile Gly Pro Ala Thr Ser Asn
                165                 170                 175
```

```
Ser Tyr Glu Ile Asn Asp Asp Ile Lys Asn Lys Phe Glu Glu Leu Thr
            180                 185                 190

Ile Asp Ser Thr Leu Tyr Ile Glu Thr Arg Gly Lys Asn Gln His Gly
            195                 200                 205

Ile Asp Leu Lys Asn Ala Asn Ala Leu Leu Leu Glu Glu Ala Gly Val
210                 215                 220

Pro Ser Lys Asn Ile Tyr Val Thr Glu Tyr Ala Thr Ser Glu Asn Leu
225                 230                 235                 240

Asp Leu Phe Phe Ser Tyr Arg Val Glu Lys Gly Gln Thr Gly Arg Met
                245                 250                 255

Leu Ala Phe Ile Gly Arg Lys
            260

<210> SEQ ID NO 32
<211> LENGTH: 10203
<212> TYPE: PRT
<213> ORGANISM: Staphylococcus epidermidis

<400> SEQUENCE: 32

Met Lys Ser Lys Pro Lys Leu Asn Gly Arg Asn Ile Cys Ser Phe Leu
1               5                   10                  15

Leu Ser Lys Cys Met Ser Tyr Ser Leu Ser Lys Leu Ser Thr Leu Lys
            20                  25                  30

Thr Tyr Asn Phe Gln Ile Thr Ser Asn Asn Lys Glu Lys Thr Ser Arg
            35                  40                  45

Ile Gly Val Ala Ile Ala Leu Asn Asn Arg Asp Lys Leu Gln Lys Phe
50                  55                  60

Ser Ile Arg Lys Tyr Ala Ile Gly Thr Phe Ser Thr Val Ile Ala Thr
65                  70                  75                  80

Leu Val Phe Met Gly Ile Asn Thr Asn His Ala Ser Ala Asp Glu Leu
                85                  90                  95

Asn Gln Asn Gln Lys Leu Ile Lys Gln Leu Asn Gln Thr Asp Asp Asp
            100                 105                 110

Asp Ser Asn Thr His Ser Gln Glu Ile Glu Asn Asn Lys Gln Asn Ser
            115                 120                 125

Ser Gly Gln Thr Glu Ser Leu Arg Ser Ser Thr Ser Gln Asn Gln Ala
130                 135                 140

Asn Ala Arg Leu Ser Asp Gln Phe Lys Asp Thr Asn Glu Thr Ser Gln
145                 150                 155                 160

Gln Leu Pro Thr Asn Val Ser Asp Asp Ser Ile Asn Gln Ser His Ser
                165                 170                 175

Glu Ala Asn Met Asn Asn Glu Pro Leu Lys Val Asp Asn Ser Thr Met
            180                 185                 190

Gln Ala His Ser Lys Ile Val Ser Asp Ser Asp Gly Asn Ala Ser Glu
            195                 200                 205

Asn Lys His His Lys Leu Thr Glu Asn Val Leu Ala Glu Ser Arg Ala
210                 215                 220

Ser Lys Asn Asp Lys Glu Lys Glu Asn Leu Gln Glu Lys Asp Lys Ser
225                 230                 235                 240

Gln Gln Val His Pro Pro Leu Asp Lys Asn Ala Leu Gln Ala Phe Phe
                245                 250                 255

Asp Ala Ser Tyr His Asn Tyr Arg Met Ile Asp Arg Asp Arg Ala Asp
            260                 265                 270

Ala Thr Glu Tyr Gln Lys Val Lys Ser Thr Phe Asp Tyr Val Asn Asp
            275                 280                 285
```

```
Leu Leu Gly Asn Asn Gln Asn Ile Pro Ser Glu Gln Leu Val Ser Ala
    290                 295                 300

Tyr Gln Gln Leu Glu Lys Ala Leu Glu Leu Ala Arg Thr Leu Ser Gln
305                 310                 315                 320

Arg Ser Thr Thr Glu Lys Arg Gly Arg Arg Ser Thr Arg Ser Val Val
                325                 330                 335

Glu Asn Arg Ser Ser Arg Ser Asp Tyr Leu Asp Ala Arg Thr Glu Tyr
            340                 345                 350

Tyr Val Ser Lys Asp Asp Asp Ser Gly Phe Pro Pro Gly Thr Phe
        355                 360                 365

Phe His Ala Ser Asn Arg Arg Trp Pro Tyr Asn Leu Pro Arg Ser Arg
    370                 375                 380

Asn Ile Leu Arg Ala Ser Asp Val Gln Gly Asn Ala Tyr Ile Thr Thr
385                 390                 395                 400

Lys Arg Leu Lys Asp Gly Tyr Gln Trp Asp Ile Leu Phe Asn Ser Asn
                405                 410                 415

His Lys Gly His Glu Tyr Met Tyr Tyr Trp Phe Gly Leu Pro Ser Asp
            420                 425                 430

Gln Thr Pro Thr Gly Pro Val Thr Phe Thr Ile Ile Asn Arg Asp Gly
        435                 440                 445

Ser Ser Thr Ser Thr Gly Gly Val Gly Phe Gly Ser Gly Ala Pro Leu
    450                 455                 460

Pro Gln Phe Trp Arg Ser Ala Gly Ala Ile Asn Ser Ser Val Ala Asn
465                 470                 475                 480

Asp Phe Lys His Gly Ser Ala Thr Asn Tyr Ala Phe Tyr Asp Gly Val
                485                 490                 495

Asn Asn Phe Ser Asp Phe Ala Arg Gly Gly Glu Leu Tyr Phe Asp Arg
            500                 505                 510

Glu Gly Ala Thr Gln Thr Asn Lys Tyr Tyr Gly Asp Glu Asn Phe Ala
        515                 520                 525

Leu Leu Asn Ser Glu Lys Pro Asp Gln Ile Arg Gly Leu Asp Thr Ile
    530                 535                 540

Tyr Ser Phe Lys Gly Ser Gly Asp Val Ser Tyr Arg Ile Ser Phe Lys
545                 550                 555                 560

Thr Gln Gly Ala Pro Thr Ala Arg Leu Tyr Tyr Ala Ala Gly Ala Arg
                565                 570                 575

Ser Gly Glu Tyr Arg Gln Ala Thr Asn Tyr Asn Gln Leu Tyr Val Glu
            580                 585                 590

Pro Tyr Lys Asn Tyr Arg Asn Arg Val Gln Ser Asn Val Gln Val Lys
        595                 600                 605

Asn Arg Thr Leu His Leu Lys Arg Thr Ile Arg Gln Phe Asp Pro Thr
    610                 615                 620

Leu Gln Arg Thr Thr Asp Val Pro Ile Leu Asp Ser Asp Gly Ser Gly
625                 630                 635                 640

Ser Ile Asp Ser Val Tyr Asp Pro Leu Ser Tyr Val Lys Asn Val Thr
                645                 650                 655

Gly Thr Val Leu Gly Ile Tyr Pro Ser Tyr Leu Pro Tyr Asn Gln Glu
            660                 665                 670

Arg Trp Gln Gly Ala Asn Ala Met Asn Ala Tyr Gln Ile Glu Glu Leu
        675                 680                 685

Phe Ser Gln Glu Asn Leu Gln Asn Ala Ala Arg Ser Gly Arg Pro Ile
    690                 695                 700

Gln Phe Leu Val Gly Phe Asp Val Glu Asp Ser His His Asn Pro Glu
```

```
                    705                 710                 715                 720
Thr Leu Leu Pro Val Asn Leu Tyr Val Lys Pro Glu Leu Lys His Thr
                725                 730                 735
Ile Glu Leu Tyr His Asp Asn Glu Lys Gln Asn Arg Lys Glu Phe Ser
                740                 745                 750
Val Ser Lys Arg Ala Gly His Gly Val Phe Gln Ile Met Ser Gly Thr
                755                 760                 765
Leu His Asn Thr Val Gly Ser Gly Ile Leu Pro Tyr Gln Gln Glu Ile
                770                 775                 780
Arg Ile Lys Leu Thr Ser Asn Glu Pro Ile Lys Asp Ser Glu Trp Ser
785                 790                 795                 800
Ile Thr Gly Tyr Pro Asn Thr Leu Thr Leu Gln Asn Ala Val Gly Arg
                805                 810                 815
Thr Asn Asn Ala Thr Glu Lys Asn Leu Ala Leu Val Gly His Ile Asp
                820                 825                 830
Pro Gly Asn Tyr Phe Ile Thr Val Lys Phe Gly Asp Lys Val Glu Gln
                835                 840                 845
Phe Glu Ile Arg Ser Lys Pro Thr Pro Arg Ile Ile Thr Thr Ala
850                 855                 860
Asn Glu Leu Arg Gly Asn Pro Asn His Lys Pro Glu Ile Arg Val Thr
865                 870                 875                 880
Asp Ile Pro Asn Asp Thr Thr Ala Lys Ile Lys Leu Val Met Gly Gly
                885                 890                 895
Thr Asp Gly Asp His Asp Pro Glu Ile Asn Pro Tyr Thr Val Pro Glu
                900                 905                 910
Asn Tyr Thr Val Val Ala Glu Ala Tyr His Asp Asn Asp Pro Ser Lys
                915                 920                 925
Asn Gly Val Leu Thr Phe Arg Ser Ser Asp Tyr Leu Lys Asp Leu Pro
930                 935                 940
Leu Ser Gly Glu Leu Lys Ala Ile Val Tyr Tyr Asn Gln Tyr Val Gln
945                 950                 955                 960
Ser Asn Phe Ser Asn Ser Val Pro Phe Ser Ser Asp Thr Thr Pro Pro
                965                 970                 975
Thr Ile Asn Glu Pro Ala Gly Leu Val His Lys Tyr Tyr Arg Gly Asp
                980                 985                 990
His Val Glu Ile Thr Leu Pro Val Thr Asp Asn Thr Gly Gly Ser Gly
                995                 1000                1005
Leu Arg Asp Val Asn Val Asn Leu Pro Gln Gly Trp Thr Lys Thr
1010                1015                1020
Phe Thr Ile Asn Pro Asn Asn Thr Glu Gly Thr Leu Lys Leu
1025                1030                1035
Ile Gly Asn Ile Pro Ser Asn Glu Ala Tyr Asn Thr Thr Tyr His
1040                1045                1050
Phe Asn Ile Thr Ala Thr Asp Asn Ser Gly Asn Thr Thr Asn Pro
1055                1060                1065
Ala Lys Thr Phe Ile Leu Asn Val Gly Lys Leu Ala Asp Asp Leu
1070                1075                1080
Asn Pro Val Gly Leu Ser Arg Asp Gln Leu Gln Leu Val Thr Asp
1085                1090                1095
Pro Ser Ser Leu Ser Asn Ser Glu Arg Glu Glu Val Lys Arg Lys
1100                1105                1110
Ile Ser Glu Ala Asn Ala Asn Ile Arg Ser Tyr Leu Leu Gln Asn
1115                1120                1125
```

```
Asn Pro Ile Leu Ala Gly Val Asn Gly Asp Val Thr Phe Tyr Tyr
    1130            1135                1140

Arg Asp Gly Ser Val Asp Val Ile Asp Ala Glu Asn Val Ile Thr
    1145            1150                1155

Tyr Glu Pro Glu Arg Lys Ser Ile Phe Ser Glu Asn Gly Asn Thr
    1160            1165                1170

Asn Lys Lys Glu Ala Val Ile Thr Ile Ala Arg Gly Gln Asn Tyr
    1175            1180                1185

Thr Ile Gly Pro Asn Leu Arg Lys Tyr Phe Ser Leu Ser Asn Gly
    1190            1195                1200

Ser Asp Leu Pro Asn Arg Asp Phe Thr Ser Ile Ser Ala Ile Gly
    1205            1210                1215

Ser Leu Pro Ser Ser Glu Ile Ser Arg Leu Asn Val Gly Asn
    1220            1225                1230

Tyr Asn Tyr Arg Val Asn Ala Lys Asn Ala Tyr His Lys Thr Gln
    1235            1240                1245

Gln Glu Leu Asn Leu Lys Leu Lys Ile Val Glu Val Asn Ala Pro
    1250            1255                1260

Thr Gly Asn Asn Arg Val Tyr Arg Val Ser Thr Tyr Asn Leu Thr
    1265            1270                1275

Asn Asp Glu Ile Asn Lys Ile Lys Gln Ala Phe Lys Ala Ala Asn
    1280            1285                1290

Ser Gly Leu Asn Leu Asn Asp Asn Asp Ile Thr Val Ser Asn Asn
    1295            1300                1305

Phe Asp His Arg Asn Val Ser Ser Val Thr Val Thr Ile Arg Lys
    1310            1315                1320

Gly Asp Leu Ile Lys Glu Phe Ser Ser Asn Leu Asn Asn Met Asn
    1325            1330                1335

Phe Leu Arg Trp Val Asn Ile Arg Asp Asp Tyr Thr Ile Ser Trp
    1340            1345                1350

Thr Ser Ser Lys Ile Gln Gly Arg Asn Thr Asp Gly Gly Leu Glu
    1355            1360                1365

Trp Ser Pro Asp His Lys Ser Leu Ile Tyr Lys Tyr Asp Ala Thr
    1370            1375                1380

Leu Gly Arg Gln Ile Asn Thr Asn Asp Val Leu Thr Leu Leu Gln
    1385            1390                1395

Ala Thr Ala Lys Asn Ser Asn Leu Arg Ser Asn Ile Asn Ser Asn
    1400            1405                1410

Glu Lys Gln Leu Ala Glu Arg Gly Ser Asn Gly Tyr Ser Lys Ser
    1415            1420                1425

Ile Ile Arg Asp Asp Gly Glu Lys Ser Tyr Leu Leu Asn Ser Asn
    1430            1435                1440

Pro Ile Gln Val Leu Asp Leu Val Glu Pro Asp Asn Gly Tyr Gly
    1445            1450                1455

Gly Arg Gln Val Ser His Ser Asn Val Ile Tyr Asn Glu Lys Asn
    1460            1465                1470

Ser Ser Ile Val Asn Gly Gln Val Pro Glu Ala Asn Gly Ala Ser
    1475            1480                1485

Ala Phe Asn Ile Asp Lys Val Val Lys Ala Asn Ala Ala Asn Asn
    1490            1495                1500

Gly Ile Met Gly Val Ile Tyr Lys Ala Gln Leu Tyr Leu Ala Pro
    1505            1510                1515

Tyr Ser Pro Lys Gly Tyr Ile Glu Lys Leu Gly Gln Asn Leu Ser
    1520            1525                1530
```

```
Asn Thr Asn Asn Val Ile Asn Val Tyr Phe Val Pro Ser Asp Lys
    1535            1540                1545

Val Asn Pro Ser Ile Thr Val Gly Asn Tyr Asp His His Thr Val
1550            1555                1560

Tyr Ser Gly Glu Thr Phe Lys Asn Thr Ile Asn Val Asn Asp Asn
    1565            1570                1575

Tyr Gly Leu Asn Thr Val Ala Ser Thr Ser Asp Ser Ala Ile Thr
1580            1585                1590

Met Thr Arg Asn Asn Asn Glu Leu Val Gly Gln Ala Pro Asn Val
    1595            1600                1605

Thr Asn Ser Thr Asn Lys Ile Val Lys Val Lys Ala Thr Asp Lys
1610            1615                1620

Ser Gly Asn Glu Ser Ile Val Ser Phe Thr Val Asn Ile Lys Pro
    1625            1630                1635

Leu Asn Glu Lys Tyr Arg Ile Thr Thr Ser Ser Ser Asn Gln Thr
1640            1645                1650

Pro Val Arg Ile Ser Asn Ile Gln Asn Asn Ala Asn Leu Ser Ile
    1655            1660                1665

Glu Asp Gln Asn Arg Val Lys Ser Ser Leu Ser Met Thr Lys Ile
1670            1675                1680

Leu Gly Thr Arg Asn Tyr Val Asn Glu Ser Asn Asn Asp Val Arg
    1685            1690                1695

Ser Gln Val Val Ser Lys Val Asn Arg Ser Gly Asn Asn Ala Thr
1700            1705                1710

Val Asn Val Thr Thr Thr Phe Ser Asp Gly Thr Thr Asn Thr Ile
    1715            1720                1725

Thr Val Pro Val Lys His Val Leu Leu Glu Val Val Pro Thr Thr
1730            1735                1740

Arg Thr Thr Val Arg Gly Gln Gln Phe Pro Thr Gly Lys Gly Thr
    1745            1750                1755

Ser Pro Asn Asp Phe Phe Ser Leu Arg Thr Gly Gly Pro Val Asp
1760            1765                1770

Ala Arg Ile Val Trp Val Asn Asn Gln Gly Pro Asp Ile Asn Ser
    1775            1780                1785

Asn Gln Ile Gly Arg Asp Leu Thr Leu His Ala Glu Ile Phe Phe
1790            1795                1800

Asp Gly Glu Thr Thr Pro Ile Arg Lys Asp Thr Thr Tyr Lys Leu
    1805            1810                1815

Ser Gln Ser Ile Pro Lys Gln Ile Tyr Glu Thr Thr Ile Asn Gly
1820            1825                1830

Arg Phe Asn Ser Ser Gly Asp Ala Tyr Pro Gly Asn Phe Val Gln
    1835            1840                1845

Ala Val Asn Gln Tyr Trp Pro Glu His Met Asp Phe Arg Trp Ala
1850            1855                1860

Gln Gly Ser Gly Thr Pro Ser Ser Arg Asn Ala Gly Ser Phe Thr
    1865            1870                1875

Lys Thr Val Thr Val Val Tyr Gln Asn Gly Gln Thr Glu Asn Val
1880            1885                1890

Asn Val Leu Phe Lys Val Lys Pro Asn Lys Pro Val Ile Asp Ser
    1895            1900                1905

Asn Ser Val Ile Ser Lys Gly Gln Leu Asn Gly Gln Gln Ile Leu
1910            1915                1920

Val Arg Asn Val Pro Gln Asn Ala Gln Val Thr Leu Tyr Gln Ser
```

-continued

```
                1925                1930                1935

Asn Gly Thr Val Ile Pro Asn Thr Asn Thr Thr Ile Asp Ser Asn
    1940                1945                1950

Gly Ile Ala Thr Val Thr Ile Gln Gly Thr Leu Pro Thr Gly Asn
    1955                1960                1965

Ile Thr Ala Lys Thr Ser Met Thr Asn Asn Val Thr Tyr Thr Lys
    1970                1975                1980

Gln Asn Ser Ser Gly Ile Ala Ser Asn Thr Thr Glu Asp Ile Ser
    1985                1990                1995

Val Phe Ser Glu Asn Ser Asp Gln Val Asn Val Thr Ala Gly Met
    2000                2005                2010

Gln Ala Lys Asn Asp Gly Ile Lys Ile Ile Lys Gly Thr Asn Tyr
    2015                2020                2025

Asn Phe Asn Asp Phe Asn Ser Phe Ile Ser Asn Ile Pro Ala His
    2030                2035                2040

Ser Thr Leu Thr Trp Asn Glu Glu Pro Asn Ser Trp Lys Asn Asn
    2045                2050                2055

Ile Gly Thr Thr Thr Lys Thr Val Thr Val Thr Leu Pro Asn His
    2060                2065                2070

Gln Gly Thr Arg Thr Val Asp Ile Pro Ile Thr Ile Tyr Pro Thr
    2075                2080                2085

Val Thr Ala Lys Asn Pro Val Arg Asp Gln Lys Gly Arg Asn Leu
    2090                2095                2100

Thr Asn Gly Thr Asp Val Tyr Asn Tyr Ile Ile Phe Glu Asn Asn
    2105                2110                2115

Asn Arg Leu Gly Gly Thr Ala Ser Trp Lys Asp Asn Arg Gln Pro
    2120                2125                2130

Asp Lys Asn Ile Ala Gly Val Gln Asn Leu Ile Ala Leu Val Asn
    2135                2140                2145

Tyr Pro Gly Ile Ser Thr Pro Leu Glu Val Pro Val Lys Val Trp
    2150                2155                2160

Val Tyr Asn Phe Asp Phe Thr Gln Pro Ile Tyr Lys Ile Gln Val
    2165                2170                2175

Gly Asp Thr Phe Pro Lys Gly Thr Trp Ala Gly Tyr Tyr Lys His
    2180                2185                2190

Leu Glu Asn Gly Glu Gly Leu Pro Ile Asp Gly Trp Lys Phe Tyr
    2195                2200                2205

Trp Asn Gln Gln Ser Thr Gly Thr Thr Ser Asp Gln Trp Gln Ser
    2210                2215                2220

Leu Ala Tyr Thr Arg Thr Pro Phe Val Lys Thr Gly Thr Tyr Asp
    2225                2230                2235

Val Val Asn Pro Ser Asn Trp Gly Val Trp Gln Thr Ser Gln Ser
    2240                2245                2250

Ala Lys Phe Ile Val Thr Asn Ala Lys Pro Asn Gln Pro Thr Ile
    2255                2260                2265

Thr Gln Ser Lys Thr Gly Asp Val Thr Val Thr Pro Gly Ala Val
    2270                2275                2280

Arg Asn Ile Leu Ile Ser Gly Thr Asn Asp Tyr Ile Gln Ala Ser
    2285                2290                2295

Ala Asp Lys Ile Val Ile Asn Lys Asn Gly Asn Lys Leu Thr Thr
    2300                2305                2310

Phe Val Lys Asn Asn Asp Gly Arg Trp Thr Val Glu Thr Gly Ser
    2315                2320                2325
```

-continued

| | | | | | | | | | | |
|---|---|---|---|---|---|---|---|---|---|---|
| Pro | Asp | Ile | Asn | Gly | Ile | Gly | Pro | Thr | Asn | Asn | Gly | Thr | Ala | Ile |
| | 2330 | | | | 2335 | | | | 2340 | |

Pro Asp Ile Asn Gly Ile Gly Pro Thr Asn Asn Gly Thr Ala Ile
    2330              2335              2340

Ser Leu Ser Arg Leu Ala Val Arg Pro Gly Asp Ser Ile Glu Ala
    2345              2350              2355

Ile Ala Thr Glu Gly Ser Gly Glu Thr Ile Ser Thr Ser Ala Thr
    2360              2365              2370

Ser Glu Ile Tyr Ile Val Lys Ala Pro Gln Pro Glu Gln Val Ala
    2375              2380              2385

Thr His Thr Tyr Asp Asn Gly Thr Phe Asp Ile Leu Pro Asp Asn
    2390              2395              2400

Ser Arg Asn Ser Leu Asn Pro Thr Glu Arg Val Glu Ile Asn Tyr
    2405              2410              2415

Thr Glu Lys Leu Asn Gly Asn Glu Thr Gln Lys Ser Phe Thr Ile
    2420              2425              2430

Thr Lys Asn Asn Asn Gly Lys Trp Thr Ile Asn Asn Lys Pro Asn
    2435              2440              2445

Tyr Val Glu Phe Asn Gln Asp Asn Gly Lys Val Val Phe Ser Ala
    2450              2455              2460

Asn Thr Ile Lys Pro Asn Ser Gln Ile Thr Ile Thr Pro Lys Ala
    2465              2470              2475

Gly Gln Gly Asn Thr Glu Asn Thr Asn Pro Thr Val Ile Gln Ala
    2480              2485              2490

Pro Ala Gln His Thr Leu Thr Ile Asn Glu Ile Val Lys Glu Gln
    2495              2500              2505

Gly Gln Asn Val Thr Asn Asp Asp Ile Asn Asn Ala Val Gln Val
    2510              2515              2520

Pro Asn Lys Asn Arg Val Ala Ile Lys Gln Gly Asn Ala Leu Pro
    2525              2530              2535

Thr Asn Leu Ala Gly Gly Ser Thr Ser His Ile Pro Val Val Ile
    2540              2545              2550

Tyr Tyr Ser Asp Gly Ser Ser Glu Glu Ala Thr Glu Thr Val Arg
    2555              2560              2565

Thr Lys Val Asn Lys Thr Glu Leu Ile Asn Ala Arg Arg Arg Leu
    2570              2575              2580

Asp Glu Glu Ile Ser Lys Glu Asn Lys Thr Pro Ser Ser Ile Arg
    2585              2590              2595

Asn Phe Asp Gln Ala Met Asn Arg Ala Gln Ser Gln Ile Asn Thr
    2600              2605              2610

Ala Lys Ser Asp Ala Asp Gln Val Ile Gly Thr Glu Phe Ala Thr
    2615              2620              2625

Pro Gln Gln Val Asn Ser Ala Leu Ser Lys Val Gln Ala Ala Gln
    2630              2635              2640

Asn Lys Ile Asn Glu Ala Lys Ala Leu Leu Gln Asn Lys Ala Asp
    2645              2650              2655

Asn Ser Gln Leu Val Arg Ala Lys Glu Gln Leu Gln Gln Ser Ile
    2660              2665              2670

Gln Pro Ala Ala Ser Thr Asp Gly Met Thr Gln Asp Ser Thr Arg
    2675              2680              2685

Asn Tyr Lys Asn Lys Arg Gln Ala Ala Glu Gln Ala Ile Gln His
    2690              2695              2700

Ala Asn Ser Val Ile Asn Asn Gly Asp Ala Thr Ser Gln Gln Ile
    2705              2710              2715

Asn Asp Ala Lys Asn Thr Val Glu Gln Ala Gln Arg Asp Tyr Val
    2720              2725              2730

-continued

```
Glu Ala Lys Ser Asn Leu Arg Ala Asp Lys Ser Gln Leu Gln Ser
2735                2740                2745

Ala Tyr Asp Thr Leu Asn Arg Asp Val Leu Thr Asn Asp Lys Lys
2750                2755                2760

Pro Ala Ser Val Arg Arg Tyr Asn Glu Ala Ile Ser Asn Ile Arg
2765                2770                2775

Lys Glu Leu Asp Thr Ala Lys Ala Asp Ala Ser Ser Thr Leu Arg
2780                2785                2790

Asn Thr Asn Pro Ser Val Glu Gln Val Arg Asp Ala Leu Asn Lys
2795                2800                2805

Ile Asn Thr Val Gln Pro Lys Val Asn Gln Ala Ile Ala Leu Leu
2810                2815                2820

Gln Pro Lys Glu Asn Asn Ser Glu Leu Val Gln Ala Lys Lys Arg
2825                2830                2835

Leu Gln Asp Ala Val Asn Asp Ile Pro Gln Thr Gln Gly Met Thr
2840                2845                2850

Gln Gln Thr Ile Asn Asn Tyr Asn Asp Lys Gln Arg Glu Ala Glu
2855                2860                2865

Arg Ala Leu Thr Ser Ala Gln Arg Val Ile Asp Asn Gly Asp Ala
2870                2875                2880

Thr Thr Gln Glu Ile Thr Ser Glu Lys Ser Lys Val Glu Gln Ala
2885                2890                2895

Met Gln Ala Leu Thr Asn Ala Lys Ser Asn Leu Arg Ala Asp Lys
2900                2905                2910

Asn Glu Leu Gln Thr Ala Tyr Asn Lys Leu Ile Glu Asn Val Ser
2915                2920                2925

Thr Asn Gly Lys Lys Pro Ala Ser Ile Arg Gln Tyr Glu Thr Ala
2930                2935                2940

Lys Ala Arg Ile Gln Asn Gln Ile Asn Asp Ala Lys Asn Glu Ala
2945                2950                2955

Glu Arg Ile Leu Gly Asn Asp Asn Pro Gln Val Ser Gln Val Thr
2960                2965                2970

Gln Ala Leu Asn Lys Ile Lys Ala Ile Gln Pro Lys Leu Thr Glu
2975                2980                2985

Ala Ile Asn Met Leu Gln Asn Lys Glu Asn Asn Thr Glu Leu Val
2990                2995                3000

Asn Ala Lys Asn Arg Leu Glu Asn Ala Val Asn Asp Thr Asp Pro
3005                3010                3015

Thr His Gly Met Thr Gln Glu Thr Ile Asn Asn Tyr Asn Ala Lys
3020                3025                3030

Lys Arg Glu Ala Gln Asn Glu Ile Gln Lys Ala Asn Met Ile Ile
3035                3040                3045

Asn Asn Gly Asp Ala Thr Ala Gln Asp Ile Ser Ser Glu Lys Ser
3050                3055                3060

Lys Val Glu Gln Val Leu Gln Ala Leu Gln Asn Ala Lys Asn Asp
3065                3070                3075

Leu Arg Ala Asp Lys Arg Glu Leu Gln Thr Ala Tyr Asn Lys Leu
3080                3085                3090

Ile Gln Asn Val Asn Thr Asn Gly Lys Lys Pro Ser Ser Ile Gln
3095                3100                3105

Asn Tyr Lys Ser Ala Arg Arg Asn Ile Glu Asn Gln Tyr Asn Thr
3110                3115                3120

Ala Lys Asn Glu Ala His Asn Val Leu Glu Asn Thr Asn Pro Thr
```

-continued

```
              3125                3130                3135
Val Asn Ala Val Glu Asp Ala Leu Arg Lys Ile Asn Ala Ile Gln
    3140                3145                3150
Pro Glu Val Thr Lys Ala Ile Asn Ile Leu Gln Asp Lys Glu Asp
    3155                3160                3165
Asn Ser Glu Leu Val Arg Ala Lys Glu Lys Leu Asp Gln Ala Ile
    3170                3175                3180
Asn Ser Gln Pro Ser Leu Asn Gly Met Thr Gln Glu Ser Ile Asn
    3185                3190                3195
Asn Tyr Thr Thr Lys Arg Arg Glu Ala Gln Asn Ile Ala Ser Ser
    3200                3205                3210
Ala Asp Thr Ile Ile Asn Asn Gly Asp Ala Ser Ile Glu Gln Ile
    3215                3220                3225
Thr Glu Asn Lys Ile Arg Val Glu Glu Ala Thr Asn Ala Leu Asn
    3230                3235                3240
Glu Ala Lys Gln His Leu Thr Ala Asp Thr Thr Ser Leu Lys Thr
    3245                3250                3255
Glu Val Arg Lys Leu Ser Arg Arg Gly Asp Thr Asn Asn Lys Lys
    3260                3265                3270
Pro Ser Ser Val Ser Ala Tyr Asn Asn Thr Ile His Ser Leu Gln
    3275                3280                3285
Ser Glu Ile Thr Gln Thr Glu Asn Arg Ala Asn Thr Ile Ile Asn
    3290                3295                3300
Lys Pro Ile Arg Ser Val Glu Glu Val Asn Asn Ala Leu His Glu
    3305                3310                3315
Val Asn Gln Leu Asn Gln Arg Leu Thr Asp Thr Ile Asn Leu Leu
    3320                3325                3330
Gln Pro Leu Ala Asn Lys Glu Ser Leu Lys Glu Ala Arg Asn Arg
    3335                3340                3345
Leu Glu Ser Lys Ile Asn Glu Thr Val Gln Thr Asp Gly Met Thr
    3350                3355                3360
Gln Gln Ser Val Glu Asn Tyr Lys Gln Ala Lys Ile Lys Ala Gln
    3365                3370                3375
Asn Glu Ser Ser Ile Ala Gln Thr Leu Ile Asn Asn Gly Asp Ala
    3380                3385                3390
Ser Asp Gln Glu Val Ser Thr Glu Ile Glu Lys Leu Asn Gln Lys
    3395                3400                3405
Leu Ser Glu Leu Thr Asn Ser Ile Asn His Leu Thr Val Asn Lys
    3410                3415                3420
Glu Pro Leu Glu Thr Ala Lys Asn Gln Leu Gln Ala Asn Ile Asp
    3425                3430                3435
Gln Lys Pro Ser Thr Asp Gly Met Thr Gln Gln Ser Val Gln Ser
    3440                3445                3450
Tyr Glu Arg Lys Leu Gln Glu Ala Lys Asp Lys Ile Asn Ser Ile
    3455                3460                3465
Asn Asn Val Leu Ala Asn Asn Pro Asp Val Asn Ala Ile Arg Thr
    3470                3475                3480
Asn Lys Val Glu Thr Glu Gln Ile Asn Asn Glu Leu Thr Gln Ala
    3485                3490                3495
Lys Gln Gly Leu Thr Val Asp Lys Gln Pro Leu Ile Asn Ala Lys
    3500                3505                3510
Thr Ala Leu Gln Gln Ser Leu Asp Asn Gln Pro Ser Thr Thr Gly
    3515                3520                3525
```

-continued

```
Met Thr Glu Ala Thr Ile Gln Asn Tyr Asn Ala Lys Arg Gln Lys
3530                3535                3540

Ala Glu Gln Val Ile Gln Asn Ala Asn Lys Ile Ile Glu Asn Ala
3545                3550                3555

Gln Pro Ser Val Gln Val Ser Asp Glu Lys Ser Lys Val Glu
3560                3565                3570

Gln Ala Leu Ser Glu Leu Asn Asn Ala Lys Ser Ala Leu Arg Ala
3575                3580                3585

Asp Lys Gln Glu Leu Gln Gln Ala Tyr Asn Gln Leu Ile Gln Pro
3590                3595                3600

Thr Asp Leu Asn Asn Lys Lys Pro Ala Ser Ile Thr Ala Tyr Asn
3605                3610                3615

Gln Arg Tyr Gln Gln Phe Ser Asn Glu Leu Asn Ser Thr Lys Thr
3620                3625                3630

Asn Thr Asp Arg Ile Leu Lys Glu Gln Asn Pro Ser Val Ala Asp
3635                3640                3645

Val Asn Asn Ala Leu Asn Lys Val Arg Glu Val Gln Gln Lys Leu
3650                3655                3660

Asn Glu Ala Arg Ala Leu Leu Gln Asn Lys Glu Asp Asn Ser Ala
3665                3670                3675

Leu Val Arg Ala Lys Glu Gln Leu Gln Gln Ala Val Asp Gln Val
3680                3685                3690

Pro Ser Thr Glu Gly Met Thr Gln Gln Thr Lys Asp Asp Tyr Asn
3695                3700                3705

Ser Lys Gln Gln Ala Ala Gln Gln Glu Ile Ser Lys Ala Gln Gln
3710                3715                3720

Val Ile Asp Asn Gly Asp Ala Thr Thr Gln Gln Ile Ser Asn Ala
3725                3730                3735

Lys Thr Asn Val Glu Arg Ala Leu Glu Ala Leu Asn Asn Ala Lys
3740                3745                3750

Thr Gly Leu Arg Ala Asp Lys Glu Glu Leu Gln Asn Ala Tyr Asn
3755                3760                3765

Gln Leu Thr Gln Asn Ile Asp Thr Ser Gly Lys Thr Pro Ala Ser
3770                3775                3780

Ile Arg Lys Tyr Asn Glu Ala Lys Ser Arg Ile Gln Thr Gln Ile
3785                3790                3795

Asp Ser Ala Lys Asn Glu Ala Asn Ser Ile Leu Thr Asn Asp Asn
3800                3805                3810

Pro Gln Val Ser Gln Val Thr Ala Ala Leu Asn Lys Ile Lys Ala
3815                3820                3825

Val Gln Pro Glu Leu Asp Lys Ala Ile Ala Met Leu Lys Asn Lys
3830                3835                3840

Glu Asn Asn Asn Ala Leu Val Gln Ala Lys Gln Gln Leu Gln Gln
3845                3850                3855

Ile Val Asn Glu Val Asp Pro Thr Gln Gly Met Thr Thr Asp Thr
3860                3865                3870

Ala Asn Asn Tyr Lys Ser Lys Lys Arg Glu Ala Glu Asp Glu Ile
3875                3880                3885

Gln Lys Ala Gln Gln Ile Ile Asn Asn Gly Asp Ala Thr Glu Gln
3890                3895                3900

Gln Ile Thr Asn Glu Thr Asn Arg Val Asn Gln Ala Ile Asn Ala
3905                3910                3915

Ile Asn Lys Ala Lys Asn Asp Leu Arg Ala Asp Lys Ser Gln Leu
3920                3925                3930
```

-continued

```
Glu Asn Ala Tyr Asn Gln Leu Ile Gln Asn Val Asp Thr Asn Gly
    3935                3940                3945

Lys Lys Pro Ala Ser Ile Gln Gln Tyr Gln Ala Ala Arg Gln Ala
    3950                3955                3960

Ile Glu Thr Gln Tyr Asn Asn Ala Lys Ser Glu Ala His Gln Ile
    3965                3970                3975

Leu Glu Asn Ser Asn Pro Ser Val Asn Glu Val Ala Gln Ala Leu
    3980                3985                3990

Gln Lys Val Glu Ala Val Gln Leu Lys Val Asn Asp Ala Ile His
    3995                4000                4005

Ile Leu Gln Asn Lys Asp Asn Asn Ser Ala Leu Val Thr Ala Lys
    4010                4015                4020

Asn Gln Leu Gln Gln Ser Val Asn Asp Gln Pro Leu Thr Thr Gly
    4025                4030                4035

Met Thr Gln Asp Ser Ile Asn Asn Tyr Glu Ala Lys Arg Asn Glu
    4040                4045                4050

Ala Gln Ser Ala Ile Arg Asn Ala Glu Ala Val Ile Asn Asn Gly
    4055                4060                4065

Asp Ala Thr Ala Lys Gln Ile Ser Asp Glu Lys Ser Lys Val Glu
    4070                4075                4080

Gln Ala Leu Ala His Leu Asn Asp Ala Lys Gln Gln Leu Thr Ala
    4085                4090                4095

Asp Thr Thr Glu Leu Gln Thr Ala Val Gln Gln Leu Asn Arg Arg
    4100                4105                4110

Gly Asp Thr Asn Asn Lys Lys Pro Arg Ser Ile Asn Ala Tyr Asn
    4115                4120                4125

Lys Ala Ile Gln Ser Leu Glu Thr Gln Ile Thr Ser Ala Lys Asp
    4130                4135                4140

Asn Ala Asn Ala Val Ile Gln Lys Pro Ile Arg Thr Val Gln Glu
    4145                4150                4155

Val Asn Asn Ala Leu Gln Gln Val Asn Gln Leu Asn Gln Gln Leu
    4160                4165                4170

Thr Glu Ala Ile Asn Gln Leu Gln Pro Leu Ser Asn Asn Asp Ala
    4175                4180                4185

Leu Lys Ala Ala Lys Leu Asn Leu Glu Asn Lys Ile Asn Gln Thr
    4190                4195                4200

Val Gln Thr Asp Gly Met Thr Gln Gln Ser Ile Glu Ala Tyr Gln
    4205                4210                4215

Asn Ala Lys Arg Val Ala Gln Asn Glu Ser Asn Thr Ala Leu Ala
    4220                4225                4230

Leu Ile Asn Asn Gly Asp Ala Asp Glu Gln Gln Ile Thr Thr Glu
    4235                4240                4245

Thr Asp Arg Val Asn Gln Gln Thr Thr Asn Leu Thr Gln Ala Ile
    4250                4255                4260

Asn Gly Leu Thr Val Asn Lys Glu Pro Leu Glu Thr Ala Lys Thr
    4265                4270                4275

Ala Leu Gln Asn Asn Ile Asp Gln Val Pro Ser Thr Asp Gly Met
    4280                4285                4290

Thr Gln Gln Ser Val Ala Asn Tyr Asn Gln Lys Leu Gln Ile Ala
    4295                4300                4305

Lys Asn Glu Ile Asn Thr Ile Asn Asn Val Leu Ala Asn Asn Pro
    4310                4315                4320

Asp Val Asn Ala Ile Lys Thr Asn Lys Ala Glu Ala Glu Arg Ile
```

```
                    4325                4330                4335

Ser Asn Asp Leu Thr Gln Ala Lys Asn Leu Gln Val Asp Thr
    4340                4345                4350

Gln Pro Leu Glu Lys Ile Lys Arg Gln Leu Gln Asp Glu Ile Asp
    4355                4360                4365

Gln Gly Thr Asn Thr Asp Gly Met Thr Gln Asp Ser Val Asp Asn
    4370                4375                4380

Tyr Asn Asp Ser Leu Ser Ala Ala Ile Ile Glu Lys Gly Lys Val
    4385                4390                4395

Asn Lys Leu Leu Lys Arg Asn Pro Thr Val Glu Gln Val Lys Glu
    4400                4405                4410

Ser Val Ala Asn Ala Gln Gln Val Ile Gln Asp Leu Gln Asn Ala
    4415                4420                4425

Arg Thr Ser Leu Val Pro Asp Lys Thr Gln Leu Gln Glu Ala Lys
    4430                4435                4440

Asn Arg Leu Glu Asn Ser Ile Asn Gln Gln Thr Asp Thr Asp Gly
    4445                4450                4455

Met Thr Gln Asp Ser Leu Asn Asn Tyr Asn Asp Lys Leu Ala Lys
    4460                4465                4470

Ala Arg Gln Asn Leu Glu Lys Ile Ser Lys Val Leu Gly Gly Gln
    4475                4480                4485

Pro Thr Val Ala Glu Ile Arg Gln Asn Thr Asp Glu Ala Asn Ala
    4490                4495                4500

His Lys Gln Ala Leu Asp Thr Ala Arg Ser Gln Leu Thr Leu Asn
    4505                4510                4515

Arg Glu Pro Tyr Ile Asn His Ile Asn Asn Glu Ser His Leu Asn
    4520                4525                4530

Asn Ala Gln Lys Asp Asn Phe Lys Ala Gln Val Asn Ser Ala Pro
    4535                4540                4545

Asn His Asn Thr Leu Glu Thr Ile Lys Asn Lys Ala Asp Thr Leu
    4550                4555                4560

Asn Gln Ser Met Thr Ala Leu Ser Glu Ser Ile Ala Asp Tyr Glu
    4565                4570                4575

Asn Gln Lys Gln Gln Glu Asn Tyr Leu Asp Ala Ser Asn Asn Lys
    4580                4585                4590

Arg Gln Asp Tyr Asp Asn Ala Val Asn Ala Ala Lys Gly Ile Leu
    4595                4600                4605

Asn Gln Thr Gln Ser Pro Thr Met Ser Ala Asp Val Ile Asp Gln
    4610                4615                4620

Lys Ala Glu Asp Val Lys Arg Thr Lys Thr Ala Leu Asp Gly Asn
    4625                4630                4635

Gln Arg Leu Glu Val Ala Lys Gln Gln Ala Leu Asn His Leu Asn
    4640                4645                4650

Thr Leu Asn Asp Leu Asn Asp Ala Gln Arg Gln Thr Leu Thr Asp
    4655                4660                4665

Thr Ile Asn His Ser Pro Asn Ile Asn Ser Val Asn Gln Ala Lys
    4670                4675                4680

Glu Lys Ala Asn Thr Val Asn Thr Ala Met Thr Gln Leu Lys Gln
    4685                4690                4695

Thr Ile Ala Asn Tyr Asp Asp Glu Leu His Asp Gly Asn Tyr Ile
    4700                4705                4710

Asn Ala Asp Lys Asp Lys Lys Asp Ala Tyr Asn Asn Ala Val Asn
    4715                4720                4725
```

-continued

Asn Ala Lys Gln Leu Ile Asn Gln Ser Asp Ala Asn Gln Ala Gln
4730                4735                4740

Leu Asp Pro Ala Glu Ile Asn Lys Val Thr Gln Arg Val Asn Thr
4745                4750                4755

Thr Lys Asn Asp Leu Asn Gly Asn Asp Lys Leu Ala Glu Ala Lys
4760                4765                4770

Arg Asp Ala Asn Thr Thr Ile Asp Gly Leu Thr Tyr Leu Asn Glu
4775                4780                4785

Ala Gln Arg Asn Lys Ala Lys Glu Asn Val Gly Lys Ala Ser Thr
4790                4795                4800

Lys Thr Asn Ile Thr Ser Gln Leu Gln Asp Tyr Asn Gln Leu Asn
4805                4810                4815

Ile Ala Met Gln Ala Leu Arg Asn Ser Val Asn Asp Val Asn Asn
4820                4825                4830

Val Lys Ala Asn Ser Asn Tyr Ile Asn Glu Asp Asn Gly Pro Lys
4835                4840                4845

Glu Ala Tyr Asn Gln Ala Val Thr His Ala Gln Thr Leu Ile Asn
4850                4855                4860

Ala Gln Ser Asn Pro Glu Met Ser Arg Asp Val Val Asn Gln Lys
4865                4870                4875

Thr Gln Ala Val Asn Thr Ala His Gln Asn Leu His Gly Gln Gln
4880                4885                4890

Lys Leu Glu Gln Ala Gln Ser Ser Ala Asn Thr Glu Ile Gly Asn
4895                4900                4905

Leu Pro Asn Leu Thr Asn Thr Gln Lys Ala Lys Glu Lys Glu Leu
4910                4915                4920

Val Asn Ser Lys Gln Thr Arg Thr Glu Val Gln Glu Gln Leu Asn
4925                4930                4935

Gln Ala Lys Ser Leu Asp Ser Ser Met Gly Thr Leu Lys Ser Leu
4940                4945                4950

Val Ala Lys Gln Pro Thr Val Gln Lys Thr Ser Val Tyr Ile Asn
4955                4960                4965

Glu Asp Gln Pro Glu Gln Ser Ala Tyr Asn Asp Ser Ile Thr Met
4970                4975                4980

Gly Gln Thr Ile Ile Asn Lys Thr Ala Asp Pro Val Leu Asp Lys
4985                4990                4995

Thr Leu Val Asp Asn Ala Ile Ser Asn Ile Ser Thr Lys Glu Asn
5000                5005                5010

Ala Leu His Gly Glu Gln Lys Leu Thr Thr Ala Lys Thr Glu Ala
5015                5020                5025

Ile Asn Ala Leu Asn Thr Leu Ala Asp Leu Asn Thr Pro Gln Lys
5030                5035                5040

Glu Ala Ile Lys Thr Ala Ile Asn Thr Ala His Thr Arg Thr Asp
5045                5050                5055

Val Thr Ala Glu Gln Ser Lys Ala Asn Gln Ile Asn Ser Ala Met
5060                5065                5070

His Thr Leu Arg Gln Asn Ile Ser Asp Asn Glu Ser Val Thr Asn
5075                5080                5085

Glu Ser Asn Tyr Ile Asn Ala Glu Pro Glu Lys Gln His Ala Phe
5090                5095                5100

Thr Glu Ala Leu Asn Asn Ala Lys Glu Ile Val Asn Glu Gln Gln
5105                5110                5115

Ala Thr Leu Asp Ala Asn Ser Ile Asn Gln Lys Ala Gln Ala Ile
5120                5125                5130

```
Leu Thr Thr Lys Asn Ala Leu Asp Gly Glu Gln Leu Arg Arg
    5135            5140                5145

Ala Lys Glu Asn Ala Asp Gln Glu Ile Asn Thr Leu Asn Gln Leu
    5150            5155                5160

Thr Asp Ala Gln Arg Asn Ser Glu Lys Gly Leu Val Asn Ser Ser
    5165            5170                5175

Gln Thr Arg Thr Glu Val Ala Ser Gln Leu Ala Lys Ala Lys Glu
    5180            5185                5190

Leu Asn Lys Val Met Glu Gln Leu Asn His Leu Ile Asn Gly Lys
    5195            5200                5205

Asn Gln Met Ile Asn Ser Ser Lys Phe Ile Asn Glu Asp Ala Asn
    5210            5215                5220

Gln Gln Gln Ala Tyr Ser Asn Ala Ile Ala Ser Ala Glu Ala Leu
    5225            5230                5235

Lys Asn Lys Ser Gln Asn Pro Glu Leu Asp Lys Val Thr Ile Glu
    5240            5245                5250

Gln Ala Ile Asn Asn Ile Asn Ser Ala Ile Asn Asn Leu Asn Gly
    5255            5260                5265

Glu Ala Lys Leu Thr Lys Ala Lys Glu Asp Ala Val Ala Ser Ile
    5270            5275                5280

Asn Asn Leu Ser Gly Leu Thr Asn Glu Gln Lys Thr Lys Glu Asn
    5285            5290                5295

Gln Ala Val Asn Gly Ala Gln Thr Arg Asp Gln Val Ala Asn Lys
    5300            5305                5310

Leu Arg Asp Ala Glu Ala Leu Asp Gln Ser Met Gln Thr Leu Arg
    5315            5320                5325

Asp Leu Val Asn Asn Gln Asn Ala Ile His Ser Thr Ser Asn Tyr
    5330            5335                5340

Phe Asn Glu Asp Ser Thr Gln Lys Asn Thr Tyr Asp Asn Ala Ile
    5345            5350                5355

Asp Asn Gly Ser Thr Tyr Ile Thr Gly Gln His Asn Pro Glu Leu
    5360            5365                5370

Asn Lys Ser Thr Ile Asp Gln Thr Ile Ser Arg Ile Asn Thr Ala
    5375            5380                5385

Lys Asn Asp Leu His Gly Val Glu Lys Leu Gln Arg Asp Lys Gly
    5390            5395                5400

Thr Ala Asn Gln Glu Ile Gly Gln Leu Gly Tyr Leu Asn Asp Pro
    5405            5410                5415

Gln Lys Ser Gly Glu Glu Ser Leu Val Asn Gly Ser Asn Thr Arg
    5420            5425                5430

Ser Glu Val Glu Glu His Leu Asn Glu Ala Lys Ser Leu Asn Asn
    5435            5440                5445

Ala Met Lys Gln Leu Arg Asp Lys Val Ala Glu Lys Thr Asn Val
    5450            5455                5460

Lys Gln Ser Ser Asp Tyr Ile Asn Asp Ser Thr Glu His Gln Arg
    5465            5470                5475

Gly Tyr Asp Gln Ala Leu Gln Glu Ala Glu Asn Ile Ile Asn Glu
    5480            5485                5490

Ile Gly Asn Pro Thr Leu Asn Lys Ser Glu Ile Glu Gln Lys Leu
    5495            5500                5505

Gln Gln Leu Thr Asp Ala Gln Asn Ala Leu Gln Gly Ser His Leu
    5510            5515                5520

Leu Glu Glu Ala Lys Asn Asn Ala Ile Thr Gly Ile Asn Lys Leu
```

```
                        5525            5530            5535

Thr  Ala  Leu  Asn  Asp  Ala  Gln  Arg  Gln  Lys  Ala  Ile  Glu  Asn  Val
     5540                5545                5550

Gln  Ala  Gln  Gln  Thr  Ile  Pro  Ala  Val  Asn  Gln  Gln  Leu  Thr  Leu
     5555                5560                5565

Asp  Arg  Glu  Ile  Asn  Thr  Ala  Met  Gln  Ala  Leu  Arg  Asp  Lys  Val
     5570                5575                5580

Gly  Gln  Gln  Asn  Asn  Val  His  Gln  Gln  Ser  Asn  Tyr  Phe  Asn  Glu
     5585                5590                5595

Asp  Glu  Gln  Pro  Lys  His  Asn  Tyr  Asp  Asn  Ser  Val  Gln  Ala  Gly
     5600                5605                5610

Gln  Thr  Ile  Ile  Asp  Lys  Leu  Gln  Asp  Pro  Ile  Met  Asn  Lys  Asn
     5615                5620                5625

Glu  Ile  Glu  Gln  Ala  Ile  Asn  Gln  Ile  Asn  Thr  Thr  Gln  Thr  Ala
     5630                5635                5640

Leu  Ser  Gly  Glu  Asn  Lys  Leu  His  Thr  Asp  Gln  Glu  Ser  Thr  Asn
     5645                5650                5655

Arg  Gln  Ile  Glu  Gly  Leu  Ser  Ser  Leu  Asn  Thr  Ala  Gln  Ile  Asn
     5660                5665                5670

Ala  Glu  Lys  Asp  Leu  Val  Asn  Gln  Ala  Lys  Thr  Arg  Thr  Asp  Val
     5675                5680                5685

Ala  Gln  Lys  Leu  Ala  Ala  Ala  Lys  Glu  Ile  Asn  Ser  Ala  Met  Ser
     5690                5695                5700

Asn  Leu  Arg  Asp  Gly  Ile  Gln  Asn  Lys  Glu  Asp  Ile  Lys  Arg  Ser
     5705                5710                5715

Ser  Ala  Tyr  Ile  Asn  Ala  Asp  Pro  Thr  Lys  Val  Thr  Ala  Tyr  Asp
     5720                5725                5730

Gln  Ala  Leu  Gln  Asn  Ala  Glu  Asn  Ile  Ile  Asn  Ala  Thr  Pro  Asn
     5735                5740                5745

Val  Glu  Leu  Asn  Lys  Ala  Thr  Ile  Glu  Gln  Ala  Leu  Ser  Arg  Val
     5750                5755                5760

Gln  Gln  Ala  Gln  Gln  Asp  Leu  Asp  Gly  Val  Gln  Gln  Leu  Ala  Asn
     5765                5770                5775

Ala  Lys  Gln  Gln  Ala  Thr  Gln  Thr  Val  Asn  Gly  Leu  Asn  Ser  Leu
     5780                5785                5790

Asn  Asp  Gly  Gln  Lys  Arg  Glu  Leu  Asn  Leu  Leu  Ile  Asn  Ser  Ala
     5795                5800                5805

Asn  Thr  Arg  Thr  Lys  Val  Gln  Glu  Glu  Leu  Asn  Lys  Ala  Thr  Glu
     5810                5815                5820

Leu  Asn  His  Ala  Met  Glu  Ala  Leu  Arg  Asn  Ser  Val  Gln  Asn  Val
     5825                5830                5835

Asp  Gln  Val  Lys  Gln  Ser  Ser  Asn  Tyr  Val  Asn  Glu  Asp  Gln  Pro
     5840                5845                5850

Glu  Gln  His  Asn  Tyr  Asp  Asn  Ala  Val  Asn  Glu  Ala  Gln  Ala  Thr
     5855                5860                5865

Ile  Asn  Asn  Asn  Ala  Gln  Pro  Val  Leu  Asp  Lys  Leu  Ala  Ile  Glu
     5870                5875                5880

Arg  Leu  Thr  Gln  Thr  Val  Asn  Thr  Thr  Lys  Asp  Ala  Leu  His  Gly
     5885                5890                5895

Ala  Gln  Lys  Leu  Thr  Gln  Asp  Gln  Gln  Ala  Ala  Glu  Thr  Gly  Ile
     5900                5905                5910

Arg  Gly  Leu  Thr  Ser  Leu  Asn  Glu  Pro  Gln  Lys  Asn  Ala  Glu  Val
     5915                5920                5925
```

-continued

| | | | | | | | | | | | |
|---|---|---|---|---|---|---|---|---|---|---|---|
|Ala|Lys|Val|Thr|Ala|Ala|Thr|Thr|Arg|Asp|Glu|Val|Arg|Asn|Ile|
| |5930| | | |5935| | | |5940| | | | | |

Ala Lys Val Thr Ala Ala Thr Thr Arg Asp Glu Val Arg Asn Ile
    5930              5935              5940

Arg Gln Glu Ala Thr Thr Leu Asp Thr Ala Met Leu Gly Leu Arg
    5945              5950              5955

Lys Ser Ile Lys Asp Lys Asn Asp Thr Lys Asn Ser Ser Lys Tyr
    5960              5965              5970

Ile Asn Glu Asp His Asp Gln Gln Ala Tyr Asp Asn Ala Val
    5975              5980              5985

Asn Asn Ala Gln Gln Val Ile Asp Glu Thr Gln Ala Thr Leu Ser
    5990              5995              6000

Ser Asp Thr Ile Asn Gln Leu Ala Asn Ala Val Thr Gln Ala Lys
    6005              6010              6015

Ser Asn Leu His Gly Asp Thr Lys Leu Gln His Asp Lys Asp Ser
    6020              6025              6030

Ala Lys Gln Thr Ile Ala Gln Leu Gln Asn Leu Asn Ser Ala Gln
    6035              6040              6045

Lys His Met Glu Asp Ser Leu Ile Asp Asn Glu Ser Thr Arg Thr
    6050              6055              6060

Gln Val Gln His Asp Leu Thr Glu Ala Gln Ala Leu Asp Gly Leu
    6065              6070              6075

Met Gly Ala Leu Lys Glu Ser Ile Lys Asp Tyr Thr Asn Ile Val
    6080              6085              6090

Ser Asn Gly Asn Tyr Ile Asn Ala Glu Pro Ser Lys Lys Gln Ala
    6095              6100              6105

Tyr Asp Ala Ala Val Gln Asn Ala Gln Asn Ile Ile Asn Gly Thr
    6110              6115              6120

Asn Gln Pro Thr Ile Asn Lys Gly Asn Val Thr Thr Ala Thr Gln
    6125              6130              6135

Thr Val Lys Asn Thr Lys Asp Ala Leu Asp Gly Asp His Arg Leu
    6140              6145              6150

Glu Glu Ala Lys Asn Asn Ala Asn Gln Thr Ile Arg Asn Leu Ser
    6155              6160              6165

Asn Leu Asn Asn Ala Gln Lys Asp Ala Glu Lys Asn Leu Val Asn
    6170              6175              6180

Ser Ala Ser Thr Leu Glu Gln Val Gln Gln Asn Leu Gln Thr Ala
    6185              6190              6195

Gln Gln Leu Asp Asn Ala Met Gly Glu Leu Arg Gln Ser Ile Ala
    6200              6205              6210

Lys Lys Asp Gln Val Lys Ala Asp Ser Lys Tyr Leu Asn Glu Asp
    6215              6220              6225

Pro Gln Ile Lys Gln Asn Tyr Asp Asp Ala Val Gln Arg Val Glu
    6230              6235              6240

Thr Ile Ile Asn Glu Thr Gln Asn Pro Glu Leu Leu Lys Ala Asn
    6245              6250              6255

Ile Asp Gln Ala Thr Gln Ser Val Gln Asn Ala Glu Gln Ala Leu
    6260              6265              6270

His Gly Ala Glu Lys Leu Asn Gln Asp Lys Gln Thr Ser Ser Thr
    6275              6280              6285

Glu Leu Asp Gly Leu Thr Asp Leu Thr Asp Ala Gln Arg Glu Lys
    6290              6295              6300

Leu Arg Glu Gln Ile Asn Thr Ser Asn Ser Arg Asp Asp Ile Lys
    6305              6310              6315

Gln Lys Ile Glu Gln Ala Lys Ala Leu Asn Asp Ala Met Lys Lys
    6320              6325              6330

```
Leu Lys Glu Gln Val Ala Gln Lys Asp Gly Val His Ala Asn Ser
    6335            6340            6345

Asp Tyr Thr Asn Glu Asp Ser Ala Gln Lys Asp Ala Tyr Asn Asn
    6350            6355            6360

Ala Leu Lys Gln Ala Glu Asp Ile Ile Asn Asn Ser Ser Asn Pro
    6365            6370            6375

Asn Leu Asn Ala Gln Asp Ile Thr Asn Ala Leu Asn Asn Ile Lys
    6380            6385            6390

Gln Ala Gln Asp Asn Leu His Gly Ala Gln Lys Leu Gln Gln Asp
    6395            6400            6405

Lys Asn Thr Thr Asn Gln Ala Ile Gly Asn Leu Asn His Leu Asn
    6410            6415            6420

Gln Pro Gln Lys Asp Ala Leu Ile Gln Ala Ile Asn Gly Ala Thr
    6425            6430            6435

Ser Arg Asp Gln Val Ala Glu Lys Leu Lys Glu Ala Glu Ala Leu
    6440            6445            6450

Asp Glu Ala Met Lys Gln Leu Glu Asp Gln Val Asn Gln Asp Asp
    6455            6460            6465

Gln Ile Ser Asn Ser Ser Pro Phe Ile Asn Glu Asp Ser Asp Lys
    6470            6475            6480

Gln Lys Thr Tyr Asn Asp Lys Ile Gln Ala Ala Lys Glu Ile Ile
    6485            6490            6495

Asn Gln Thr Ser Asn Pro Thr Leu Asp Lys Gln Lys Ile Ala Asp
    6500            6505            6510

Thr Leu Gln Asn Ile Lys Asp Ala Val Asn Asn Leu His Gly Asp
    6515            6520            6525

Gln Lys Leu Ala Gln Ser Lys Gln Asp Ala Asn Asn Gln Leu Asn
    6530            6535            6540

His Leu Asp Asp Leu Thr Glu Glu Gln Lys Asn His Phe Lys Pro
    6545            6550            6555

Leu Ile Asn Asn Ala Asp Thr Arg Asp Glu Val Asn Lys Gln Leu
    6560            6565            6570

Glu Ile Ala Lys Gln Leu Asn Gly Asp Met Ser Thr Leu His Lys
    6575            6580            6585

Val Ile Asn Asp Lys Asp Gln Ile Gln His Leu Ser Asn Tyr Ile
    6590            6595            6600

Asn Ala Asp Asn Asp Lys Lys Gln Asn Tyr Asp Asn Ala Ile Lys
    6605            6610            6615

Glu Ala Glu Asp Leu Ile His Asn His Pro Asp Thr Leu Asp His
    6620            6625            6630

Lys Ala Leu Gln Asp Leu Leu Asn Lys Ile Asp Gln Ala His Asn
    6635            6640            6645

Glu Leu Asn Gly Glu Ser Arg Phe Lys Gln Ala Leu Asp Asn Ala
    6650            6655            6660

Leu Asn Asp Ile Asp Ser Leu Asn Ser Leu Asn Val Pro Gln Arg
    6665            6670            6675

Gln Thr Val Lys Asp Asn Ile Asn His Val Thr Thr Leu Glu Ser
    6680            6685            6690

Leu Ala Gln Glu Leu Gln Lys Ala Lys Glu Leu Asn Asp Ala Met
    6695            6700            6705

Lys Ala Met Arg Asp Ser Ile Met Asn Gln Glu Gln Ile Arg Lys
    6710            6715            6720

Asn Ser Asn Tyr Thr Asn Glu Asp Leu Ala Gln Gln Asn Ala Tyr
```

```
                6725                6730                6735

Asn His Ala Val Asp Lys Ile Asn Asn Ile Ile Gly Glu Asp Asn
    6740                6745                6750

Ala Thr Met Asp Pro Gln Ile Ile Lys Gln Ala Thr Gln Asp Ile
    6755                6760                6765

Asn Thr Ala Ile Asn Gly Leu Asn Gly Asp Gln Lys Leu Gln Asp
    6770                6775                6780

Ala Lys Thr Asp Ala Lys Gln Gln Ile Thr Asn Phe Thr Gly Leu
    6785                6790                6795

Thr Glu Pro Gln Lys Gln Ala Leu Glu Asn Ile Ile Asn Gln Gln
    6800                6805                6810

Thr Ser Arg Ala Asn Val Ala Lys Gln Leu Ser His Ala Lys Phe
    6815                6820                6825

Leu Asn Gly Lys Met Glu Glu Leu Lys Val Ala Val Ala Lys Ala
    6830                6835                6840

Ser Leu Val Arg Gln Asn Ser Asn Tyr Ile Asn Glu Asp Val Ser
    6845                6850                6855

Glu Lys Glu Ala Tyr Glu Gln Ala Ile Ala Lys Gly Gln Glu Ile
    6860                6865                6870

Ile Asn Ser Glu Asn Asn Pro Thr Ile Ser Ser Thr Asp Ile Asn
    6875                6880                6885

Arg Thr Ile Gln Glu Ile Asn Asp Ala Glu Gln Asn Leu His Gly
    6890                6895                6900

Asp Asn Lys Leu Arg Gln Ala Gln Glu Ile Ala Lys Asn Glu Ile
    6905                6910                6915

Gln Asn Leu Asp Gly Leu Asn Ser Ala Gln Ile Thr Lys Leu Ile
    6920                6925                6930

Gln Asp Ile Gly Arg Thr Thr Thr Lys Pro Ala Val Thr Gln Lys
    6935                6940                6945

Leu Glu Glu Ala Lys Ala Ile Asn Gln Ala Met Gln Gln Leu Lys
    6950                6955                6960

Gln Ser Ile Ala Asp Lys Asp Ala Thr Leu Asn Ser Ser Asn Tyr
    6965                6970                6975

Leu Asn Glu Asp Ser Glu Lys Lys Leu Ala Tyr Asp Asn Ala Val
    6980                6985                6990

Ser Gln Ala Glu Gln Leu Ile Asn Gln Leu Asn Asp Pro Thr Met
    6995                7000                7005

Asp Ile Ser Asn Ile Gln Ala Ile Thr Gln Lys Val Ile Gln Ala
    7010                7015                7020

Lys Asp Ser Leu His Gly Ala Asn Lys Leu Ala Gln Asn Gln Ala
    7025                7030                7035

Asp Ser Asn Leu Ile Ile Asn Gln Ser Thr Asn Leu Asn Asp Lys
    7040                7045                7050

Gln Lys Gln Ala Leu Asn Asp Leu Ile Asn His Ala Gln Thr Lys
    7055                7060                7065

Gln Gln Val Ala Glu Ile Ala Gln Ala Asn Lys Leu Asn Asn
    7070                7075                7080

Glu Met Gly Thr Leu Lys Thr Leu Val Glu Glu Gln Ser Asn Val
    7085                7090                7095

His Gln Gln Ser Lys Tyr Ile Asn Glu Asp Pro Gln Val Gln Asn
    7100                7105                7110

Ile Tyr Asn Asp Ser Ile Gln Lys Gly Arg Glu Ile Leu Asn Gly
    7115                7120                7125
```

-continued

```
Thr Thr Asp Asp Val Leu Asn Asn Lys Ile Ala Asp Ala Ile
    7130            7135            7140

Gln Asn Ile His Leu Thr Lys Asn Asp Leu His Gly Asp Gln Lys
    7145            7150            7155

Leu Gln Lys Ala Gln Gln Asp Ala Thr Asn Glu Leu Asn Tyr Leu
    7160            7165            7170

Thr Asn Leu Asn Asn Ser Gln Arg Gln Ser Glu His Asp Glu Ile
    7175            7180            7185

Asn Ser Ala Pro Ser Arg Thr Glu Val Ser Asn Asp Leu Asn His
    7190            7195            7200

Ala Lys Ala Leu Asn Glu Ala Met Arg Gln Leu Glu Asn Glu Val
    7205            7210            7215

Ala Leu Glu Asn Ser Val Lys Lys Leu Ser Asp Phe Ile Asn Glu
    7220            7225            7230

Asp Glu Ala Ala Gln Asn Glu Tyr Ser Asn Ala Leu Gln Lys Ala
    7235            7240            7245

Lys Asp Ile Ile Asn Gly Val Pro Ser Ser Thr Leu Asp Lys Ala
    7250            7255            7260

Thr Ile Glu Asp Ala Leu Leu Glu Leu Gln Asn Ala Arg Glu Ser
    7265            7270            7275

Leu His Gly Glu Gln Lys Leu Gln Glu Ala Lys Asn Gln Ala Val
    7280            7285            7290

Ala Glu Ile Asp Asn Leu Gln Ala Leu Asn Pro Gly Gln Val Leu
    7295            7300            7305

Ala Glu Lys Thr Leu Val Asn Gln Ala Ser Thr Lys Pro Glu Val
    7310            7315            7320

Gln Glu Ala Leu Gln Lys Ala Lys Glu Leu Asn Glu Ala Met Lys
    7325            7330            7335

Ala Leu Lys Thr Glu Ile Asn Lys Lys Glu Gln Ile Lys Ala Asp
    7340            7345            7350

Ser Arg Tyr Val Asn Ala Asp Ser Gly Leu Gln Ala Asn Tyr Asn
    7355            7360            7365

Ser Ala Leu Asn Tyr Gly Ser Gln Ile Ile Ala Thr Thr Gln Pro
    7370            7375            7380

Pro Glu Leu Asn Lys Asp Val Ile Asn Arg Ala Thr Gln Thr Ile
    7385            7390            7395

Lys Thr Ala Glu Asn Asn Leu Asn Gly Gln Ser Lys Leu Ala Glu
    7400            7405            7410

Ala Lys Ser Asp Gly Asn Gln Ser Ile Glu His Leu Gln Gly Leu
    7415            7420            7425

Thr Gln Ser Gln Lys Asp Lys Gln His Asp Leu Ile Asn Gln Ala
    7430            7435            7440

Gln Thr Lys Gln Gln Val Asp Ile Val Asn Asn Ser Lys Gln
    7445            7450            7455

Leu Asp Asn Ser Met Asn Gln Leu Gln Gln Ile Val Asn Asn Asp
    7460            7465            7470

Asn Thr Val Lys Gln Asn Ser Asp Phe Ile Asn Glu Asp Ser Ser
    7475            7480            7485

Gln Gln Asp Ala Tyr Asn His Ala Ile Gln Ala Ala Lys Asp Leu
    7490            7495            7500

Ile Thr Ala His Pro Thr Ile Met Asp Lys Asn Gln Ile Asp Gln
    7505            7510            7515

Ala Ile Glu Asn Ile Lys Gln Ala Leu Asn Asp Leu His Gly Ser
    7520            7525            7530
```

```
Asn Lys Leu Ser Glu Asp Lys Lys Glu Ala Ser Glu Gln Leu Gln
    7535            7540            7545
Asn Leu Asn Ser Leu Thr Asn Gly Gln Lys Asp Thr Ile Leu Asn
    7550            7555            7560
His Ile Phe Ser Ala Pro Thr Arg Ser Gln Val Gly Glu Lys Ile
    7565            7570            7575
Ala Ser Ala Lys Gln Leu Asn Asn Thr Met Lys Ala Leu Arg Asp
    7580            7585            7590
Ser Ile Ala Asp Asn Asn Glu Ile Leu Gln Ser Ser Lys Tyr Phe
    7595            7600            7605
Asn Glu Asp Ser Glu Gln Gln Asn Ala Tyr Asn Gln Ala Val Asn
    7610            7615            7620
Lys Ala Lys Asn Ile Ile Asn Asp Gln Pro Thr Pro Val Met Ala
    7625            7630            7635
Asn Asp Glu Ile Gln Ser Val Leu Asn Glu Val Lys Gln Thr Lys
    7640            7645            7650
Asp Asn Leu His Gly Asp Gln Lys Leu Ala Asn Asp Lys Thr Asp
    7655            7660            7665
Ala Gln Ala Thr Leu Asn Ala Leu Asn Tyr Leu Asn Gln Ala Gln
    7670            7675            7680
Arg Gly Asn Leu Glu Thr Lys Val Gln Asn Ser Asn Ser Arg Pro
    7685            7690            7695
Glu Val Gln Lys Val Val Gln Leu Ala Asn Gln Leu Asn Asp Ala
    7700            7705            7710
Met Lys Lys Leu Asp Asp Ala Leu Thr Gly Asn Asp Ala Ile Lys
    7715            7720            7725
Gln Thr Ser Asn Tyr Ile Asn Glu Asp Thr Ser Gln Gln Val Asn
    7730            7735            7740
Phe Asp Glu Tyr Thr Asp Arg Gly Lys Asn Ile Val Ala Glu Gln
    7745            7750            7755
Thr Asn Pro Asn Met Ser Pro Thr Asn Ile Asn Thr Ile Ala Asp
    7760            7765            7770
Lys Ile Thr Glu Ala Lys Asn Asp Leu His Gly Val Gln Lys Leu
    7775            7780            7785
Glu Gln Ala Gln Gln Gln Ser Ile Asn Thr Ile Asn Gln Met Thr
    7790            7795            7800
Gly Leu Asn Gln Ala Gln Lys Glu Gln Leu Asn Gln Glu Ile Gln
    7805            7810            7815
Gln Thr Gln Thr Arg Ser Glu Val His Gln Val Ile Lys Lys Ala
    7820            7825            7830
Gln Ala Leu Asn Asp Ser Met Asn Thr Leu Arg Gln Ser Ile Thr
    7835            7840            7845
Asp Glu Asn Glu Val Lys Gln Thr Ser Asn Tyr Ile Asn Glu Thr
    7850            7855            7860
Val Gly Asn Gln Thr Ala Tyr Asn Asn Ala Val Asp Arg Val Lys
    7865            7870            7875
Gln Ile Ile Asn Gln Thr Ser Asn Pro Thr Met Asn Pro Leu Glu
    7880            7885            7890
Val Glu Arg Ala Thr Ser Asn Val Lys Thr Ser Lys Asp Ala Leu
    7895            7900            7905
His Gly Glu Arg Glu Leu Asn Asp Asn Lys Asn Ser Lys Thr Phe
    7910            7915            7920
Ala Val Asn His Leu Asp Asn Leu Asn Gln Ala Gln Lys Glu Ala
```

```
                      7925                7930                7935

Leu  Thr  His  Glu  Ile  Glu  Gln  Ala  Thr  Ile  Val  Ser  Gln  Val  Asn
     7940                7945                7950

Asn  Ile  Tyr  Asn  Lys  Ala  Lys  Ala  Leu  Asn  Asn  Asp  Met  Lys  Lys
     7955                7960                7965

Leu  Lys  Asp  Ile  Val  Ala  Gln  Gln  Asp  Asn  Val  Arg  Gln  Ser  Asn
     7970                7975                7980

Asn  Tyr  Ile  Asn  Glu  Asp  Ser  Thr  Pro  Gln  Asn  Met  Tyr  Asn  Asp
     7985                7990                7995

Thr  Ile  Asn  His  Ala  Gln  Ser  Ile  Ile  Asp  Gln  Val  Ala  Asn  Pro
     8000                8005                8010

Thr  Met  Ser  His  Asp  Glu  Ile  Glu  Asn  Ala  Ile  Asn  Asn  Ile  Lys
     8015                8020                8025

His  Ala  Ile  Asn  Ala  Leu  Asp  Gly  Glu  His  Lys  Leu  Gln  Gln  Ala
     8030                8035                8040

Lys  Glu  Asn  Ala  Asn  Leu  Leu  Ile  Asn  Ser  Leu  Asn  Asp  Leu  Asn
     8045                8050                8055

Ala  Pro  Gln  Arg  Asp  Ala  Ile  Asn  Arg  Leu  Val  Asn  Glu  Ala  Gln
     8060                8065                8070

Thr  Arg  Glu  Lys  Val  Ala  Glu  Gln  Leu  Gln  Ser  Ala  Gln  Ala  Leu
     8075                8080                8085

Asn  Asp  Ala  Met  Lys  His  Leu  Arg  Asn  Ser  Ile  Gln  Asn  Gln  Ser
     8090                8095                8100

Ser  Val  Arg  Gln  Glu  Ser  Lys  Tyr  Ile  Asn  Ala  Ser  Asp  Ala  Lys
     8105                8110                8115

Lys  Glu  Gln  Tyr  Asn  His  Ala  Val  Arg  Glu  Val  Glu  Asn  Ile  Ile
     8120                8125                8130

Asn  Glu  Gln  His  Pro  Thr  Leu  Asp  Lys  Glu  Ile  Ile  Lys  Gln  Leu
     8135                8140                8145

Thr  Asp  Ala  Val  Asn  Gln  Ala  Asn  Asn  Asp  Leu  Asn  Gly  Val  Glu
     8150                8155                8160

Leu  Leu  Asp  Ala  Asp  Lys  Gln  Asn  Ala  His  Gln  Ser  Ile  Pro  Thr
     8165                8170                8175

Leu  Met  His  Leu  Asn  Gln  Ala  Gln  Gln  Asn  Ala  Leu  Asn  Glu  Lys
     8180                8185                8190

Ile  Asn  Asn  Ala  Val  Thr  Arg  Ala  Glu  Val  Ala  Ala  Ile  Ile  Gly
     8195                8200                8205

Gln  Ala  Lys  Ile  Leu  Asp  His  Ala  Met  Glu  Asn  Leu  Glu  Glu  Ser
     8210                8215                8220

Ile  Lys  Asp  Lys  Glu  Gln  Val  Lys  Gln  Ser  Ser  Asn  Tyr  Ile  Asn
     8225                8230                8235

Glu  Asp  Pro  Asp  Val  Gln  Glu  Thr  Tyr  Asn  Asn  Ala  Val  Asp  His
     8240                8245                8250

Val  Thr  Glu  Ile  Leu  Asn  Gln  Thr  Val  Asn  Pro  Thr  Leu  Ser  Ile
     8255                8260                8265

Glu  Asp  Ile  Glu  His  Ala  Ile  Asn  Glu  Val  Asn  Gln  Ala  Lys  Lys
     8270                8275                8280

Gln  Leu  Arg  Gly  Lys  Gln  Lys  Leu  Tyr  Gln  Thr  Ile  Asp  Leu  Ala
     8285                8290                8295

Asp  Lys  Glu  Leu  Ser  Lys  Leu  Asp  Asp  Leu  Thr  Ser  Gln  Gln  Ser
     8300                8305                8310

Ser  Ser  Ile  Ser  Asn  Gln  Ile  Tyr  Thr  Ala  Lys  Thr  Arg  Thr  Glu
     8315                8320                8325
```

-continued

```
Val Ala Gln Ala Ile Glu Lys Ala Lys Ser Leu Asn His Ala Met
    8330              8335              8340

Lys Ala Leu Asn Lys Val Tyr Lys Asn Thr Asp Lys Val Leu Asp
    8345              8350              8355

Ser Ser Arg Phe Ile Asn Glu Asp Gln Pro Glu Lys Glu Ala Tyr
    8360              8365              8370

Gln Gln Ala Ile Asn His Val Asp Ser Ile Ile His Arg Gln Thr
    8375              8380              8385

Asn Pro Glu Met Asp Pro Thr Val Ile Asn Ser Ile Thr His Glu
    8390              8395              8400

Leu Glu Thr Ala Gln Asn Asn Leu His Gly Asp Gln Lys Leu Ala
    8405              8410              8415

His Ala Gln Gln Asp Ala Ala Asn Val Ile Asn Gly Leu Ile His
    8420              8425              8430

Leu Asn Val Ala Gln Arg Glu Val Met Ile Asn Ala Asn Thr Asn
    8435              8440              8445

Ala Thr Thr Arg Glu Lys Val Ala Lys Asn Leu Asp Asn Ala Gln
    8450              8455              8460

Ala Leu Asp Lys Ala Met Glu Thr Leu Gln Gln Val Val Ala His
    8465              8470              8475

Lys Asn Asn Ile Leu Asn Asp Ser Lys Tyr Leu Asn Glu Asp Ser
    8480              8485              8490

Lys Tyr Gln Gln Gln Tyr Asp Arg Val Val Ala Asp Ala Glu Gln
    8495              8500              8505

Leu Leu Asn Gln Thr Thr Asn Pro Thr Leu Glu Pro Tyr Lys Ile
    8510              8515              8520

Asp Ile Val Lys Asp Asn Val Leu Ala Asn Glu Lys Ile Leu Phe
    8525              8530              8535

Gly Ala Glu Lys Leu Ser Tyr Asp Lys Ser Asn Ala Asn Asp Glu
    8540              8545              8550

Ile Lys His Met Asn Tyr Leu Asn Asn Ala Gln Lys Gln Ser Ile
    8555              8560              8565

Lys Asp Met Ile Ser His Ala Ala Leu Arg Thr Glu Val Lys Gln
    8570              8575              8580

Leu Leu Gln Gln Ala Lys Thr Leu Asp Glu Ala Met Lys Ser Leu
    8585              8590              8595

Glu Asp Lys Thr Gln Val Val Ile Thr Asp Thr Thr Leu Ser Asn
    8600              8605              8610

Tyr Thr Glu Ala Ser Glu Asp Lys Lys Glu Lys Val Asp Gln Thr
    8615              8620              8625

Val Ser His Ala Gln Ala Ile Ile Asp Lys Ile Asn Gly Ser Asn
    8630              8635              8640

Val Ser Leu Asp Gln Val Arg Gln Ala Leu Glu Gln Leu Thr Gln
    8645              8650              8655

Ala Ser Glu Asn Leu Asp Gly Asp Gln Arg Val Glu Glu Ala Lys
    8660              8665              8670

Val His Ala Asn Gln Thr Ile Asp Gln Leu Thr His Leu Asn Ser
    8675              8680              8685

Leu Gln Gln Gln Thr Ala Lys Glu Ser Val Lys Asn Ala Thr Lys
    8690              8695              8700

Leu Glu Glu Ile Ala Thr Ala Ser Asn Asp Ala Leu Ala Leu Asn
    8705              8710              8715

Lys Val Met Gly Lys Leu Glu Gln Phe Ile Asn His Ala Asp Ser
    8720              8725              8730
```

```
Val Glu Asn Ser Asp Asn Tyr Arg Gln Ala Asp Asp Lys Ile
    8735            8740            8745

Ile Ala Tyr Asp Asp Ala Leu Glu His Gly Gln Asp Ile Gln Lys
    8750            8755            8760

Ser Asn Ala Thr Gln Asn Glu Ala Lys Gln Ala Leu Gln Gln Leu
    8765            8770            8775

Ile Asn Ala Glu Thr Ser Leu Asn Gly Phe Glu Arg Leu Asn His
    8780            8785            8790

Ala Arg Pro Arg Ala Leu Glu Tyr Ile Lys Ser Leu Glu Lys Ile
    8795            8800            8805

Asn Asn Ala Gln Lys Ser Ala Leu Glu Asp Lys Val Thr Gln Ser
    8810            8815            8820

His Asp Leu Leu Glu Leu Glu His Leu Val Asn Glu Gly Thr Asn
    8825            8830            8835

Leu Asn Asp Ile Met Gly Glu Leu Ala Asn Ala Ile Val Asn Asn
    8840            8845            8850

Tyr Ala Pro Thr Lys Ala Ser Ile Asn Tyr Ile Asn Ala Asp Asn
    8855            8860            8865

Leu Arg Lys Asp Asn Phe Thr Gln Ala Ile Asn Asn Ala Arg Asp
    8870            8875            8880

Ala Leu Asn Lys Thr Gln Gly Gln Asn Leu Asp Phe Asn Ala Ile
    8885            8890            8895

Asp Thr Phe Lys Asp Ile Phe Lys Thr Lys Asp Ala Leu Asn
    8900            8905            8910

Gly Ile Glu Arg Leu Thr Ala Ala Lys Ser Lys Ala Glu Lys Leu
    8915            8920            8925

Ile Asp Ser Leu Lys Phe Ile Asn Lys Ala Gln Phe Thr His Ala
    8930            8935            8940

Asn Asp Glu Ile Met Asn Thr Asn Ser Ile Ala Gln Leu Ser Arg
    8945            8950            8955

Ile Val Asn Gln Ala Phe Asp Leu Asn Asp Ala Met Lys Ser Leu
    8960            8965            8970

Arg Asp Glu Leu Asn Asn Lys Ala Phe Pro Val Gln Ala Ser Ser
    8975            8980            8985

Asn Tyr Ile Asn Ser Asp Glu Asp Leu Lys Gln Gln Phe Asp His
    8990            8995            9000

Ala Leu Ser Asn Ala Arg Lys Val Leu Ala Lys Glu Asn Gly Lys
    9005            9010            9015

Asn Leu Asp Glu Ile Gln Ile Glu Gly Leu Lys Gln Val Ile Glu
    9020            9025            9030

Asp Thr Lys Asp Ala Leu Asn Gly Ile Gln Arg Leu Ser Lys Ala
    9035            9040            9045

Lys Ala Lys Ala Ile Gln Tyr Val Gln Ser Leu Ser Tyr Ile Asn
    9050            9055            9060

Asp Ala Gln Arg His Ile Ala Glu Asn Asn Ile His Asn Ser Asp
    9065            9070            9075

Asp Leu Ser Ser Leu Ala Asn Thr Leu Ser Lys Ala Ser Asp Leu
    9080            9085            9090

Asp Asn Ala Met Lys Asp Leu Arg Asp Thr Leu Glu Ser Asn Ser
    9095            9100            9105

Thr Ser Val Pro Asn Ser Val Asn Tyr Ile Asn Ala Asp Lys Asn
    9110            9115            9120

Phe Gln Ile Glu Phe Asp Glu Ala Leu Gln Gln Ala Ser Ala Thr
```

-continued

```
                    9125                9130                9135

Ser Ser Lys Thr Ser Glu Asn Pro Ala Thr Ile Glu Glu Val Leu
    9140                9145                9150

Gly Leu Ser Gln Ala Ile Tyr Asp Thr Lys Asn Ala Leu Asn Gly
    9155                9160                9165

Glu Gln Arg Leu Ala Thr Glu Lys Ser Lys Asp Leu Lys Leu Ile
    9170                9175                9180

Lys Gly Leu Lys Asp Leu Asn Lys Ala Gln Leu Glu Asp Val Thr
    9185                9190                9195

Asn Lys Val Asn Ser Ala Asn Thr Leu Thr Glu Leu Ser Gln Leu
    9200                9205                9210

Thr Gln Ser Thr Leu Lys Leu Asn Asp Lys Met Lys Leu Leu Arg
    9215                9220                9225

Asp Lys Leu Lys Thr Leu Val Asn Pro Val Lys Ala Ser Leu Asn
    9230                9235                9240

Tyr Arg Asn Ala Asp Tyr Asn Leu Lys Arg Gln Phe Asn Lys Ala
    9245                9250                9255

Leu Lys Glu Ala Lys Gly Ile Leu Asn Lys Asn Ser Gly Pro Asn
    9260                9265                9270

Val Asn Ile Asn Asp Ile Gln His Leu Leu Thr Gln Ile Asp Asn
    9275                9280                9285

Ala Lys Asp Gln Leu Asn Gly Glu Arg Arg Leu Lys Glu His Gln
    9290                9295                9300

Gln Lys Ser Glu Val Phe Ile Ile Lys Glu Leu Asp Ile Leu Asn
    9305                9310                9315

Asn Ala Gln Lys Ala Ala Ile Ile Asn Gln Ile Arg Ala Ser Lys
    9320                9325                9330

Asp Ile Lys Ile Ile Asn Gln Ile Val Asp Asn Ala Ile Glu Leu
    9335                9340                9345

Asn Asp Ala Met Gln Gly Leu Lys Glu His Val Ala Gln Leu Thr
    9350                9355                9360

Ala Thr Thr Lys Asp Asn Ile Glu Tyr Leu Asn Ala Asp Glu Asp
    9365                9370                9375

Leu Lys Leu Gln Tyr Asp Tyr Ala Ile Asn Leu Ala Asn Asn Val
    9380                9385                9390

Leu Asp Lys Glu Asn Gly Thr Asn Lys Asp Ala Asn Ile Ile Ile
    9395                9400                9405

Gly Met Ile Gln Asn Met Asp Asp Ala Arg Ala Leu Leu Asn Gly
    9410                9415                9420

Ile Glu Arg Leu Lys Asp Ala Gln Thr Lys Ala His Asn Asp Ile
    9425                9430                9435

Lys Asp Thr Leu Lys Arg Gln Leu Asp Glu Ile Glu His Ala Asn
    9440                9445                9450

Ala Thr Ser Asn Ser Lys Ala Gln Ala Lys Gln Met Val Asn Glu
    9455                9460                9465

Glu Ala Arg Lys Ala Phe Ser Asn Ile Asn His Ala Thr Ser Asn
    9470                9475                9480

Asp Leu Val Asn Gln Ala Lys Asp Glu Gly Gln Ser Ala Ile Glu
    9485                9490                9495

His Ile His Ala Asp Glu Leu Pro Lys Ala Lys Leu Asp Ala Asn
    9500                9505                9510

Gln Met Ile Asp Gln Lys Val Glu Asp Ile Asn His Leu Ile Ser
    9515                9520                9525
```

```
Gln Asn Pro Asn Leu Ser His Asp Glu Lys Asn Lys Leu Ile Ser
9530                9535                9540

Gln Ile Asn Lys Leu Val Asn Gly Ile Lys Asp Glu Ile Gln Gln
9545                9550                9555

Ala Ile Asn Lys Gln Gln Ile Glu Asn Ala Thr Thr Lys Leu Asp
9560                9565                9570

Glu Val Ile Glu Thr Thr Lys Lys Leu Ile Ile Ala Lys Ala Glu
9575                9580                9585

Ala Lys Gln Val Ile Lys Glu Leu Ser Gln Lys Lys Arg Asp Ala
9590                9595                9600

Ile Asn Asn Asn Thr Asp Leu Thr Pro Ser Gln Lys Ala His Ala
9605                9610                9615

Leu Ala Asp Ile Asp Lys Thr Glu Lys Asp Ala Leu Gln His Ile
9620                9625                9630

Glu Asn Ser Asn Ser Ile Asp Asp Ile Asn Asn Asn Lys Lys His
9635                9640                9645

Ala Phe Asn Thr Leu Ala His Ile Ile Ile Trp Asp Thr Asp Gln
9650                9655                9660

Gln Pro Leu Val Phe Glu Leu Pro Glu Leu Ser Leu Gln Asn Ala
9665                9670                9675

Leu Val Thr Ser Glu Val Val Val His Arg Asp Glu Thr Ile Ser
9680                9685                9690

Leu Glu Ser Ile Ile Gly Ala Met Thr Leu Thr Asp Glu Leu Lys
9695                9700                9705

Val Asn Ile Val Ser Leu Pro Asn Thr Asp Lys Val Ala Asp His
9710                9715                9720

Leu Thr Ala Lys Val Lys Val Ile Leu Ala Asp Gly Ser Tyr Val
9725                9730                9735

Thr Val Asn Val Pro Val Lys Val Val Glu Lys Glu Leu Gln Ile
9740                9745                9750

Ala Lys Lys Asp Ala Ile Lys Thr Ile Asp Val Leu Val Lys Gln
9755                9760                9765

Lys Ile Lys Asp Ile Asp Ser Asn Asn Glu Leu Thr Ser Thr Gln
9770                9775                9780

Arg Glu Asp Ala Lys Ala Glu Ile Glu Arg Leu Lys Lys Gln Ala
9785                9790                9795

Ile Asp Lys Val Asn His Ser Lys Ser Ile Lys Asp Ile Glu Thr
9800                9805                9810

Val Lys Arg Thr Asp Phe Glu Ile Asp Gln Phe Asp Pro Lys
9815                9820                9825

Arg Phe Thr Leu Asn Lys Ala Lys Lys Asp Ile Ile Thr Asp Val
9830                9835                9840

Asn Thr Gln Ile Gln Asn Gly Phe Lys Glu Ile Glu Thr Ile Lys
9845                9850                9855

Gly Leu Thr Ser Asn Glu Lys Thr Gln Phe Asp Lys Gln Leu Thr
9860                9865                9870

Glu Leu Gln Lys Glu Phe Leu Glu Lys Val Glu His Ala His Asn
9875                9880                9885

Leu Val Glu Leu Asn Gln Leu Gln Gln Glu Phe Asn Asn Arg Tyr
9890                9895                9900

Lys His Ile Leu Asn Gln Ala His Leu Leu Gly Glu Lys His Ile
9905                9910                9915

Ala Glu His Lys Leu Gly Tyr Val Val Val Asn Lys Thr Gln Gln
9920                9925                9930
```

```
Ile Leu Asn Asn Gln Ser Ala Ser Tyr Phe Ile Lys Gln Trp Ala
    9935            9940                9945

Leu Asp Arg Ile Lys Gln Ile Gln Leu Glu Thr Met Asn Ser Ile
    9950            9955                9960

Arg Gly Ala His Thr Val Gln Asp Val His Lys Ala Leu Leu Gln
    9965            9970                9975

Gly Ile Glu Gln Ile Leu Lys Val Asn Val Ser Ile Ile Asn Gln
    9980            9985                9990

Ser Phe Asn Asp Ser Leu His Asn Phe Asn Tyr Leu His Ser Lys
    9995            10000               10005

Phe Asp Ala Arg Leu Arg Glu Lys Asp Val Ala Asn His Ile Val
    10010           10015               10020

Gln Thr Glu Thr Phe Lys Glu Val Leu Lys Gly Thr Gly Val Glu
    10025           10030               10035

Pro Gly Lys Ile Asn Lys Glu Thr Gln Gln Pro Lys Leu His Lys
    10040           10045               10050

Asn Asp Asn Asp Ser Leu Phe Lys His Leu Val Asp Asn Phe Gly
    10055           10060               10065

Lys Thr Val Gly Val Ile Thr Leu Thr Gly Leu Leu Ser Ser Phe
    10070           10075               10080

Trp Leu Val Leu Ala Lys Arg Arg Lys Lys Glu Glu Glu Glu Lys
    10085           10090               10095

Gln Ser Ile Lys Asn His His Lys Asp Ile Arg Leu Ser Asp Thr
    10100           10105               10110

Asp Lys Ile Asp Pro Ile Val Ile Thr Lys Arg Lys Ile Asp Lys
    10115           10120               10125

Glu Glu Gln Ile Gln Asn Asp Asp Lys His Ser Ile Pro Val Ala
    10130           10135               10140

Lys His Lys Lys Ser Lys Glu Lys Gln Leu Ser Glu Glu Asp Ile
    10145           10150               10155

His Ser Ile Pro Val Val Lys Arg Lys Gln Asn Ser Asp Asn Lys
    10160           10165               10170

Asp Thr Lys Gln Lys Lys Val Thr Ser Lys Lys Lys Lys Thr Pro
    10175           10180               10185

Gln Ser Thr Lys Lys Val Val Lys Thr Lys Lys Arg Ser Lys Lys
    10190           10195               10200

<210> SEQ ID NO 33
<211> LENGTH: 1014
<212> TYPE: DNA
<213> ORGANISM: Staphylococcus epidermidis

<400> SEQUENCE: 33
ttgcgaaaag acgtgataga agtggttaat aaagttgaag attactactt taaaagttat      60
ccaattcaat acaatccaat aattgaatat tttaaccaaa ttaaaaataa aaaagtaatt     120
gtgtcattaa aaatatataa ggtttataaa aaaattgtgg aaaatattca tgatactgaa     180
agtcaatgga tatattctcc tgaacatgca ttacacccaa tagaatttat agaatcattt     240
tgtaaacata taagggaaa gtatgctgga acaccaattg aattagaatt atggcaaaaa     300
gcaggaatag caactatttt tggtttcatt aataaaaaa ctaaagaaag aaaatatcaa     360
gaaatctttt gggtggtggc tcgtaaaaat ggtaagtcaa ctatatctag tggaatagcg     420
ttatatttgc tcggtgctga tggtgaaggt ggcccagaag tatacacagt ggctaccaaa     480
aaagatcaag caaaaatagt atggaacgat gctaaaaaga tggtgaataa atcgccgtta     540
```

```
ttaaaactcg atttcgtaac taaagtagct gagatattaa cacctttaa tgatggacaa      600 ttaattcccc ttggtcgaga tagtgatact acagatgggt taaatgtaca tggtgctatt      660
atggatgaag tgcatgcttg gaaaacaatg caaatgtacg atgtggtttt tgacggaata      720
tctgcacgtg ataatccttt aattctagca ataactactg cgggaacaat aagaaactct      780
gtgtatgata taaatatgaa agaatcagaa aatataatca atgggttatg gaagatgaa       840 ggatataaaa atgaacgatt tttacctttg atatatgaat tagattcacg agaagaatgg      900
atagatgaaa gttgttggct aaaagccaat ccaggattag gttcaataaa gaaaatagat      960
gctatcaaaa ctaaagtaaa tagagctaag aagaatgctt tatttagagc aacc           1014

<210> SEQ ID NO 34
<211> LENGTH: 930
<212> TYPE: DNA
<213> ORGANISM: Staphylococcus epidermidis

<400> SEQUENCE: 34
gtgaaaaaaa ttctcgcttt agcaatagca tttttaatta tccttgccgc atgtgggaat       60
cacagtaacc atgaacatca ctcacatgaa ggaaaattaa agttgtaac tacaaactct       120 attctctatg acatggttaa acgtgtcggt ggaaataagg tcgatgttca tagcatcgtt      180
ccagtaggac aagatccaca tgaatatgag gttaaaccta agatattaa agcattaaca      240 gatgctgacg ttgtatttta taatggttta aacctagaaa ctggaaatgg ttggtttgaa      300
aaagcacttg accaagcagg aaaatcaaca aaagataaaa atgtgatagc agcatcaaat      360
aatgttaaac caatatactt aaatggtgag gaaggtaaca aaaacaaaca agatccacat      420
gcatggttaa gtttagagaa tggaattaaa tacgtaaaaa caatacaaaa atcactagaa      480
catcatgata aaaaagataa gtctacatat gaaaaacaag ggaatgcata tatatcaaaa      540
ttagaagaac ttaataaaga tagtaaaaat aaatttgatg acatacccaa aaatcaacgt      600
gccatgatga caagtgaagg tgcatttaaa tattttgctc aacaattcga tgttaaacca      660
ggttatattt gggagataaa cacagaaaaa caaggtacac ctggtcaaat gaaacaagcc      720
attaaatttg ttaaagataa tcatttaaaa catttattag tcgaaacaag cgtagataaa      780
aaagctatgc aaagtttatc agaagaaact aagaaagata tttatggtga agtatttacc      840
gactctatag gtaaggcagg tactaaaggt gactcatact ataaaatgat gaaatctaat      900
attgatacaa tacatggtag tatgaaataa                                       930

<210> SEQ ID NO 35
<211> LENGTH: 1131
<212> TYPE: DNA
<213> ORGANISM: Staphylococcus epidermidis

<400> SEQUENCE: 35
ttggaggtag ataatatgaa aattgggatt cctaaagaaa taagaataa tgagaatcga        60 gtggggttat ccccaagtgg tgtacatgca cttgtagacc aaggacatga agttttagta      120
gaaacaaatg ctggtctagg atcttacttt gaagatggtg attatcaaga agccggtgcc      180
aaaattgttg atgagcagtc aaaagcttgg gatgttgata tggtcatcaa agttaaagaa      240
ccacttgaat cggaatacaa attctttaaa gaagagttaa tcttatttac ttatttacac      300
cttgcgaatg aacagaaatt aactcaggca cttgtggaca acaaggttat atctattgcc      360
tatgaaactg tacaattacc agacggttct ttaccgttat taacaccaat gagtgaagtg      420
gctggtagaa tgtctacaca agtgggagct gaatttttac aaagatttaa tggaggtatg      480
```

| | |
|---|---|
| ggtatcttac taggtggcat acctggagta cctaaaggca aagtcactat cattggtggt | 540 |
| ggtcaagcag gtacaaatgc agctaagata gctttaggat tgggagctga agtgacaata | 600 |
| ctagatgtta atcctaaacg tttagaagaa ttagaggact tatttgatgg cagagtaaga | 660 |
| acaattatgt ctaatccatt aaatatagaa atgtatgtga agaaagcga tttagtgatt | 720 |
| ggagcagtcc ttattccagg tgctaaagct ccaaacttag tgactgaaga tatgataaaa | 780 |
| gaaatgaaag atggatcagt gattgtagat attgcgatag atcaaggtgg aattttttgaa | 840 |
| acaactgata agattactac tcatgataat ccgacttaca ctaaacatgg tgtcgtgcat | 900 |
| tatgctgtag ctaatatgcc aggtgccgtt ccacgtacat ctacaattgg attgaacaat | 960 |
| gcaacattac cttatgcgca attattggct aataaaggtt atcgtgaagc atttaaagta | 1020 |
| aatcatccat tatctctagg tctgaataca tttaatggac atgtgactaa taagaatgta | 1080 |
| gctgatacat ttaattttga atacacttca attgaagatg cattgaaata a | 1131 |

<210> SEQ ID NO 36
<211> LENGTH: 1203
<212> TYPE: DNA
<213> ORGANISM: Staphylococcus epidermidis

<400> SEQUENCE: 36

| | |
|---|---|
| atggaagcga tcgatacatg tccaaacaaa tattcaacta taaggagagt tttaataatg | 60 |
| aataaaaaaa cgcaaatgat acatggggga catacgacag acaactatac tggagcagtg | 120 |
| acaacccta tttatcaaac aagtacttat ttacaagatg atattggtga tttaagacaa | 180 |
| gggtacgaat attcacgtac tgcaaatcct acacgtgcgt ctcttgaaag tgttattgct | 240 |
| aatttagaac atggtaagca tggttttgct tttggttcag gaatggcagc aattagtgca | 300 |
| gttatcatgt tattagataa aggagatcac ttagttctta attctgatgt ttatggtggc | 360 |
| acatatcgtg cattaactaa agtatttact cgctttggta tagacgtaga ttttgttgat | 420 |
| acaactaaaa ttgaaaacat tgaacaatat attaaacctg aaactaaaat gttatatgta | 480 |
| gaaacacctt caaatccatt attgcgtgtg actgatatta agcatcagc aaaaattgca | 540 |
| aaaaaatatg atttgatatc tgtagtcgat aatacattta tgacaccttta ctaccaaaac | 600 |
| cctttagact ttggtattga tatcgtattg cattcggcta ctaaatatat tggaggccat | 660 |
| agtgatgttg tagctggtct tgttgctact gctgatgatg atttagcaga acgtctaggc | 720 |
| tttatttcaa attctacagg tggtgtactt ggacctcaag atagctattt attaatcaga | 780 |
| ggtattaaaa cgctaggtct aagaatggag caaataaacc gaaacgttga aggtattgtg | 840 |
| caaatgttac aaaagcaccc taagttcaa caagtattcc atcctagtat taaggaacat | 900 |
| atgaactata ctatccatca aaatcaagca actgggcata caggggtagt atcttttgaa | 960 |
| gttaaagata cagaagcggc taaacaagtg attcacgcaa caaactactt tacactggca | 1020 |
| gagagtttag gggcagttga aagtctaatt tctgtaccgg cacttatgac gcatgcgtcc | 1080 |
| atcccatcag atgtaagagc caaggaaggt attacggatg gtctcattcg tttatctatt | 1140 |
| ggtattgaag acacagaaga cttagttaat gatttagaac aagccttaaa tactttgaga | 1200 |
| taa | 1203 |

<210> SEQ ID NO 37
<211> LENGTH: 633
<212> TYPE: DNA
<213> ORGANISM: Staphylococcus epidermidis

<400> SEQUENCE: 37

| | |
|---|---:|
| ttggaactac aattagccat tgatttatta aataaagaag aagcagcaaa attagctcaa | 60 |
| aaagttgaag aatatgtaga tattgttgaa attggtacgc caattgtaat taatgaaggg | 120 |
| ttacctgcag ttcaacattt aaatgaaaat attaataatg ctaaagtatt agctgacttg | 180 |
| aaaattatgg atgcagcaga ttacgaagtg agccaagcag taaaatatgg tgcagatatt | 240 |
| gttacaattt taggtgttgc tgaagatgct tcaattaaag cagcagttga agaagcgcat | 300 |
| aaacatggaa aagcattgct tgttgatatg atagcagtgc aaaacttaga caacgtgct | 360 |
| aaagaactag atgagatggg tgcagactat atcgcagttc atacaggtta cgacttacaa | 420 |
| gctgaaggaa atctccatt agacagcttg cgtacagtta atctgttat caaaaactct | 480 |
| aaggttgcag tagcaggtgg tattaaacca gatactatca agatattgt tgctgaagat | 540 |
| ccagatttag ttattgttgg tggcggtatt gcgaatgctg acgatcctgt agaagcagca | 600 |
| aaacaatgta gagcagctat tgaaggtaaa taa | 633 |

<210> SEQ ID NO 38
<211> LENGTH: 714
<212> TYPE: DNA
<213> ORGANISM: Staphylococcus epidermidis

<400> SEQUENCE: 38

| | |
|---|---:|
| atgacaaaat taaatgttaa agtgtttgcg gatggtgcag atattgaaga aatgaaatca | 60 |
| gcatataaga atcaactcgt tgatggtttt acaacgaatc caagcttgat ggctaaagcg | 120 |
| ggtgtaactg attataaagc ttttgcagag gaagtggtta gtgaaatacc agacgcttca | 180 |
| atttcttttg aggtgtttgc tgacgattta cctactatgg aaaaagaagc tgagatttta | 240 |
| aaacaatatg gtgataatgt atttgtaaaa attcctattg ttacaacaac tggtgagtct | 300 |
| acactaccat taattaaacg tttatcatcg aaacaggtaa ggttgaatgt cacggctgtc | 360 |
| tatactatag agcaagtaaa agcaattact gacgctgtaa ctgaaggtgt gccaacatat | 420 |
| gtgtcagtat ttgcaggacg cattgcagat actggggttg atccacttcc tttgatgaaa | 480 |
| gaatcagtta aggtaactca tagtaaagaa ggcgttcaat tattatgggc aagttgtcgt | 540 |
| gaagtatata atgtaatcca agctgatgaa attggagctg atattattac ttgcccagct | 600 |
| gatgttgtaa aaaaggttaa taacaattta ggccgggata taggagaact ttcagtagat | 660 |
| acagtcaaag gttttgccaa agacattcaa agttccggtt tgtcaatttt ataa | 714 |

<210> SEQ ID NO 39
<211> LENGTH: 795
<212> TYPE: DNA
<213> ORGANISM: Staphylococcus epidermidis

<400> SEQUENCE: 39

| | |
|---|---:|
| gtgaatatat tgaaaatcca aatacttcaa ttcaatgtag aacgtggaaa tgttgataaa | 60 |
| aatatgcaaa atatcaaaac taagtttaat caatacttag ataaagatac cagtgtcgtc | 120 |
| gtgcttccag aaatgtggaa taacggttat gcattagaag aattagaaca aaaagctgat | 180 |
| aaaaatctta agacagctc tctctttata aaagacttag cacatacatt taatgtagat | 240 |
| atcattgcag gttcagtatc aaatataaga gaaaaccata tatataatac tgcttttgca | 300 |
| attaataaaa acaaagaatt gattaatgaa tatgacaaag tacatctcgt gccaatgtta | 360 |
| cgtgagccag acttttatg tggtggaaat gtagtccctg aaccttttta tttatctgat | 420 |
| caaacacttg tgacgcaaat catttgttat gacttacgat ttccagagat attgcgctat | 480 |
| ccagctagaa aaggtgctaa aattgctttt tatgtagcac agtggcctag ctcaagacta | 540 |

```
gatcattggt tatcattact aaaagcgaga gcaatcgaaa atgatatttt tattgtagct      600
tgtaatagtt gtggtgatga tggtcacacc aattatgctg gaaattcaat tgtcattaat      660
cctaatggtg aaattttagg ccatttagat gataaagaag gtgtactaac aacacatatc      720
gatgtagact tagtagatca acaaagagaa tatattccag ttttcagaaa tctaaaacca      780
catctttata aatag                                                      795
```

<210> SEQ ID NO 40
<211> LENGTH: 888
<212> TYPE: DNA
<213> ORGANISM: Staphylococcus epidermidis

<400> SEQUENCE: 40

```
atgtctaaaa tagtaggatc agatcgagtt aaaagaggaa tggctgaaat gcaaaaaggc       60
ggtgtcatta tggacgtcgt taatgcagaa caagctaaaa ttgctgaaga agccggagct      120
gttgccgtaa tggcattaga gcgtgtacca tcagatattc gtgctgctgg cggtgttgca      180
cgtatggcga atcctaaaat agttgaagaa gttatgaatg ccgtatcaat tccggttatg      240
gctaaagcca gaattggtca tattacagaa gctagagttt tagaatcgat gggtgttgac      300
tatatagatg agtctgaagt attaacgcct gcagacgaag aatatcattt aagaaaagat      360
caatttacag ttccttttgt gtgtggctgt cgtaacttag gtgaagcagc acgacgcatt      420
ggtgaaggtg cggcgatgtt gcgtacgaaa ggtgaacctg gtactggtaa tattgttgaa      480
gctgtccgtc atatgagacg tgttaattct gaagttagcc gcttaacagt tatgaatgat      540
gatgaaatta tgacatttgc aaaagatttg ggtgcacctt atgaagtatt aaaacaaatt      600
aaagataatg gacgtcttcc tgtagttaat tttgcagctg gtggtgttgc tacgcctcag      660
gatgcagcac taatgatgga attaggtgca gatggtgtat tgttggttc aggtatatttt     720 aaatctgaag atcctgaaaa atttgctaaa gctatcgttc aagctacaac acattatcaa      780
gattatgagt taatcggaaa attggctagt gagctaggta cggctatgaa aggtctagat      840
attaatcaaa tttcactaga agaagaatg caagagcgtg ttggtaa                    888
```

<210> SEQ ID NO 41
<211> LENGTH: 1746
<212> TYPE: DNA
<213> ORGANISM: Staphylococcus epidermidis

<400> SEQUENCE: 41

```
atggaggatg ctgtggtgga gatggatgct gttaaatact taaataaatt gaatttagat       60
aacattgagt taacaaaata tttgtttttt actggtaaag gcggcgtagg taaaacgacg      120
atatcaagtt ttattgcttt aaacttagca gagaatggaa agaaagtagc tttagtaagt      180
actgatccag ctagtaattt acaagatgta tttcaaatgg aattatctaa taaattaact      240
aaatatcaac ctatacctaa tctctctata gccaattttg acccgattgt tgctgcagac      300
gattataaag cacaatctat agaaccttat gagggtattc taccagaaga tgtgctttct      360
gaaatgaaag aacagttaag tggttcatgt acagttgaag tagcagcatt taatgaattt      420
acaaattttt tatccgataa aactttagaa caagaatttg atttcattat atttgataca      480
gctcccacag gtcacacctt gagaatgctt gaattacctt ctgcatggac agattattta      540
aatacaacga gtaatgacgc ttcttgctta ggtcaattat caggtttaaa tgaaaataga      600
gttaaatata attcagcact tgaaaaacta cgtaaccaag atgatacgac catgatgtta      660
gttgcgagac ctactcactc ttctatatat gaaattcaaa gagcgcaaca agaattacaa      720
```

```
caactgtcaa tttctaaatt caaagtaatc attaacaact atatagaaga aagtcacggt    780
ttaatttcga gtcagatgaa atcagaacaa gataaaaaca ttaatcattt tactgaatgg    840
ttaaataaca atcatgctta ttacgttcca tataaaaatc agaaagaaga aggtatagaa    900
agtttaacta atctattaaa tgatgataac ttaattgaaa atgatgactt tattgttgaa    960
gatcatccgc aattcaataa attaatcgat gaaattgaaa atagtaaagt tcaatattta   1020
tttacaatgg gaaaaggtgg cgttggtaaa acgacagtag caacgcaatt agctacaacg   1080
ttatctaata aaggatatcg tgttcttttta gcaactactg accctactaa agaaattaat   1140
gttgaaacta caagtaattt aaatactgct tatattgatg aagaacaagc attagaaaag   1200
tataaaaaag aagtactagc cacagtgaat gatgatacac cacaagacga tattgattat   1260
attatggaag atttaaaatc accttgtaca gaagaaatag catttttcaa agcctttagt   1320
gacattatgg agaatcaaga cgacatggat tacgtcattg tagatacagc tcctacaggc   1380
cataccttgc tgttacttga ttctagtgaa aatcatcata gagaattaaa gaaaaaatca   1440
actcaaacta ccagtaatgt tgaaacatta ttacccaaaa ttcaaaataa aaatttaaca   1500
cagatgataa ttgtaacatt agcagaaaaa acaccttatt tagaatctaa acgtttagta   1560
gaagatttaa atagagctaa tataggccat aattggtggg ttgttaatca atcgttagtt   1620
acgctaaatc aacgtgatga cctttttagt aacaaaaaag aagatgaatc attttggata   1680
aacaagatta aaaatgaaag tcttgataat tactttgtca taccttatcg agtattagaa   1740
tattga                                                              1746

<210> SEQ ID NO 42
<211> LENGTH: 1011
<212> TYPE: DNA
<213> ORGANISM: Staphylococcus epidermidis

<400> SEQUENCE: 42
atggcaatta aagtagcaat taatggtttt ggtagaattg gtcgtttagc attcagaaga     60
attcaagatg tagaaggtct tgaagtagtt gcagttaacg acttaacaga tgacgatatg    120
ttagctcatt tattaaaata cgatactatg caaggtcgtt tcactggaga agttgaagtt    180
atcgaaggtg gattccgtgt gaacggtaaa gaaattaaat cattcgatga accagatgct    240
ggtaaattac catggggcga tttagatatc gacgtagtat tagaatgtac tggtttctat    300
actgataaag aaaaagcaca agctcacatc gatgcaggtg ctaaaaaagt attaatctca    360
gctccagcta aaggtgatgt aaaaacaatc gtattcaaca ctaaccatga tacattagat    420
ggttcagaaa cagttgtttc aggtgcttct tgtactacta actcattagc accagttgca    480
aaagttttaa gtgacgaatt cggtttagtt gaaggtttca tgactacaat tcacgcttac    540
actggtgacc aaaatacaca agacgcacct cacagaaaag gtgacaaacg tcgtgcacgt    600
gcagcagctg aaaatattat ccctaactca acaggtgctg ctaaagctat cggtaaagtt    660
attccagaaa tcgatggtaa attagacggt ggagcacaac gtgttccagt tgctactggt    720
tctttaactg aattaactgt agtattagac aaacaagatg taactgttga ccaagttaac    780
agtgctatga acaagcttc tgacgaatca ttcggttaca ctgaagacga aatcgtatct    840
tctgatattg ttggtatgac ttacggttca ttatttgatg cgactcaaac tcgtgttatg    900
actgttggag atcgtcaatt agttaaagtt gcagcttggt acgacaatga aatgtcttac    960
actgctcaat tagtacgtac attagctcac ttagctgaac tttctaaata a            1011
```

```
<210> SEQ ID NO 43
<211> LENGTH: 1305
<212> TYPE: DNA
<213> ORGANISM: Staphylococcus epidermidis

<400> SEQUENCE: 43
atgccaatta ttacagatgt ttacgctcgc gaagtcttag actcacgtgg taacccaaca      60
gttgaagttg aagtattaac tgaaagcggt gctttcggac gtgcattagt accttctggt     120
gcttctactg gtgaacatga agcagttgaa ttacgtgatg gagataaatc acgttattta     180
ggtaaaggtg tgactaaagc ggtagaaaat gttaacgaaa tgatcgcacc agaaatcgtt     240
gaaggtgaat tttcagtttt agatcaagta tctattgata aaatgatgat tcaattagac     300
ggtacacaca acaaaggtaa attaggtgca atgccatttt aggtgtttc tattgccgta     360 gctcgtgcag ctgctgactt attaggtcaa ccattatata aatatttagg tggatttaat     420
ggtaaacaat tgccagtacc tatgatgaat attgttaatg gtggttctca ctcagatgca     480
ccaattgctt tccaagagtt catgatttta cctgtaggtg ctgagtcatt caagaatca     540 ttacgttggg gtgcagaaat cttccataac cttaaatcaa tcttaagtga acgtggttta     600
gaaactgcag taggtgatga aggtggtttc gctcctagat ttgaaggcac tgaagacgct     660
gtagaaacta ttattaaagc tatcgaaaaa gcaggataca aaccaggtga agatgtattc     720
ttaggatttg actgtgcttc ttctgaattc tatgaaaatg gtgtttatga ttacactaaa     780
ttcgaaggtg aacacggtgc taaacgtagt gcagcagagc aagttgacta cttagaagaa     840
ttaattggta aatatccaat catcactatt gaagatggta tggatgaaaa cgattgggaa     900
ggttggaaac aattaactga tcgtatcggt gataaagttc aattagttgg tgatgattta     960
ttcgtaacta cacactgaaat tttatctaaa ggtatcgaac aaggtattgg taactcaatc    1020
ttaatcaaag taaaccaaat cggtacatta actgaaacat tcgatgctat tgaaatggct    1080
caaaaagctg atatactgc ggttgtatct caccgttctg gtgaaactga agatactaca    1140
attgctgata tcgcagttgc tacaaatgca ggccaaatta aaacaggttc attatctaga    1200
actgaccgta ttgctaaata caatcaatta ttacgtattg aagatgaatt atacgaaaca    1260
gctaaatttg aaggaattaa atctttctac aatttagata ataa                     1305

<210> SEQ ID NO 44
<211> LENGTH: 1407
<212> TYPE: DNA
<213> ORGANISM: Staphylococcus epidermidis

<400> SEQUENCE: 44
atggtagttg gagatttccc aattgaaaca gatactattg taataggagc aggtccaggt      60
ggatatgtcg cagccattcg cgcggctcaa ttaggacaaa aggtaacaat cgttgagaaa     120
ggtaatttag gtggtgtatg cttaaacgtt ggttgtatac cttcaaaagc attactacat     180
gcttctcatc gctttgttga agcgcaaaat tcagaaaact taggggtaat tgctgaaagc     240
gtttcgttaa actatcaaaa agttcaagaa ttcaagactt ctgtagttaa taaattaact     300
ggcggtgttg aaggactttt aaaaggtaac aaagtagaga ttgttagagg tgaagcttat     360
ttcgttgata caatagttt acgtgtcatg gacgaaaaga gtgctcaaac ttacaatttc     420
aaacatgcga ttatagctac aggttcaaga ccaattgaaa ttccaaattt tgaatttggt     480
aaacgtgtta tcgattcaac aggagcttta aatctacaag aagtacctaa caaactagtt     540
gtagttggtg gcggatatat cggttctgaa ttaggtactg cttttgcaaa ctttggctct    600
gaagttacta tccttgaagg tgcaaaagat attttaggcg gatttgaaaa gcaaatgaca    660
```

```
caacctgtta aaaaaggtat gaaagaaaaa ggtatcgaaa tcgttactga agcaatggca    720
aaatctgcag aagaaactga aatggtgtc  aaagtaactt atgaggcaaa aggtgaggaa    780
caaactatcg aagctgatta tgtattagtt acagttggcc gtcgccctaa tactgatgaa    840
ttaggattag aagaacttgg tctgaaattt gctgatcgtg gattactaga agtggacaaa    900
caaagtcgta cttctattga aaatatcttt gcgattggag atattgtacc tggattacca    960
ttagctcaca aagctagtta tgaaggtaaa gttgctgctg aagcgataga tggtcaagcc   1020
gcagaggtag actatattgg tatgccagca gtttgctta  cagaaccaga attagcacaa   1080
gttggttata ctgaagctca agcaaaagaa gaaggtttat caattaaagc ttctaaattc   1140
ccttatgcag ctaatggacg agctttatca ttagatgata caaatggttt tgttaagtta   1200
attacactta aagaagatga tacgcttatt ggagcacaag ttgtaggtac tggcgcatct   1260
gatattatct ctgaattagg tttagctatt gagtcaggta tgaatgctga agatatcgca   1320
ttaactgtac atgcacaccc aactttaggt gaaatgacaa tggaagctgc tgaaaaagca   1380
attggttatc caattcatac tatgtaa                                       1407
```

<210> SEQ ID NO 45
<211> LENGTH: 840
<212> TYPE: DNA
<213> ORGANISM: Staphylococcus epidermidis

<400> SEQUENCE: 45

```
atggacttag caactaaata tttaatcaa  atcaactggc gttatgtcga tcattcaagt     60
ggtttagagc ccatgcaatc ttttgcgttt gatgacactt tttccgaaag cgttggtaaa    120
gatttatctt gtaatgtagt acgaacgtgg atacatcaac acaccgtgat tgggcatt     180 catgattcgc gttaccatt  tttaagtgat ggtattcgtt ttcttacaga tgaacaagga    240
tataatgcaa ttgttaggaa ttctggtggc ttgggtgtcg tattagatca aggaatttta    300
aacatatctt tgattttaa  aggacaaacc gaaacgacta ttgatgaagc ctttacagtg    360
atgtatttat tgattaataa aatgtttgag gatgaagatg ttagtatcga tactaaagaa    420
attgagcaat cgtattgccc aggaaaattt gatttaagta ttaatgataa gaaatttgcc    480
gggatttcgc agcgacgagt acgtggtggt atcgcagtgc aaatatactt atgtattgaa    540
ggttctggct cagaacgggc attaatgatg caacagtttt atcaacgtgc gcttaaaggg    600
gagactacta aatttcacta tccagacata gatccctcat gtatggcatc tttagaaacc    660
cttttaaata gagaaattaa agtgcaagat gttatgtttt tattattata tgcactaaaa    720
gatttagggg caaacttaaa tatggatcct attacagaag acgagtggac acgttacgaa    780
gggtattatg ataagatgtt agaacgcaat gcgaaaatga atgaaaaatt agattttag    840
```

<210> SEQ ID NO 46
<211> LENGTH: 933
<212> TYPE: DNA
<213> ORGANISM: Staphylococcus epidermidis

<400> SEQUENCE: 46

```
atggcacaaa aacctgtaga ttatgttaca caaattattg gaatacacc  tgtagtcaaa     60 ttaagaaacg ttgttgatga tgatgcagct gatatttatt taagttaga  atatcaaaat    120 ccaggtggtt cggtaaaaga tcgtatcgct ttagcgatga ttgaaaaagc tgagcgtgaa    180
gggaaaatta aacctggtga tacaatcgtt gagcctacga gtggtaacac tggtatagt    240 ctagcatttg tatgtgctgc caaggggtac aaagcagttt ttacaatgcc tgaaacaatg    300
```

```
agccaagagc gccgtaactt attaaaagct tatggtgctg aactagtatt aacaccagga      360
tctgaagcta tgaaaggtgc aataaaaaaa gctaaagaat aaaagaaga gcacggctat       420 tttgaaccac aacaattcga aaatccagca aatcctgaaa ttcatgaact tacaactgga      480
ccagaattag ttgaacaatt tgaaggtcga caaattgatg cattttttagc tggtgtagga    540 actggtggta cgttatctgg tgttggtaaa gtattgaaga agaatatcc aaatgtggaa      600 atagtagcta ttgaacctga agcttctcca gtattaagcg gtggtgaacc aggccctcat    660
aaattacaag gattgggagc aggtttcgta cctgatactt aaatacaga agtttatgac     720 agcatcatca aagtaggtaa tgatactgct atggatatgg cacgtcgtgt tgctagagaa    780
gaaggtatat tagcaggtat ttcatctggt gctgcaatat atgctgctat tcaaaaagca    840
aaagaattag gtaaaggtaa aacagttgta acagtattac caagtaatgg ggaacgttac    900
ttatcaacac cattatattc atttgataat taa                                 933

<210> SEQ ID NO 47
<211> LENGTH: 1428
<212> TYPE: DNA
<213> ORGANISM: Staphylococcus epidermidis

<400> SEQUENCE: 47
atgcattttg aaacagtaat cggacttgaa gttcatgttg agttaaaaac ggactcaaaa     60
atgttctctc catcacccgc acattttgga gctgaaccaa attcaaatac aaatgttatc   120
gacttagctt atccaggtgt attaccagta gttaatagac gtgcagtaga ttgggcaatg   180
agagcttcaa tggcattaaa tatggatatt gctacaaatt caaaatttga tcgtaaaaac   240
tatttctatc cagataatcc aaaagcatat caaatttctc agtttgatca acctattgga   300
gaaaatggct atattgatat tgaagttgat ggagaaacaa aacgtatcgg tattacacgt   360
cttcatatgg aagaagatgc aggtaaatca acacataaag atggttattc tctagtagac   420
ttaaaccgtc aaggtacgcc attaattgaa attgtatctg aacccgatat tcgttcacct   480
aaagaagcat atgcttatct agaaaaaacta cgttcaatca ttcaatatac aggtgtatct   540
gattgtaaaa tggaagaggg atccctacgt tgtgatgcta atatttcact tcgtccatat   600
ggtcaaaagg aatttggtac aaaaaactga ttgaaaaacc ttaactcatt taactacgtt    660
aaaaaaggtt tagaatatga agagaaacgt caagaagaag aattattaaa tggtggagag   720
attggtcaag aaacacgtcg atttgatgaa tctactggta aaacaatttt aatgcgtgtg    780
aaagaaggtt cagatgatta tagatatttc cctgaaccag atattgtacc attatatgta   840
gatgaagatt ggaaagcacg tgtaagaaa acaattccag aattgccaga tgaacgtaaa   900
gctaaatacg taaatgatct tggactacca gaatatgatg cgcatgtatt aacattaact   960
aaagaaatgt ctgatttctt tgaaggcgca attgaccatg gtgcagatgt taaacttact   1020
tccaactggt taatgggagg tgttaacgag tatcttaata aaaatcaagt tgaattaaaa   1080
gatacgcaac taacacctga aaatttagct ggtatgatta attaatagag acggaaca     1140 atgagtagta aaatcgctaa aaaagttttt ccagaactag cagaaaatgg tggagatgct   1200
aaacaaatta tggaagataa aggtttagta caaatttctg atgaagcaac actacttaaa   1260
tttgtaacag atgcattaga taataatcca caatcaatag aagattataa aaatggtaaa   1320
ggtaaagcta tgggattctt agtgggccaa attatgaaag cttctaaagg tcaagctaac   1380
ccacaaaaag ttaatagcct attaaaacaa gaattagata accgttaa                 1428
```

<210> SEQ ID NO 48
<211> LENGTH: 1095
<212> TYPE: DNA
<213> ORGANISM: Staphylococcus epidermidis

<400> SEQUENCE: 48

| | | |
|---|---|---|
| atgttaaaac gtgcaaatga aaatgaagag gcttggaata tatgcttaa aaattatagt | 60 |
| gaagcctatc cggaattagc tgaagaattt aaattagcaa tgagtggtaa gttaccaaat | 120 |
| aattacgctg atgccttacc agaatatgat ttaaatcaca gtggtgcttc tagagctgat | 180 |
| tcaggagaaa taattcaaaa attaagcgag tttgtacctt cattctttgg tggatcagca | 240 |
| gacttagcag gttcaaataa atctaacgtt aaagaagcta agattataa taagatact | 300 |
| ccagaaggta aaaacgtatg gtttggtgta cgtgaatttg caatgggagc agcaataaac | 360 |
| ggcatggcag cacatggtgg acttcatcca tatgcagcaa cattctttgt attcagtgat | 420 |
| tacctaaaac cagctttacg attatcatca atcatgggac tcaattcaac gttcatcttt | 480 |
| actcatgatt caattgctgt aggtgaagat ggccctacac acgaacctat tgaacaatta | 540 |
| gcaggtcttc gtgctattcc taacatgaat gttattcgtc cagctgatgg taatgaaaca | 600 |
| cgtgtagctt gggaagttgc acttgaatca gaacaaacac caacatcatt agtgttaact | 660 |
| cgtcaaaatt taccaacttt ggatgttgat aaacaaacag ttgaaaatgg tgtgagaaaa | 720 |
| ggtgcatata ttgtttttga aacagaacaa caacttgaat attattatt ggcatctgga | 780 |
| tcagaagtta atttagctgt agaagccgca aagaattag agcaacaagg taaaggtgta | 840 |
| cgagttattc tatgccaaa ctggtacgca tttgaacaac aatcttctga atataaagaa | 900 |
| tcaattttac cttctgatgt tactaaacgt atagctatcg aaatggcatc accacttggt | 960 |
| tggcataaat atgttggaat tgaaggtaaa gtcattggta taaatagttt tggcgctagt | 1020 |
| gctcctggag atttagtagt tgaaaagtat ggattcacta agaaaatat tttaaaacaa | 1080 |
| gtccgttcat tataa | 1095 |

<210> SEQ ID NO 49
<211> LENGTH: 1005
<212> TYPE: DNA
<213> ORGANISM: Staphylococcus epidermidis

<400> SEQUENCE: 49

| | | |
|---|---|---|
| gtggaatcag tgagaggttt aaaaattta agtgtaattg gcttattgtt tgttttaatt | 60 |
| gcaactgcag catgtggaaa taatagttca agtaactcaa gtaaagagtc atcaaaagat | 120 |
| ggagttgaaa tcaagcacga agaaggtact acgaaagtac ctaaacaccc taaacgtgtt | 180 |
| gttgttcttg agtattcatt tgttgatgcg ttagttgctt tagatgttaa acctgttggg | 240 |
| atagcggatg ataacaaaaa aaatcgtatt attaaaccat taagagataa aattggaaaa | 300 |
| tacacttctg taggaacacg taagccacct aacttagaag aaatcagtaa acttaaacca | 360 |
| gatttaatta ttgctgataa taatagacac aaaggtattt ataaagactt aaataaaatt | 420 |
| gctcctacga ttgaactgaa agtttcgat ggagattata tgaaaatat tgatgctttt | 480 |
| aaaacaattt caaaagcttt aggtaaagaa gaagaaggta aaaacgctt agaagaacac | 540 |
| gataagaaaa ttgaagaata taaaaagaa ataactatgg ataaaaatca aaaggtattg | 600 |
| cctgcagtag ctgctaaatc aggtttgctt gctcatccaa gcaactctta tgttggtcaa | 660 |
| ttcctaagtc aactaggttt taagaagca ttaagtgatg atgttactaa aggtttaagt | 720 |
| aagtatctta aaggacctta cttacaaatg aacactgaaa cttatctca agtgaatcct | 780 |
| gagcgtatgt tcataatgac aaacaaagca agttctaacg aaccttcact aaaagaacta | 840 |

```
gaaaaagatc ctgtatggaa gaaattaaac gctgtgaaaa atcaacgtgt tgatatttta      900
gaccgtgact tatgggcaag atcacgtggt ttaatttctt cagaagaaat ggcaaaagaa      960
cttgttgaat tatctaagac agatagtaaa aaagataata agtaa                    1005

<210> SEQ ID NO 50
<211> LENGTH: 1236
<212> TYPE: DNA
<213> ORGANISM: Staphylococcus epidermidis

<400> SEQUENCE: 50
atgagagata aatttgaaat aactttatt aagaatagga gagatttaat aatggcaaaa       60
gaaaaatttg atcgctcaaa agaacatgcc aatattggta ctatcggtca cgttgaccat     120
ggtaaaacaa ctttaacagc tgctatcgca actgtattag ctaaaaatgg tgacactgtt     180
gcacaatcat acgatatgat tgacaacgct ccagaagaaa aagaacgtgg tattacaatc     240
aatactgcac atatcgaata ccaaactgac aaacgtcact atgctcacgt tgactgccca     300
ggacacgctg actatgttaa aaacatgatc actggtgcag ctcaaatgga cggcggtatc     360
ttagttgtat ctgctgctga cggtccaatg ccacaaactc gtgaacacat cttattatca     420
cgtaacgttg gtgtaccagc attagttgta ttcttaaaca agttgacat ggtagacgac     480 gaagaattat tagaattagt tgaaatggaa gttcgtgact tattaagcga atatgacttc     540
ccaggtgacg atgtacctgt aatcgctggt tctgcattaa aagcattaga aggcgatgct     600
gaatacgaac aaaaaatctt agacttaatg caagcagttg atgattacat tccaactcca     660
gaacgtgatt ctgacaaacc attcatgatg ccagttgagg acgtattctc aatcactggt     720
cgtggtactg ttgctacagg ccgtgttgaa cgtggtcaaa tcaaagttgg tgaagaagtt     780
gaaatcatcg gtatgcacga aacttctaaa caactgtta ctggtgtaga atgttccgt      840 aaattattag actacgctga agctggtgac aacatcggtg cttttattcg tggtgttgca     900
cgtgaagacg tacaacgtgg tcaagtatta gctgctcctg gttctattac accacacaca     960
aaattcaaag ctgaagtata cgtattatct aaagatgaag gtggacgtca cactccattc    1020
ttcactaact atcgcccaca attctatttc cgtactactg acgtaactgg tgttgtaaac    1080
ttaccagaag gtacagaaat ggttatgcct ggcgacaacg ttgaaatgac agttgaatta    1140
atcgctccaa tcgctatcga agacggaact cgtttctcaa ttcgtgaagg tggacgtact    1200
gttggatcag gcgttgtaac tgaaatcttt gaataa                              1236

<210> SEQ ID NO 51
<211> LENGTH: 1287
<212> TYPE: DNA
<213> ORGANISM: Staphylococcus epidermidis

<400> SEQUENCE: 51
atgatgagtt ttgaaaaatc tattaaagca atggagcaag ctgagaaatt aatgcctggc       60
ggtgttaaca gtcccgtaag agcatttaaa tcagtagaca caccagctat ttttatggat     120
catggtgaag gatctaaaat atatgatatt gatggaaatg aatacattga ttatgtgcta     180
agttggggcc cattaattct gggacataaa atcaacaag ttatatccaa attacatgaa      240
gcagtagata aaggtacaag cttcggcgct tcaacacttc aagaaaataa acttgctgaa     300
cttgtgattg accgtgtacc ttcaattgaa aaagtaagaa tggtttcctc aggaactgaa     360
gctactttag acacacttcg tttagctagg ggttatacag gacgtaataa aattataaaa     420
tttgaagggt gttatcatgg acacagtgat tctttattga ttaaagcagg atcaggtgtt    480
```

| | |
|---|---|
| gcaacactag gtttacctga ttcaccaggc gtccctgaag gtattgctaa aaacactatc | 540 |
| acggtgccat ataatgattt agattcactt aaattagcgt tcgaaaaata tggcgatgat | 600 |
| attgctggtg ttattgttga accggttgct ggaaatatgg gtgtagtgcc tccagtgaat | 660 |
| ggatttctac aaggtttaag agatattact aatgaatatg gagcattact tatatttgat | 720 |
| gaagtgatga ctggtttccg tgtaggttat aattgtgcgc aaggatactt tggtgtaaca | 780 |
| cctgatttaa cttgcttagg aaaagtgata ggtggaggtt tacccgttgg agcttttggt | 840 |
| ggtaaaaaag aaattatgga ttacattgct cctgttggga ctatttatca agctggcaca | 900 |
| ctttcaggta atcctttagc aatgactagt ggttatgaaa cattgagtca acttactcct | 960 |
| gaatcttatg agtattttaa ttctctagga gatatacttg aaaaaggatt aaaagaggta | 1020 |
| tttgctaagt ataatgttcc aatcacagta aatcgcgctg gttcaatgat tggttacttc | 1080 |
| ttaaatgagg ggcctgtaac aaattttgag gaagcaaata aaagtgattt aaaattattt | 1140 |
| agtaatatgt atagagaaat ggctaaggaa ggtgtttaca taccaccttc acaatttgaa | 1200 |
| ggaacatttt tatcaactgc acatactaaa gatgatattg agaaaactat ccaagcattt | 1260 |
| gataatgcat taagtcgtat tgtgtga | 1287 |

<210> SEQ ID NO 52
<211> LENGTH: 861
<212> TYPE: DNA
<213> ORGANISM: Staphylococcus epidermidis

<400> SEQUENCE: 52

| | |
|---|---|
| atgcctttag tttcaatgaa agaaatgtta atcgatgcga agaaaacgg ttatgcggtt | 60 |
| ggtcaataca atcttaataa cctcgaattt acacaagcta ttttagaagc gtctcaagaa | 120 |
| gagaatgcgc cagttatttt aggtgtttct gaaggggcag ctcgttatat gagtggtttt | 180 |
| tatacagttg tgaaaatggt agaaggttta atgcatgact aaacatcac aatcccagta | 240 |
| gcaattcatt tagaccacgg ttcaagcttt gaaaaatgta agaagcaat tgatgctgga | 300 |
| ttcacatctg taatgattga tgcatctcat agtccttttg aagaaaatgt tgaaatcact | 360 |
| tctaaagtag ttgagtatgc tcatgataga ggcgtttctg tagaagctga attaggtaca | 420 |
| gttggtggac aagaagacga cgtagttgct gatggcgtta tctatgcaga ccctaaagaa | 480 |
| tgtcaagaat tagtagaaaa aactggaatt gatactttag ctccagcatt aggttctgta | 540 |
| catggaccat ataaaggtga acctaaatta ggatttaaag agatggaaga aattggtgct | 600 |
| tcaactggat tacctttagt attacacggt ggtacaggta ttccaactaa agatattcaa | 660 |
| aaagctattc cttatggtac tgctaaaatt aacgtgaata ctgaaaatca aattgcgtct | 720 |
| gctaaagcag ttcgtgaagt attaaacaac gacaaagatg tgtatgatcc acgtaaatat | 780 |
| ttaggaccag cacgtgaagc aattaaagag acagttaaag gtaaaattag agaattcggt | 840 |
| acttctaatc gcgctaaata a | 861 |

<210> SEQ ID NO 53
<211> LENGTH: 1407
<212> TYPE: DNA
<213> ORGANISM: Staphylococcus epidermidis

<400> SEQUENCE: 53

| | |
|---|---|
| atgacacaac aaattggagt agtgggttta gcagtaatgg ggaaaaacct agcttggaat | 60 |
| attgaatcac gtggttatag tgtttctgtt tataaccgat caagacaaaa aactgatgaa | 120 |
| atggttaaag aatcgcctgg aagagaaatt tacccaacat actcattaga agaatttgta | 180 |

```
gaatctttag agaaacctcg taagatttta ttaatggtaa aagctggacc tgcaacagat    240
gccactatag atggtttatt acctttatta gacgatgatg atattttaat tgatggtggt    300
aatactaatt accaagatac gattcgtcga aataaagctt tagctgaaag tagtattaac    360
tttattggta tgggagtttc tggtggagaa atcggcgcac tcacgggccc ttctttaatg    420
ccaggtggtc aaaagatgc ttataacaaa gtcagcgata tcttggacgc aattgctgct    480
aaggcacaag atggtgcttc atgtgtaact tacattggcc ctaatggtgc aggacattat    540
gttaagatgg tacacaatgg tatcgaatat gcagatatgc aattaattgc tgaaagttat    600
gcaatgatga aagatttatt aggcatgtca cataaagaaa tttctcaaac ttttaaagaa    660
tggaatgctg agaacttga aagttattta atagaaatta caggtgatat tttcaataaa    720
ttagatgatg acaatgaagc acttgtagaa aaaatattag atactgcagg tcaaaaaggc    780
acaggtaaat ggacttcaat taacgcacta gaattaggtg ttcctttaac aatcattaca    840
gaatctgtat ttgcgagatt catctcatca attaaagaag aacgtgttac tgcttctaaa    900
tctttaaaag gacctaaagc acattttgaa ggcgataaaa aaacattctt agaaaaaata    960
cgtaaggcac tttatatgag taaaatatgc tcatatgcac aaggtttcgc tcaaatgaga   1020
aaagccagtg aagataatga gtggaatttg aaattaggcg aattagcaat gatttggcgt   1080
gaaggttgta ttattcgtgc acaattccta caaaaaatta agatgccta cgataataat   1140 gaaaacttac aaaacttatt attagaccct tacttcaaaa acattgttat ggaatatcaa   1200
gatgcactac gtgaagtagt agctactagc gtgtacaatg gcgtgccaac acctggtttt   1260
tcagcaagta taaattatta tgatagttat cgctcagagg atttacctgc aaacttaatt   1320
caagcacaac gtgattactt tggcgcacat acttatgaac gtaaagaccg tgaaggtatt   1380
ttccatacac aatgggtaga agaataa                                      1407

<210> SEQ ID NO 54
<211> LENGTH: 789
<212> TYPE: DNA
<213> ORGANISM: Staphylococcus epidermidis

<400> SEQUENCE: 54
atgaaaagac ttttactttg cattgttgca cttgtttttg ttttagcagc ctgtggcaac     60
aattcatcta caataaaga taatcaatca agcagtaaag acaaggatac gttaagagtt    120
ggtacggaag gtacatatgc gcccttact taccataata aaaaagatca attaacaggt    180
tatgatattg atgtgattaa agcagttgca aaagaagaaa tcttaaaact taagtttaat    240
gaaacgtcat gggattcaat gtttgcagga ttagatgctg gtcgttttga tgttattgca    300
aatcaagtgg gtgtgaataa agatagagag aaaaaatata aattctctga accttacaca    360
tattcaagtg ctgtacttgt tgttcgtgaa atgaaaaag atattacatc attcaatgat    420
gtaaaaggta aaaagttagc acaaacgttt acgtctaatt atggtcaatt ggctaaagat    480
aagggtgcgg acattactaa ggtagatgga tttaatcaat caatggactt actattatct    540
aaacgtgtag atggtacatt taacgacagt ttatcttact tagattacag aaaacaaaag    600
cctaatgcta aaattaaagc aatcaaagga catgcagaac aaaataaatc agcatttgca    660
ttctctaaga aggttgatga aaaaacgatt gagaaattta taaaggcct agaaaaaatt    720 agagataatg gtgaattagc taaaattggt aagaaatggt ttggtcaaga tgtttctaaa    780
cctgaataa                                                          789
```

```
<210> SEQ ID NO 55
<211> LENGTH: 933
<212> TYPE: DNA
<213> ORGANISM: Staphylococcus epidermidis

<400> SEQUENCE: 55
gtgtatatga ctaaatatgt gttgaaacga ttgtgttata tgtttgtgtc gttatttatt      60
gttataacaa ttacattttt cttaatgaaa ttaatgccag gatctccgtt taatgacaca     120
aaacttaatg cgcaacaaaa agaaatatta aatgaaaagt acggtttgaa tgatccagta     180
gcattacaat atgttaatta tttgaaaaat gtagtaacag gtgattttgg caactcattt     240
caatatcata atatgccagt gtgggattta gttaaaccac gattgatacc ttcaatggag     300
atgggaataa cagctatggt tattggtgtt gttttaggtt tagtattagg tgttgctgct     360
gctactaaac aaaatacatg ggtagactat acaacaacaa ttatctctgt tatcgcagta     420
tcagtgccgt catttgtctt agcagtttta ttgcagtatg tatttgcagt taagttagaa     480
tggtttccag ttgcaggatg ggaaggtttt tctacagcta ttttaccttc tctagcacta     540
tcagctacag ttttagcaac tgttgcaaga tatattagag ctgaaatgat tgaagtactc     600
agttcagatt acatactttt agctcgagct aaaggaaatt ctactttaaa agtgctcttt     660
ggacatgcat tacgaaatgc attaattcct attattacaa tcattgtacc tatgttagca     720
ggtatattaa caggaacatt aacaattgaa atatctttg gtgttccagg attaggtgat      780
caatttgttc gttctataac tacaaatgat ttttcagtca tcatggctac aacgatatta     840
ttcagtactt tatttattgt ttcgatcttt attgtagaca ttttatatgg tgttatcgat     900
ccaagaattc gtgtacaagg gggcaagaaa taa                                   933

<210> SEQ ID NO 56
<211> LENGTH: 1545
<212> TYPE: DNA
<213> ORGANISM: Staphylococcus epidermidis

<400> SEQUENCE: 56
gtgaatgaag agcaaagaaa ggctggaacg ataaatattc tagcagaacg tgatcgtaaa      60
gctgagaaag attatagtaa atactttgaa caagtgtatc agccacctag cttaaaagaa     120
gctaaaaaaa gaggaaaaca agaagttcaa tataacagag atttttcatat agatgaaaaa     180 tacaaaggta tgggtaaagg tcgcactttt ttaattaaaa catatggatg tcaaatgaat     240
gcacatgaca ctgaagttat ggcaggaata ttaaatgcat taggatatag tgctacttcg     300
gatattaatg aagcggatgt gattttaatt aatacatgcg ccattagaga aaatgctgaa     360
aataaagtct ttagtgaaat aggaaattta aaacatttaa aaaagaacg cccagattgt     420 ttaattgggg tgtgtggttg catgtctcaa gaagaatcag tcgtaaataa aatattaaaa     480
tcttatcaaa atgtagatat ggttttttggg acacacaaca ttcatcatttt acctgagatt     540 ttagaagagg catatttatc taaagcgatg gtagttgaag tatggtctaa agagggagac     600
atcatcgaaa atttacctaa agtgcgtgac ggtcacatta aagcttgggt taatattatg     660
tatggttgcg ataagttttg tacttattgt attgttccat ttactagagg aaaagaacgt     720
agtcgtcgtc cagaggacat cattgatgag gttagagaat tagcaagaga aggttatcaa     780
gaaattacct tattaggtca aaatgtaaat tcatatggta agatatcga aggtctggat     840 tatgaattag gtgacttatt ggaagatatt tctaaaattg atataccctcg tgttcgtttt     900 acaacaagtc atcctggga ctttacagat cgaatgatag aagttatagc taaaggtggg     960
aacatagtac cgcatatcca tttaccggta caatcaggta ataaccaagt attaaagata    1020
```

| atgggggcgta aatatacaag agagagttat cttgatttag tttcaagaat aaaggaagct | 1080 |
| atccctaacg tagctctaac tactgatatc atagtaggtt atcctaatga aactgtagaa | 1140 |
| caatttgaag aaacattatc attatatgat gacgttcaat ttgagcatgc atacacatat | 1200 |
| ttatattcac aaagagatgg aacaccagca gctaaaatga aggataacgt acctttagaa | 1260 |
| gtgaaaaaag aacgtttgca aaggcttaat aagaaggttg aatatattc tcaacaagca | 1320 |
| atgagtcagt atgaaggtaa gattgttacg gtattatgtg aaggttctag taaaaaagat | 1380 |
| gagaatgttc tagcaggcta tactgataaa aataaacttg tgaattttaa aggaccaaga | 1440 |
| gagagcattg gtaaactcgt tgatgtcaaa attgacgagg caaaacaata ttctttaaat | 1500 |
| ggaacattta tacaagaaca tcaacgttca atggtgacac aataa | 1545 |

<210> SEQ ID NO 57
<211> LENGTH: 1185
<212> TYPE: DNA
<213> ORGANISM: Staphylococcus epidermidis

<400> SEQUENCE: 57

| atgtcacgca tagtattagc tgaagcatat cgaacaccta taggcgtgtt tggtggtgta | 60 |
| tttaaggata tacctgccta tgaactaggt gcaacagtta ttcgtcaaat tttagaacat | 120 |
| agtcaaatag atcctaatga aatcaatgaa gttattctag aaacgtatt acaggcaggt | 180 |
| caaggacaaa atcctgctcg tattgctgcg attcatggtg gtgtgccaga agcggtacct | 240 |
| tcttttactg taaataaagt ttgcggttct ggattaaaag cgattcaact tgcctatcaa | 300 |
| tctattgtag cgggagataa tgagattgtt atcgctggag gcatggaaag tatgtctcaa | 360 |
| tctccaatgc ttcttaaaaa tagtcgtttc ggttttaaaa tgggaaatca aactttagaa | 420 |
| gatagtatga tagctgatgg tttaactgat aagtttaatg attaccatat gggtatcaca | 480 |
| gccgaaaatc tagttgaaca gtatcagatt agtcgtaaag aacaagatca atttgcattc | 540 |
| gattctcaac aaaaagcatc acgtgcacaa caagctggtg tatttgatgc tgaaattgta | 600 |
| cctgtagagg taccacaacg taaaggcgac cccctaatta tttctcaaga tgaaggcatt | 660 |
| agacctcaaa cgacaattga taagttagca caactccgtc cagcatttaa aaaagatgga | 720 |
| tcagtaactg ctggtaatgc atccggtatc aatgacggtg ctgctgctat gctcgttatg | 780 |
| acggaggaca aagcgaaagc attgggctta caacctatag ctgtattaga tagttttggt | 840 |
| gcgagtggtg tggcgccttc aattatgggt attggtccag ttgaagcgat acataaagct | 900 |
| ttaaaacgtt ctaataaagt gataaatgat gttgatattt ttgaattaaa cgaagctttt | 960 |
| gcagcgcaat caattgctgt aaaccgtgag ttgcaattac cgcaagataa agtcaatgtt | 1020 |
| aatggtggtg cgattgcact aggacatccg ataggggctt cgggtgcgcg tacttagtt | 1080 |
| tcattattac atcaattaag tgatgctaag ccaacaggtg tggcatcttt atgtatcggt | 1140 |
| ggcggtcaag gtatcgctac ggttgtatct aaatatgaag tttaa | 1185 |

<210> SEQ ID NO 58
<211> LENGTH: 879
<212> TYPE: DNA
<213> ORGANISM: Staphylococcus epidermidis

<400> SEQUENCE: 58

| atggcaattt cagcaaaact tgttaaagaa ttacgtgaaa aaactggcgc aggaatgatg | 60 |
| gattgtaaaa aagcgctaac tgaaactgat ggtgacatcg ataaagcgat tgactactta | 120 |
| cgtgaaaaag gtattgcaaa agcagctaaa aaagctgacc gtatcgcagc agaaggactt | 180 |

```
gtacacgttg aagtaaaaga taatgaagct gcaatcgttg agattaattc agaaacagac        240
ttcgtagcac gtaacgaagg tttccaagaa ttagttaaag aaattgctaa ccatatttta        300
gatagcaagg tagaaacagt agacgctttg atggaatcta aattatctag cggtaaaact        360
gttgatgaaa gaatgaaaga agctatctca acaattggtg aaaaattaag tatccgtcgt        420
ttctctatca gaacaaaaac tgataatgat gcatttggtg catatttaca catgggtgga        480
cgtattggtg tgttaactgt agtggaaggt actactgatg aagaagctgc taaagacgta        540
gcaatgcaca ttgcggcaat caaccctaag tatgtttctt ctgaacaagt aagcgaagaa        600
gaaatcaatc atgaaagaga agtattaaaa caacaagcat taaacgaagg taaaccagag        660
aaaatcgttg aaaaaatggt tgaaggtcgt ttacgtaaat atttacaaga atttgtgct         720 gtagatcaaa acttcgttaa aaatccagac gaaactgttg aagctttctt aaaagctaaa        780
ggtggtaaac ttactgattt cgttcgttat gaagttggag aaggtatgga aaaacgtgaa        840
gaaaactttg ctgaagaagt taaaggacaa atgaaataa                              879

<210> SEQ ID NO 59
<211> LENGTH: 933
<212> TYPE: DNA
<213> ORGANISM: Staphylococcus epidermidis

<400> SEQUENCE: 59
atgactgaag tagattttga tgtagcaata atcggtgcag gtcctgccgg tatgacagca         60
gcagtatatg catctcgtgc caatttaaaa actgtcatga ttgaacgcgg tatgccaggc        120
ggtcaaatgg caaacactga agaagtagag aattttccag gatttgagat gatcacaggt        180
cctgacttat ctactaaaat gtttgaacat gctaaaaaat ttggtgcgga ataccaatat        240
ggcgatatta atctgttga agataaaggc gactataaag ttatcaattt agggaataaa        300
gagataacag cacatgcagt tattatctca actggagcag agtataaaaa gattggcgtt        360
cctggtgaac aagaattagg aggacgtgga gtaagttatt gtgcggtttg tgatggagca        420
ttctttaaaa ataaacgtct tttcgtaatt ggcggcggag attcagcggt agaagaaggt        480
actttcttaa ctaaatttgc agataaagta acgattgttc accgtagaga tgaattacgt        540
gcacaaaaca tcttgcaaga acgtgccttc aaaaatgata agttgactt tatttggagt        600 catacactta aaacaattaa tgaaaaagat ggtaaagttg gttcagttac acttgaatca        660
actaaagatg gtgctgaaca gacttatgat gccgacggtg tattcattta tattggaatg        720
aaaccactca cagcaccatt taaaaatctt ggtattacaa atgacgcggg atacattgtc        780
acacaagatg acatgagtac taaagtcgga ggtatttttg ctgcaggtga cgttcgtgat        840
aaagggttac gtcaaattgt tactgctaca ggagacggta gtattgcggc tcaaagtgca        900
gctgattata ttacagaatt aaaagataat taa                                    933

<210> SEQ ID NO 60
<211> LENGTH: 1398
<212> TYPE: DNA
<213> ORGANISM: Staphylococcus epidermidis

<400> SEQUENCE: 60
atgactcaaa agtatagata tcctactttt ttagaatcta tttctactat tttagttatg         60
gttgtcgttg tagtaattgg ttttgttttc tttaatgtcc cgatacaaat attattatta        120
atttcttcag cttatgcagc attgattgca catagagtgg gattaaaatg gaaggattta        180
gaagagggga ttactcatcg attgagcacg gcgatgccag ctatctttat tattttagct        240
```

```
gttggaatca ttgtaggaag ttggatgtat tctggaacag ttccagcgtt aatttactat        300
ggacttaaat ttttaaaccc aagttattta ttagtatctg catttataat cagtgcaatg        360
acttcaatcg ctacaggaac ggcttgggga tcggcatcta cagcaggcat tgcactcata        420
tcaattgcta atcaattagg tgtgccagca ggtatggctg ctggtgccat tattgcaggg        480 gcggttttg tgataaaat gtctccatta tctgatacta caaatttggc agctcttgta         540
actaaagtta atattttgc tcacattaaa tcgatgatgt ggacaacaat ccctgcttct        600
ataataggat tggctatatg gtttattgtt ggattacaat ataagggaga cgcaaataca        660
caacaaattc aaaatctatt aaaagaatta acaacaattt aacttgaa ttttgggta         720 tggatcccac ttattatcat agttttatgt ttaatattta gaatctctac agtaccgtca        780
atgcttatct ctagtatcag tgctttagtt attggaacat tcgatcatca atttaatatg        840
aaagatggtt ttaaagcttc ttttgatgga tttaatcata caatgctaca ccagtctcat        900
atttcagata atgctaagac gttgattgag caggggtggta tgatgagtat gactcaaatc       960
attgtaacta tattttgtgg ttatgctttt gctggtattg ttgaaaaggc aggttgttta      1020
gacgtaattt tagagacaat agctaaaggc gtaaagtcag ttggaacact aatattaata       1080
actgtagttt gtagtattat gctagtattt gcagctggag ttgcttcaat agttattatt      1140
atggtaggcg tacttatgaa agatatgttc gaaaagatga atgtctcaaa gtcagtgtta      1200
tctcgtacac ttgaagattc aagtacaatg gtattgccac tcattccatg gggcacatct      1260
ggtatatatt atgcacacca acttaatgtt tcagttgatc agttctttat atgggcaatc      1320
ccatgttact tatgtgcatt cattgcaata atttatggct ttacaggtat aggaattaaa      1380
aaaataagta gaaaataa                                                     1398
```

<210> SEQ ID NO 61
<211> LENGTH: 708
<212> TYPE: DNA
<213> ORGANISM: Staphylococcus epidermidis

<400> SEQUENCE: 61

```
atgaaaaaaa cagttatcgc ttctacatta gcagtatctt taggaattgc aggttacggt         60
ttatcaggac atgaagcaca cgcttcagaa actacaaacg ttgataaagc acacttagta        120
gatttagcac aacataatcc tgaagaatta aatgctaaac cagttcaagc tggtgcttac        180
gatattcatt tcgtagacaa tggataccaa tacaacttca cttcaaatgg ttctgaatgg        240
tcatggagct acgctgtagc tggttcagat gctgattaca cagaatcatc atcaaaccaa        300
gaagtaagtg caaatacaca atctagtaac acaaatgtac aagctgtttc agctccaact        360
tcttcagaaa gtcgtagcta cagcacatca actacttcat actcagcacc aagccataac        420
tacagctctc acagtagttc agtaagatta tcaaatggta atactgctgg ttctgtaggt        480
tcatatgctg ctgctcaaat ggctgcacgt actggtgtat ctgcttcaac atgggaacac        540
atcattgcta gagaatcaaa tggtcaatta catgcacgta atgcttcagg tgctgctgga        600
ttattccaaa ctatgccagg ttggggttca actggttcag taaatgatca aatcaatgcc        660
gcttataaag catataaagc acaaggttta tctgcttggg gtatgtaa                     708
```

<210> SEQ ID NO 62
<211> LENGTH: 891
<212> TYPE: DNA
<213> ORGANISM: Staphylococcus epidermidis

<400> SEQUENCE: 62

```
atgaataaag aacaattaga aaaaatgact catggtaaag gattcattgc tgcattagac    60
caaagtggtg gtagtacacc taaagcactt aaagaatatg gtgtgaatga agaccaatac   120
agtaatgaag acgaaatgtt ccaacttgtt cacgatatgc gtacacgtgt tgtaacttca   180
ccttcatttt cacctgataa aattttaggt gcgattttat tcgaacaaac tatggatcgc   240
gaagttgaag gtaaatacac tggagactat ttagcggaca aaggcgttgt tcctttctta   300
aaagtcgaca aaggtcttgc tgaagagaaa aatggcgtac aattaatgaa acctattgat   360
gatttagatg aaactttaga tcgtgcaaat gaacgtcata tcttcggtac taaaatgcgt   420
tctaacatcc ttgaacttaa tgaacaagga atcaaagatg ttgttgaaca acaatttgaa   480
ttcgctaaaa aaatcatcgc taaaggttta gtacctatta tcgaaccaga agttaatatt   540
aatgctaaag ataaatctga aattgagaaa gttttaaaag ctgaaatcaa aaaaggttta   600
gattcattaa acgatgatca attagttatg ttaaaattaa ctattcctac tgaagctaac   660
ttatataaag atttagctga ccaccctaat gttgtacgtg tagtagtatt atcaggtggt   720
tacagccgag atgaagctaa caaattgtta aaagataacg atgaattaat tgcaagcttc   780
tcacgtgcat tagcaagtga cttacgtgct agccaatcac aagaagaatt cgataaagca   840
ttaggcgatg ctgtagattc aatctatgat gcgtcagtaa ataaaaacta a            891
```

<210> SEQ ID NO 63
<211> LENGTH: 792
<212> TYPE: DNA
<213> ORGANISM: Staphylococcus epidermidis

<400> SEQUENCE: 63

```
ttgaaagaga gatttattaa gaaaactcat tatttagact atcaatttga tgagcctact    60
gatattaagt taggtttcac tactcgagaa aatgggttaa gtccttatcc taatcatagt   120
tttaatatgg cgagatatat cagtgacagt gcacatcata ttacacatca tcaagatatc   180
ttagcgaatc ttattggtta tccaagagat gaatgggttt ttcctataca aacacatgat   240
agtcgtatcg ttgaagttac aagtgaacat aaaggaacaa atattgatga actaactgat   300
gatttacatg gcatagatgg aatgtatact tttgattctc acattcttct tactatgtgt   360
tatgcggatt gcgtacctgt atatttttat agtgaaccac atggatatat aggattagca   420
catgcaggtt ggcgaggaac atatggtcaa atagtaaaag acatgctaaa aaaagtggat   480
tttgattatg aagacttaaa gattgtaatt ggtccagcaa cttcaaattc ttatgaaatc   540
aatgatgata taaaaaataa gtttgaggaa ttaaccattg attcaacttt atatattgag   600
accagaggta aaaatcaaca tggtattgat ttgaaaaacg ctaacgcact tcttctagaa   660
gaagctggag ttccatcaaa aaacatatac gttacggaat atgcaacttc agaaaactta   720
gatttattct tttcatatcg tgttgaaaaa ggacagacgg gacgtatgtt agcatttatt   780
ggacggaagt aa                                                        792
```

<210> SEQ ID NO 64
<211> LENGTH: 30612
<212> TYPE: DNA
<213> ORGANISM: Staphylococcus epidermidis

<400> SEQUENCE: 64

```
atgaagagca aaccgaaatt aaacggtcgg aacatctgct cttttttatt gagcaaatgt    60
atgagttatt cattgtcaaa attatcaaca ttaaaaacgt ataattttca aatcacatca   120
aacaacaaag aaaaaacatc aagaatagga gtggcaatag ctttgaataa tcgtgataaa   180
```

```
ttacaaaaat ttagtattcg aaaatacgca attggaacat tttctactgt gattgcaaca    240
cttgtgttca tgggtatcaa tacaaaccat gcaagtgccg acgagttgaa tcaaaatcaa    300
aagttaatta aacaattaaa tcaaacagat gatgatgatt cgaatacgca tagtcaagaa    360
atcgaaaata acaaacaaaa ttctagtggg cagactgaat cattacgttc atcaactagt    420
caaaatcaag caaatgcacg actgtcggat caattcaaag acactaatga acatcgcaa     480 caattaccta caaatgtttc ggatgatagt atcaatcaat cgcatagtga agcaaatatg    540
aataacgaac cattgaaagt tgataatagt actatgcaag cacatagtaa aatagtaagc    600
gatagcgatg ggaatgcttc tgaaaataaa catcataaac taacagaaaa tgtacttgca    660
gaaagccgag caagtaaaaa tgacaaagag aaagagaatc tacaagagaa agataaatcg    720
cagcaagtac atccaccatt agataaaaat gcattacaag cttttttttga cgcatcatat    780 cacaattaca gaatgattga tagagatcgt gcggatgcaa cagaatatca aaaagtcaaa    840
tctacttttg actacgtcaa tgacttacta ggtaataatc aaaatattcc ttcagaacag    900
cttgtttcgg catatcaaca attagagaaa gcattagaac ttgcacgtac gttatcacaa    960
cgatctacta cagaaaaacg tggtagaaga agtacgagaa gtgttgttga gaatcgttca   1020
tcaagaagcg attacttaga tgctagaact gaatatttatg tttcaaaaga cgatgatgat   1080 tctggttttcc ctcctggtac tttcttccat gcttcaaata gaagatggcc ttataattta   1140
ccaagatcta ggaacatctt acgtgcttct gatgtacaag gtaatgctta tatcactaca   1200
aaacgactta agatggata tcaatgggat atttttattta atagtaatca taagggcat    1260 gaatatatgt actattggtt tggacttcca agtgatcaaa caccaactgg tccagtaact   1320
ttcactatta tcaaccgtga tggttcaagt acatctactg gtggcgttgg atttggatca   1380
ggtgcaccac tacctcaatt ttggagatca gcaggtgcta ttaattctag cgtagcgaat   1440
gattttaaac atggctccgc tacaaattat gcatttatg atggtgttaa taattttctt    1500
gactttgcta gagggggaga attatacttc gacagagaag gcgctacaca aactaataaa   1560
tattatggcg atgaaaactt cgcattgcta aatagtgaga aaccagatca aataagagga   1620
ttagatacaa tatatagttt taaaggtagt ggtgatgtaa gttatcgtat ttcatttaaa   1680
actcaaggag ctccaactgc aagattgtat tatgctgctg gcgcgcgttc tggtgaatat   1740
agacaagcaa cgaactataa ccaactctat gtcgaacctt ataagaatta tcgaaatcga   1800
gtacagtcaa atgtccaagt taaaaatcgt acacttcatt taaaaagaac aatcagacaa   1860
ttcgatccta cattacagag aactactgat gttcctattt tggatagtga cggttccgga   1920
agtattgatt cggtatacga cccattaagt tatgtaaaga atgtgactgg tacagtccta   1980
ggtatttatc catcttatct tccgtataat caggaaagat ggcagggagc taatgcaatg   2040
aatgcctatc aaattgaaga actttttttca caagaaaatc ttcaaaatgc agcacgttca   2100
ggtcgtccaa ttcaatttct tgtaggtttt gatgttgaag atagccatca taaccctgaa   2160
actcttttac cagtaaattt atatgtaaaa cctgagttaa acatacaat tgagttatat     2220 cacgataatg aaaaacaaaa tagaaaggaa ttttcagtat cgaaacgagc gggccatggt   2280
gttttccaaa taatgagtgg aacgcttcat aacactgtag gatcaggaat attaccttat   2340
caacaagaga ttcgtatcaa acttactagt aatgaaccaa ttaaagatag tgaatggtct   2400
attacaggat atcctaacac gcttacatta caaaacgctg tgggtagaac aaataatgct   2460
actgaaaaaa acttagctct tgttggtcat attgatccag gaattatttt catcactgtt   2520
aagtttggtg ataaagtaga acaatttgaa attagatcaa aaccaactcc accaagaatc   2580
```

```
attacaactg ctaatgaatt acgtggaaat cctaaccaca agcctgaaat aagagtaaca    2640
gatataccaa atgatactac tgctaaaatc aaacttgtga tgggcggaac cgatggtgat    2700
catgatccag aaataaatcc atatactgtc cctgaaaact acacagtagt tgcagaagca    2760
taccatgata atgatccaag taaaaatggg gtcttaacat tccgttcatc agactacctt    2820
aaagatctac cattaagcgg tgaattaaag gcaattgttt attacaatca atatgtacaa    2880
tcaaacttta gtaatagcgt tccgtttagt agcgatacaa caccacctac aattaatgaa    2940
ccagcaggac tagttcataa gtattacagg ggagatcatg tagaaattac tcttccagtc    3000
actgataata ctggcggttc aggtttaaga gatgtaaacg tcaatttacc tcaaggttgg    3060
acaaaaacct ttacaatcaa tcctaataat aatactgagg gtacgcttaa gttaattggt    3120 aatatatccta gtaatgaagc ataataacg acatatcatt tcaatattac tgcaaccgat    3180
```

```
caaaacaatg ctaacctttc aattgaagat caaaatagag taaaatcttc actcagcatg   5040
actaaaattt taggtacaag aaattatgtc aatgagtcaa ataatgacgt tcgtagtcaa   5100
gttgtaagta aagtaaatag aagtgggaac aatgctacag ttaatgttac aactacattt   5160
tctgatggta caactaatac aataaccgtt ccagttaaac atgtgttatt agaagttgta   5220
cctactacta gaacaacagt aagaggacaa caatttccaa ccggcaaagg aacttcccca   5280
aatgatttct ttagtttaag aacgggaggt ccagttgatg cgagaatagt ttgggttaat   5340
aatcagggac ccgatataaa tagtaatcaa attggtagag atttaacatt acacgctgaa   5400
atattctttg atggtgaaac aacaccaatt agaaaagata cgacttacaa acttagtcaa   5460
tctattccaa agcaaatata tgaaacaact atcaatggtc gatttaattc atcaggtgat   5520
gcatatccag gaaattttgt tcaagcagta atcaatatt ggccagaaca tatggacttc   5580
agatgggccc aaggatcagg cacaccaagt tctcgtaatg caggttcatt tactaaaaca   5640
gttacggtag tttatcaaaa cggccaaact gaaaacgtta atgtactatt caaagtcaaa   5700
ccaaataaac ctgttattga tagtaatagt gtgatttcaa aaggacaatt aaatggtcaa   5760
caaattttag ttcgaaatgt tccacaaaat gcacaagtca ctctatatca atcaaatgga   5820
actgttattc ctaatacaaa tacaactata gattctaatg gtatagctac tgtaacaatt   5880
caaggcactc taccaaccgg aaatattact gctaaaacct caatgacaaa taatgtaacg   5940
tacactaaac aaaatagtag tggaattgct tcaaatacaa ctgaagatat aagtgttttt   6000
tcagaaaaca gtgatcaagt aaatgttacc gctggcatgc aagctaaaaa tgatggtatt   6060
aaaataatta aggtacaaa ctataatttt aatgacttca atagtttcat aagtaatata   6120
ccagcccatt ctactcttac atggaacgag gagcctaata gttggaaaaa caacatcggt   6180
actacaacaa aaactgttac agttactcta cctaatcatc aaggtacgag aactgtagat   6240
attccaataa caatctatcc aacagttaca gctaagaatc cagtaagaga tcaaaaagga   6300
cgaaacttaa ccaatggtac tgacgtttat aattatatta tttttgaaaa taataaccgt   6360
cttggaggaa cagcttcttg gaaagacaat cgtcaacctg ataaaaacat agccggtgta   6420
caaaatttaa ttgcacttgt taattatcct ggcatatcta caccattaga agttcctgtt   6480
aaagtgtggg tatataattt tgatttcact caacctatct acaaaattca agtaggagat   6540
acattcccta aaggaacatg ggcaggctat acaaacatc ttgaaaatgg agagggatta   6600
ccaatagatg gttggaaatt ttattggaac cagcaaagta caggaactac tagtgatcaa   6660
tggcaatcat tagcatatac tagaactcct tttgttaaaa ctggtactta tgatgtcgtt   6720
aatcctagca actggggtgt ttggcaaaca tcacaatcag ctaaatttat agttacaaat   6780
gctaaaccta atcaaccaac cataactcag tctaaaactg gtgatgtaac agtaacacct   6840
ggtgctgtgc gtaatatact aataagtggg acaaatgatt atatccaagc atctgcagat   6900
aagattgtta ttaataaaaa tggaaataaa ttaactacat tgttaagaa taatgatggt   6960 cgttggactg ttgaaactgg gtcacctgac ataaatggta tcggaccaac aaataacgga   7020
actgctatat ctttaagtcg attagcagtt agacctgggg attcaataga agcaatagcg   7080
actgaaggtt ccggagaaac tataagtact tcagcaacta gtgaaattta tattgtcaaa   7140
gctccacaac ctgaacaagt agcaactcat acttatgata tggaacatt cgatatatta   7200 cctgacaatt cacgtaattc tttaaatcca actgaacgtg tcgaaattaa ttacactgaa   7260
aaattaaatg gcaatgaaac acaaaaatca ttcactatta ctaaaaataa caacggcaaa   7320
tggacgataa ataataaacc aaattatgtc gagttcaatc aggataatgg taaagttgta   7380
```

```
ttttcggcca atacaattaa acctaattct caaattacaa taactcctaa agcaggtcag   7440
ggtaacactg aaaacacaaa tcctactgta attcaagcac ctgcgcaaca tactttaaca   7500
atcaatgaaa ttgttaaaga acagggtcaa aatgtgacta atgatgatat taataatgcg   7560
gttcaagtgc caaataaaaa tagagttgcg attaaacaag gaaacgctct tccaacaaat   7620
ttagctggtg gtagtacatc acatattcca gtagttattt attacagtga tggaagttct   7680
gaagaagcta ctgagactgt tagaactaaa gttaataaaa ccgaattaat caatgctcgt   7740
cgtcgactag atgaagaaat tagtaaagag aacaaaacac catcaagtat cagaaacttt   7800
gatcaagcta tgaatcgtgc tcaatcacaa attaatacag ctaaaagtga tgctgaccaa   7860
gttataggca cagaatttgc aacacctcaa caagtaaatt cagctttatc taaagttcaa   7920
gcggcacaaa ataaaataaa tgaagctaaa gcattattac aaaacaaggc tgataatagt   7980
caacttgtga gagcaaaaga acaattacaa caatcgattc aaccagccgc ttcaactgat   8040
ggtatgactc aagatagcac aaggaactac aaaaataaac gccaagcagc tgaacaagca   8100
atacaacatg caaatagcgt tataaataat ggagatgcaa catcccaaca aattaatgat   8160
gctaaaaaca cagttgaaca ggcacagaga gattatgttg aagctaaaag caacttacgt   8220
gctgataagt cacagttaca aagcgcttat gatacgttaa atagagatgt tttaacaaat   8280
gataaaaagc cagcatctgt aagacgctat aatgaagcca tttcaaatat tagaaaagaa   8340
ttagatacag ctaaagcgga tgcaagtagt actttgcgaa acaccaatcc ttccgttgaa   8400
caagttagag acgctttaaa taaaataaat actgttcaac ctaaagtgaa tcaagcaatt   8460
gctttacttc aaccaaaaga aaataattca gaacttgtac aagctaaaaa acgtttacaa   8520
gacgctgtaa atgacatacc tcaaacacaa ggtatgacac aacaaacaat taataattat   8580
aatgacaaac aacgtgaagc tgaaagagca cttacatctg cacaaagagt gattgataat   8640
ggggatgcta caactcaaga aattacttct gaaaaatcta agtagagca agcaatgcaa   8700 gctttaacta atgctaaaag taatctgaga gctgataaga atgagttaca gactgcatat   8760
aacaaattaa ttgagaacgt atctaccaat ggtaaaaaac cggcgagtat acgtcaatac   8820
gaaacagcca agccagaat acaaaatcaa attaatgatg ctaaaaatga agcggagcga   8880
attttaggta atgataatcc acaagtatca caagtaactc aagcattgaa caaaatcaaa   8940
gctattcaac caaaattaac agaagctatc aacatgcttc aaaacaaaga aataataca   9000 gaattagtca atgctaaaaa cagacttgaa aatgcagtaa atgatacaga tccaacacac   9060
ggtatgactc aagaaacaat taataattac aacgctaaaa agcgagaagc tcaaaatgaa   9120
atacaaaaag cgaacatgat tattaataat ggagatgcta ctgctcaaga tatttcttct   9180
gaaaaatcta agtagagca agtattacaa gcattacaaa atgctaagaa tgacttaaga   9240
gctgataaaa gagaattaca gactgcatac aataaactta tacaaatgt taataccaat   9300 ggtaaaaaac catctagtat tcaaaactat aagtctgcaa gacgaaatat cgaaaaccaa   9360
tataataccg ctaaaaatga agcacataat gttcttgaaa atacaaaccc tactgtaaat   9420
gcagtagaag atgctttacg taagataaat gcaattcaac cagaggttac aaaagctatt   9480
aatatacttc aagataaaga agataatagc gaacttgtta gagcaaaaga aaattagat   9540 caagcgatta atagtcaacc atcactaaat ggtatgactc aagaatctat taataattac   9600
acaacaaaac gtagagaagc acaaaatata gcaagttctg ctgacactat tattaataat   9660
ggggatgcat ctattgaaca aataacagaa aataaaattc gagttgaaga ggcaactaat   9720
gcacttaacg aagcaaaaca acatttaacg gcagatacaa cttcttaaa aactgaagta   9780
```

```
cggaaattaa gtaggagagg cgacacaaac aacaaaaagc ctagcagtgt tagtgcttat    9840
aacaatacta ttcattcgct acaatctgaa attacacaga ctgaaaatag agcaaatact    9900
atcatcaata agcctattcg ttctgttgaa gaagtaaata atgcattgca tgaagtaaac    9960
caattgaacc aacgcttaac agatacaatt aacttattac aacctttagc gaataaagaa   10020
agcttaaaag aagctcgtaa tcgacttgaa agtaaaatta atgaaaccgt tcaaacagac   10080
ggtatgactc aacaatctgt tgagaattat aagcaagcta aaataaaagc tcaaaatgaa   10140
tctagtattg cacaaactct tattaataat ggtgatgcat ctgatcaaga agtttctaca   10200
gaaatagaaa aattaaatca aaagctgtct gaattaacaa attcaatcaa tcacttaaca   10260
gttaataaag aacctttaga aactgccaaa atcagttac  aagcaaatat tgaccaaaaa   10320
cctagcactg atggtatgac gcaacaatct gtacaaagct atgaacgtaa actacaagaa   10380
gccaaagata aaataaactc aattaataat gtcttagcta acaatccaga tgttaatgct   10440
atcagaacaa acaaagttga gacggaacaa atcaataatg aattaacaca ggcgaaacaa   10500
ggtcttactg ttgataaaca accattgatt aatgcaaaaa ctgctttgca acaaagtcta   10560
gataatcaac caagtactac tggtatgact gaagcaacaa ttcaaaatta taacgctaaa   10620
cgtcaaaaag cagagcaagt tatacaaaat gcaaataaaa ttattgaaaa cgctcaacct   10680
agtgtacaac aagtgtctga tgagaaatct aaggtagagc aagcactcag tgaattgaac   10740
aacgccaaat cagcgcttag agctgataaa caagaattac agcaagcata taatcagttg   10800
attcaaccaa cggatttaaa taataagaaa ccagcttcta tcactgcgta caatcaaaga   10860
tatcaacaat ttagtaacga attgaacagc actaaaacaa atacagatcg catttttaaaa  10920 gagcaaaatc caagtgtagc tgatgtcaac aatgcactaa ataagtaag  agaagtacaa   10980 caaaaattaa acgaagccag agcactttta caaaataaag aagataatag tgcactagtt   11040
cgagccaaag aacaacttca acaggcagtt gaccaagtcc cttcaacaga aggtatgacg   11100
caacaaacta agatgattca caattcaaaa caacaagctg ctcaacaaga aatatcaaaa   11160
gcacaacaag ttatcgataa tggcgatgcg actacacaac aaatttctaa cgccaaaaca   11220
aatgttgaac gcgctttaga agcattaaat aatgcaaaaa ctggtttaag agcagataaa   11280
gaggaacttc aaaatgcata taatcaatta actcaaaata ttgatacgag cggtaaaacg   11340
cctgcaagta tcaggaaata caatgaagct aagtcacgta ttcaaactca aattgattca   11400
gctaaaaatg aagcaaacag tattttaaca aatgacaatc ctcaagtatc acaagtgact   11460
gctgcgttaa acaaaataaa agctgttcaa cctgaattag ataaagcgat agcaatgctt   11520
aaaaataaag agaataataa tgcattggtt caagcgaaac aacaacttca acaaattgtt   11580
aatgaagtag atccaacaca aggcatgaca acagatactg ctaataacta taaatcaaaa   11640
aaacgtgaag ctgaagatga aatacaaaaa gctcaacaaa tcattaacaa tggcgatgcc   11700
actgagcaac aaattactaa cgaaacaaat agagtaaatc aagcgattaa tgcaataaac   11760
aaagccaaaa acgatttacg tgctgataag tctcaattgg aaaatgctta taccaatta    11820 atacaaaatg ttgatacaaa tggtaaaaaa cctgctagta ttcaacaata ccaagctgct   11880
cgacaagcta ttgagacgca atacaataac gctaaatcag aagcacatca aattcttgaa   11940
aatagtaacc cttcagttaa tgaagtagca caagcattac aaaaagttga agctgtacaa   12000
cttaaagtta atgacgcgat tcatatactt caaaataaag ataataatag tgcacttgtc   12060
acagctaaaa atcaacttca gcaatcagtt aatgatcaac cattaacaac aggtatgact   12120
caagattcta ttaataacta tgaagctaag agaaatgagg ctcaaagtgc tatcagaaat   12180
```

```
gcagaagctg tcatcaacaa tggcgatgca actgcaaaac aaatttcaga cgagaaatct    12240
aaagttgaac aagcactagc acatttgaat gatgctaaac agcaattaac tgcagatact    12300
actgaattac aaacagcagt tcaacaatta aacagaagag gcgatacaaa taataaaaag    12360
ccaagaagta tcaatgcata taataaagca attcaatcat tagaaacaca aattacttct    12420
gctaaagata tgccaacgc tgtgatacaa aaacctatac gtactgttca agaggtaaat    12480
aatgcattac aacaagtaaa tcagttgaat caacaattaa ctgaagcaat taatcaactt    12540
caaccgctat caaataatga tgcattaaaa gctgcaaaat taaatttaga aaataaaatt    12600
aatcaaactg tacaaactga tggtatgaca caacaatcta tagaggctta tcaaaacgct    12660
aaacgcgtag cccaaaatga atctaacact gctttagcat taattaataa cggcgatgcc    12720
gatgaacaac aaattacaac tgaaacagac cgagtcaatc agcaaactac aaacttaact    12780
caagcaatta acgggttaac agttaataaa gaaccattag aaaccgctaa acagcgtta    12840 caaaataaca tcgaccaggt acctagtaca gatggtatga ctcagcaatc tgttgcaaat    12900
tataatcaaa aactacaaat agctaaaaac gaaattaaca caattaataa cgttttagcg    12960
aacaatccag atgttaatgc aatcaaaacg aataaagcag aagcggaacg aatcagtaac    13020
gatttaacac aagctaagaa taacttacaa gttgatactc aacctttaga aaaaataaaa    13080
agacaacttc aagatgaaat tgatcaaggt actaacacag atggaatgac tcaagattca    13140
gtggataatt acaatgatag cttaagtgca gcaattatag aaaaaggcaa agtaaataaa    13200
ttacttaaac gtaatccgac agtagaacaa gttaaagaga gcgttgctaa tgcacaacaa    13260
gtcatacaag atttacaaaa tgctcgaact tcacttgttc cagacaaaac tcaacttcaa    13320
gaagctaaaa atagattaga aaacagtatt aaccaacaaa cagatactga cggcatgact    13380
caagattcgc ttaacaatta taatgataaa ttagcaaaag ctagacaaaa ccttgaaaaa    13440
atatctaaag tttaggtgg tcaacctact gtagctgaaa ttagacaaaa tacagatgaa    13500
gcaaatgcac ataaacaagc attagacact gcacgttctc aacttacatt aaatagagag    13560
ccatatatca atcatattaa taatgaaagt catttaaata acgcgcaaaa agataatttt    13620
aaagctcaag ttaactcagc acctaatcat aatactttag aaacgattaa aataaggct    13680 gatactttaa atcaatctat gacagcatta agtgaaagta ttgcagatta cgaaaatcaa    13740
aaacaacaag aaaattattt agatgcatct aacaataaac gtcaagacta tgacaatgca    13800
gtcaatgcgg ctaaaggtat tttaaaccaa actcaaagtc cgacaatgag tgctgatgtg    13860
attgatcaaa aagctgaaga tgttaaacgt acgaaaactg cgttagatgg aaatcaaaga    13920
ttagaagttg ctaaacaaca agcacttaat catttaaata ccttaaatga tttaaacgat    13980
gctcagcgac aaactttaac tgatactata aatcactctc caaacatcaa ttcagtgaat    14040
caagctaaag aaaaagctaa tactgttaac acagcaatga ctcaactgaa acaaactatt    14100
gctaactatg acgatgaatt gcatgacggc aattacatta atgcagataa agacaaaaaa    14160
gatgcttata taacgctgt taacaatgct aaacaactga ttaatcaatc tgatgctaat    14220
caagcacaac ttgatccagc tgaaattaat aaagttacac aaagagtcaa tacgactaaa    14280
aatgatctaa atggtaatga caaattggct gaagctaaaa gagatgctaa tacaaccatt    14340
gatggtttaa cttatctaaa tgaagctcaa cgtaacaaag ctaaagaaaa tgtaggcaaa    14400
gcttctacaa aaacaaatat tacgagtcag ttacaagatt acaatcaatt gaatattgct    14460
atgcaagcat tacgtaacag tgtgaacgac gttaacaatg ttaaagcaaa tagcaattat    14520
ataaatgaag ataatggtcc aaaagaagct tacaatcaag ccgttactca tgctcaaaca    14580
```

```
ttgataaatg cacaatctaa ccctgaaatg agccgtgacg tagtaaatca aaaacacaa    14640 gcagtaaata ctgcccatca gaatttacat ggacaacaaa agttagaaca agcacaaagt   14700
agtgctaata cagaaatcgg taacttacca aacttaacta atactcaaaa agctaaagaa   14760
aaggaactgg taaatagtaa acaaactcgt acggaagtac aagaacaact taaccaagct   14820
aagtcactag atagttctat gggcacgtta aaatcattag ttgctaaaca acctacagta   14880
caaaaaacaa gtgtttatat taacgaagat caacctgagc aatctgccta caatgattcc   14940
attacaatgg gacaaactat aattaataaa acagctgatc cagtacttga taaaacttta   15000
gttgataacg caatcagtaa catttcaact aaagagaatg cactgcatgg tgaacaaaaa   15060
ttaacaactg ctaaaacgga agcaattaat gcacttaata cattagctga tttaaacaca   15120
cctcagaaag aggctattaa aacagctatt aacactgctc atacaagaac tgatgtaact   15180
gcagagcaaa gtaaggctaa tcaaataaat agtgcaatgc acacgttgag acaaaacatt   15240
tctgacaacg aatcagtaac aaacgaaagt aattatatta cgctgaacc cgaaaaacaa    15300 catgccttta ctgaggctct aaataatgct aagaaatag ttaatgaaca acaagccact     15360
cttgatgcca attcaattaa ccaaaaagca caagcgattc ttactactaa aaatgcttta   15420
gatggtgaag aacaattacg tcgtgctaaa gaaaatgccg atcaagaaat caatacgtta   15480
aatcaattga ctgatgcgca aagaaatagt gaaaaggtt tagtcaacag ttctcaaact     15540
agaacagaag ttgcttctca attagcaaaa gctaagaaac taaataaggt gatggaacaa   15600
ctgaatcacc ttatcaatgg taaaaaccaa atgataaata gcagtaaatt tatcaatgaa   15660
gatgcgaacc aacaacaagc atattcaaat gcgattgcaa gtgcagaagc gcttaaaaac   15720
aaatcacaaa accctgaatt agataaagta acaattgaac aagcaattaa taatattaat   15780
tctgcaatta acaatctaaa cggtgaagct aaactgacta agctaaaga agatgctgtt    15840 gcttcaataa acaacctaag cggattaaca aacgagcaaa aaacaaaaga aaatcaagcc   15900
gttaatggcg ctcaaactag agaccaagtt gctaataaat tacgtgatgc tgaagcatta   15960
gatcaatcaa tgcaaacatt acgtgactta gttaacaatc aaaatgcaat acattcaaca   16020
agtaattatt ttaacgagga ttcaactcaa aagaatactt atgataatgc aattgataat   16080
ggctcgacat atataactgg tcaacacaat ccagaattaa ataaatctac tattgatcaa   16140
acgattagcc gaattaacac agctaaaaat gatttacatg gtgtagaaaa gttacaaaga   16200
gataagggaa ctgctaatca agaaattgga caattaggtt atttaaatga ccctcaaaaa   16260
tctggtgagg aatccttagt caacggttca aatacacgtt ctgaagtaga agagcatctt   16320
aatgaagcta atcattaaa taatgcaatg aaacaattaa gagataaagt agctgaaaag    16380
actaatgtca aacaaagtag cgattacatt aatgattcaa ctgaacatca acgtgggtat   16440
gatcaagcac ttcaagaagc agaaaatatt attaatgaaa tcggtaatcc aacattaaat   16500
aaatcggaaa ttgaacaaaa gttacaacaa ttgactgacg ctcaaaatgc gttacaaggt   16560
tcacatctat tagaagaagc taaaaataat gcgattactg gaatcaataa acttacagca   16620
ttaaatgatg cacaacgtca aaaagcaatt gaaaatgttc aagcacagca gacaatccca   16680
gcagttaatc aacaattaac tttggataga gaaataaata ctgcaatgca agctttacga   16740
gataaagtag gccaacaaaa taacgttcac caacaaagta attatttcaa tgaagatgaa   16800
caaccaaaac ataactatga taattctgta caagccggtc aaactattat tgataaactt   16860
caagatccaa tcatgaacaa aaatgaaatt gagcaggcta ttaatcaaat caatacgact   16920
caaacagcgt taagtggaga aaataaatta cacactgacc aagaaagcac aaatagacaa   16980
```

```
atagaaggtt tatctagttt gaacacagct caaatcaacg ccgaaaaaga tttagtcaat    17040
caagctaaaa caagaacaga tgttgctcaa aagttagctg cagctaaaga aataaattct    17100
gctatgagta atttaagaga tggcattcaa aataaagagg acatcaaacg tagcagtgca    17160
tatatcaacg cagatccgac taaagttaca gcttacgatc aagcactaca gaacgcagaa    17220
aatatcatca atgccacacc aaacgtagag cttaataaag ctacaattga acaagcgcta    17280
tcacgcgttc aacaagcaca acaagatctt gatggtgttc aacaattagc taatgctaaa    17340
caacaagcta cacaaactgt caatgggtta aatagcttaa atgacggtca aaagcgtgaa    17400
ttaaatctat taattaattc agctaatacc cgtacaaaag tacaagaaga attaaacaaa    17460
gcaactgaat tgaaccatgc gatggaagct ttaagaaaca gtgttcaaaa cgttgatcaa    17520
gtaaaacaaa gtagcaatta tgtcaatgaa gatcaacctg aacagcacaa ttatgataat    17580
gctgtcaatg aagctcaagc tacaatcaac aacaatgctc aacctgttct agacaaatta    17640
gctatagaac gtttaactca aactgttaac actacaaaag atgcattaca tggtgctcaa    17700
aaactgacac aagaccaaca agctgctgaa actggaatac gtggtttaac gagtctcaat    17760
gaacctcaga aaaatgctga agtagctaaa gtaactgcag caacaacacg tgatgaagtg    17820
agaaatattc gtcaagaagc aacaacatta gatactgcaa tgcttggttt acgtaaaagc    17880 attaagata aaaacgatac taaaaatagt agtaaatata ttaatgagga tcatgaccaa    17940
caacaagctt atgacaatgc tgtaaataat gctcaacaag ttatcgatga aactcaagca    18000
acgttaagct cagatacaat caatcaattg gcaaatgccg taactcaagc taaatctaat    18060
cttcatggag atactaaact acaacacgat aaagatagtg ctaaacaaac gattgctcaa    18120
ttacagaatt tgaattcagc tcaaaaacat atggaagatt cttaattga taatgaatct    18180 acacgtacgc aagtccaaca cgatttaaca gaagctcaag ctttagatgg tttaatgggt    18240
gccttaaaag aaagtattaa agattatact aatattgttt caaacggtaa ttacatcaat    18300
gcggaaccat ctaagaaaca agcatatgat gcagctgtac aaaatgctca aaatataata    18360
aatggaacga atcaaccaac aattaataaa ggtaatgtca ctacagcaac acaaaccgtg    18420
aaaaatacta aagatgcctt agacggtgat catagattag aggaagctaa aaataatgcc    18480
aatcaaacaa tcagaaatct atctaatttg aacaatgccc aaaaagatgc agagaaaaat    18540
ctagttaata gcgcatcaac attagaacaa gttcaacaaa acttacaaac cgctcaacaa    18600
ttagataatg ctatgggtga gttacgacaa agtattgcta aaaaagatca agtgaaagca    18660
gatagtaaat atctaaatga agatcctcaa attaagcaaa actatgatga tgcagttcaa    18720
cgtgttgaaa ctattattaa cgaaactcaa aaccctgaat tacttaaagc aaacattgac    18780
caagcaactc aatccgttca aaatgcagaa caagctttac atggtgctga aaaattaaat    18840
caagacaaac aaacgtcttc gacagaacta gatggattaa cagatttaac agatgcacaa    18900
cgtgaaaaac tcagagaaca aattaacact tctaatagta gagatgatat taagcaaaaa    18960
attgagcaag caaagcact aaatgacgca atgaaaaaac ttaaagaaca agttgcgcaa    19020
aaagatggtg ttcatgctaa cagtgattat acaaatgaag attctgcaca aaaagatgcg    19080
tataataatg cacttaaaca agcggaagac attattaata acagctcaaa tcctaactta    19140
aatgcacaag acattactaa tgctttaaat aatattaaac aagcacaaga taaccttcat    19200
ggagctcaaa aattacagca agacaaaaat acaactaatc aagccattgg taacttaaat    19260
catcttaatc aacctcaaaa agatgcgctt atacaagcta ttaatggagc tacatctagg    19320
gaccaagttg cagaaaaact taaagaggcc gaagcgcttg atgaagctat gaacaacctt    19380
```

```
gaagatcaag tgaatcaaga tgatcaaatt tcaaatagca gcccattcat aaatgaagac    19440
tcagacaaac aaaaaactta taatgataaa atccaagctg caaaagaaat aattaatcaa    19500
acatctaatc caaccttaga taaacaaaaa attgctgata cacttcaaaa tattaaagat    19560
gcagtgaata atttacatgg tgatcaaaaa ttagctcaat ctaaacaaga tgctaataat    19620
caattaaatc atttagatga cttaaccgaa gaacaaaaaa accattttaa accgttaatt    19680
aataatgctg atactcgaga tgaggtaaat aaacaactag agattgctaa acaattaaat    19740
ggtgatatga gtacacttca taaagtcata aatgataaag atcaaattca catttaagc    19800 aattacatta atgctgataa tgataaaaaa caaaattatg ataatgctat taaagaagct    19860
gaggatttaa ttcataatca tccagataca ttagatcata aagcattaca agatttatta    19920
aacaagatag accaagcgca taacgaatta aatggagaat ccagatttaa acaggcttta    19980
gacaatgctt taaacgacat agatagctta aacagtctca atgttccaca acgccaaact    20040
gttaaggata acatcaacca tgtgacaact ctagaaagtt tagctcaaga attgcagaaa    20100
gcaaaagagc ttaatgatgc tatgaaagca atgagagata gcattatgaa tcaagagcaa    20160
attcgtaaaa atagcaatta tactaatgaa gacttagctc aacaaaatgc ctataatcat    20220
gcagtagata aaataaataa cattattggt gaagacaatg cgacgatgga tcctcaaata    20280
atcaaacaag caactcaaga tataaataca gctataaatg gattaaatgg agatcaaaaa    20340
cttcaagatg caaagacaga tgctaaacaa caaattacta actttactgg tttaactgaa    20400
ccacaaaaac aagcattgga aaacatcatt aaccaacaaa caagcagagc aaatgttgct    20460
aaacagttaa gtcatgctaa attcttaaat ggaaaaatgg aagaattaaa agttgcagta    20520
gccaaagcgt cattagtaag acaaaatagt aactatatta tgaagatgt ctctgaaaaa    20580 gaagcatatg aacaagctat cgcaaaaggt caggaaataa ttaattcaga aaataatcca    20640
acaataagta gtactgatat caatcgtacc attcaagaaa ttaatgatgc tgaacaaaat    20700
cttcatggtg ataataaatt aagacaagca caggaaattg caaagaatga aatacaaaat    20760
ctagacggat taaattcagc tcaaataaca aaattaatcc aagatatagg cagaacaaca    20820
actaaacctg cagtaactca gaaactagaa gaagcaaaag caataaacca agctatgcaa    20880
caacttaaac aaagtatagc cgataaggat gctactctaa attctagtaa ctatctcaat    20940
gaagattctg agaaaaagtt agcgtacgat aatgctgtaa gccaagctga caactcata    21000 aatcaactta acgacccaac tatggatata agtaatattc aagctattac tcaaaaggtc    21060
attcaagcaa aagattcatt gcacggtgcg aataaacttg cacaaaatca agcagattca    21120
aatttaataa taaatcaatc aacaaattta atgataaac aaaagcaagc attaaatgac    21180
ttaattaatc atgctcaaac taaacagcaa gtggcagaaa taattgcaca agctaataag    21240
ttaaataacg aaatgggcac actaaaaaca ctcgtagaag aacagtcaaa cgttcatcaa    21300
caaagtaaat atattaatga agatccgcaa gttcaaaata tttataatga ctccattcaa    21360
aaaggtcgag aaatattaaa cggcactaca gatgatgttt taaacaacaa taaaatagca    21420
gatgccattc aaaacattca tttaactaaa aacgatttac atggtgatca aaaattacaa    21480
aaagcacaac aagatgcaac caatgaatta aactatttaa caaatctaaa caattctcaa    21540
agacaaagcg agcatgatga gattaactct gctccttcaa gaactgaagt ttctaatgat    21600
ttaaatcatg ctaaagcact taatgaagct atgcgtcaac ttgagaatga agttgctctt    21660
gaaaacagtg ttaaaaaatt aagcgacttt atcaatgaag atgaagcggc acaaaatgaa    21720
tatagtaatg cacttcaaaa agctaaagac attatcaacg gcgttccaag tagcacttta    21780
```

```
gataaagcta caattgaaga tgctttatta gaattgcaaa atgctagaga aagtttacat    21840
ggtgagcaaa aacttcaaga ggctaaaaat caagctgttg ctgaaattga taatttacaa    21900
gcattaaatc ctggacaggt tcttgctgaa aaaacattag ttaaccaagc atcaaccaaa    21960
ccagaagttc aagaagcctt acaaaaagca aaagaactta atgaagctat gaaagcactg    22020
aaaactgaaa taaataaaaa agaacaaatc aaggctgata gtagatatgt aaatgctgac    22080
agtggtcttc aagcaaatta caattctgcg ttaaattatg gttctcaaat tattgcaact    22140
acccaaccac cagagcttaa taaagatgta ataaatagag caactcaaac gattaaaact    22200
gctgaaaata atttaaatgg gcaatctaaa ttagcagagg ctaagtcaga cggaaatcaa    22260
agcatcgaac atttgcaagg attaacacaa tcacaaaaag ataaacaaca tgatttaatt    22320
aatcaagctc aaactaaaca acaggtagat gatatcgtaa ataactctaa acaattagat    22380
aactctatga atcaactaca acaaattgtt aacaatgaca atacagtaaa acaaaatagt    22440
gatttcatta atgaagattc cagccaacag gatgcttata atcatgcaat tcaagcagca    22500
aaagatttga taactgctca tcctactatc atggataaaa atcaaataga tcaagctatt    22560
gaaaatatca acaagcact taatgattta cacggtagta ataaactatc agaagataaa    22620
aaagaagctt cagaacaact acaaaacctt aatagcttga cgaacgggca aaaagatacg    22680
attttaaatc atattttcag tgcaccaaca agaagccaag taggagaaaa aattgcaagt    22740
gctaaacaat taaataatac aatgaaagca cttagagatt ctattgctga taataatgaa    22800
attttacaaa gtagtaagta cttcaatgaa gattctgaac aacaaaatgc ttataatcaa    22860
gccgtaaata aagctaaaaa tataattaat gatcaaccaa caccagtaat ggcaaatgat    22920
gagattcaaa gtgtcctaaa tgaagttaaa caaactaaag ataatttaca tggtgatcaa    22980
aaacttgcta acgacaagac agatgcccaa gcaacattaa atgcgttaaa ttacttaaat    23040
caagcgcaaa gaggtaatct tgaaactaaa gttcaaaact ctaattctag accagaagta    23100
caaaaagtag ttcaattagc aaatcaactt aatgatgcga tgaaaaaatt agatgatgct    23160
ttaactggta atgacgcaat aaaacaaacg agtaattata ttaatgaaga tacttctcaa    23220
caagttaact ttgatgagta tacagataga ggtaaaaaca tagttgctga acaaacaaat    23280
ccaaatatgt ctccaactaa tattaacact attgctgata aaattactga agctaaaaat    23340
gatttacatg gcgtacaaaa actagaacaa gctcaacaac agtccatcaa tactattaat    23400
caaatgactg gtctaaacca agctcaaaaa gaacaattaa atcaagaaat tcaacaaact    23460
caaacccgtt ctgaagtaca tcaagtaatt aaaaaagcac aagctttaaa tgattcaatg    23520
aatactttac gtcaaagtat cactgatgag aatgaagtta acaaacaag taactacatc    23580 aatgaaactg ttggtaatca aactgcatat aacaatgccg ttgatcgtgt aaaacaaata    23640
atcaatcaaa catctaatcc aactatgaat cctttagagg tggaacgtgc aacatcaaat    23700
gtaaaaactt ctaaagatgc acttcatggt gaacgtgaat tgaatgacaa taaaaattca    23760 aaaactttg cagtcaatca cttagataac ctcaatcaag ctcaaaaga agcattaact    23820 catgaaattg aacaagcaac tatagtttca caagtaaata atatctataa caaagcgaaa    23880 gcttttaaata atgatatgaa aaacttaaa gatatcgttg ctcaacaaga taatgtgaga    23940
caatcaaaca attatataaa cgaggatagt acacctcaaa atatgtacaa cgatacaatt    24000
aatcatgcac aatcaatcat tgatcaagta gcaaacccta cgatgtctca tgacgaaata    24060
gagaatgcaa tcaataacat aaagcatgcc atcaatgcac tcgatggaga acataaatta    24120
caacaagcaa aagaaaatgc aaacttattg attaatagtt taaacgattt aaatgcacca    24180
```

```
caaagagatg ccataaatag attggttaat gaagctcaaa caagagaaaa agtagctgaa    24240
caacttcaaa gtgctcaagc tctaaatgat gctatgaagc atttaagaaa cagcattcaa    24300
aatcaatcat ccgtaagaca agagagcaaa tatattaatg caagtgatgc taaaaaagag    24360
caatataatc acgcagttag agaagtcgaa aatattatca atgaacaaca tccaacattg    24420
gataaagaaa taattaagca actaacggat gctgtaaatc aagcgaataa tgacttaaat    24480
ggcgttgaat tattagatgc tgataagcaa aacgcacatc aatcgatacc tacattgatg    24540
cacttaaatc aagcacaaca aaacgcatta aatgaaaaaa ttaataacgc agttaccaga    24600
gctgaagttg cggctattat tggccaagca aaaatactcg atcatgctat ggagaattta    24660
gaagaaagta tcaaagataa agagcaagtc aaacagtcaa gtaactatat taatgaagac    24720
cctgatgttc aagaaacata caataacgcc gttgatcatg tgacagaaat acttaatcaa    24780
acagtaaatc caactttatc tattgaagat atagagcatg ctatcaacga agttaatcaa    24840
gcgaaaaaac aactcagagg taaacaaaaa ctttatcaaa ctatcgattt agctgataaa    24900
gaattaagta aattggatga tttaacatca caacaaagca gttcaatatc taatcaaata    24960
tatactgcta aaacgagaac agaagttgcc caagcaattg aaaaagcaaa atcattaaat    25020
catgcaatga aagcacttaa caaagtatat aaaaatacag ataaagtgtt agatagtagt    25080
cgattcatta acgaagatca acccgaaaaa gaggcgtatc aacaagctat aaatcacgtt    25140
gattcaatca ttcatagaca aacaaatcct gaatggatc caacagtaat caatagcata    25200
actcatgaac tcgaaacagc tcaaaataac ttacatggtg atcagaaact tgctcatgca    25260
caacaagatg ccgctaatgt aattaatggt ctaattcatc ttaatgttgc tcaacgcgag    25320
gtaatgataa atgcgaatac aaatgctaca acacgcgaaa aagttgcaaa gaacttagat    25380
aatgctcaag ctcttgataa agctatggaa acactacaac aagtagttgc tcataaaaat    25440
aatatattga acgatagtaa atatttaaat gaagattcaa aatatcaaca acaatacgat    25500
cgagttgttg ctgacgccga caactactt aatcagacaa caaatccaac attagaacct    25560
tataaaatcg atattgttaa ggataatgtc ctagctaacg aaaaaatact atttggcgca    25620
gaaaaactat catatgacaa atcaaatgca aatgatgaaa ttaaacatat gaattatctt    25680
aataatgcac aaaagcaatc tataaaagat atgatttctc acgcagcatt aagaactgaa    25740
gttaaacaac ttctgcaaca agctaaaacc cttgatgaag ctatgaaatc acttgaagat    25800
aaaactcaag tagtgattac agatactact ttgtctaatt acactgaagc ttcagaggat    25860
aaaaaggaaa aagtagacca aactgtatca catgctcaag caatcattga taaaataaat    25920
ggctcaaatg taagtttaga tcaagtacga caagcactag aacaattaac tcaagcatca    25980
gaaaacctcg atggtgatca gcgagttgaa gaagctaaag ttcatgctaa tcaaacaatt    26040
gaccaattaa cacatcttaa ttcattacaa caacaaactg cgaaagaaag tgttaaaaac    26100
gcaacaaaac tagaagaaat cgctactgct agtaacgatg ctctggcatt aaacaaagta    26160
atgggtaaat tagaacaatt cattaatcat gctgattctg ttgaaaatag tgataattat    26220
agacaagccg acgacgacaa aattatcgct tatgatgatg cactagaaca tggacaagat    26280
atacaaaaat ctaatgcaac ccaaaatgaa gcaaacaag cgttacaaca attaataaat    26340
gcagaaacat cgttaaatgg tttcgaaaga ttaaatcatg ctagaccacg agctttgaaa    26400
tatattaaat cactagaaaa aataaacaat gctcaaaagt ctgctttaga ggataaagta    26460
acgcaatcgc atgattttatt agaattagaa catcttgtca acgagggcac aaaccctcaat    26520 gacattatgg gtgaattagc taacgcaatc gttaataact atgctccaac caaagcaagt    26580
```

```
ataaattata ttaacgccga taacctacgc aaagataact ttactcaagc tatcaacaat    26640
gcacgtgatg cactcaacaa aactcaaggt cagaacttag atttcaatgc aattgataca    26700
tttaaagatg atatattcaa aactaaagat gcacttaacg gtattgaacg tttaacagct    26760
gcaaaatcaa aagcagaaaa actaattgat agtttaaaat ttattaataa agctcaattc    26820
acacatgcaa atgatgaaat tatgaatact aattctattg cacaattgtc tagaatcgtg    26880
aatcaagcat ttgatttaaa tgatgcaatg aaatctttaa gagatgaact taataataaa    26940
gcttttcctg tccaagcaag ctcaaattat ataaattcag atgaagattt aaaacaacaa    27000
tttgaccatg ctttaagtaa tgctcgaaaa gtacttgcaa aagaaaatgg taaaaattta    27060
gatgaaatac aaattgaggg actcaaacaa gtgattgagg atactaaaga tgctttaaat    27120
ggtatccaac gtttatcaaa agctaaagct aaagcaattc aatacgtaca atctttatct    27180
tatatcaatg atgcacagcg tcatattgct gaaaataata ttcacaactc tgatgattta    27240
tcatctttag caaatacatt atctaaagct agtgatttag ataatgcaat gaaagactta    27300
cgagatactc tagaaagtaa ttcaacttct gttccaaata gtgtgaatta tattaatgct    27360
gataagaatt ttcaaattga atttgatgag gcgctacaac aagcaagtgc aacaagttct    27420
aaaacttcag aaaatccagc aacgattgaa gaagtattag gtcttagtca agccatttac    27480
gatacaaaaa atgcattgaa tggtgaacaa cgacttgcaa ctgagaagag caaagatcta    27540
aaattaataa aaggattaaa agatttaaat aaagcacaac ttgaagatgt cacaaacaag    27600
gtaaattcag caaatacttt aacagagtta tctcagctca ctcaatcaac gttaaaatta    27660
aacgataaaa tgaaattatt gagagataag cttaaaacct tagtaaatcc tgttaaagca    27720
agtttaaatt atagaaacgc tgattataat ttaaaacgtc aatttaacaa agctttaaaa    27780
gaagctaaag gcatattaaa taaaaatagc ggtccaaatg tcaatatcaa tgacattcaa    27840
catcttttaa cacaaataga taatgctaaa gaccaattaa atggtgaacg acgtctaaaa    27900
gaacatcaac aaaaatctga agtatttatt attaaagaat tagatatact taataatgct    27960
caaaaagctg caataattaa tcagattaga gcgtctaaag acattaaaat aattaatcaa    28020
atcgttgata atgcaataga attaaatgat gctatgcaag gtttaaaaga acatgtagct    28080
caattaacag caactacaaa agacaacatt gaatatttaa atgctgatga agaccttaaa    28140
ttacaatatg attacgctat caacttagcg aataatgttc ttgacaaaga aaacggtaca    28200
aataaagacg ctaatatcat aattggaatg attcaaaaca tggatgatgc tagagcactt    28260
ctaaatggaa ttgaaagact taaagatgct caaacaaaag cacataatga cattaaagat    28320
acgctcaaac gtcaacttga tgaaattgaa cacgctaatg caacatcaaa ttctaaggct    28380
caagcaaaac aaatggtaaa tgaggaagct agaaaagcgt tttctaatat taatcacgca    28440
acatcaaatg atttagttaa tcaagcaaaa gatgaagggc aatctgcaat tgaacacata    28500
catgcagatg aattacctaa agcgaaacta gatgctaatc aaatgattga ccaaaaagtt    28560
gaagatataa atcacttaat tagtcaaaat ccaaacttat cacatgatga aaaaaataaa    28620
ctaatatctc aaattaataa gttagtaaat ggaattaagg atgaaattca acaagctata    28680
aacaaacaac aaatagaaaa tgctacaaca aaactagatg aagtcattga aactactaaa    28740
aaattaatta tcgccaaagc tgaagctaaa caagtgataa aagagttatc acaaaagaaa    28800
cgagatgcaa taaataacaa cactgattta acaccttctc aaaaggcaca tgctttagca    28860
gatattgata aaacagaaaa agatgcactt caacatatcg aaaattctaa ttcaattgat    28920
gatatcaata acaataaaaa gcatgcattt aatactttag ctcatatcat tatttgggat    28980
```

```
actgatcagc aaccattagt ttttgaacta cctgaattga gccttcaaaa tgctttagta    29040
acaagtgagg tggttgttca cagagatgaa actatttcat tagaatctat aattggagct    29100
atgactttaa ctgatgaact taaagtcaat attgtttcat taccgaacac tgataaagta    29160
gctgatcacc taaccgctaa agttaaggtt attttagctg atggctcata tgtcactgta    29220
aatgttccag tcaaagttgt agaaaaagaa ttacaaatag ctaaaaagga tgctataaaa    29280
acaattgatg ttctggtaaa acaaaaaatc aaagatatag attctaataa cgaattaacg    29340
tctactcaac gtgaagatgc aaaagctgaa attgaaagat tgaaaaagca agccatcgat    29400
aaagtgaatc attcaaaatc gattaaagat attgaaacag taaaacgaac tgattttgaa    29460
gaaatagatc agtttgatcc taaacgcttt acgctaaata aagctaaaaa ggatatcatt    29520
actgatgtta atactcaaat ccaaaatggt ttcaaagaaa ttgaaacaat aaaaggttta    29580
acttctaatg aaaaaactca gtttgataaa caattaactg aactacaaaa agaattttta    29640 gaaaagtcg agcatgctca taatttagta gaattaaatc aattacaaca agagtttaat    29700
aatagatata aacatatttt aaaccaagca catttactag gtgaaaaaca tatagcagaa    29760
cataaattag gatatgttgt agtaaacaaa actcagcaaa tactaaataa tcaatctgct    29820
tcttacttta taaaacaatg ggcacttgat agaattaaac aaattcaact agaaacgatg    29880
aattcaattc gtggtgcgca taccgtacaa gatgtacaca aagcattatt acaaggtata    29940
gagcaaatct tgaaagtaaa tgtaagtatt ataaatcaat ctttcaacga ttccttgcat    30000
aactttaatt atcttcattc aaaatttgat gctagattaa gagaaaagga tgttgcaaac    30060
catatcgtac aaactgaaac attcaaagaa gttctaaaag gaacgggtgt tgaaccaggt    30120
aaaatcaaca aagaaacaca gcaaccaaaa cttcataaga atgataatga tagcctattc    30180
aaacatttag ttgataattt cggcaaaact gtaggtgtta ttacattaac tggtttactt    30240
tctagtttct ggttagtttt ggctaaaaga cgtaaaaaag aagaagaaga aaaacaatcg    30300
ataaaaaatc atcacaaaga tattcgtctt tcagatactg ataaaataga tccaattgta    30360
ataactaagc gtaaaataga taagaagaaa caaattcaaa acgatgacaa acattcaatt    30420
ccagttgcta aacataagaa atctaaagaa aagcaattga gtgaagagga tattcattca    30480
atccccgtcg ttaagcgtaa acaaaacagt gataacaaag atacaaaaca gaagaaagtt    30540
acttctaaaa agaagaaaac gcctcaatca actaaaaaag ttgtaaaaac caaaaagcgt    30600
tctaaaaagt aa                                                       30612
```